(12) United States Patent
Choi et al.

(10) Patent No.: US 10,215,756 B2
(45) Date of Patent: Feb. 26, 2019

(54) COMPOSITION FOR DIAGNOSING PANCREATIC CANCER AND METHOD FOR DIAGNOSING PANCREATIC CANCER USING THE SAME

(71) Applicants: SK TELECOM CO., LTD., Seoul (KR); Seoul National University R&DB Foundation, Seoul (KR)

(72) Inventors: Yonghwan Choi, Seoul (KR); Junghyun Namkung, Seoul (KR); Sung Gon Yi, Seoul (KR); Sangjo Han, Seoul (KR); Jin-Young Jang, Seoul (KR); Taesung Park, Seoul (KR); Youngsoo Kim, Seoul (KR)

(73) Assignees: SK TELECOM CO., LTD., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 15/988,027

(22) Filed: May 24, 2018

(65) Prior Publication Data
US 2018/0267045 A1  Sep. 20, 2018

Related U.S. Application Data

(62) Division of application No. 14/915,658, filed as application No. PCT/KR2015/009827 on Sep. 18, 2015, now Pat. No. 9,983,208.

(30) Foreign Application Priority Data

Oct. 17, 2014 (KR) .................. 10-2014-0140695
Oct. 17, 2014 (KR) .................. 10-2014-0140714
Jun. 29, 2015 (KR) .................. 10-2015-0092393

(51) Int. Cl.
*G01N 35/10* (2006.01)
*G01N 33/574* (2006.01)
*C12Q 1/6886* (2018.01)

(52) U.S. Cl.
CPC ..... *G01N 33/57438* (2013.01); *C12Q 1/6886* (2013.01); *C12Q 2600/112* (2013.01); *C12Q 2600/118* (2013.01); *C12Q 2600/158* (2013.01); *G01N 2333/4728* (2013.01)

(58) Field of Classification Search
CPC .................................................. G01N 33/00
See application file for complete search history.

(56) References Cited

U.S. PATENT DOCUMENTS

| 2005/0260639 | A1* | 11/2005 | Nakamura | C12Q 1/6886 435/6.14 |
| 2010/0092476 | A1* | 4/2010 | Hanash | G01N 33/57438 424/141.1 |
| 2011/0294136 | A1 | 12/2011 | Meyer | |
| 2014/0073522 | A1 | 3/2014 | Williams et al. | |
| 2014/0080782 | A1* | 3/2014 | Palmon | G01N 33/57438 514/49 |
| 2014/0271621 | A1* | 9/2014 | Hemken | G01N 33/57438 424/133.1 |
| 2016/0033511 | A1* | 2/2016 | Pannell | G01N 33/57438 514/266.4 |
| 2016/0252512 | A1* | 9/2016 | Han | G01N 33/57438 506/9 |

FOREIGN PATENT DOCUMENTS

| CN | 102713623 | 10/2012 |
| JP | 2009-521215 | 6/2009 |
| KR | 10-2007-0119250 | 12/2007 |
| KR | 10-0819122 | 3/2008 |
| KR | 10-2009-0003308 | 1/2009 |
| KR | 10-2012-0009781 | 2/2012 |
| KR | 10-2012-0082372 | 7/2012 |
| WO | 2013-152989 | 10/2013 |

OTHER PUBLICATIONS

Shields et al., RBBP9: a tumor-associated serine hydrolase activity required for pancreatic neoplasia, Proc Natl Acad Sci U S A. Feb. 2, 2010;107(5):2189-94. Epub Dec. 28, 2009.*
Nie et al., Glycoprotein biomarker panel for pancreatic cancer discovered by quantitative proteomics analysis, J Proteome Res. Apr. 4, 2014;13(4):1873-84. Epub Mar. 10, 2014.*
Kakisaka et al., Plasma proteomics of pancreatic cancer patients by multi-dimensional liquid chromatography and two-dimensional difference gel electrophoresis (2D-DIGE): up-regulation of leucine-rich alpha-2-glycoprotein in pancreatic cancer, J Chromatogr B Analyt Technol Biomed Life Sci. Jun. 1, 2007;852(1-2):257-6.*
Makawita et al., Integrated proteomic profiling of cell line conditioned media and pancreatic juice for the identification of pancreatic cancer biomarkers, Mol Cell Proteomics. Oct. 2011;10(10):M111. 008599. Epub Jun. 7, 2011.*

(Continued)

*Primary Examiner* — Aaron A Priest
(74) *Attorney, Agent, or Firm* — :Lex IP Meister, PLLC

(57) ABSTRACT

The present invention relates to: a composition for diagnosing pancreatic cancer, containing a preparation for measuring the expression level of a protein or a gene thereof, and capable of being used for determining whether there is a risk of pancreatic cancer; a kit; and a method for diagnosing pancreatic cancer by using the same. The present invention can significantly predict or identify the risk of pancreatic cancer or a precancerous lesion of pancreatic cancer, the early diagnosis thereof and the extent of diseases thereof by providing a diagnostic marker of pancreatic cancer, and can be utilized in the research of pancreatic cancer oncogenesis. In addition, the diagnostic method of the present invention can provide simple and early diagnosis of pancreatic cancer from the blood and the like in a non-invasive manner.

13 Claims, 100 Drawing Sheets

(56) References Cited

OTHER PUBLICATIONS

Chen et al., Identification and verification of transthyretin as a potential biomarker for pancreatic ductal adenocarcinoma, J Cancer Res Clin Oncol. Jul. 2013;139(7):1117-27. Epub Apr. 2, 2013).*

Chen, J. et al., 'Identification and verification of transthyretin as a potential biomarker for pancreatic ductal adenocarcinoma', Journal of Cancer Research and Clinical Oncology, Apr. 2, 2013, vol. 139, pp. 1117-1127.

Furukawa, K. et al., 'Clinicopathological significance of leucine-rich α2-glycoprotein-1 in sera of patients with pancreatic cancer', Pancreas[online], Jul. 2014, vol. 44, Iss. 1, pp. 1-6. < https://www.researchgate.net/publication/264201094_Clinicopathological_Significance_of_Leucine-Rich_a2Glycoprotein-1_in_Sera_of_Patients_With_Pancreatic_Cancer>.

Fritz, S. et al., 'Role of serum carbohydrate antigen 19-9 and carcinoembryonic antigen in distinguishing between benign and invasive intraductal papillary mucinous neoplasm of the pancreas', British Journal of Surgery, Oct. 14, 2010(published online), vol. 98, pp. 104-110.

Makawita, S. et al., Validation of four candidate pancreatic cancer serological biomarkers that improve the performance of CA 19.9, BioMed Central, Sep. 3, 2013, vol. 13, No. 404, p. 1-11.

Yan, L. et al., "Confounding Effect of Obstructive Jaundice in the Interpretation of Proteomic Plasma Profiling Data for Pancreatic Cancer" Journal of Proteome Research, Dec. 4, 2008, vol. 8, No. 1, p. 142-148.

Nolen, B.M. et al., "Prediagnostic Serum Biomarkers as Early Detection Tools for Pancreatic Cancer in a Large Prospective Cohort Study" PLOS ONE, Apr. 2014, vol. 9, Issue 4, p. 1-11.

Furukawa et al., "Clinicopathological Significance of Leucine-Rich α2-Glycoprotein-1 in Sera of Patients With Pancreatic Cancer" Pancreas [Online], vol. 00, No. 00, pp. 1-6, Jul. 2014, [Publication] Pancreas: Jan. 2015 vol. 44, No. 1, pp. 93-98.

Jin Soo Lim et al., "Breast Cancer Classification Using Optimal Support Vector Machine" Journal of The Korea Society of Health Informatics and Statistics, 2013, vol. 38, No. 1, p. 108-121.

Tatsuhiko Kakisaka et al., "Plasma proteomics of pancreatic cancer patients by multi-dimensional liquid chromatography and two-dimensional difference gel electrophoresis (2D-DIGE): Up-regulation of leucine-rich alpha-2-glycoprotein in pancreatic cancer", Journal of Chromatography B, vol. 852, pp. 257-267, Feb. 2007.

Xu Shu-jian et al., "Screening serum biomarkers for pancreatic cancer by serum proteomics techniques", ACTA Universitatis Medicinalis Nanjing vol. 29 No. 4, pp. 534-538, Apr. 2009.

SIPO, Search Report of Chinese Patent Application No. 201580002481.2, dated Jan. 29, 2018.

Klaus Felix et al., "Serum Protein Signatures Differentiating Autoimmune Pancreatitis versus Pancreatic Cancer", PLOS ONE, vol. 8 No. 12, p. e82755, XP055355208, Dec. 2013.

Song Nie et al., "Glycoprotein Biomarker Panel for Pancreatic Cancer Discovered by Quantitative Proteomics Analysis", Journal of Proteome Research., vol. 13, No. 4, p. 1873-1884, XP055463005, Mar. 2014.

Ehmann Michael et al., "Identification of potential markers for the detection of pancreatic cancer through comparative serum protein expression profiling", PANC, Lippincott Williams & Wilkins, US, vol. 34, No. 2, p. 205-214, XP008183746, Mar. 2007.

Junshuo Jin et al., "Clinical significance of clusterin expression in pancreatic adenocarcinoma", World Journal of Surgical Oncology, Biomed Central, London, GB, val. 10, No., p. 146, XP021116055, Jul. 2012.

Hustinx S R et al., "Differentially expressed genes in pancreatic ductal adenocarcinomas identified through serial analysis of gene expression", Cancer Biology & Therapy, Landes Bioscience, US, vol. 3, No. 12, p. 1254-1261, XP002552474, Dec. 2004.

Bin Xu et al., "Predictive Value of Serum Carbohydrate Antigen 19-9 in Malignant Intraductal Papillary Mucinous Neoplasms", World Journal of Surgery; Official Journal of the Internationalsociety of Surgery/Societe Internationale De Chirurgie, Springer-Verlag, NE, vol. 35, No. 5, p. 1103-1109, XP019893705, Mar. 2011.

Extended European Search Report of the corresponding European Patent Application No. 15850998.4, dated Apr. 9, 2018.

* cited by examiner

[Fig. 1]
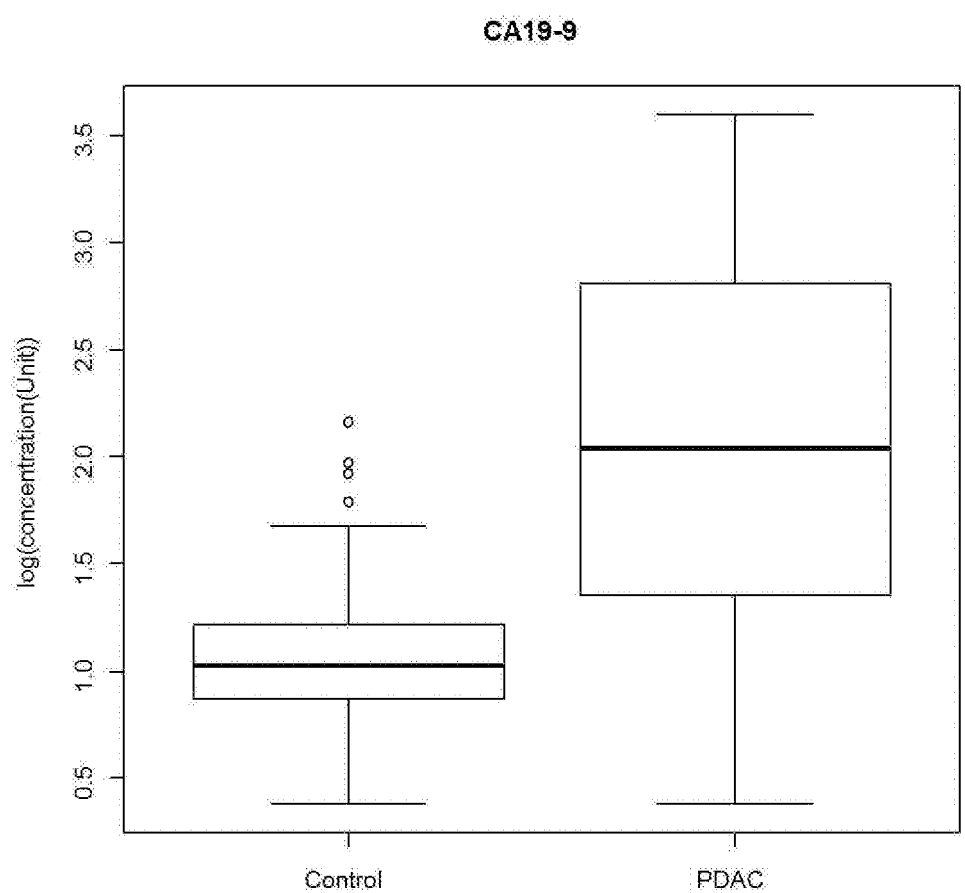

[Fig. 2]
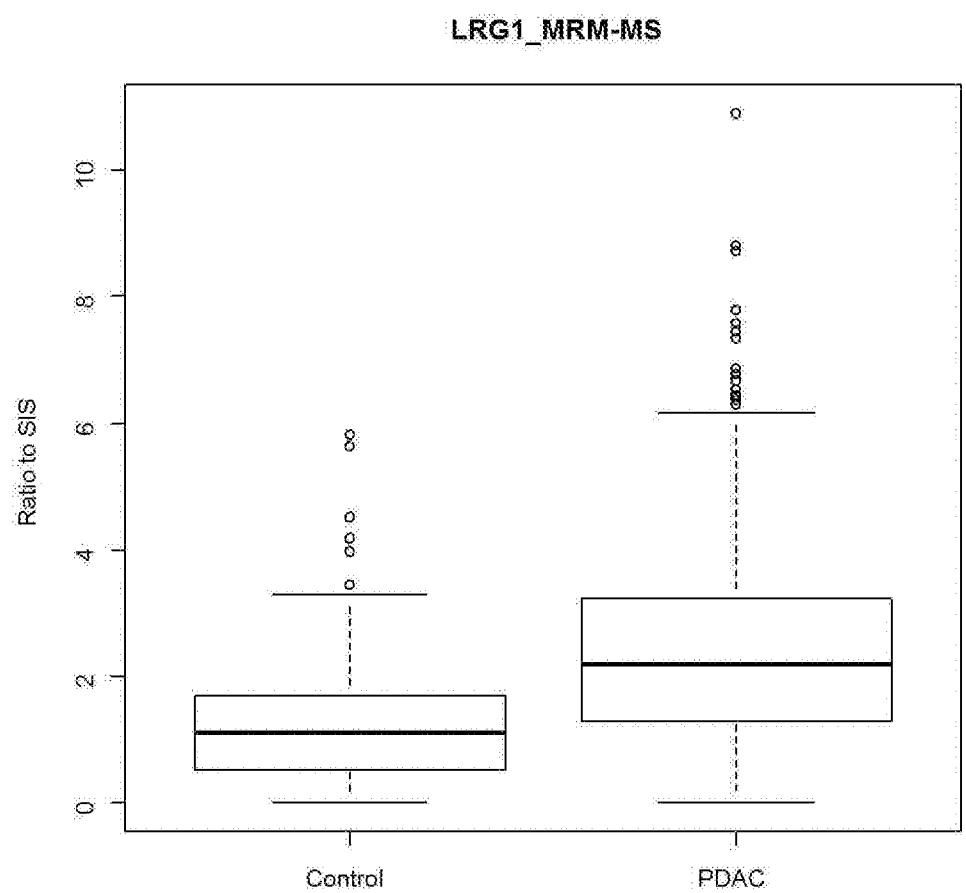

[Fig. 3]
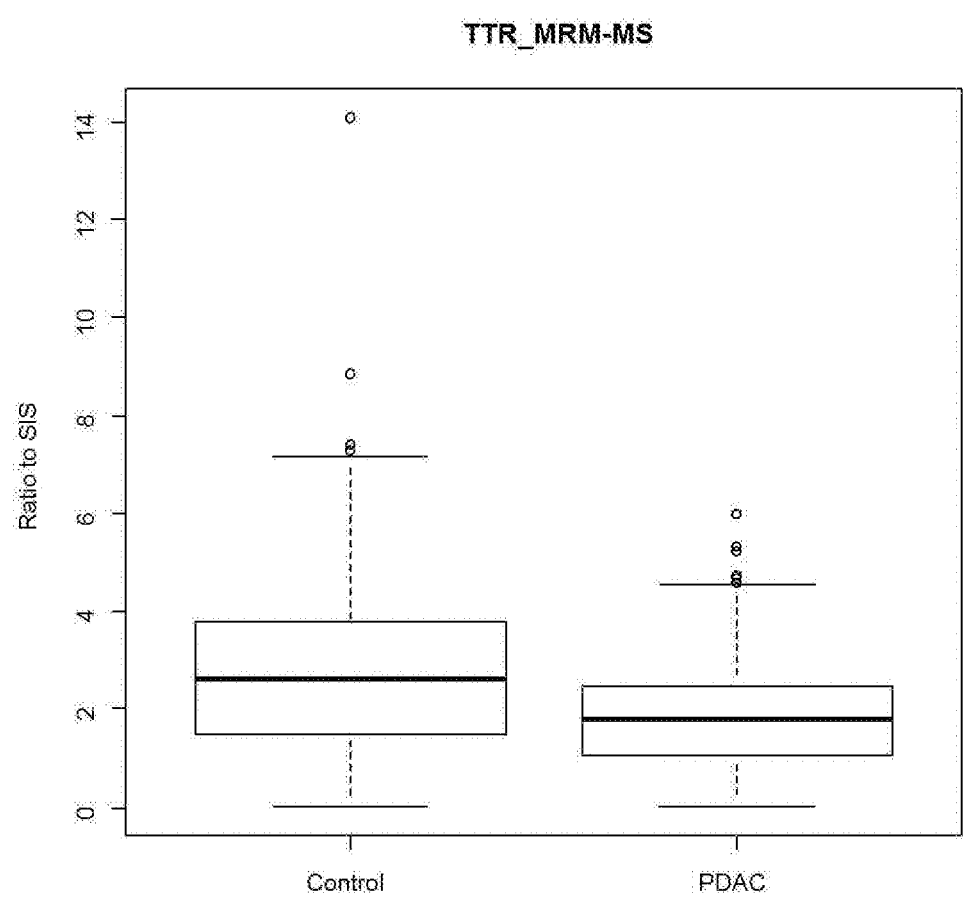

[Fig. 4]
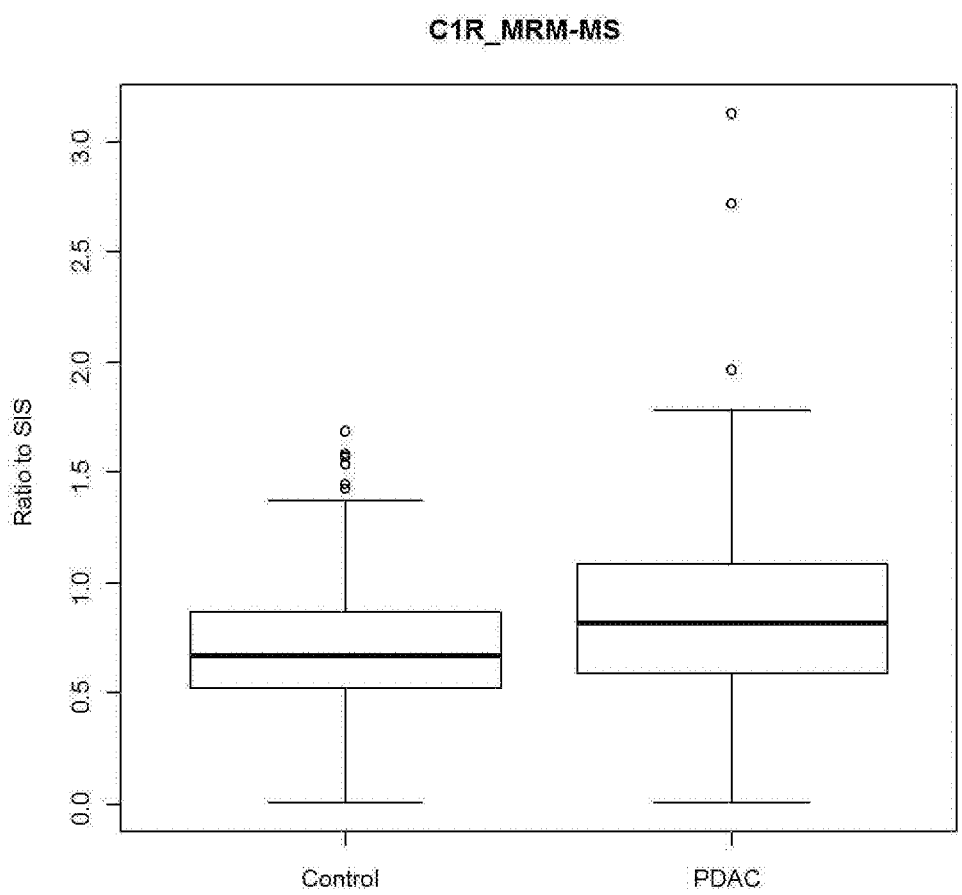

[Fig. 5]
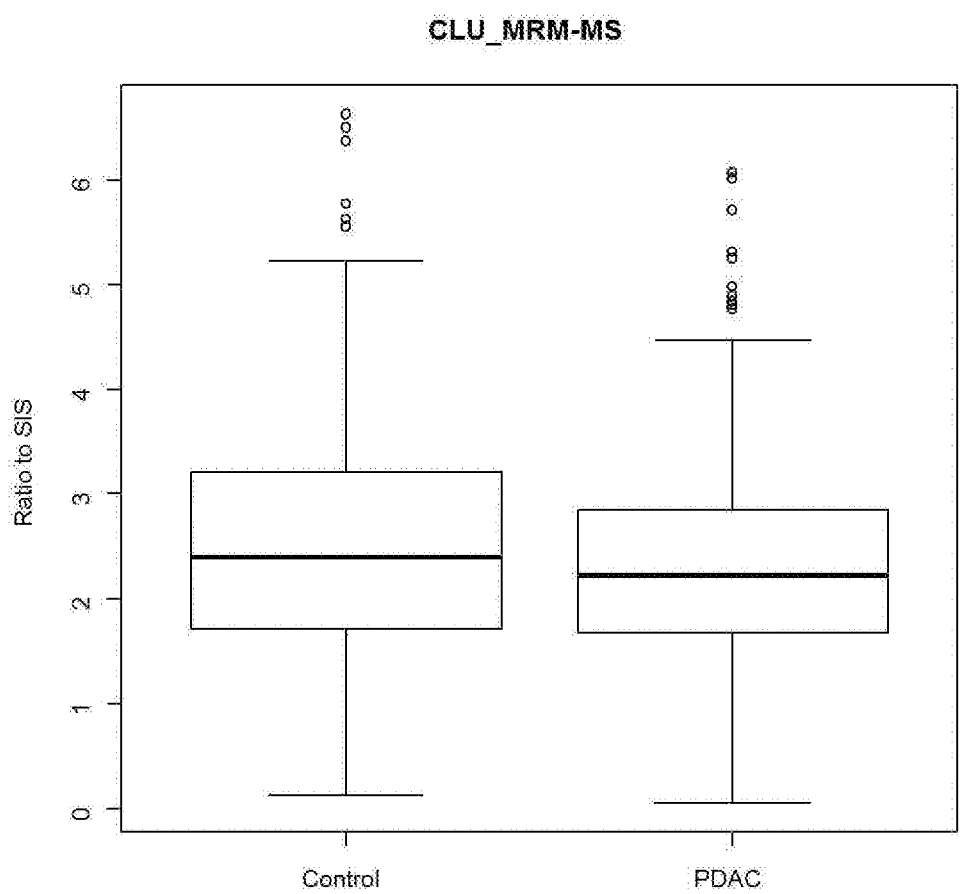

[Fig. 6]
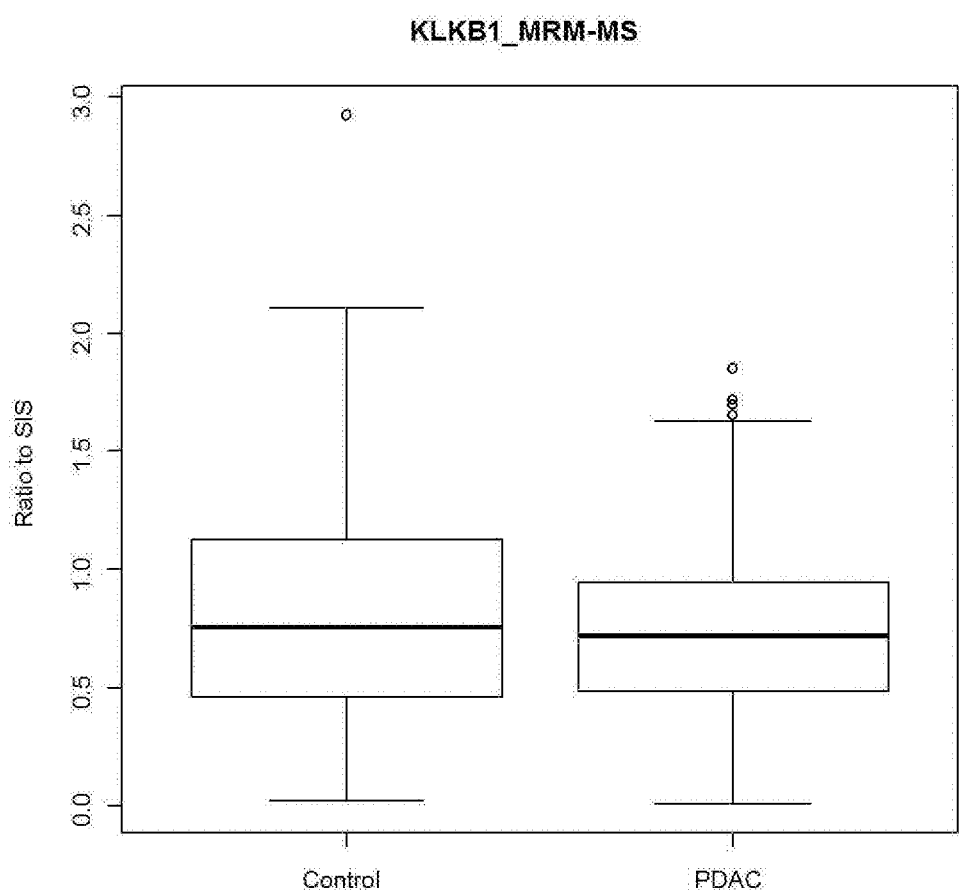

[Fig. 7]
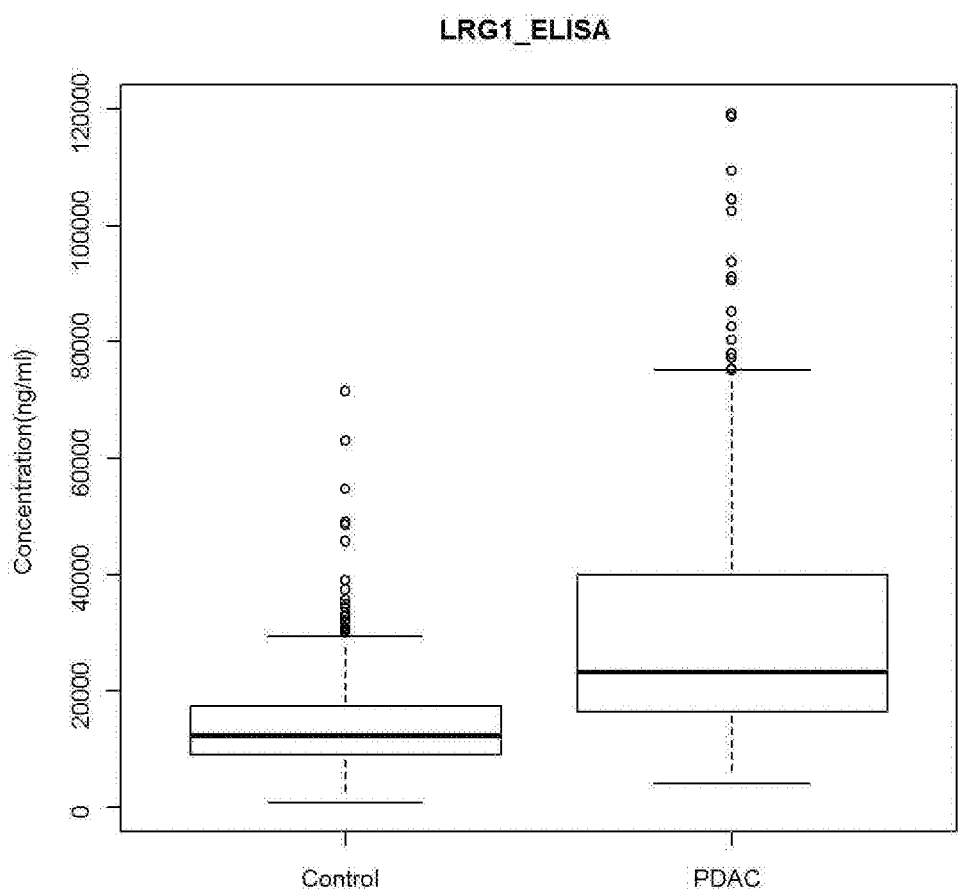

[Fig. 8]
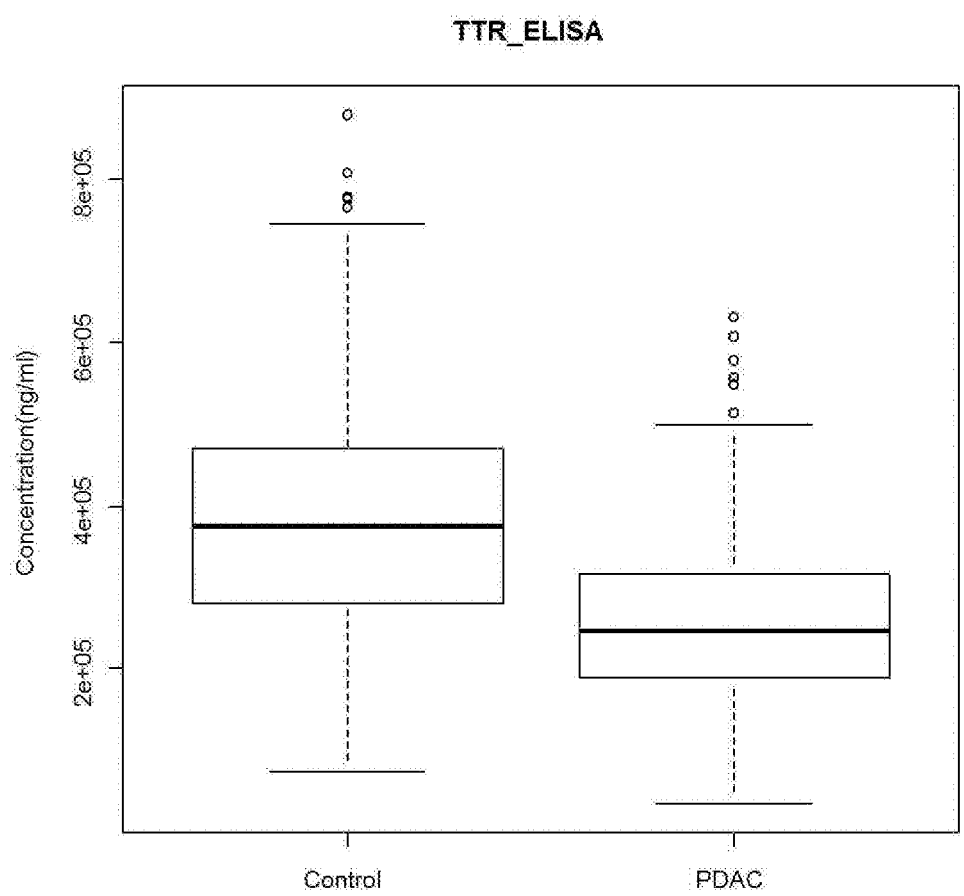

【Fig. 9】
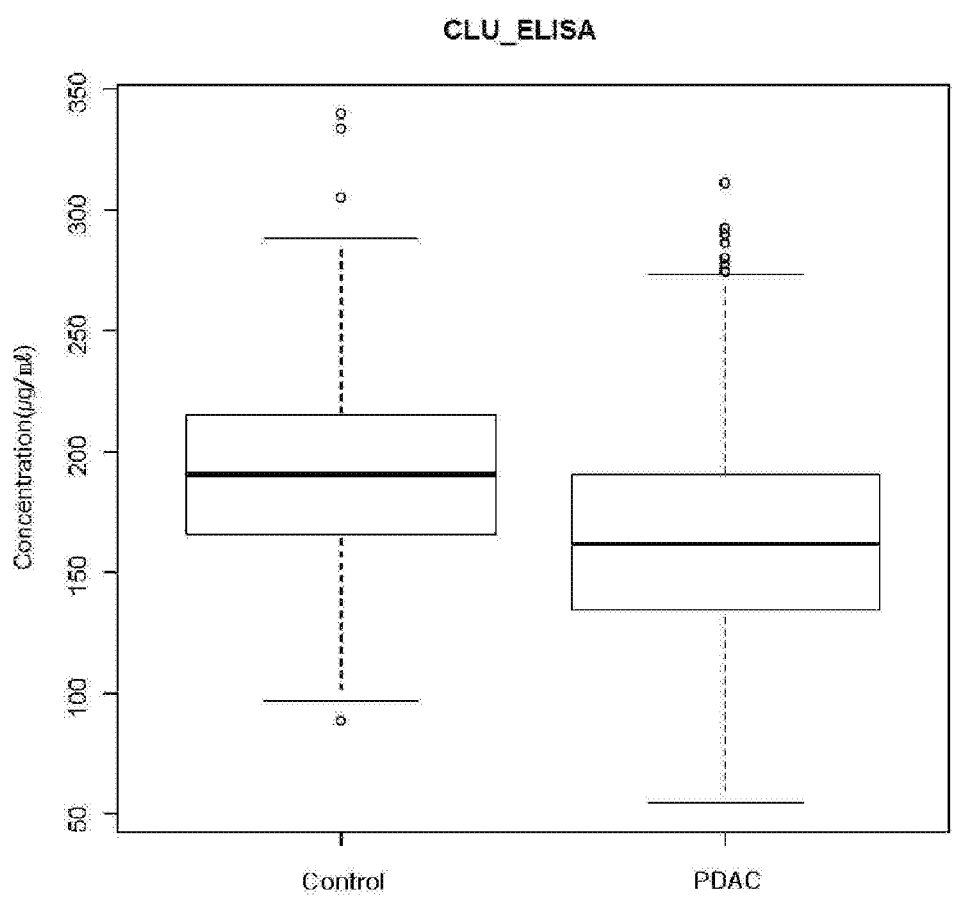

[Fig. 10]
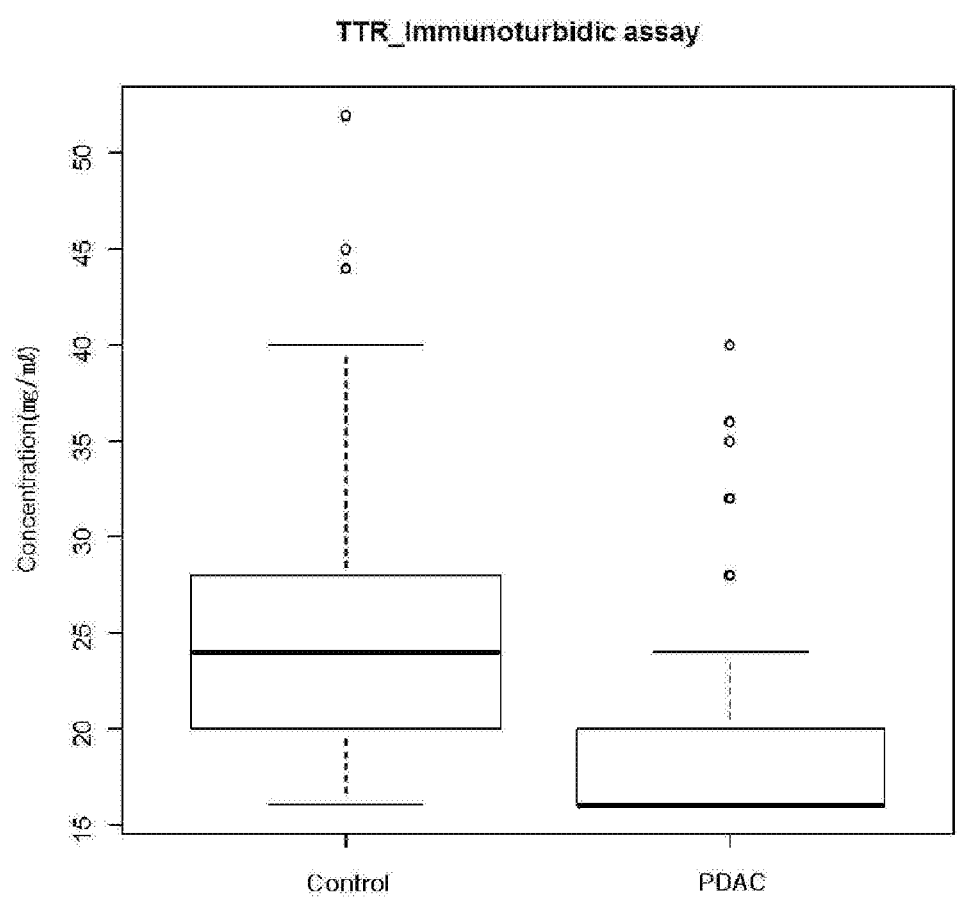

[Fig. 11]
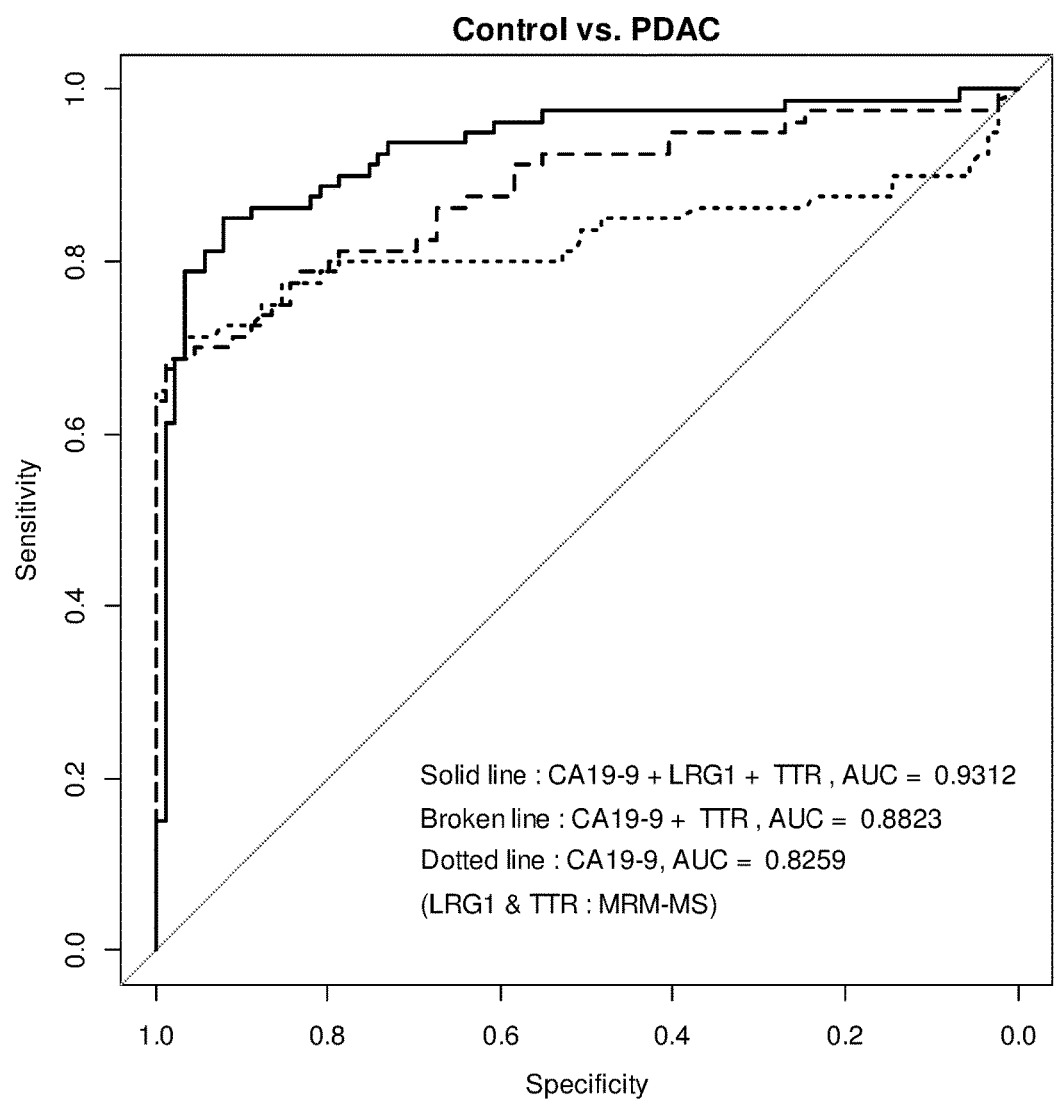

[Fig. 12]
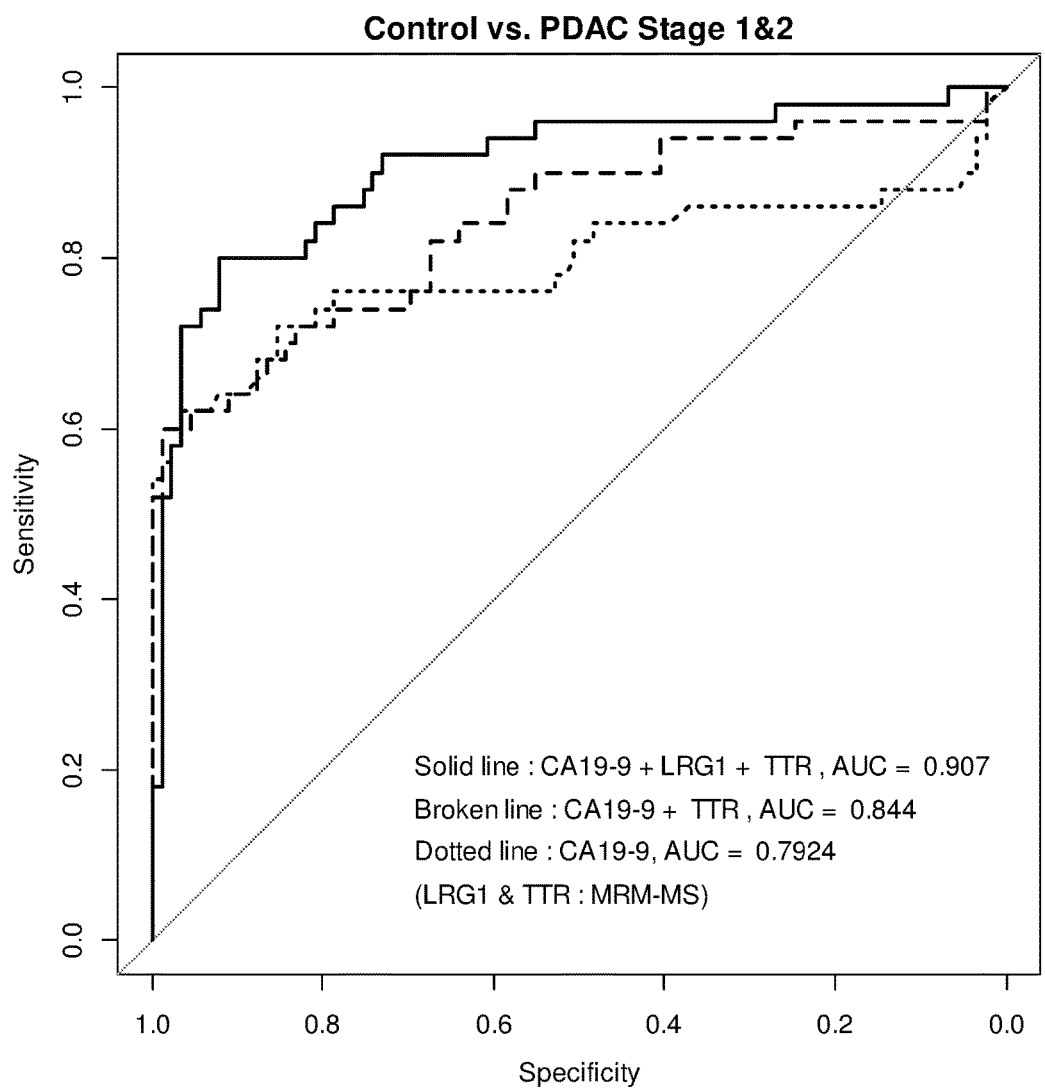

[Fig. 13]
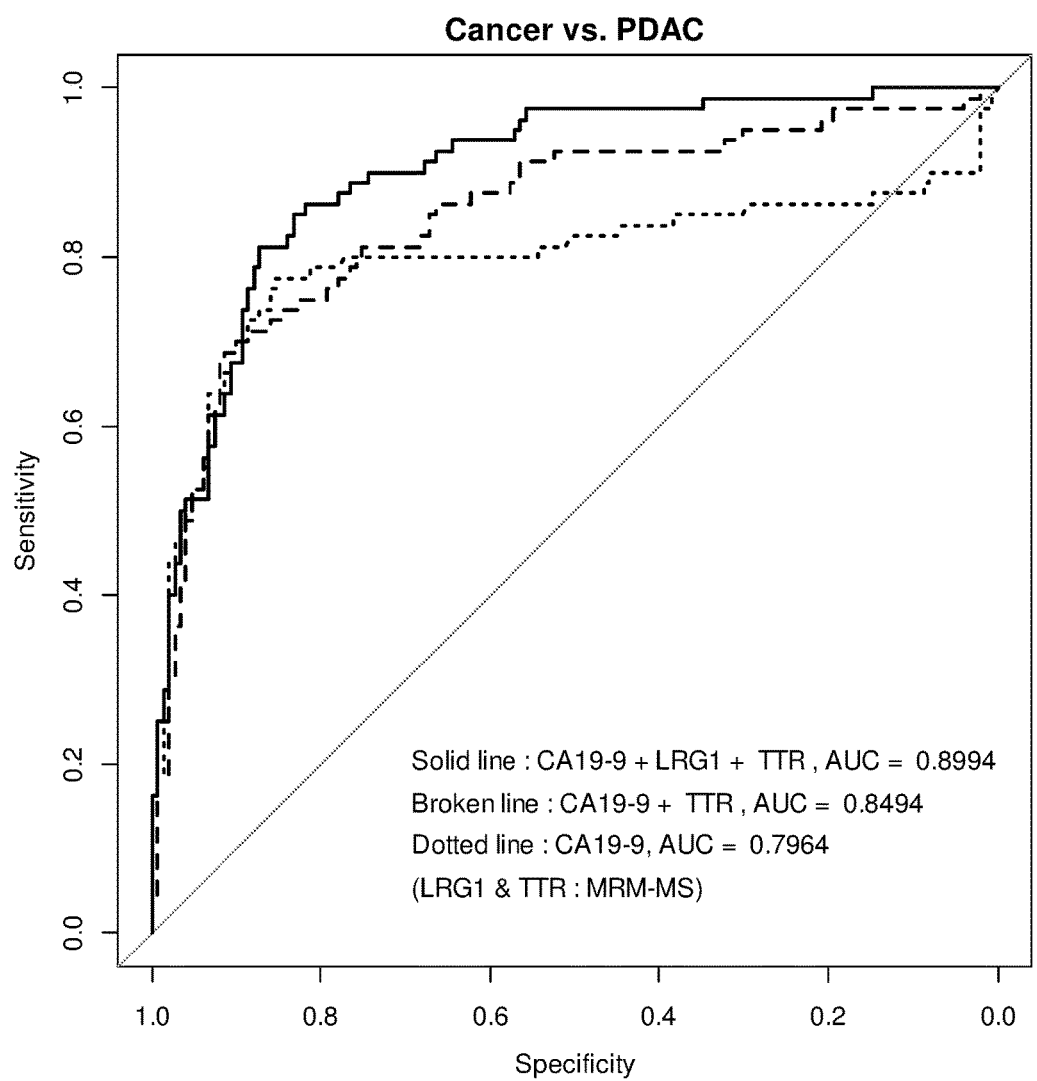

[Fig. 14]
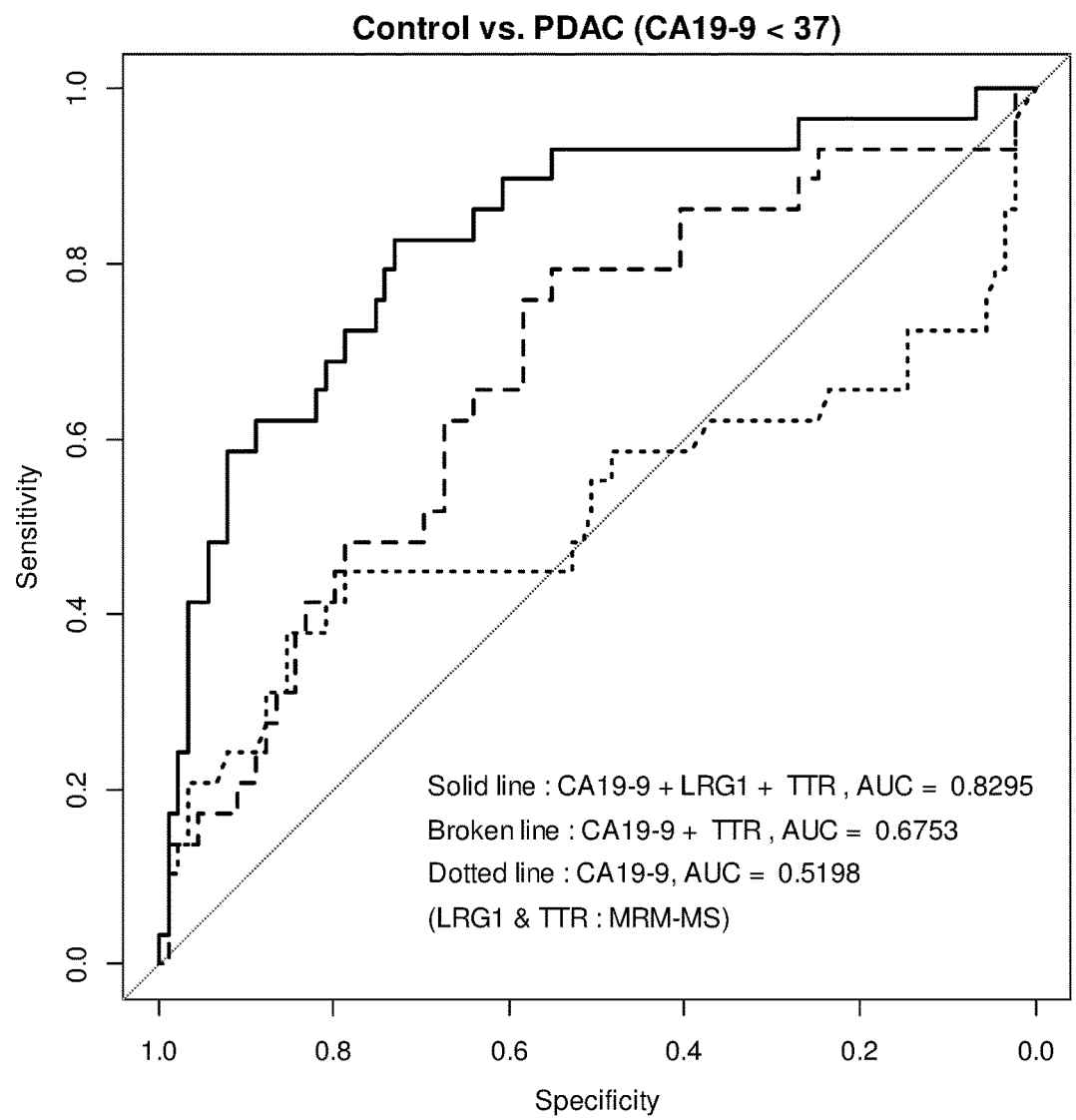

[Fig. 15]
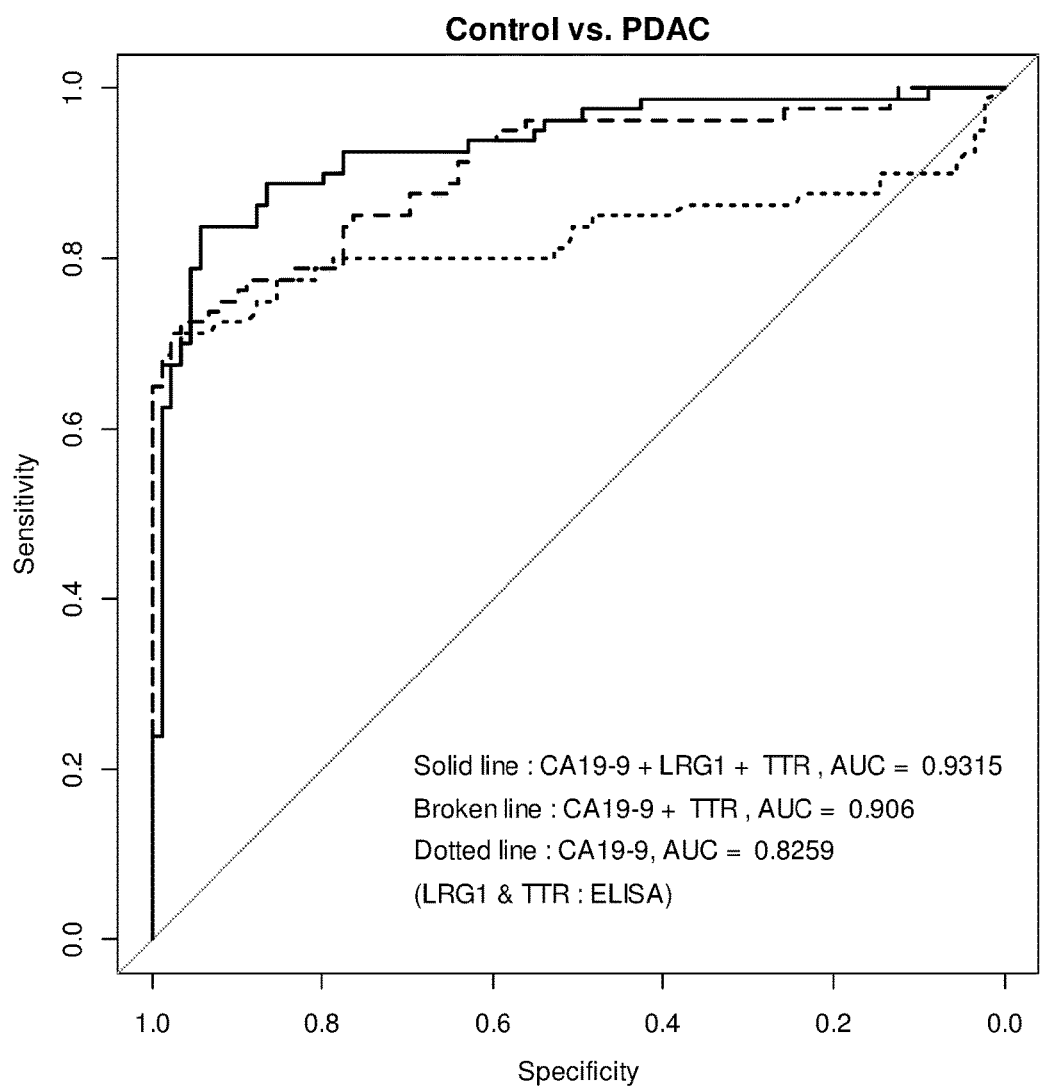

[Fig. 16]
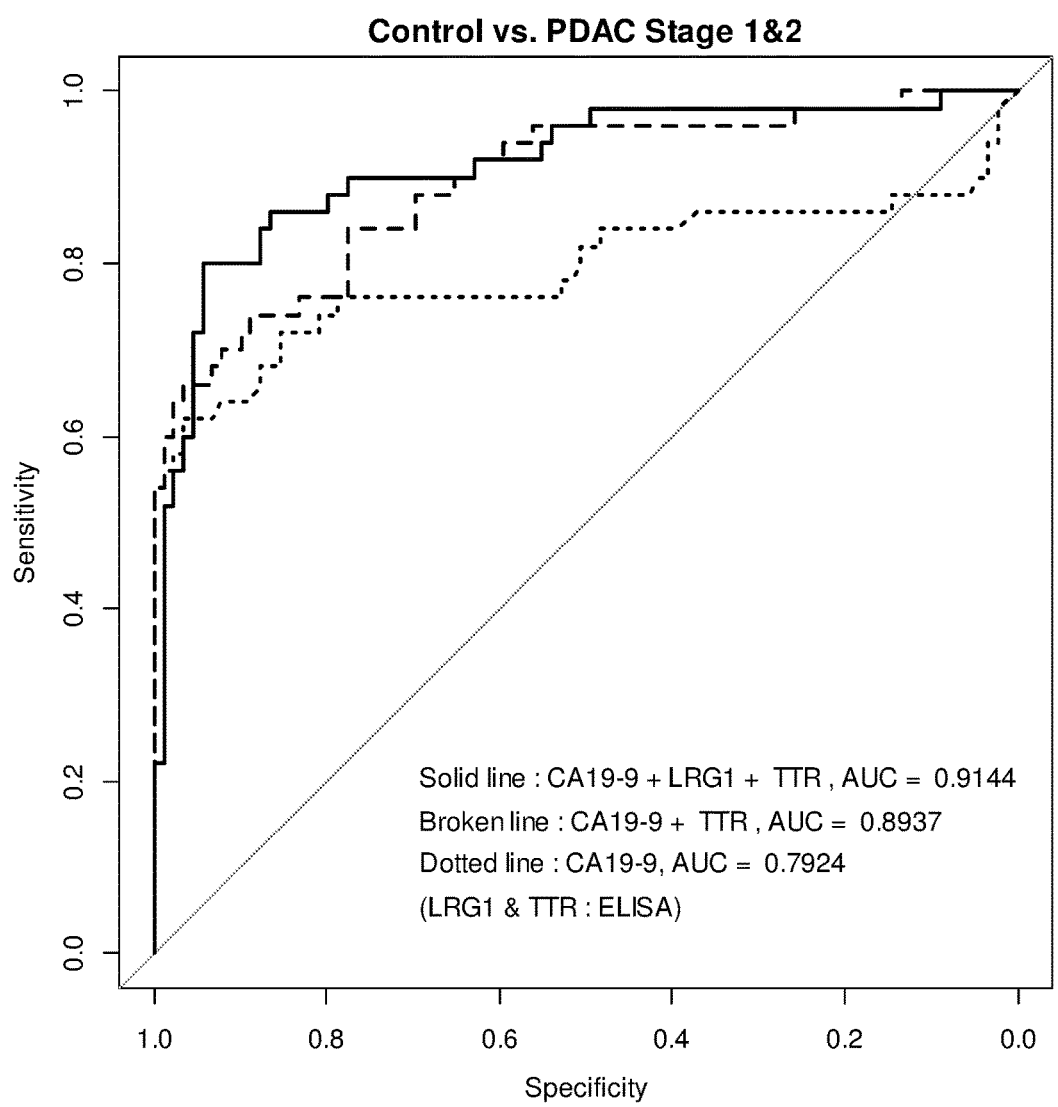

[Fig. 17]
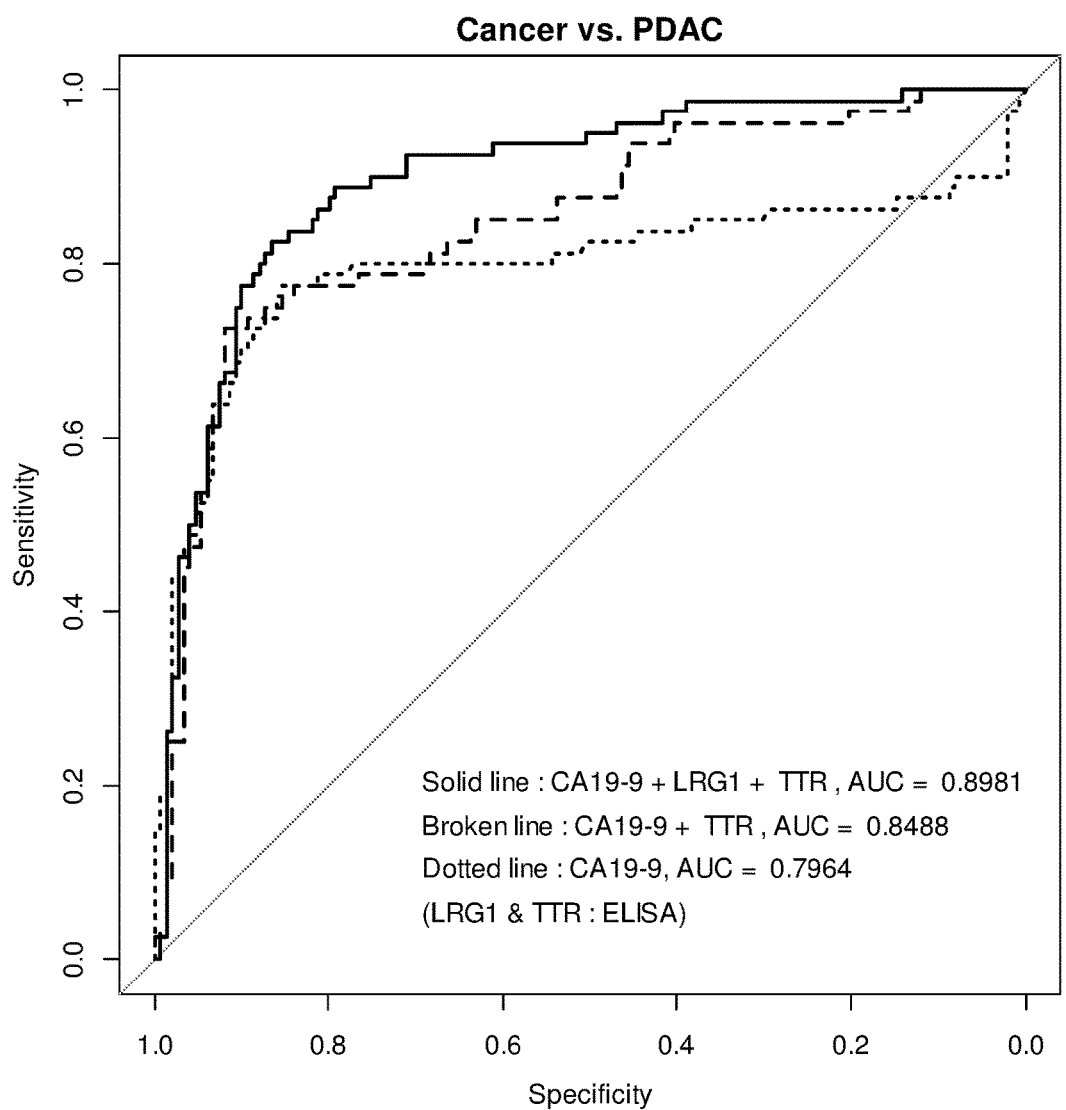

[Fig. 18]
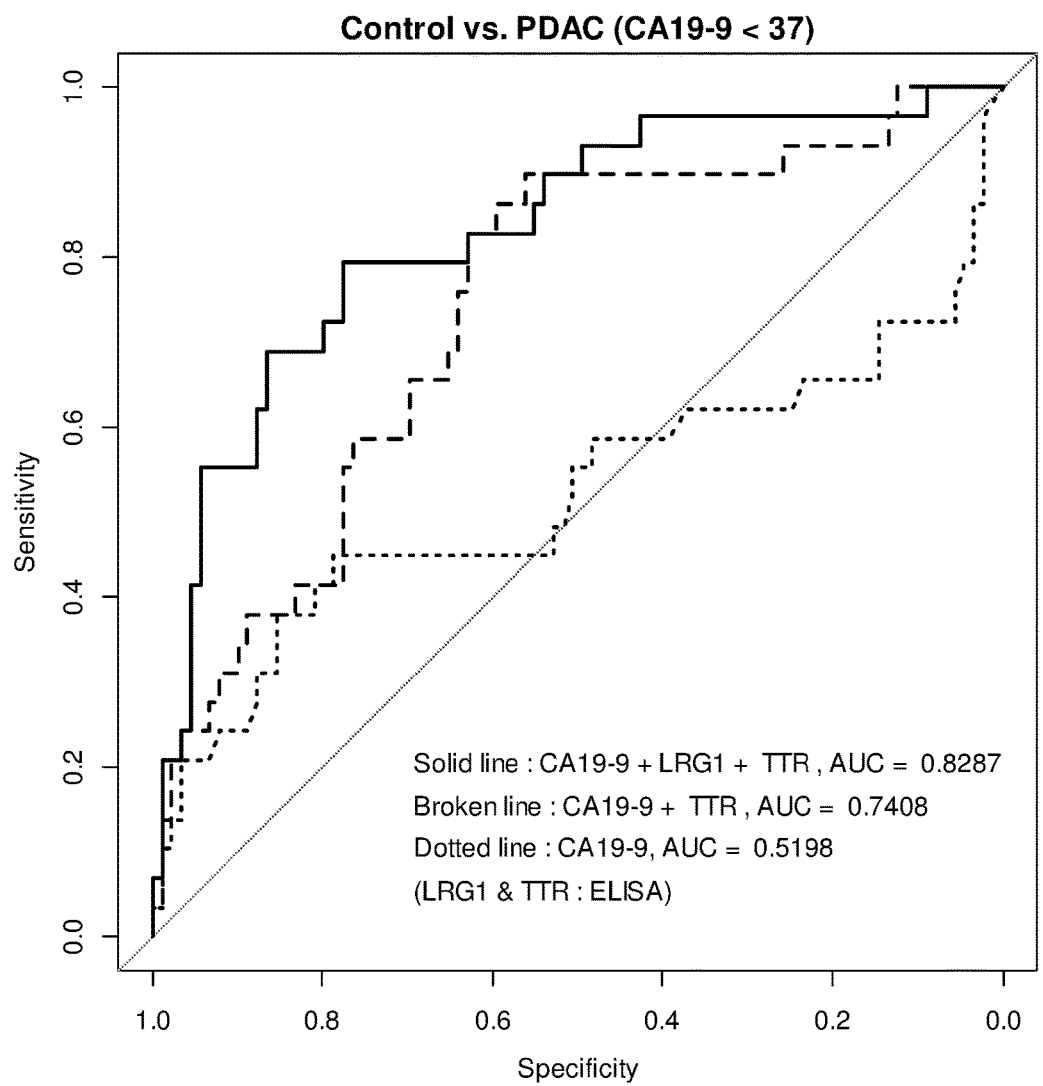

[Fig. 19]
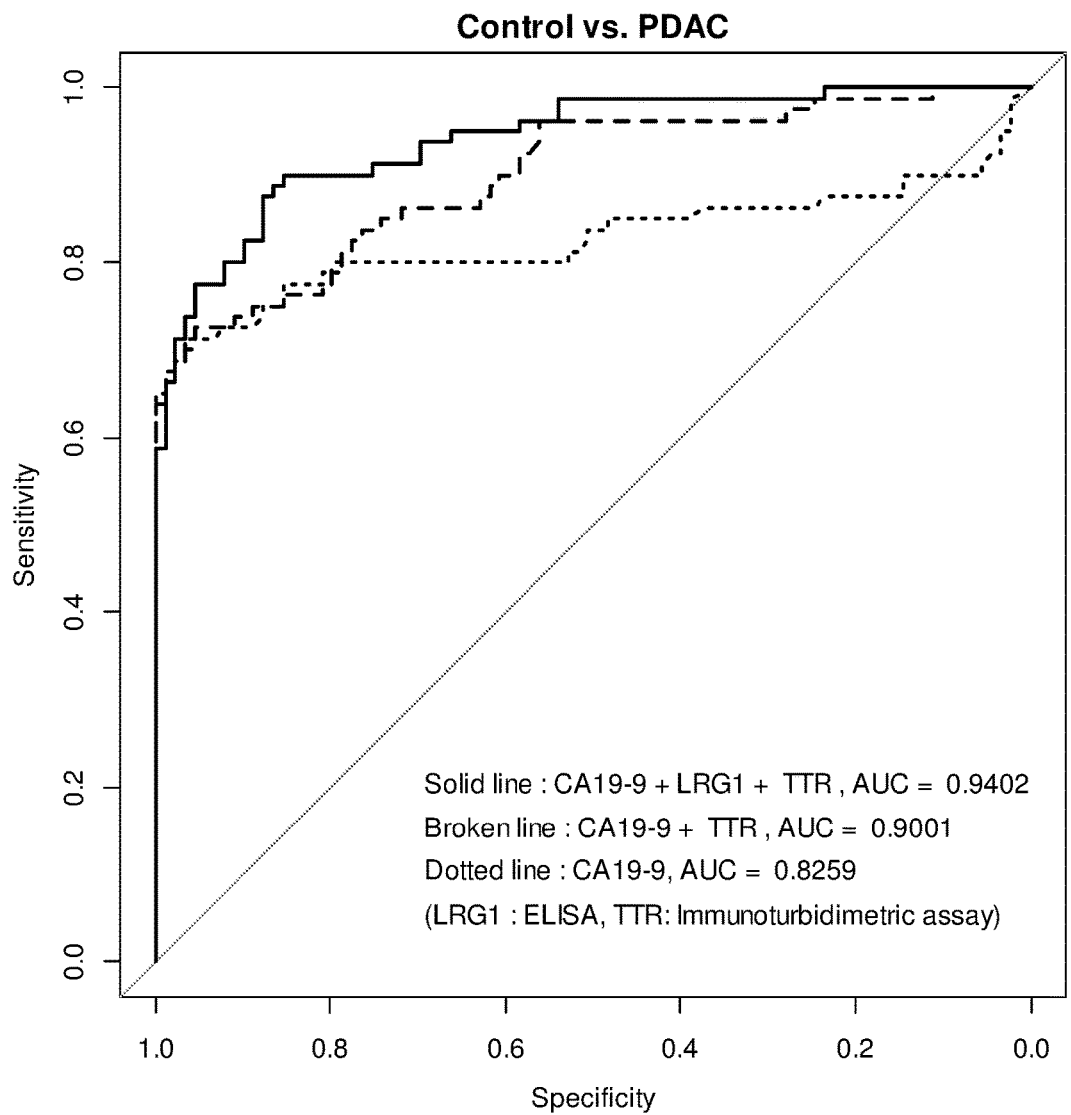

[Fig. 20]
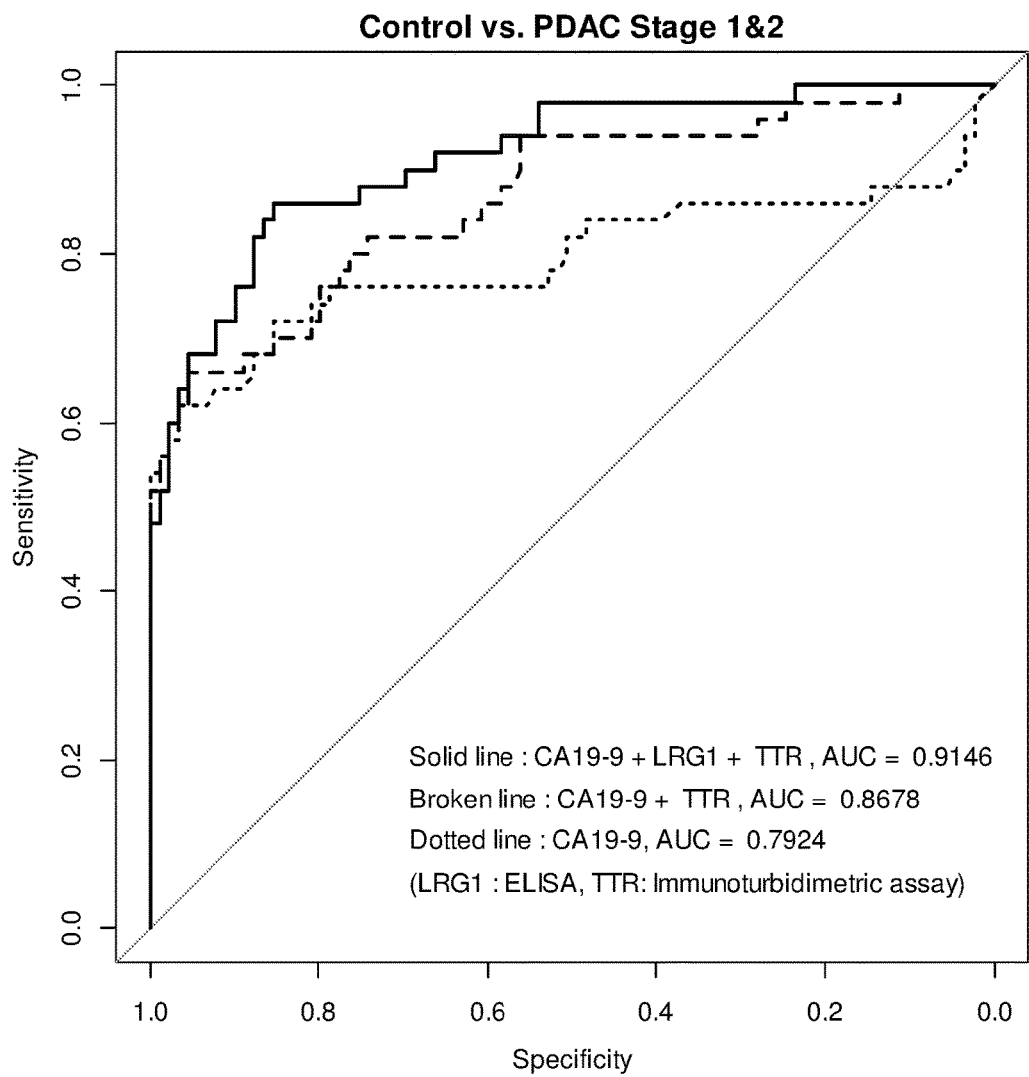

[Fig. 21]
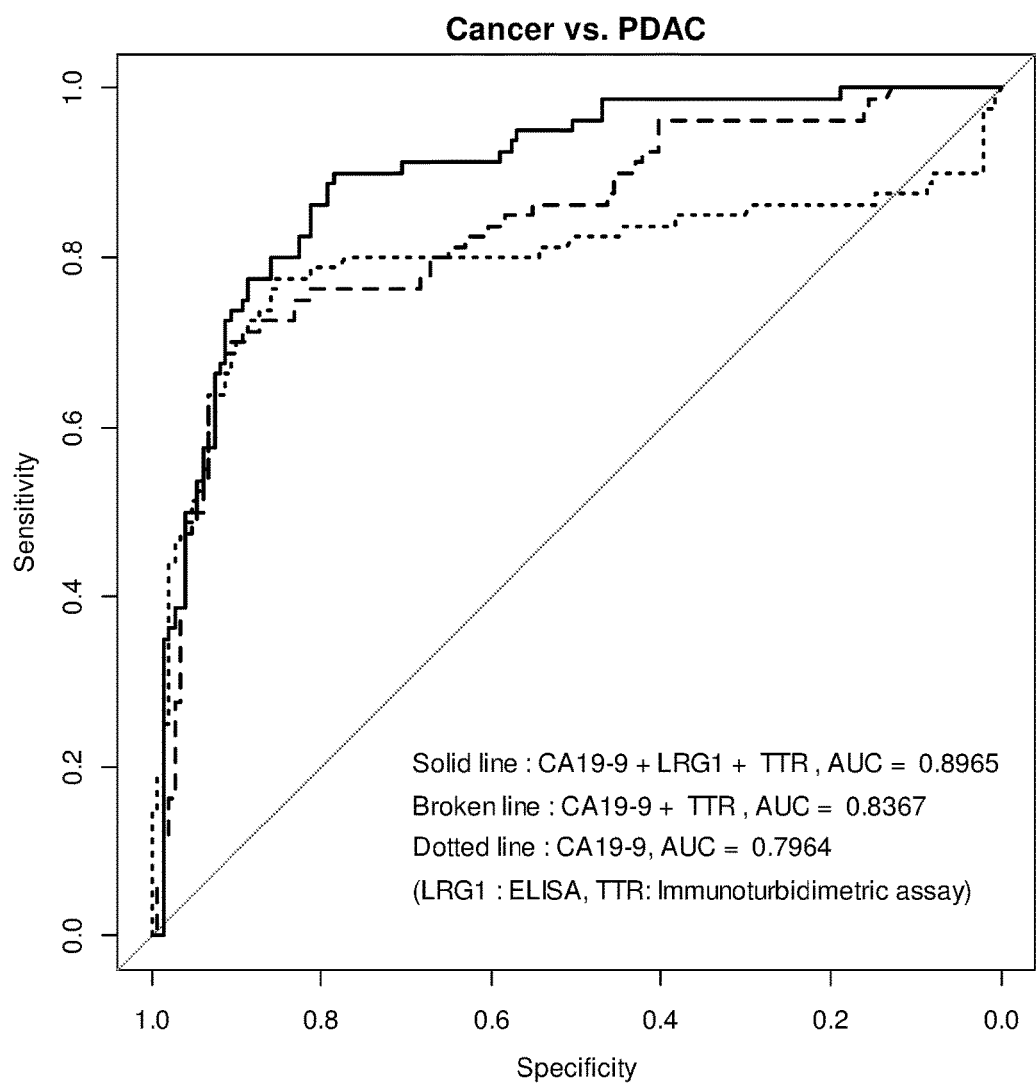

[Fig. 22]
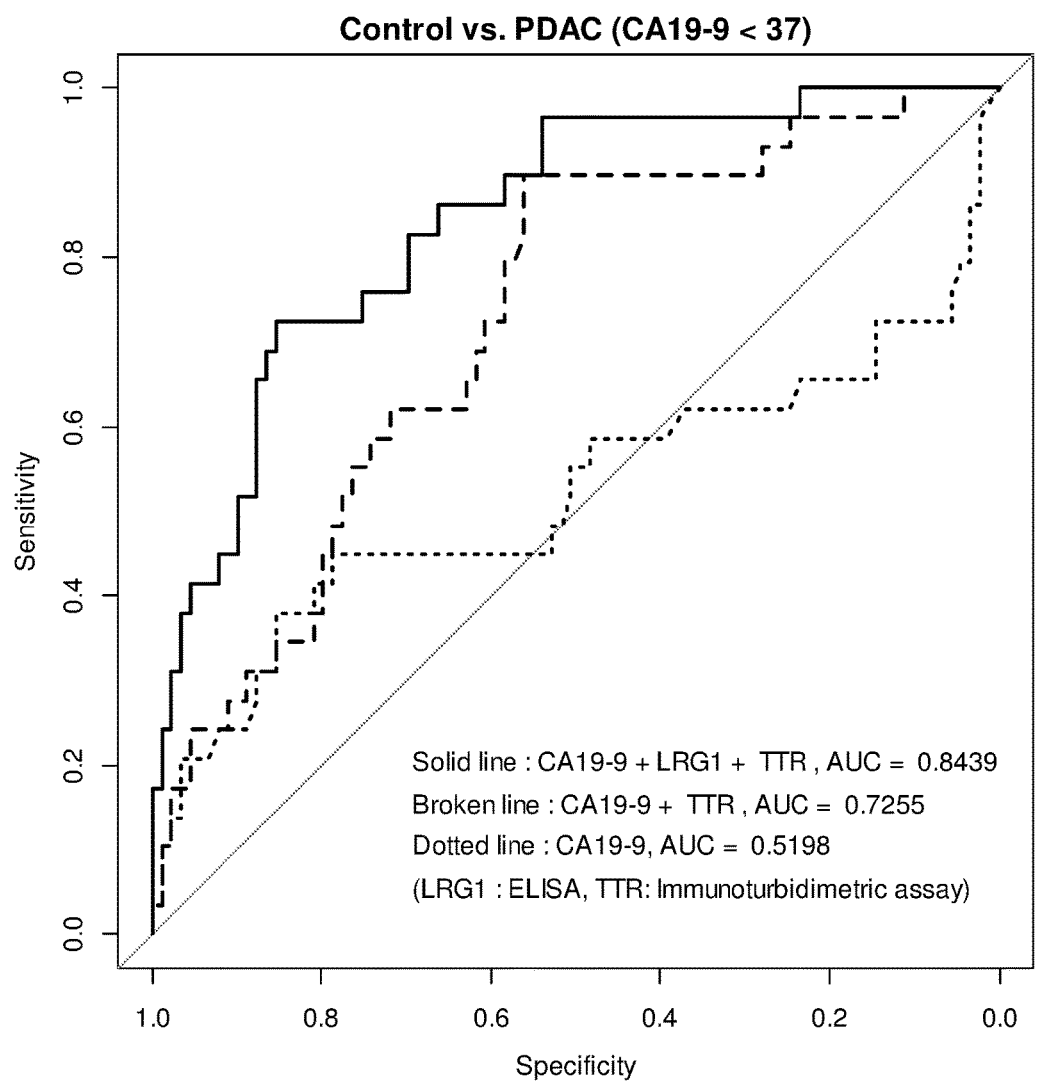

【Fig. 23】
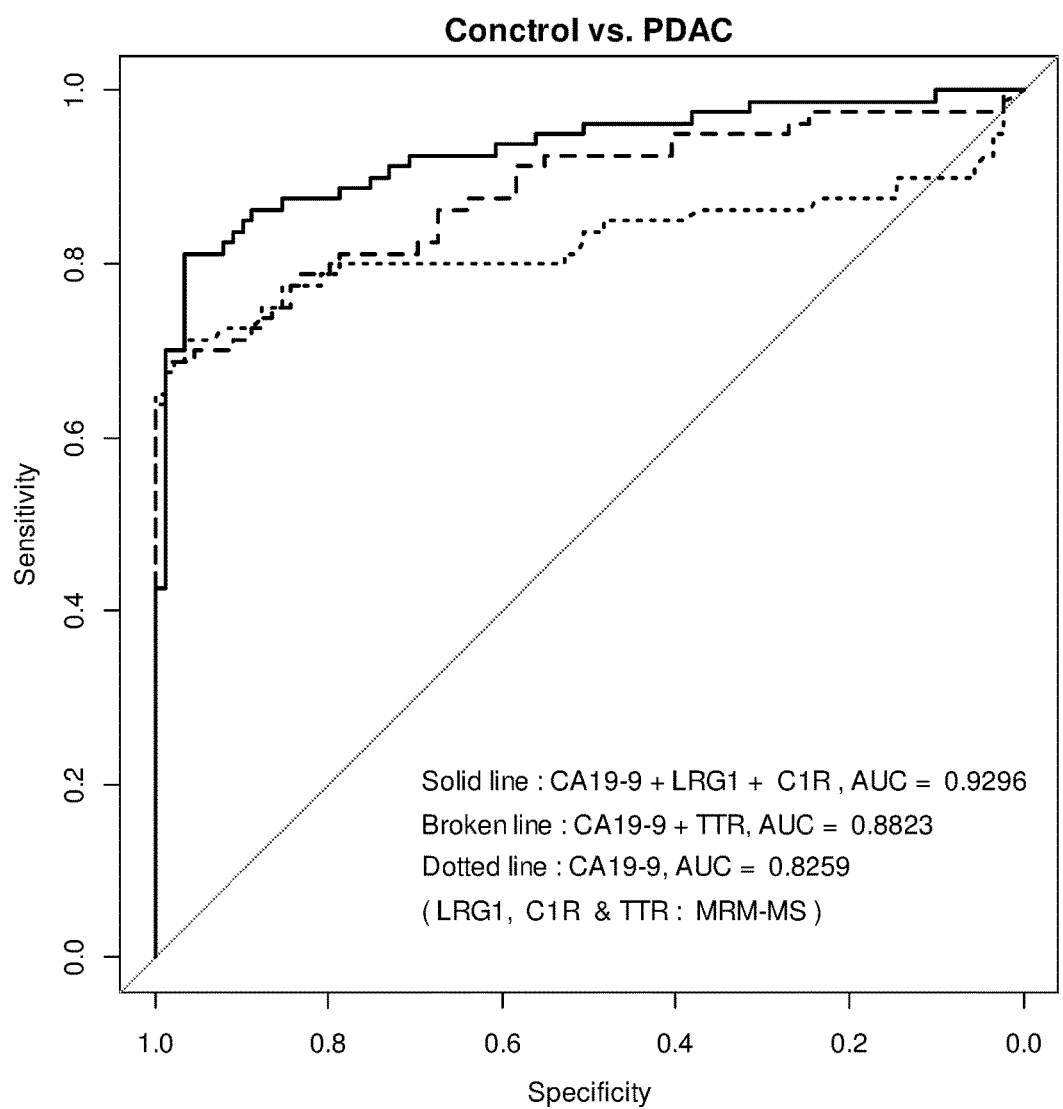

[Fig. 24]
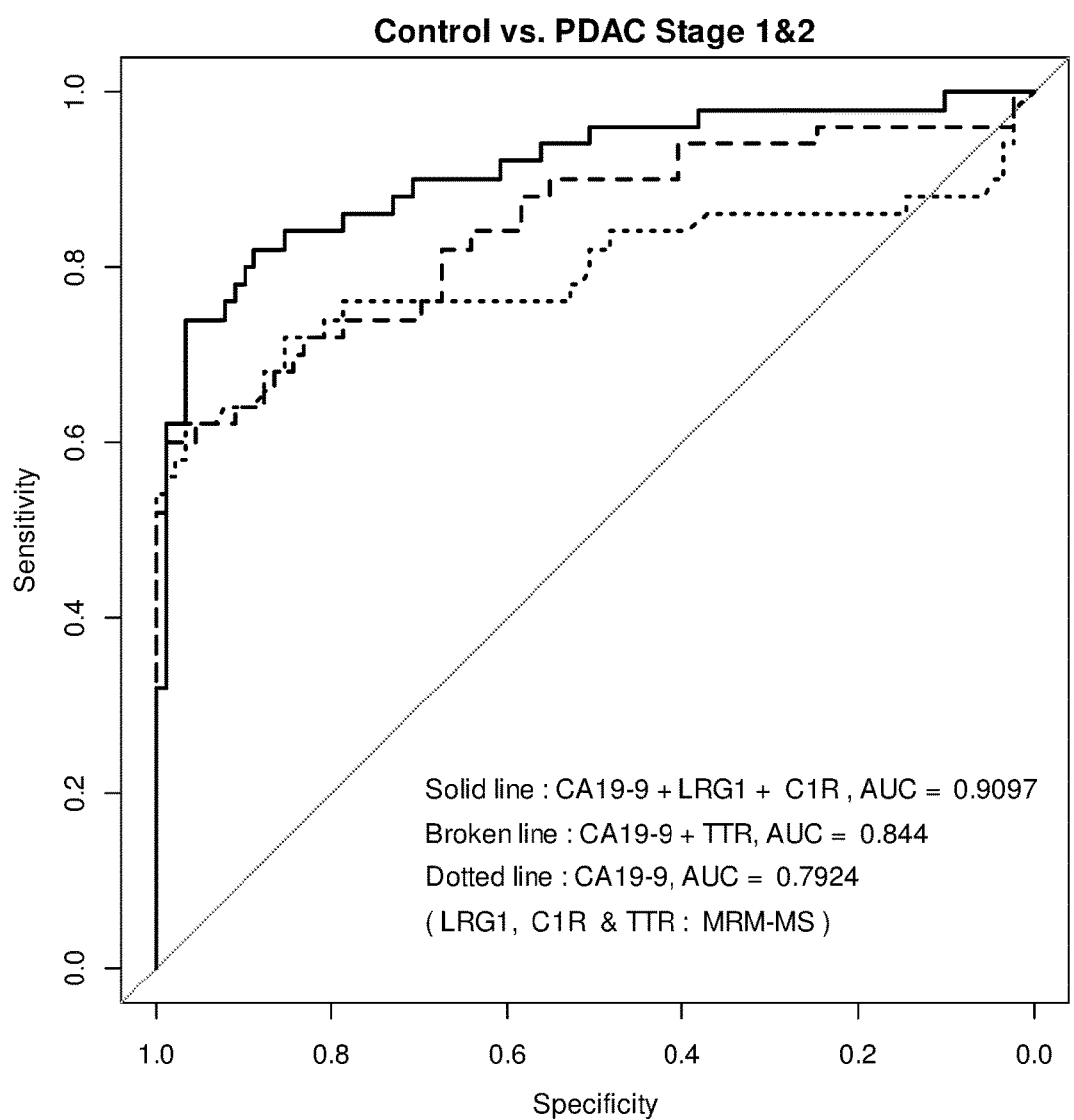

【Fig. 25】
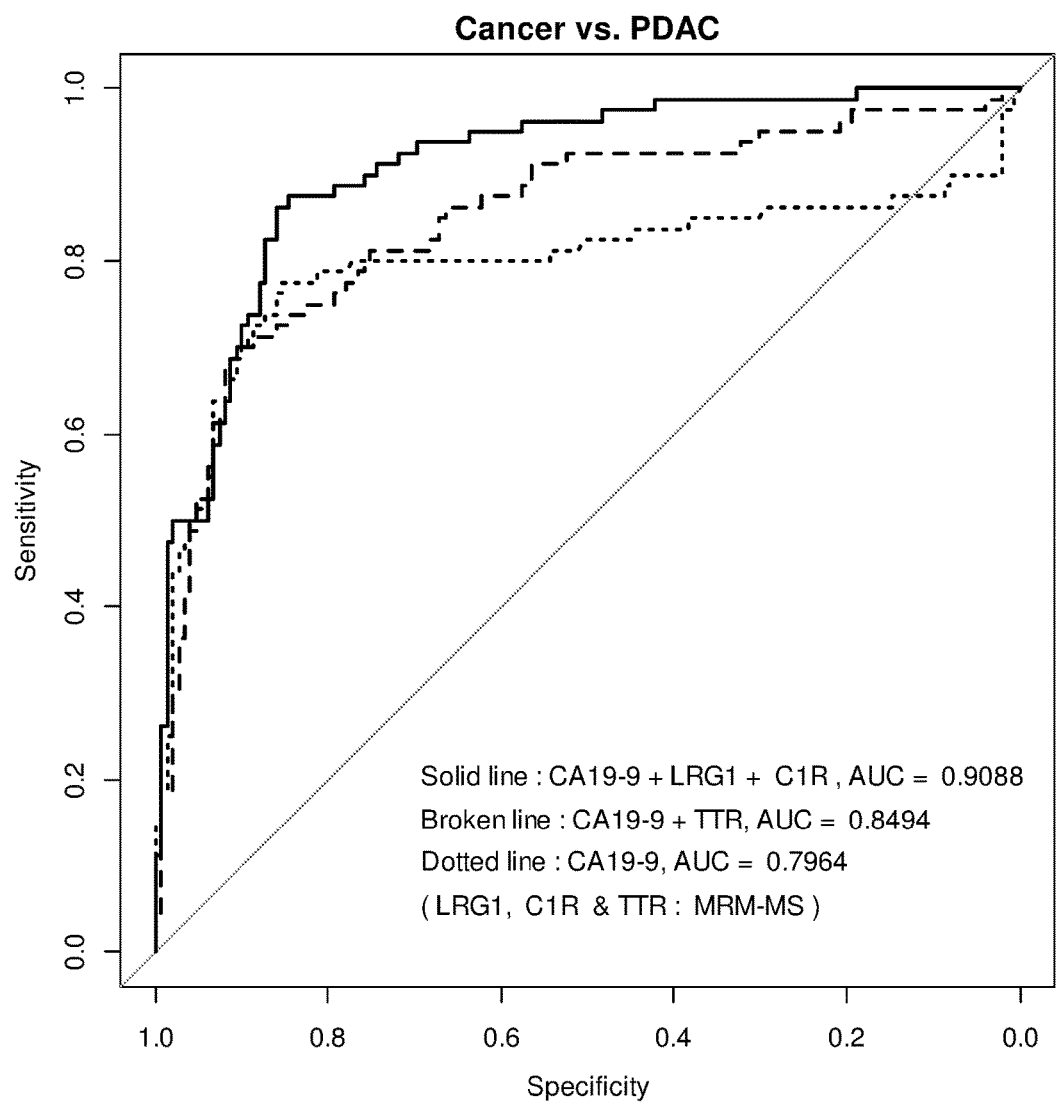

[Fig. 26]
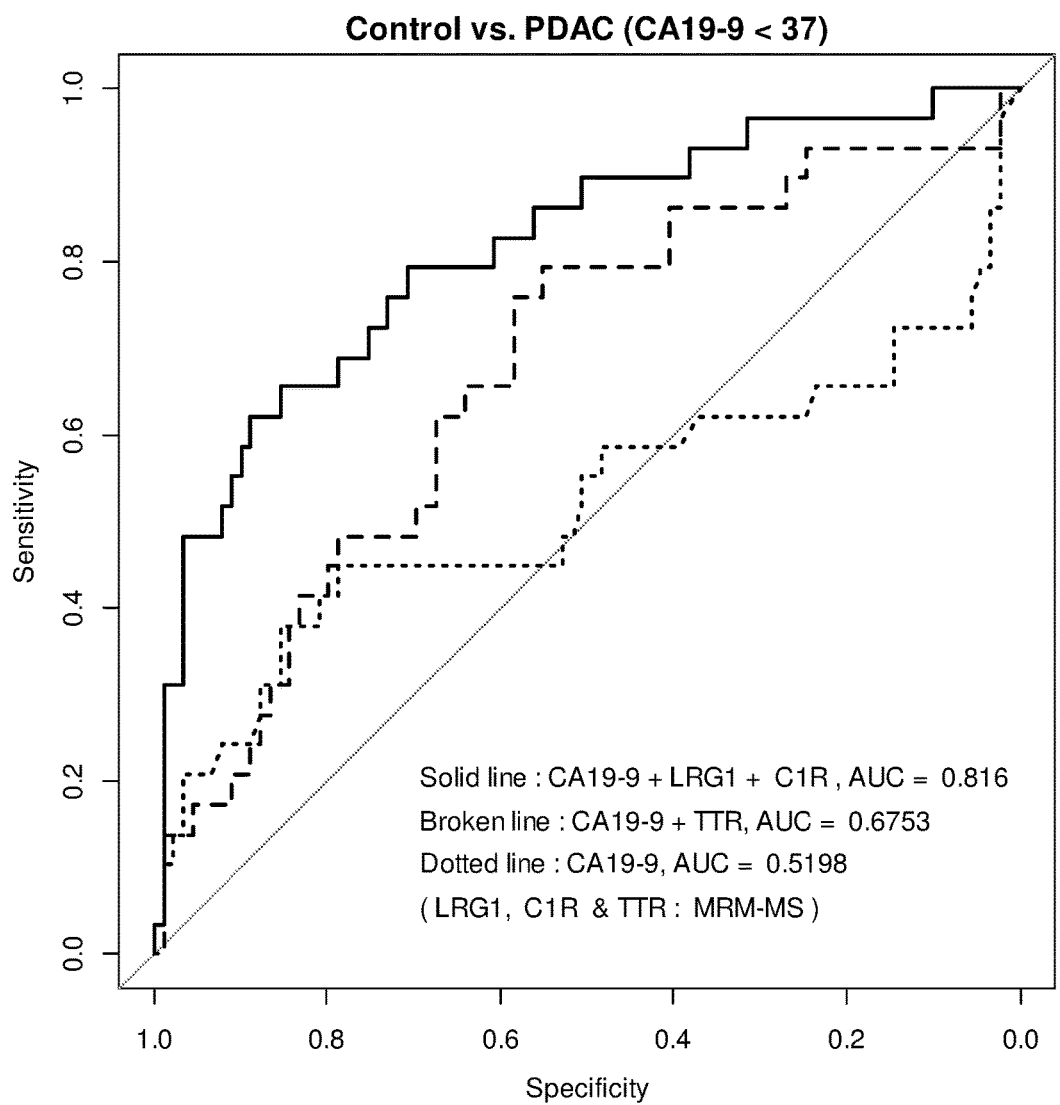

[Fig. 27]
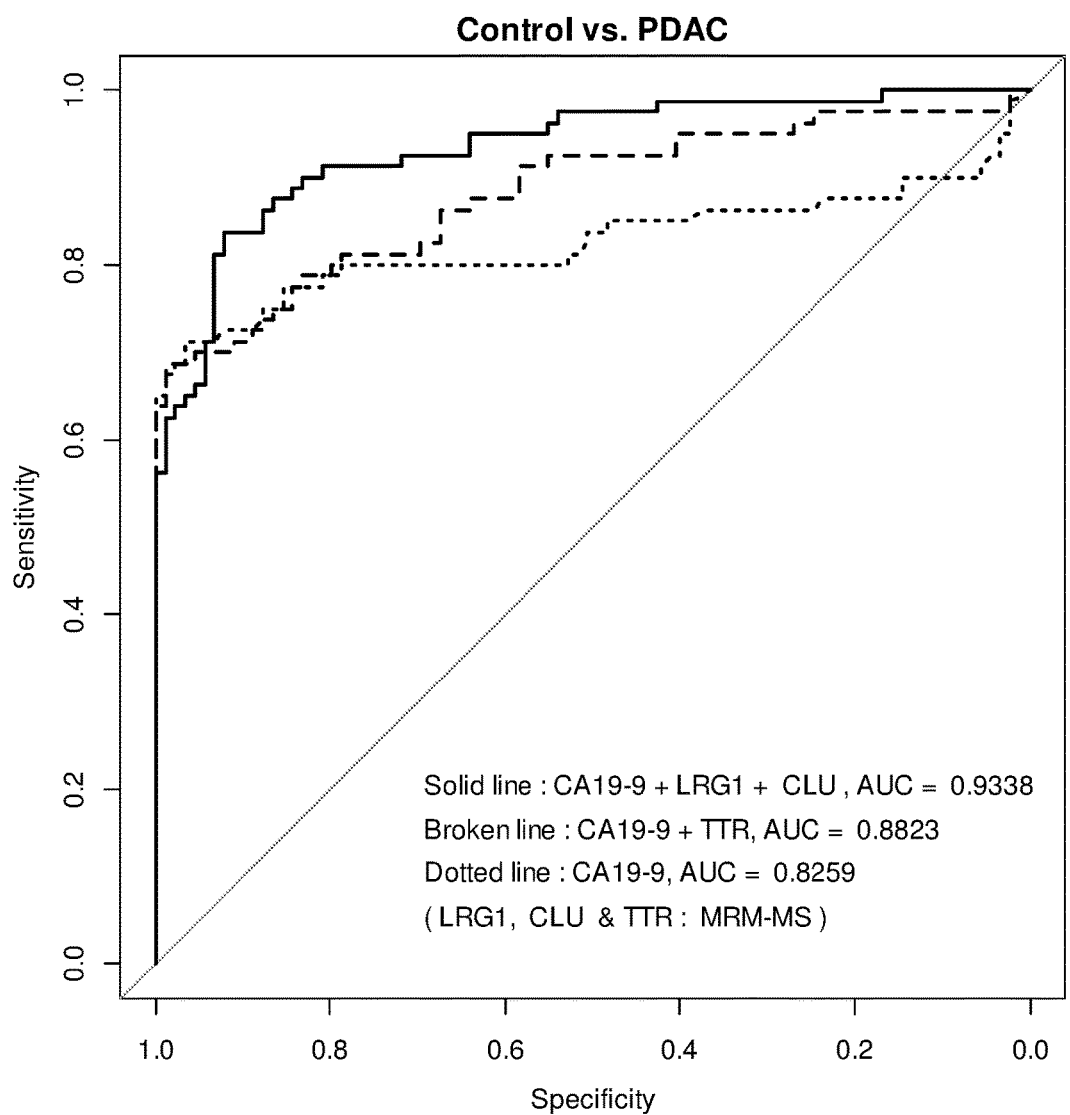

[Fig. 28]
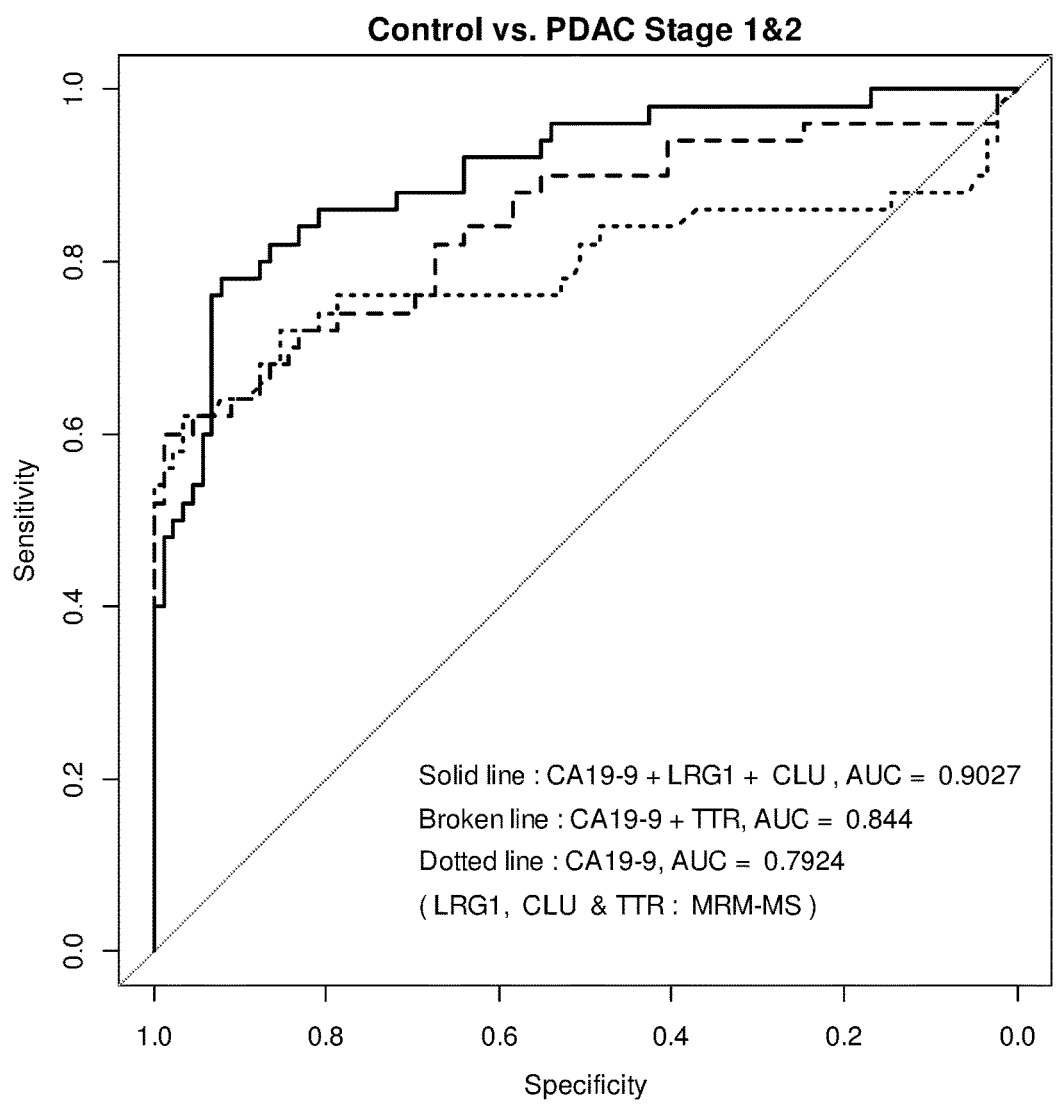

【Fig. 29】
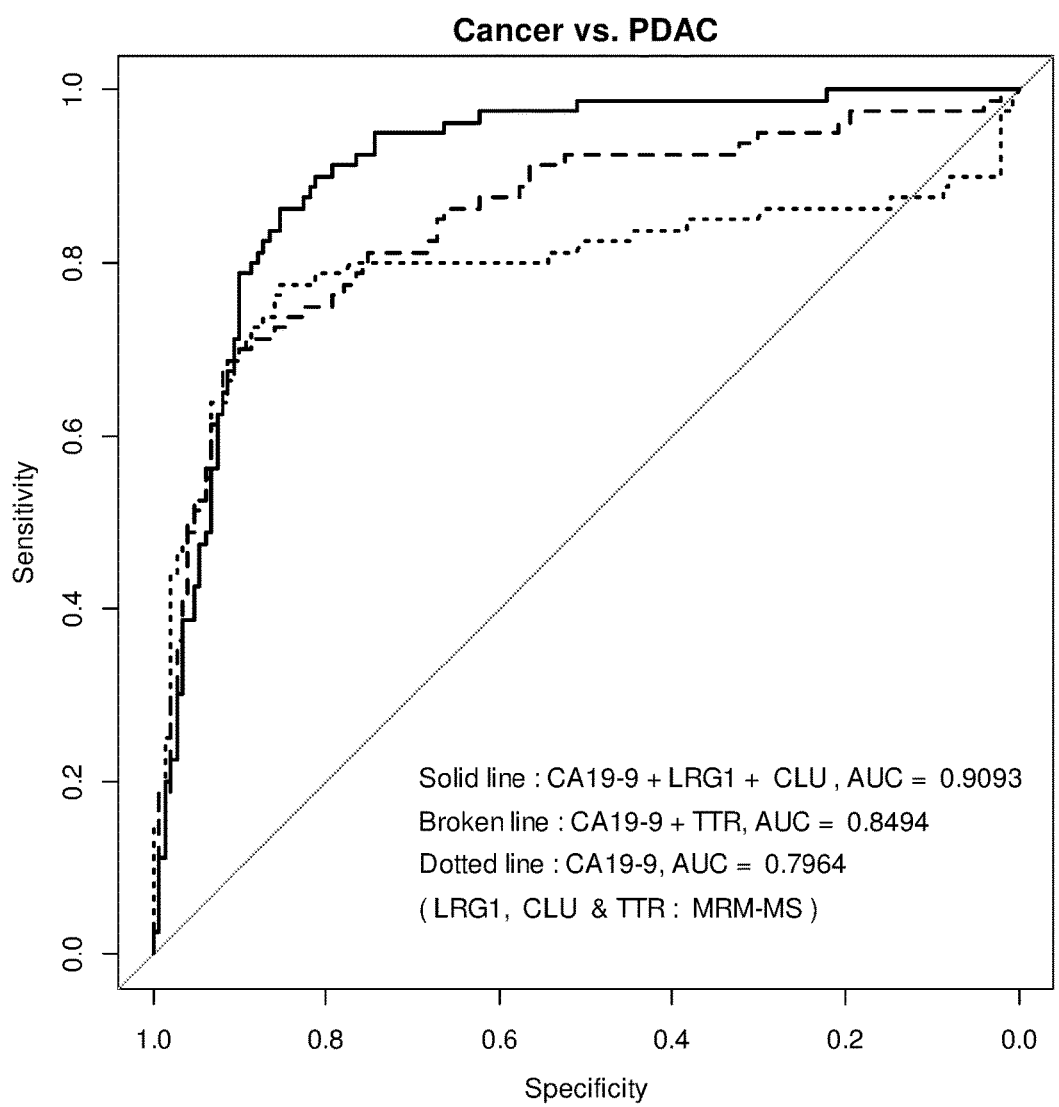

[Fig. 30]
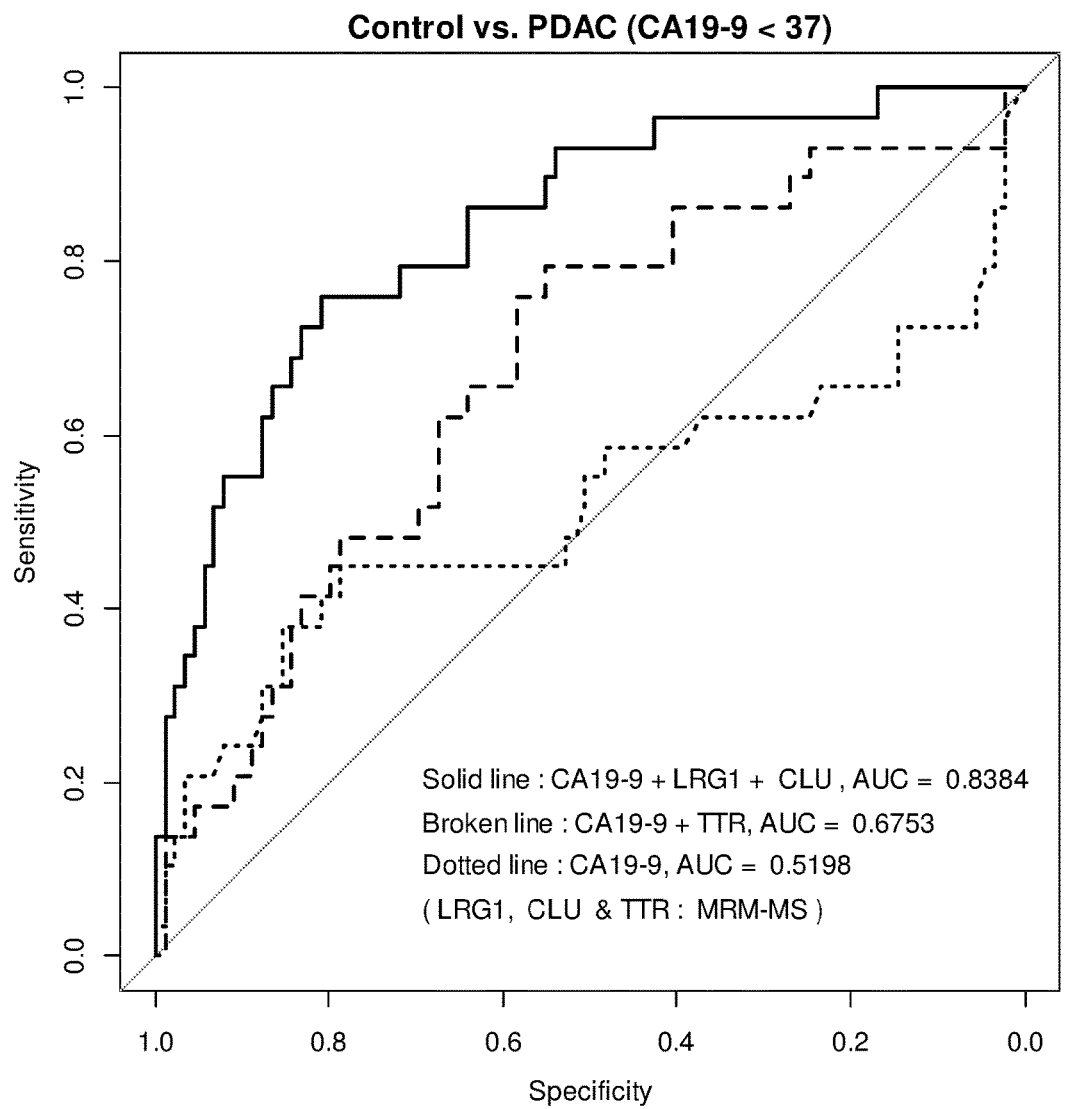

[Fig. 31]
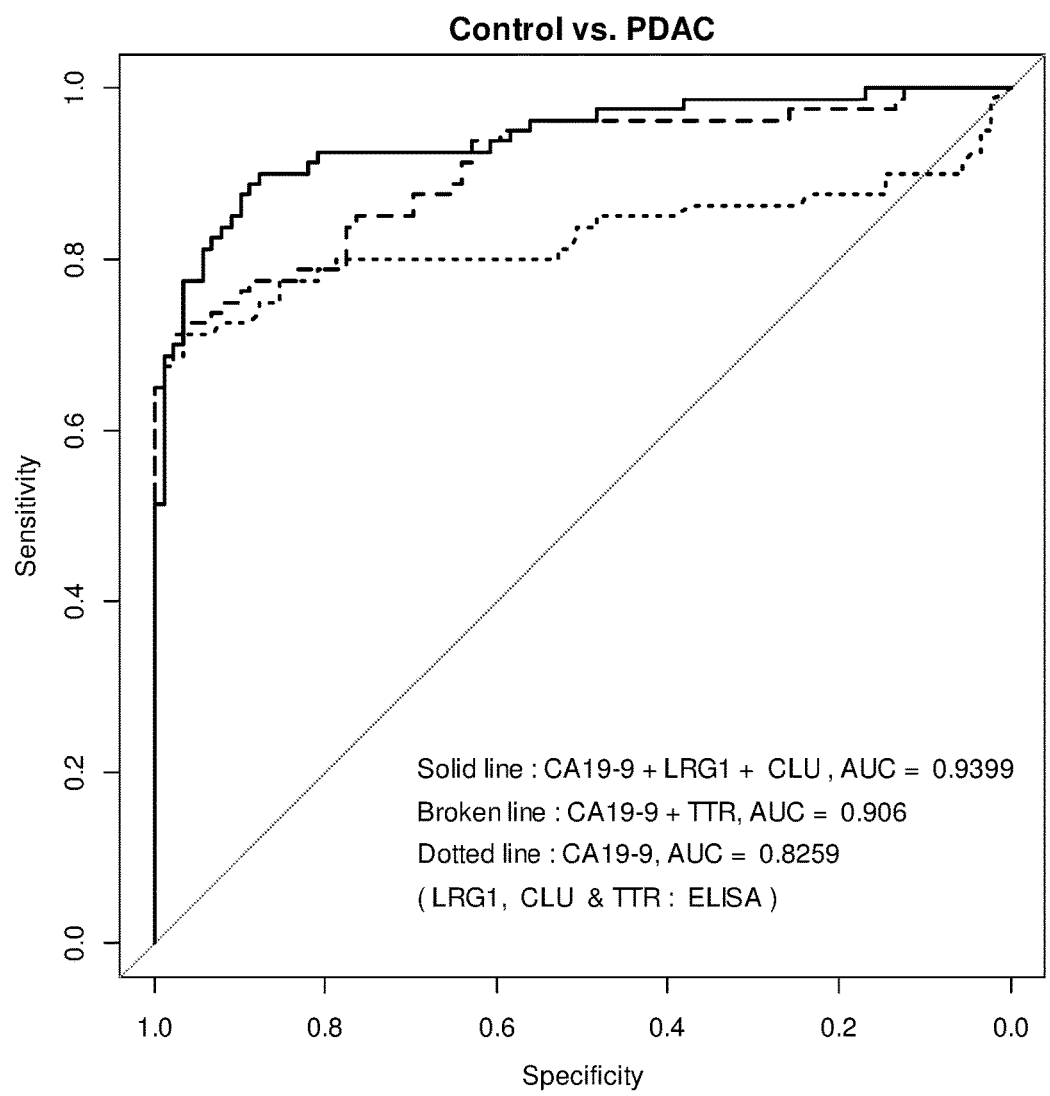

[Fig. 32]
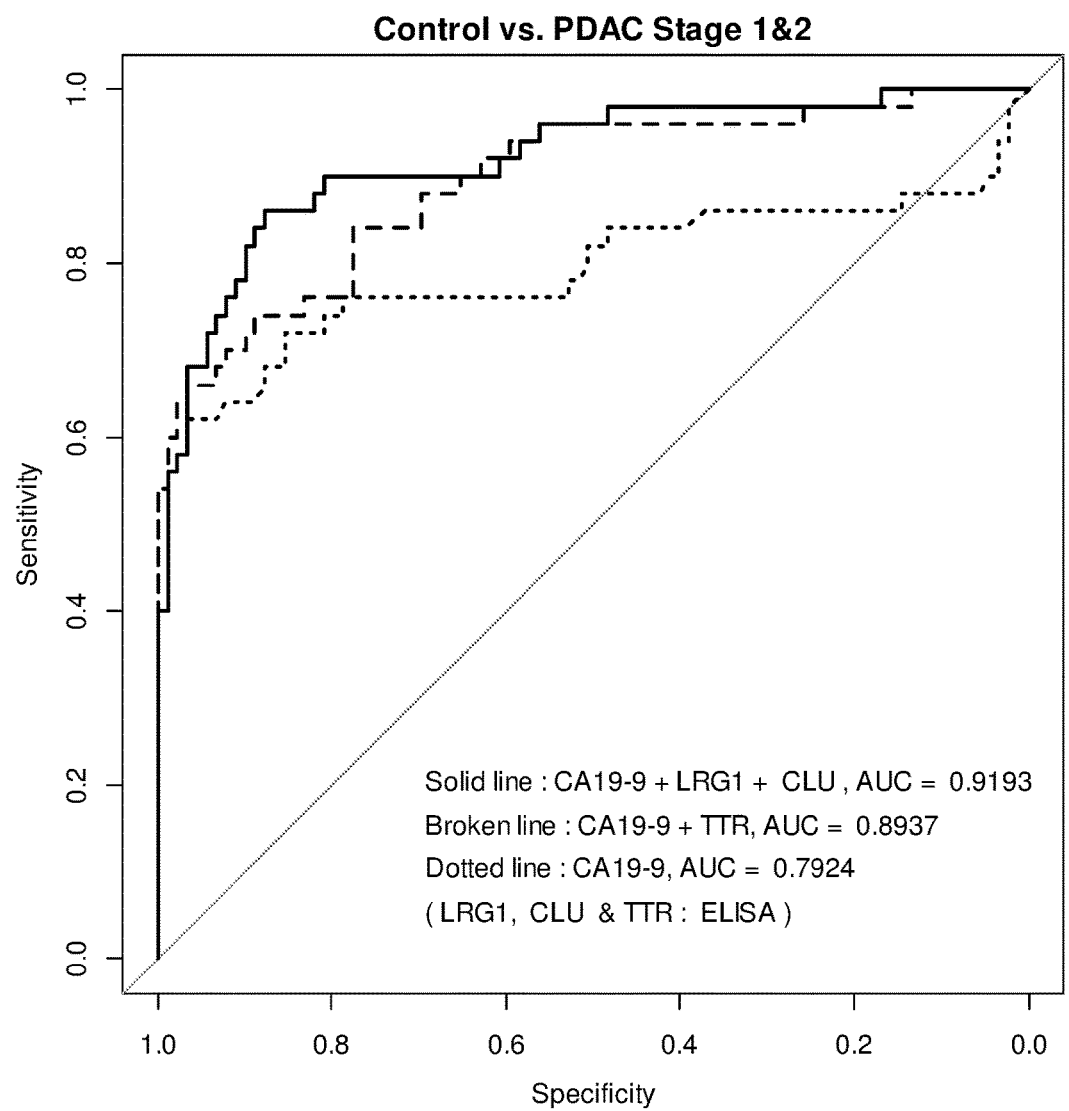

[Fig. 33]
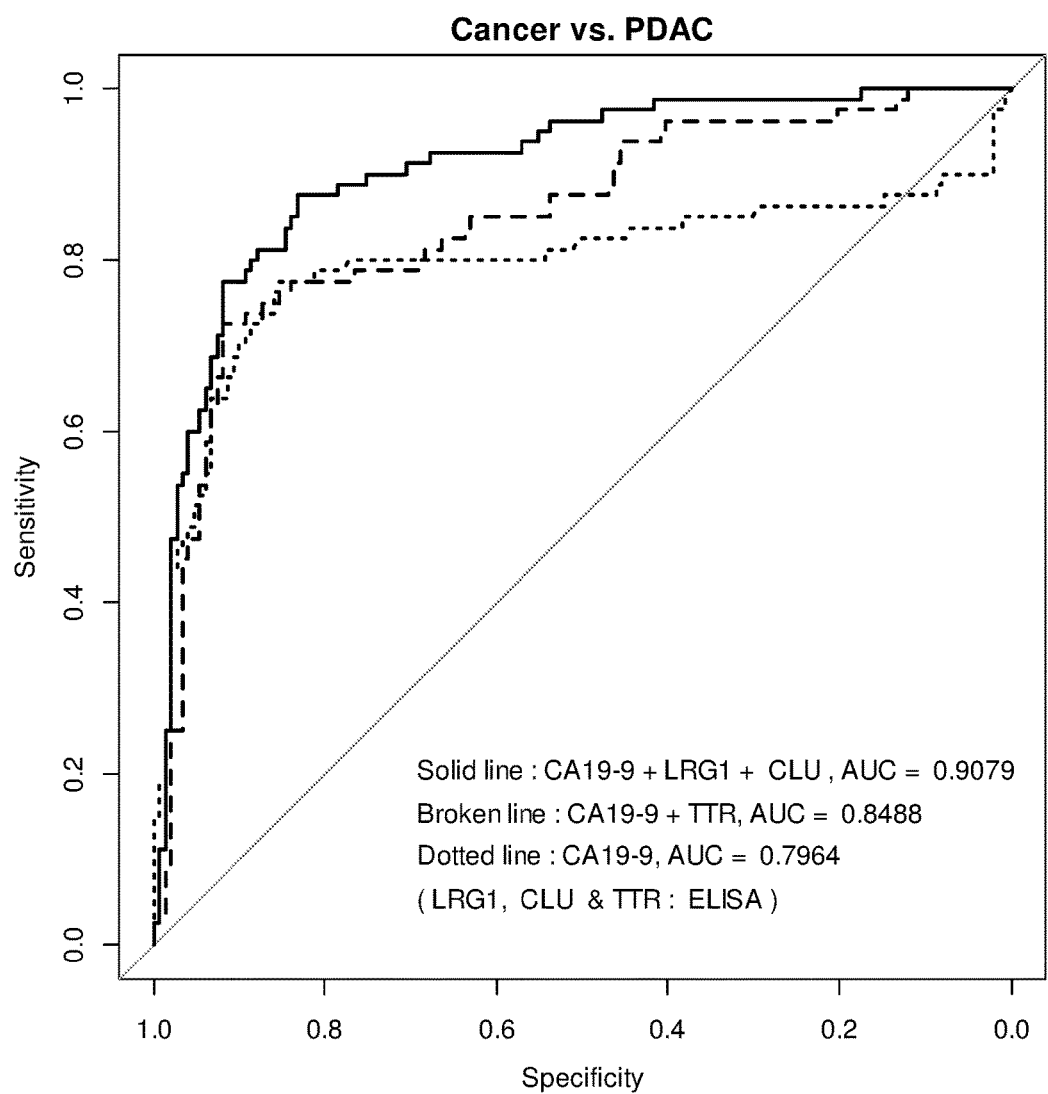

[Fig. 34]
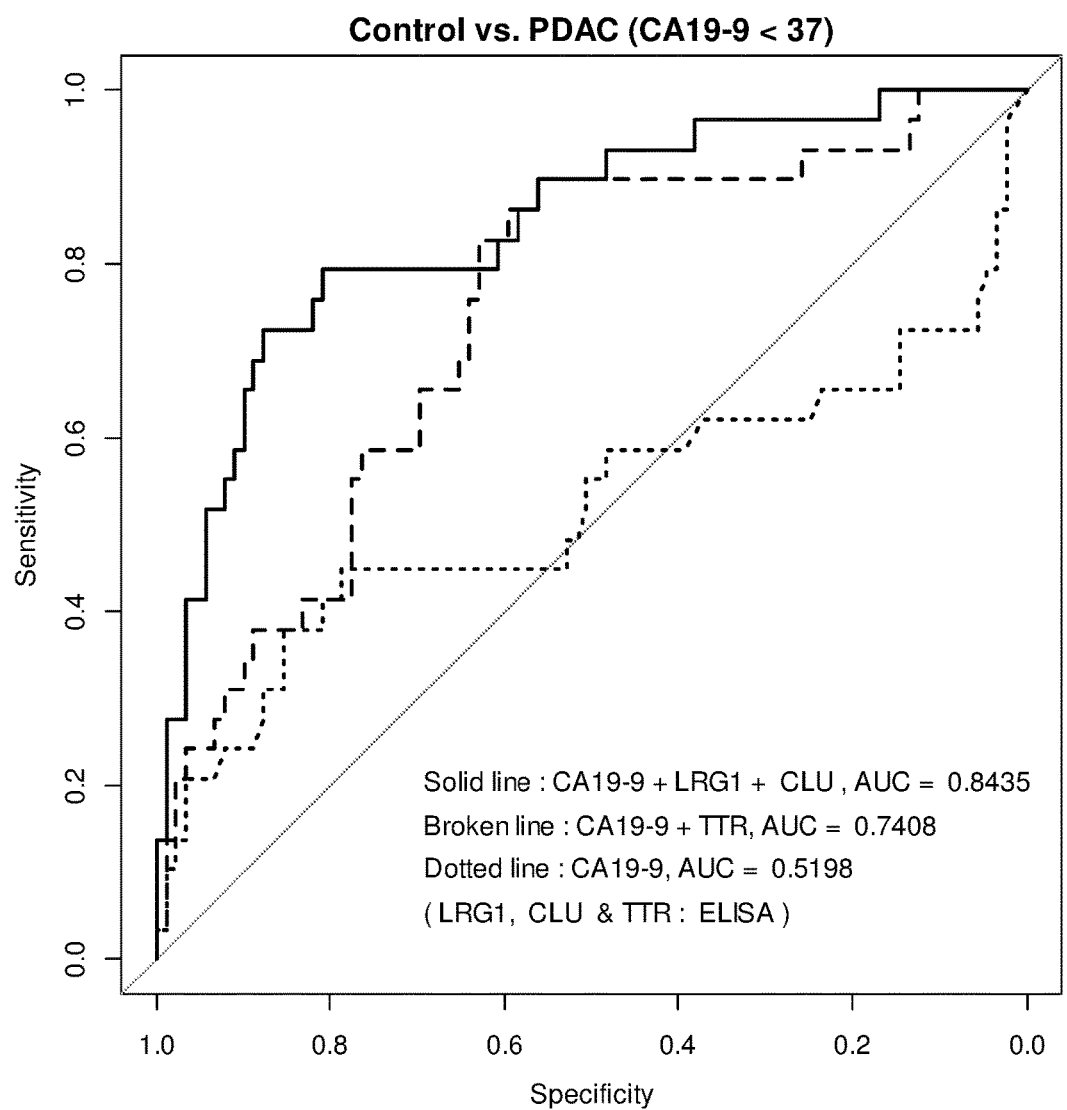

[Fig. 35]
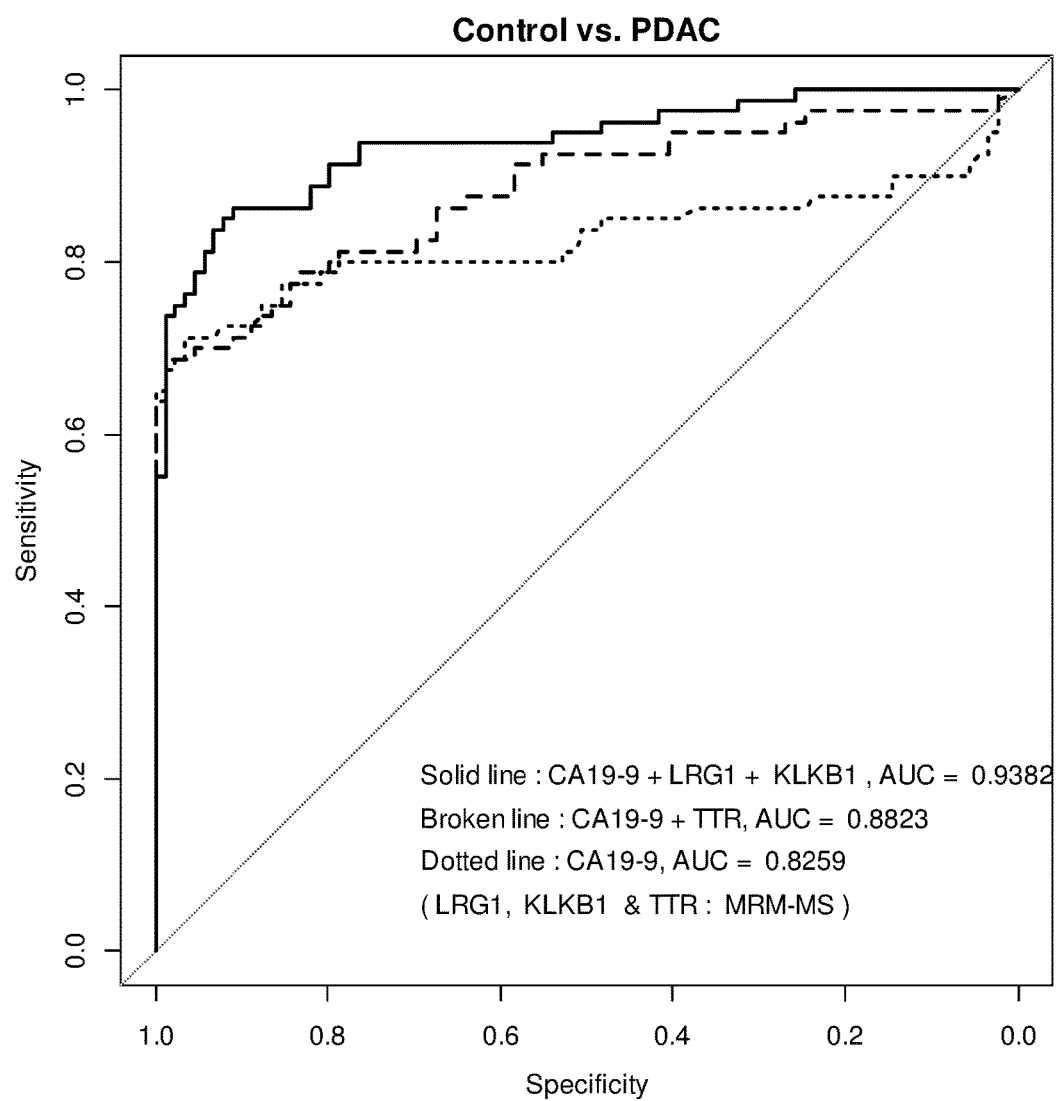

[Fig. 36]
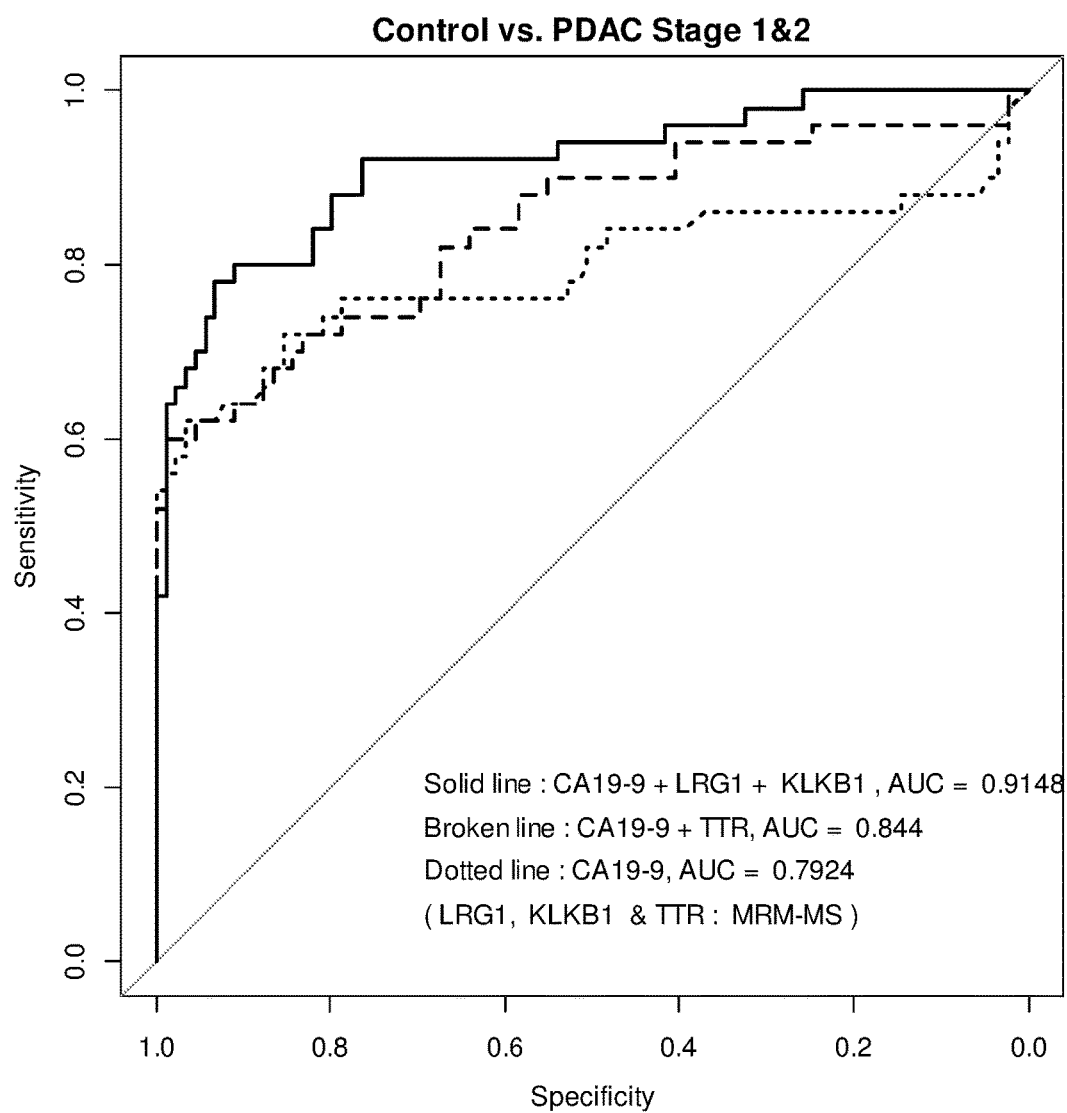

[Fig. 37]
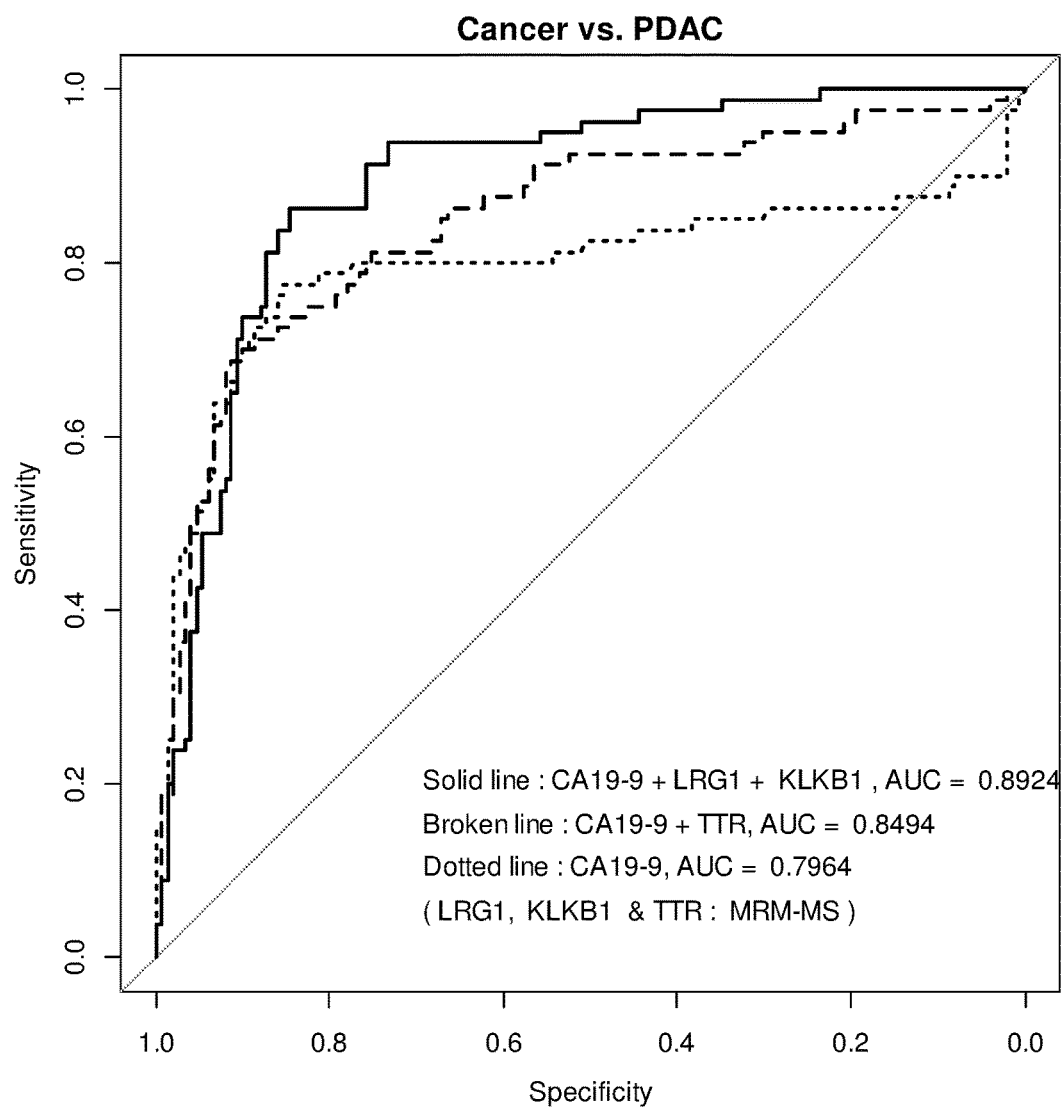

[Fig. 38]
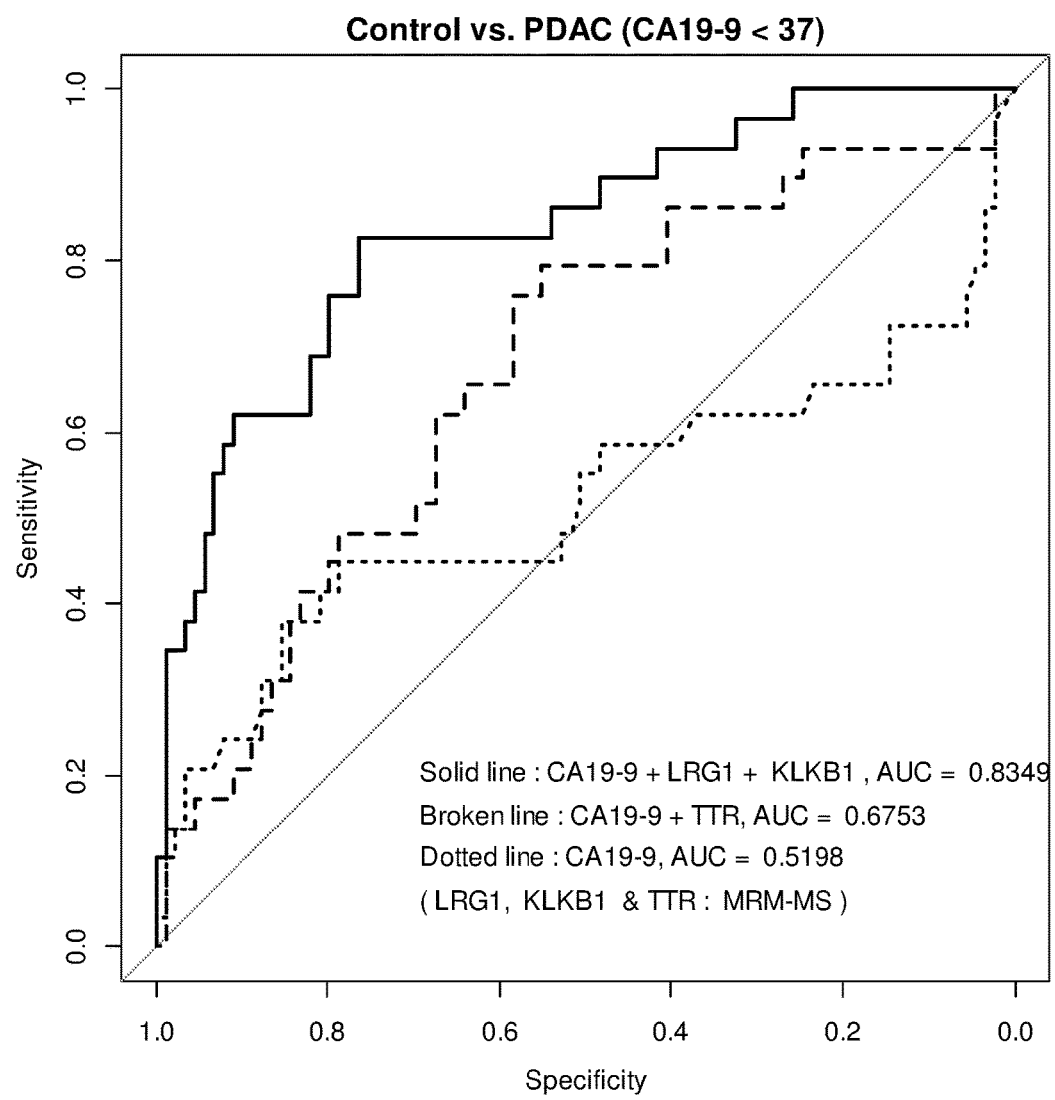

[Fig. 39]
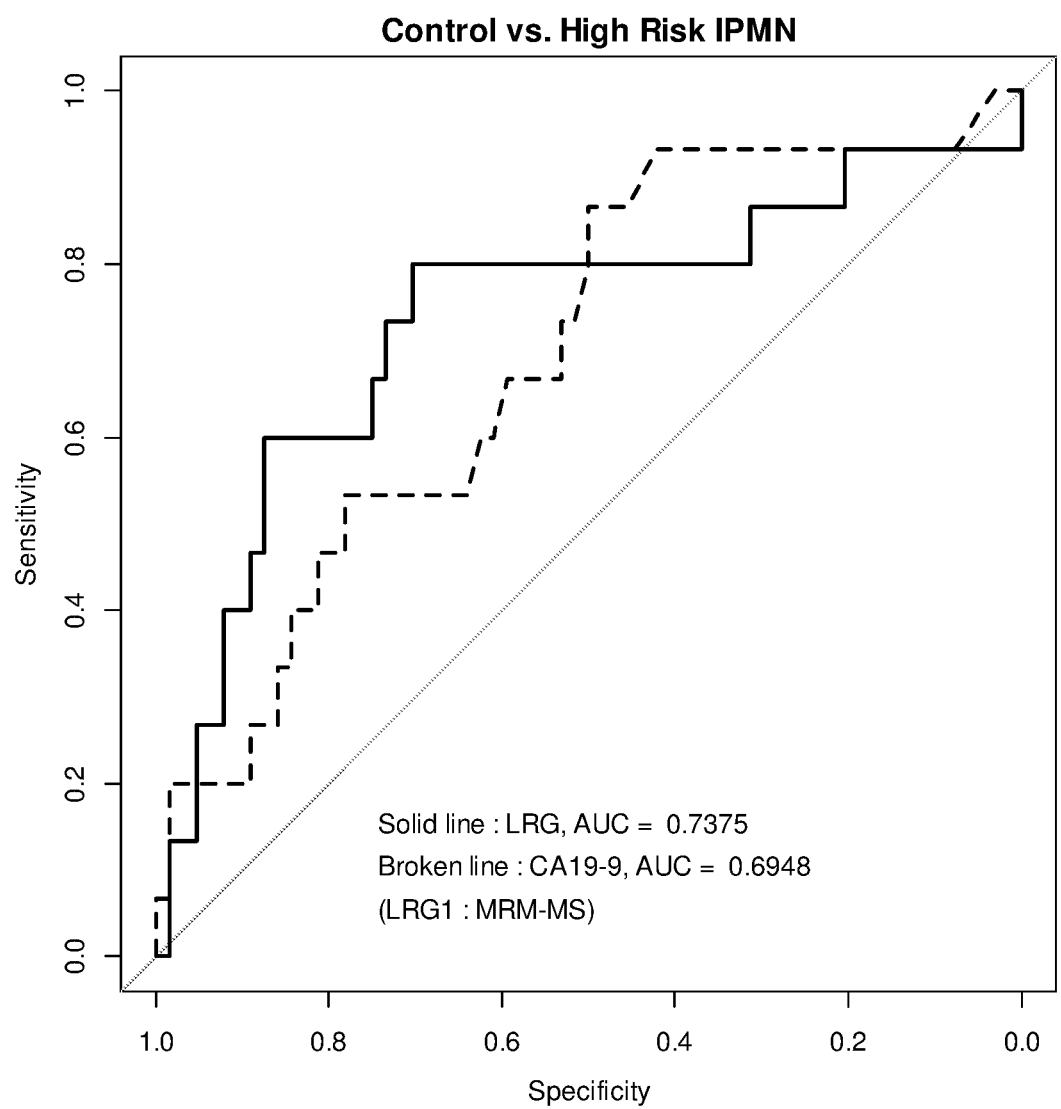

【Fig. 40】
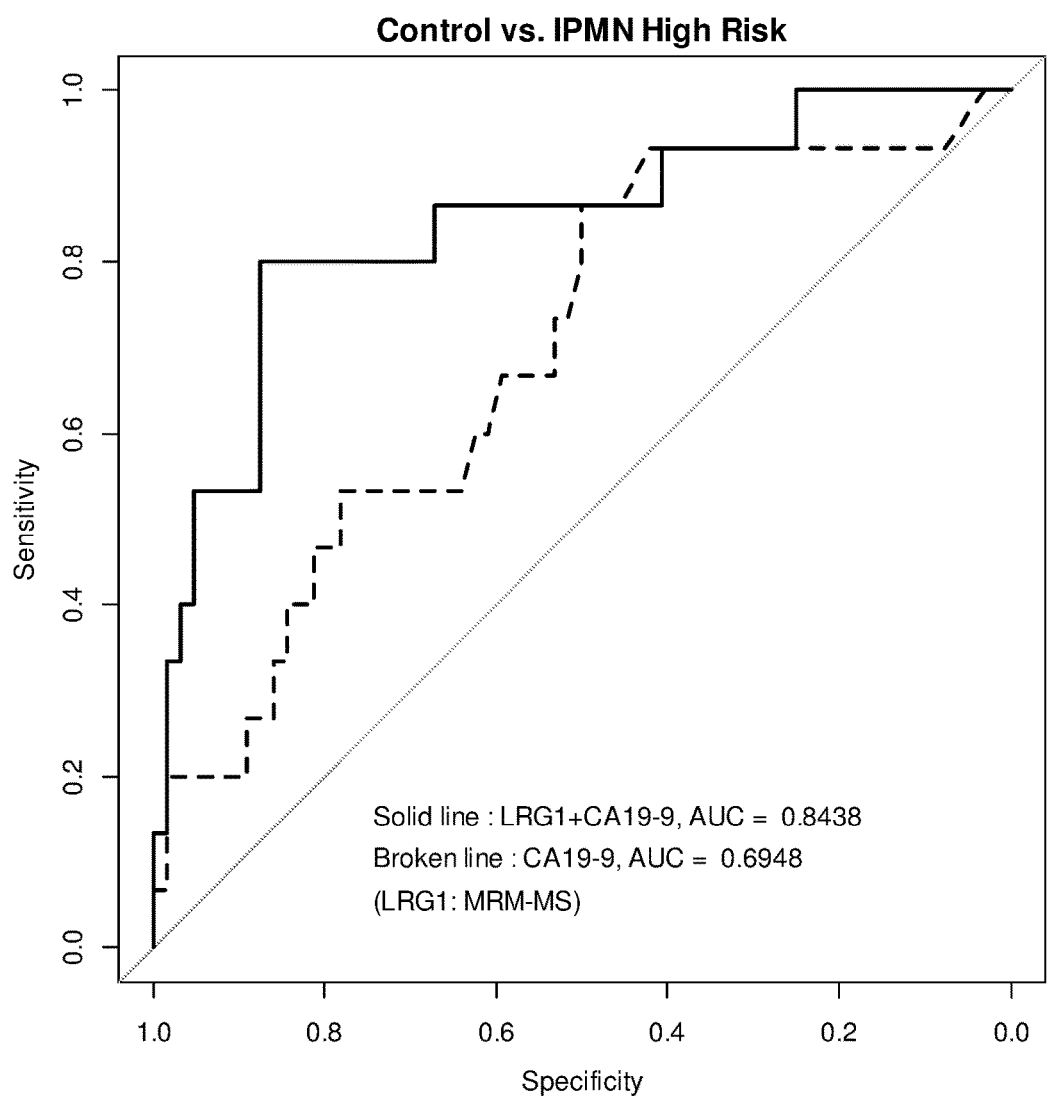

【Fig. 41】
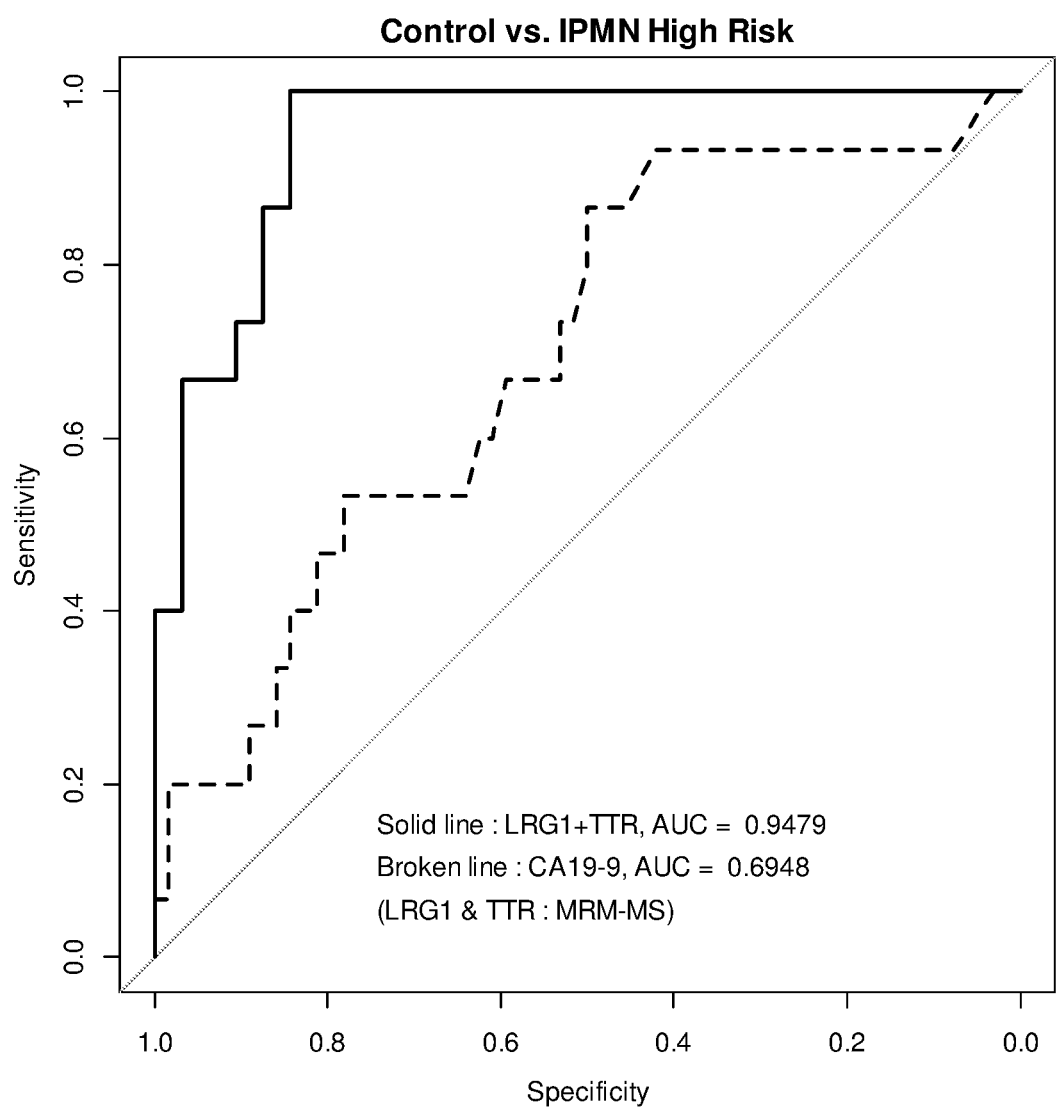

[Fig. 42]
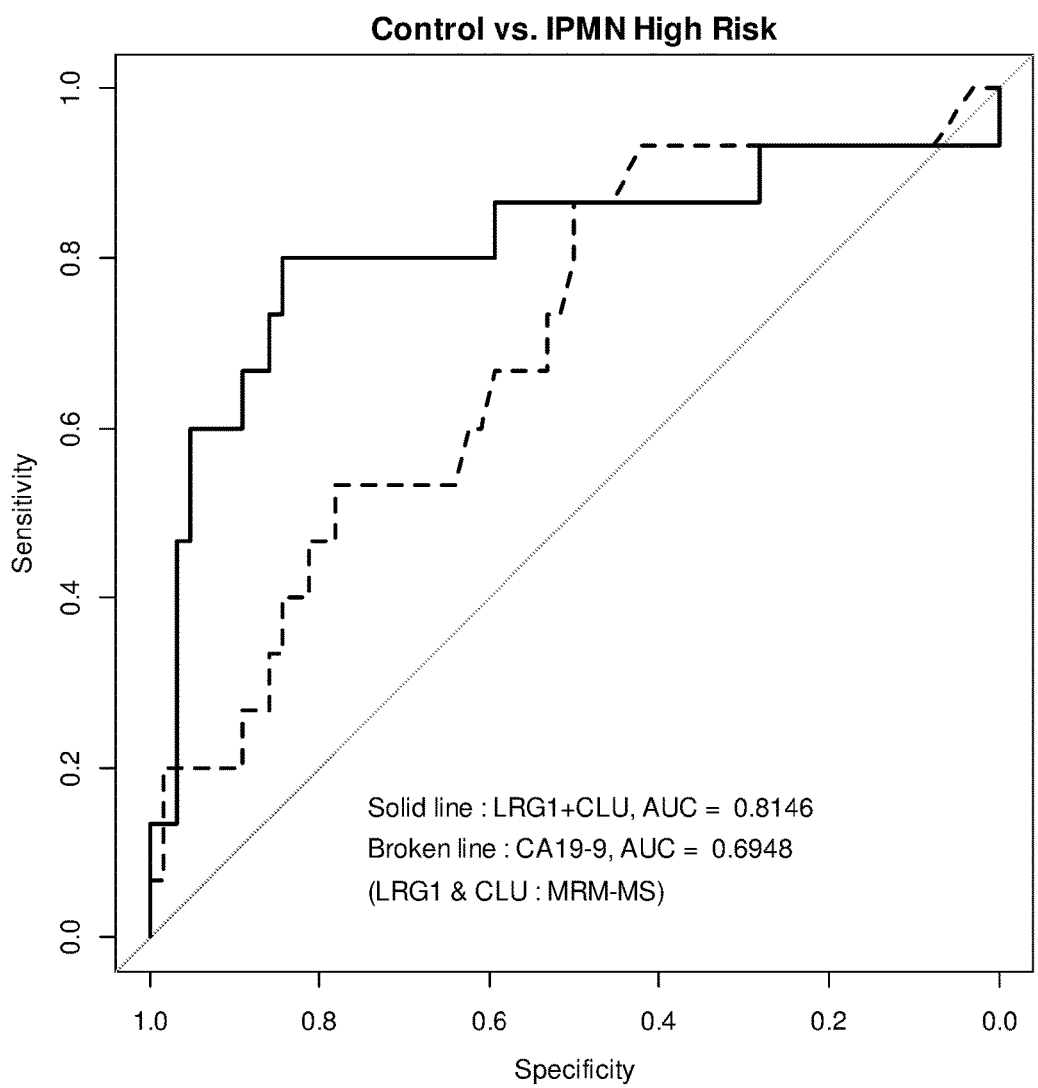

[Fig. 43]
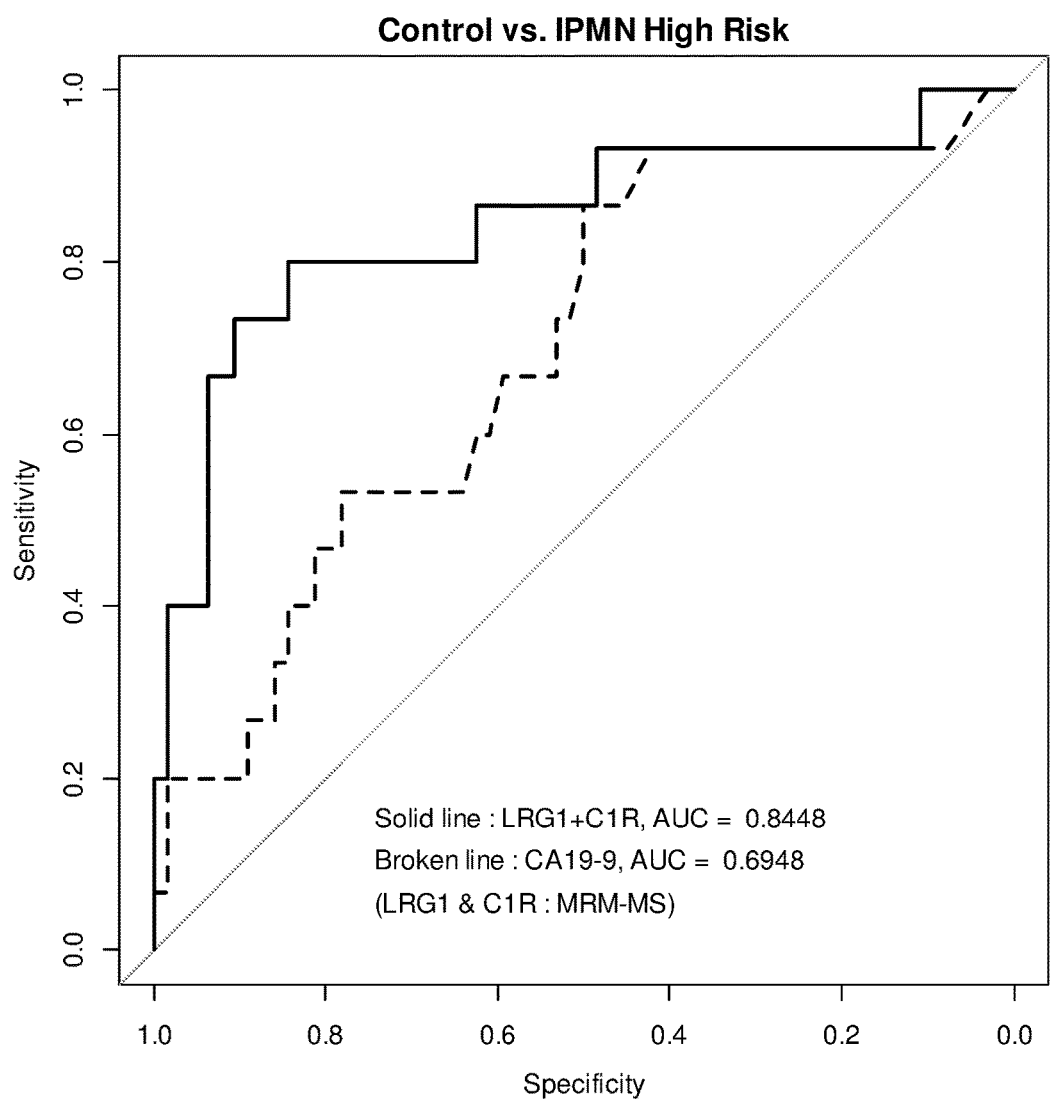

[Fig. 44]
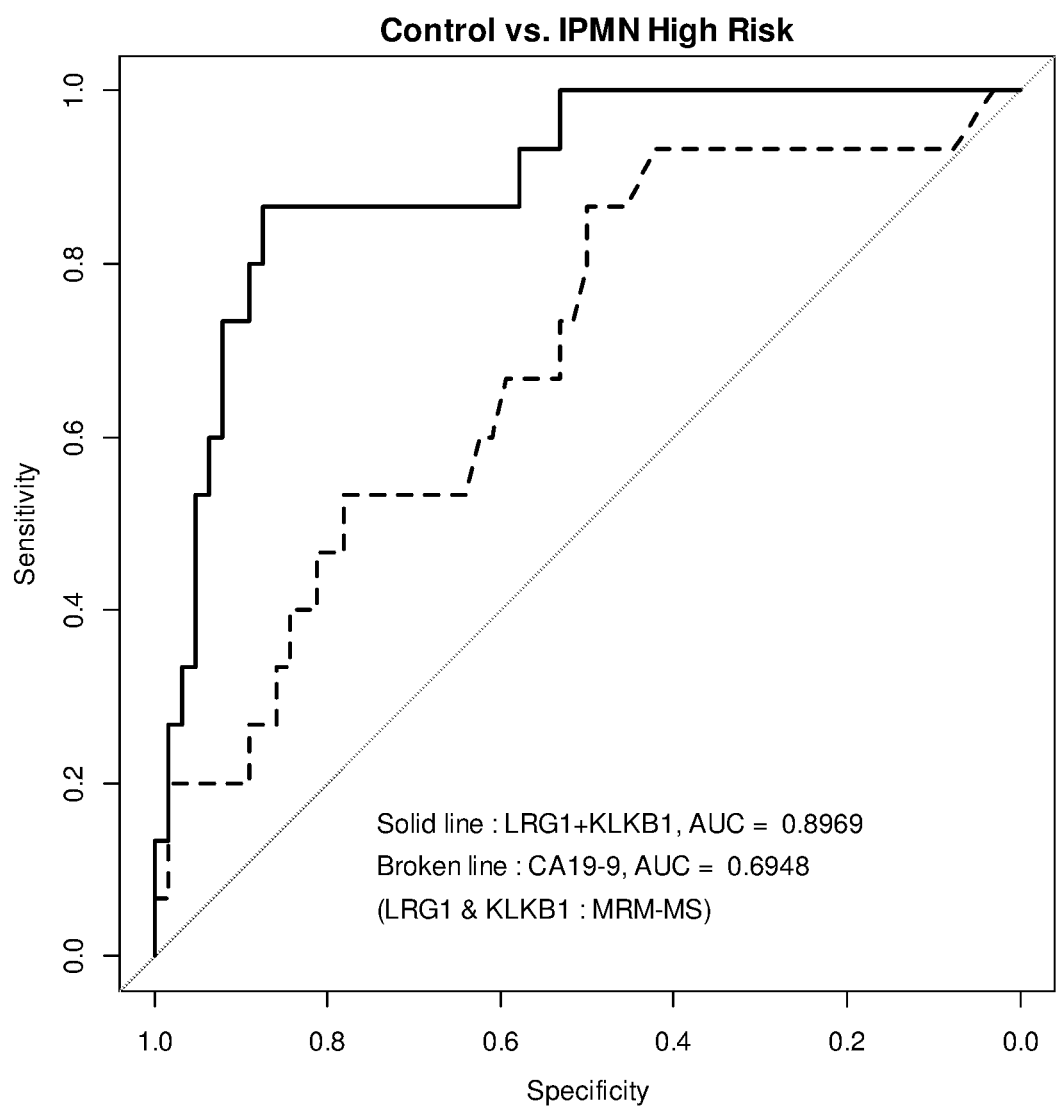

[Fig. 45]
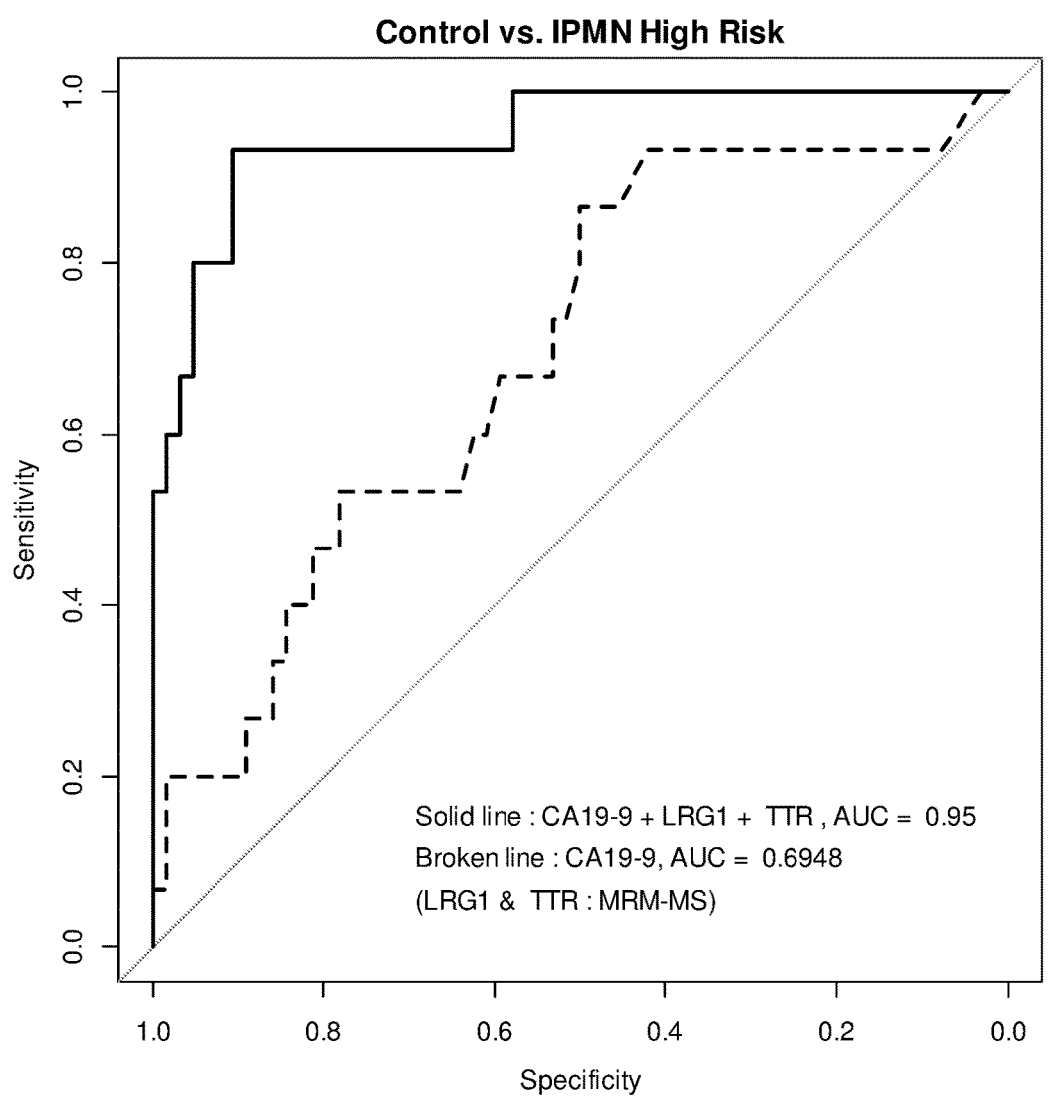

【Fig. 46】
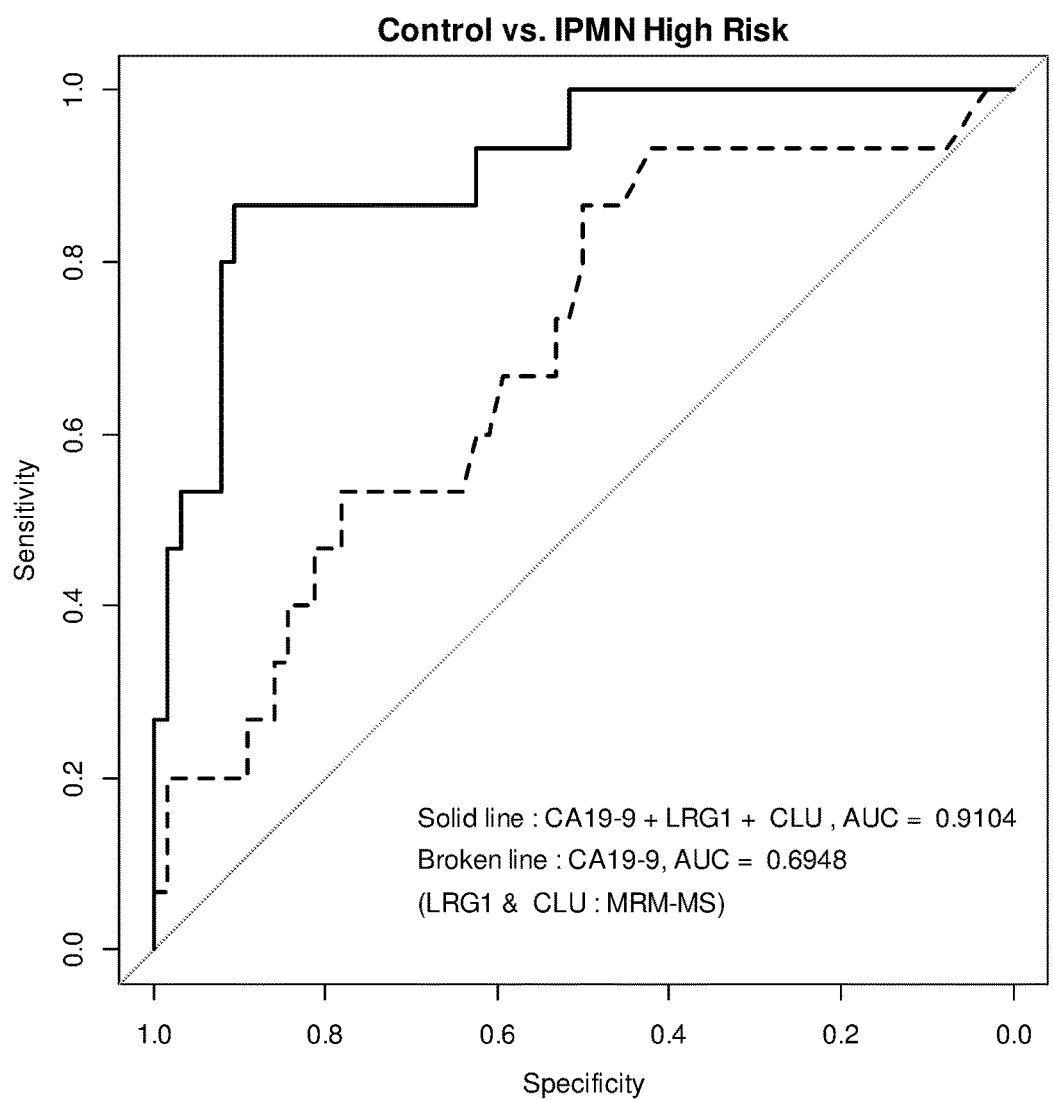

【Fig. 47】
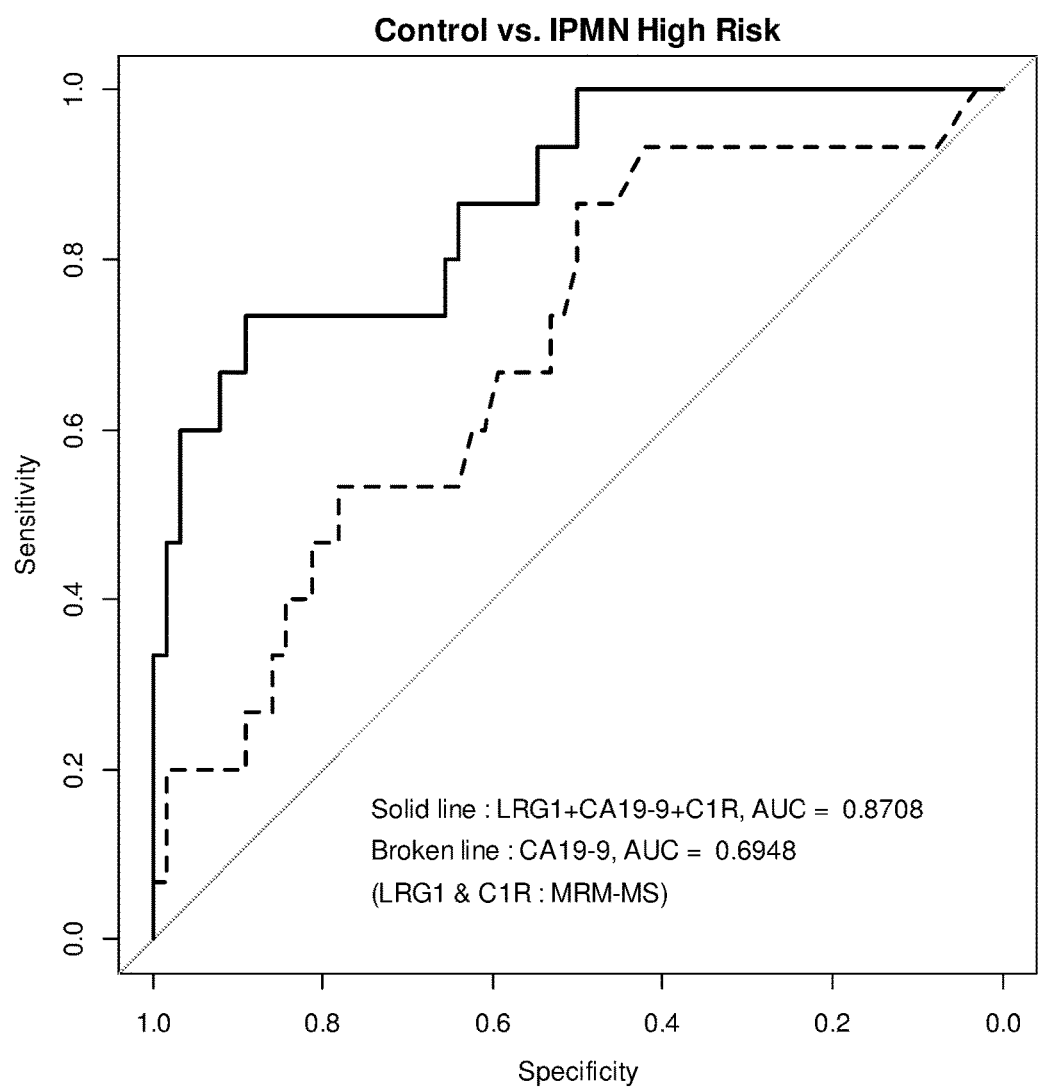

【Fig. 48】
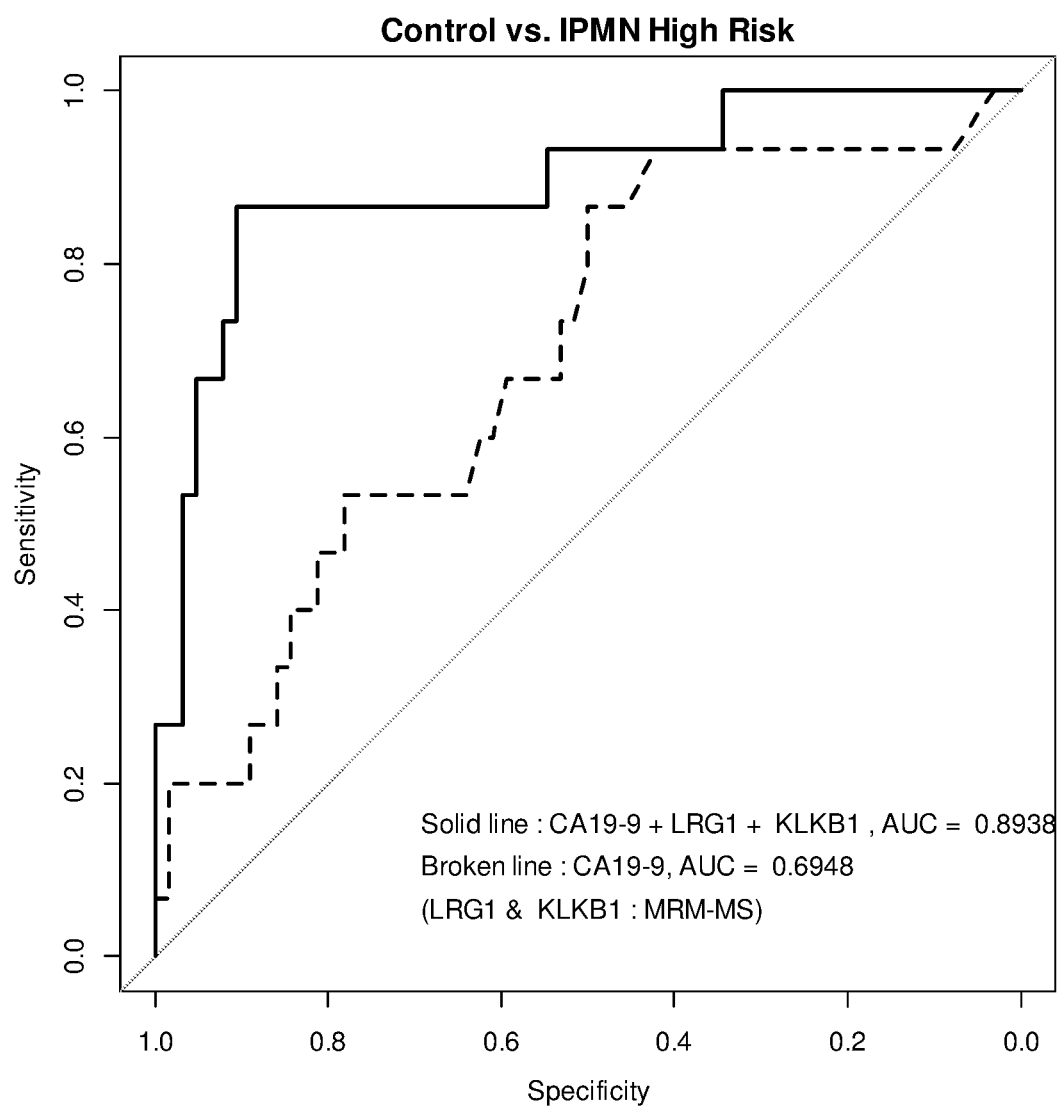

【Fig. 49】
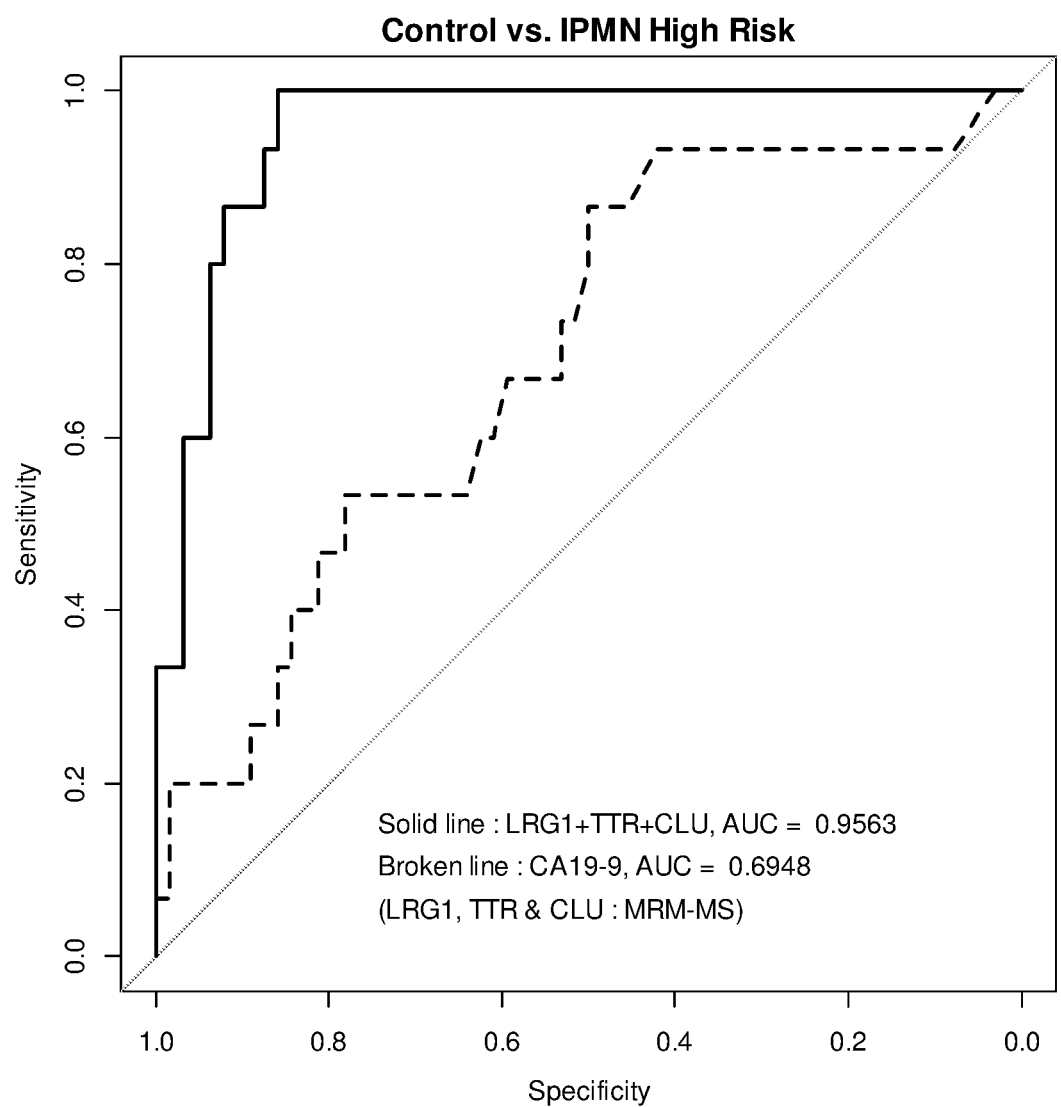

[Fig. 50]
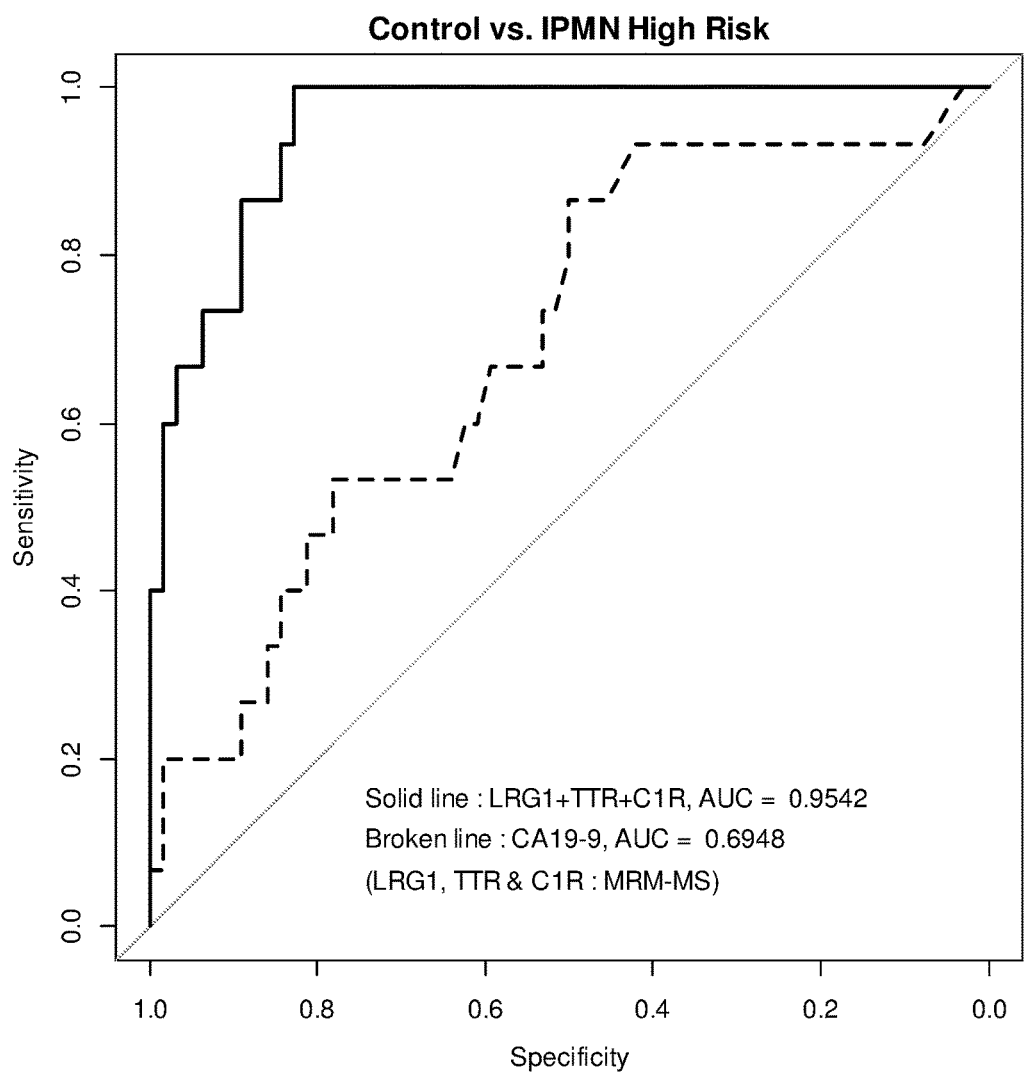

[Fig. 51]
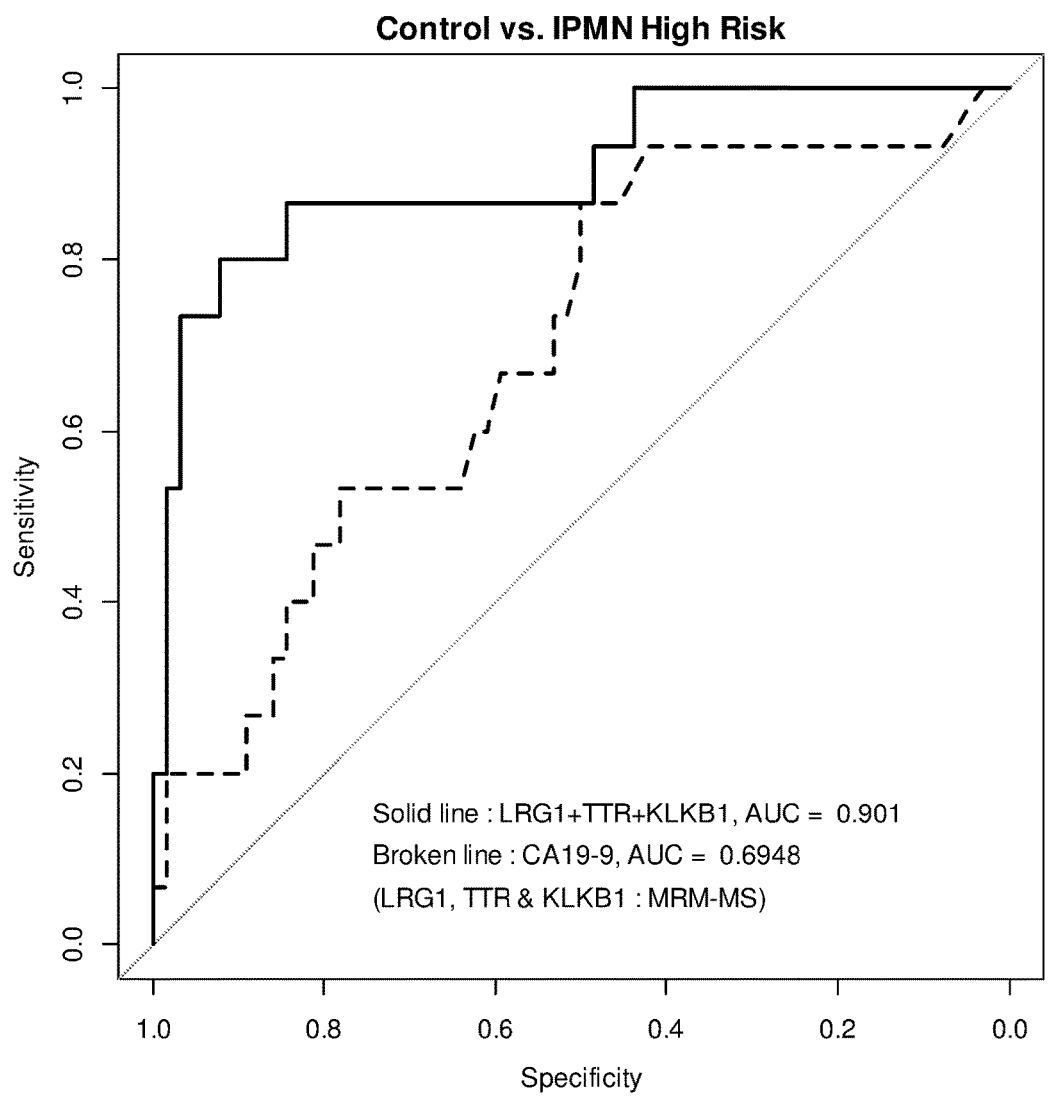

【Fig. 52】
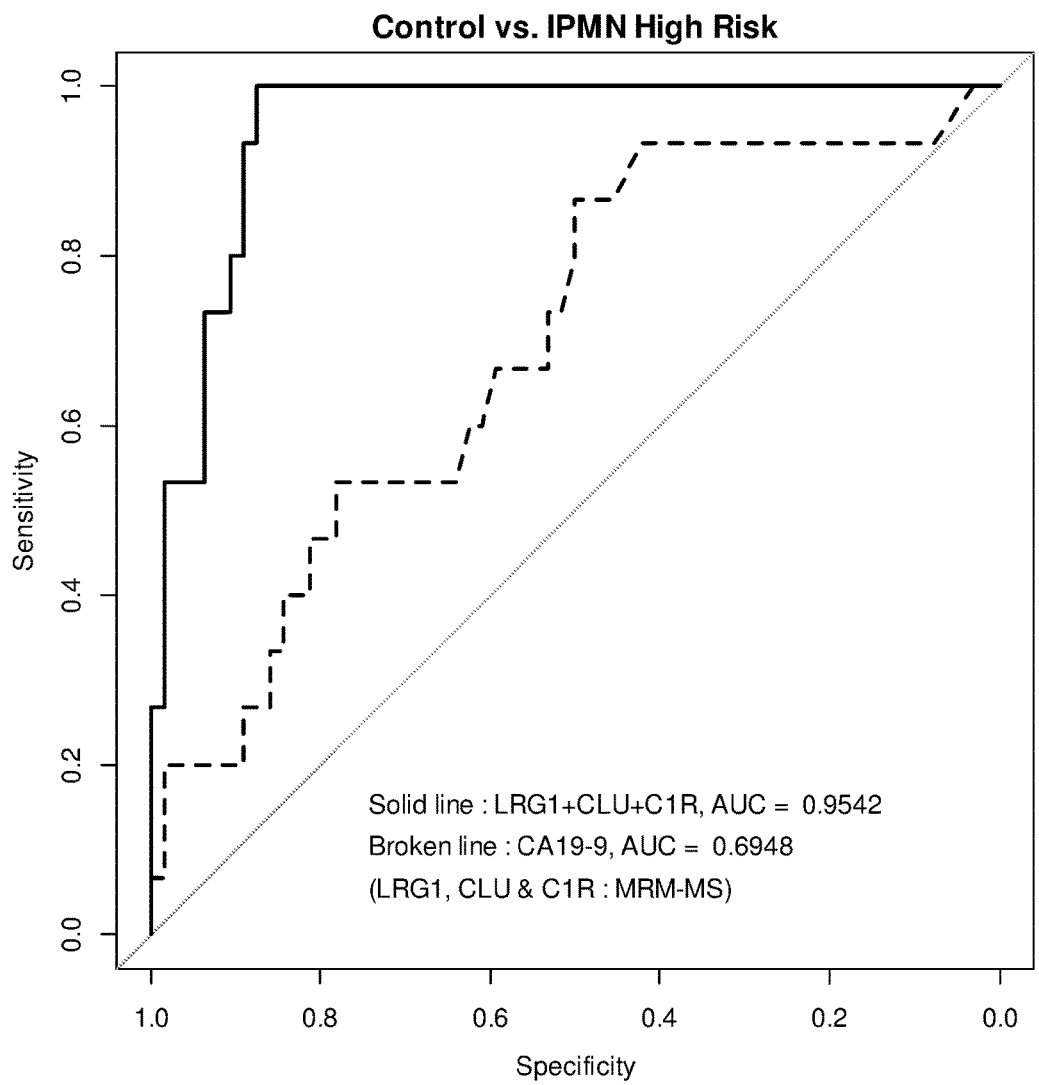

[Fig. 53]
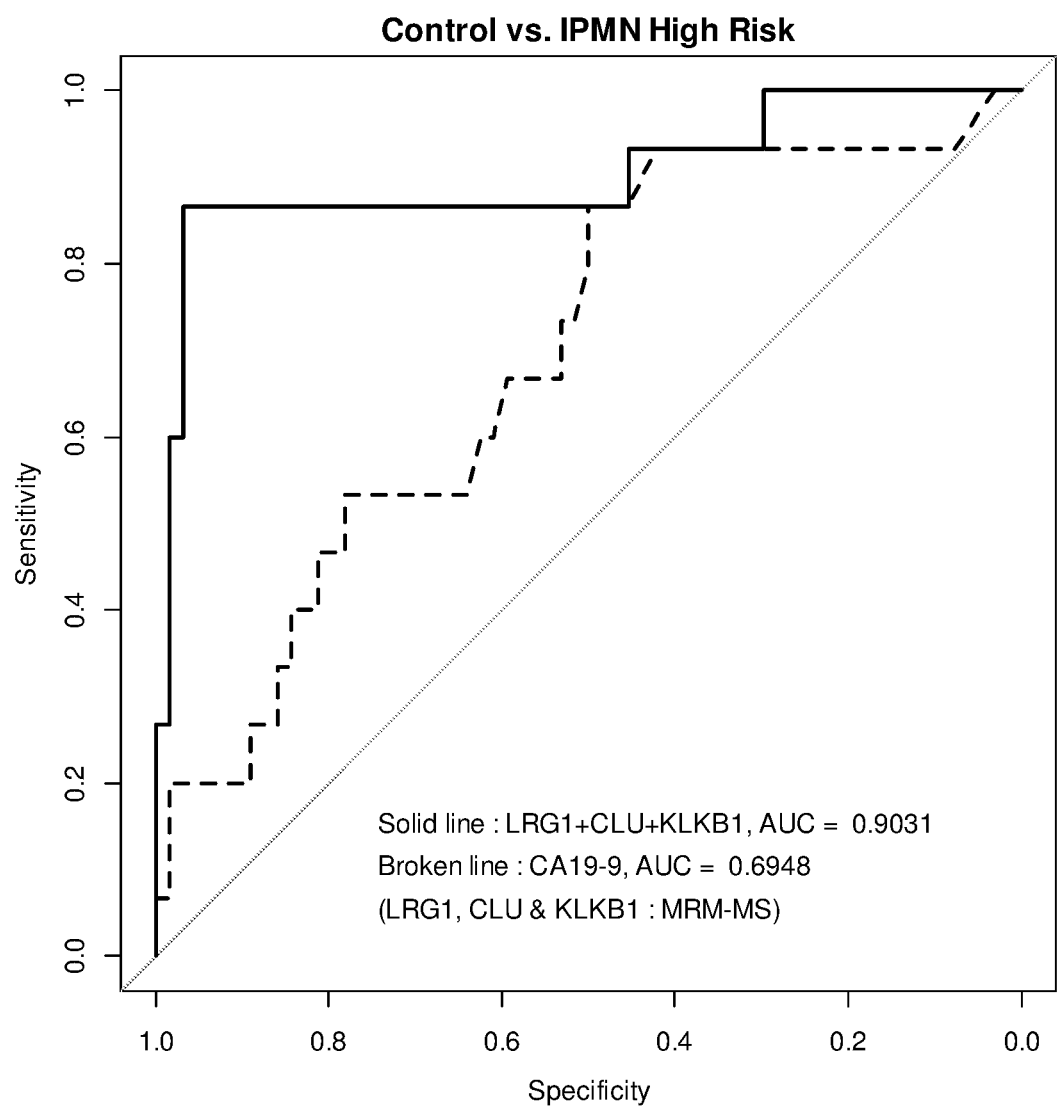

[Fig. 54]
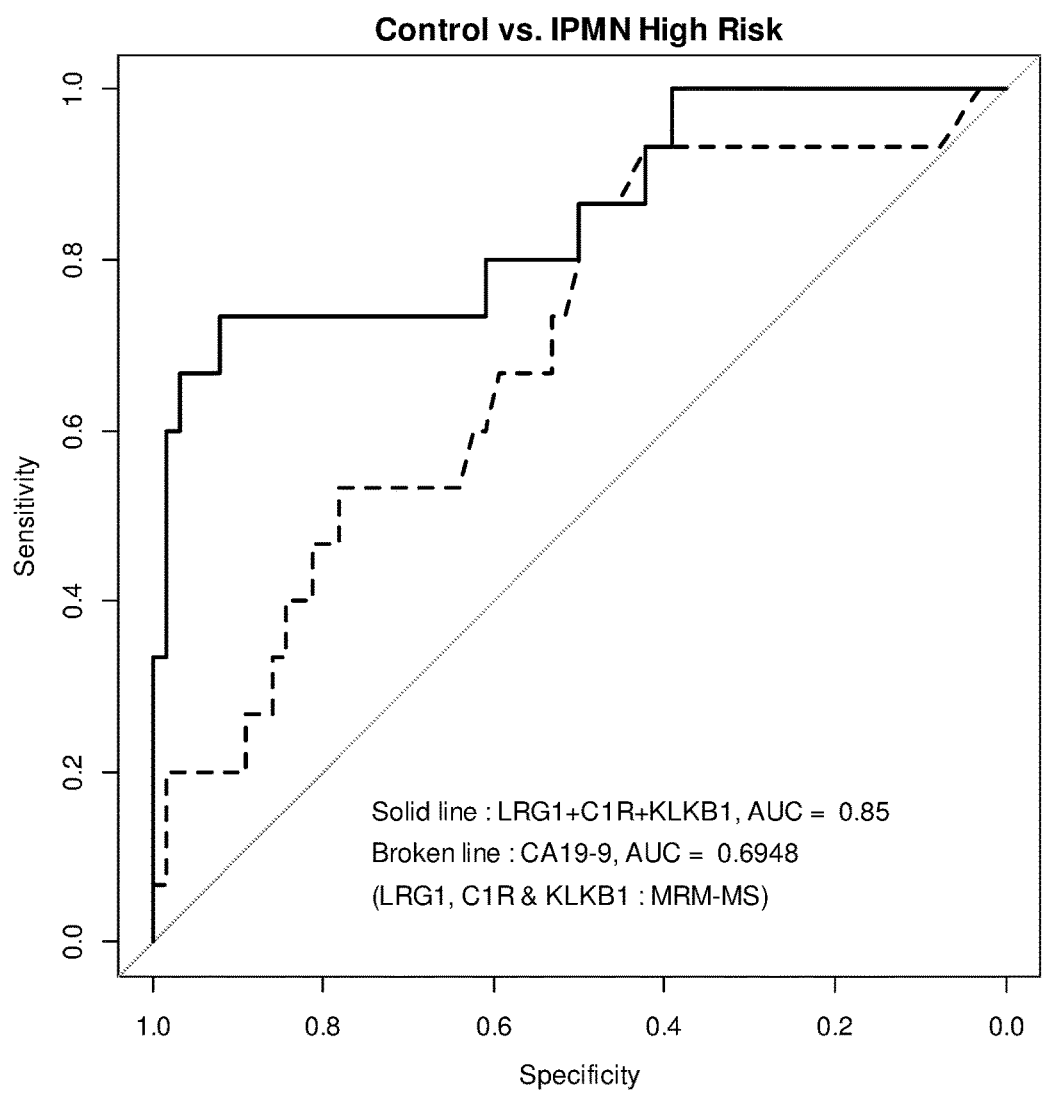

[Fig. 55]
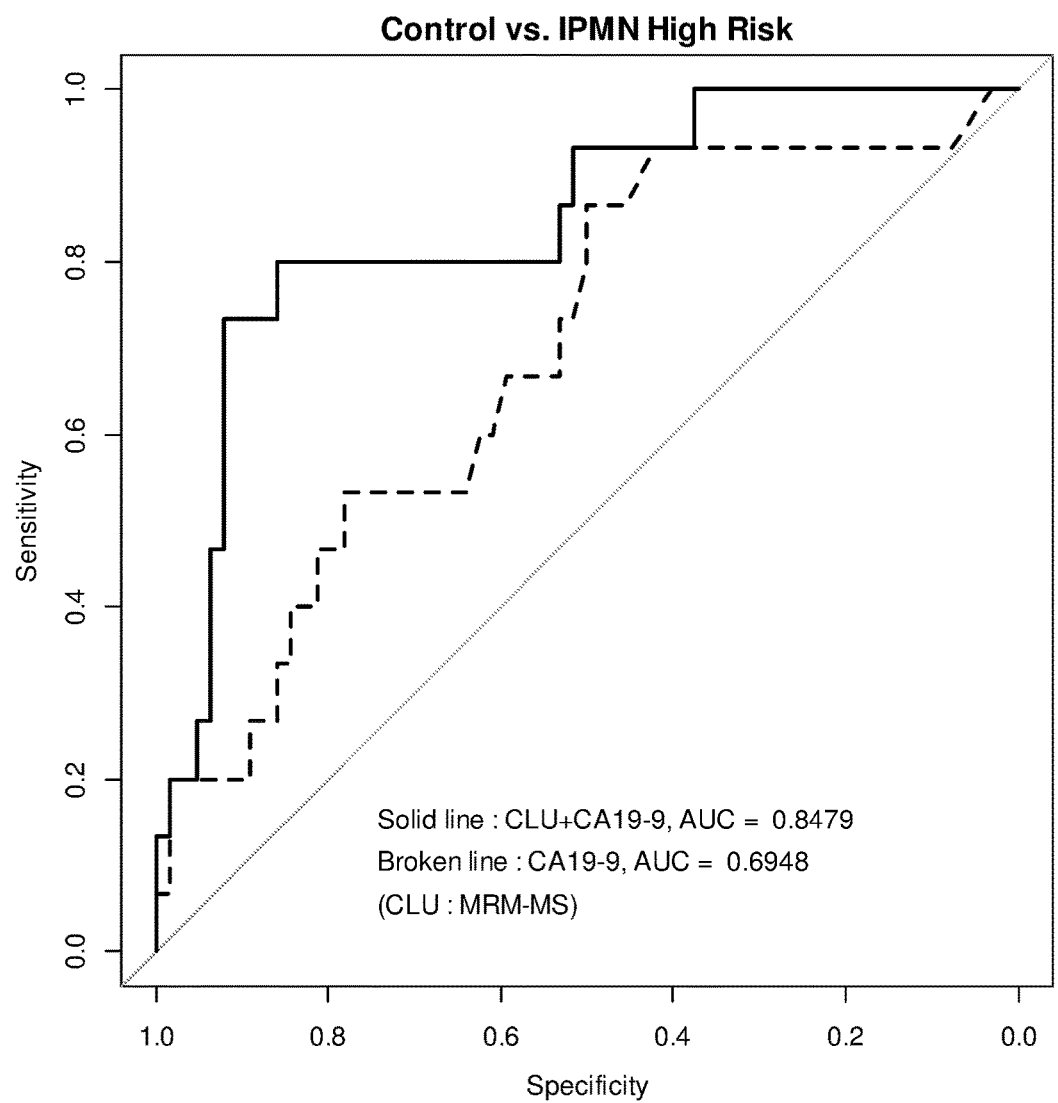

[Fig. 56]
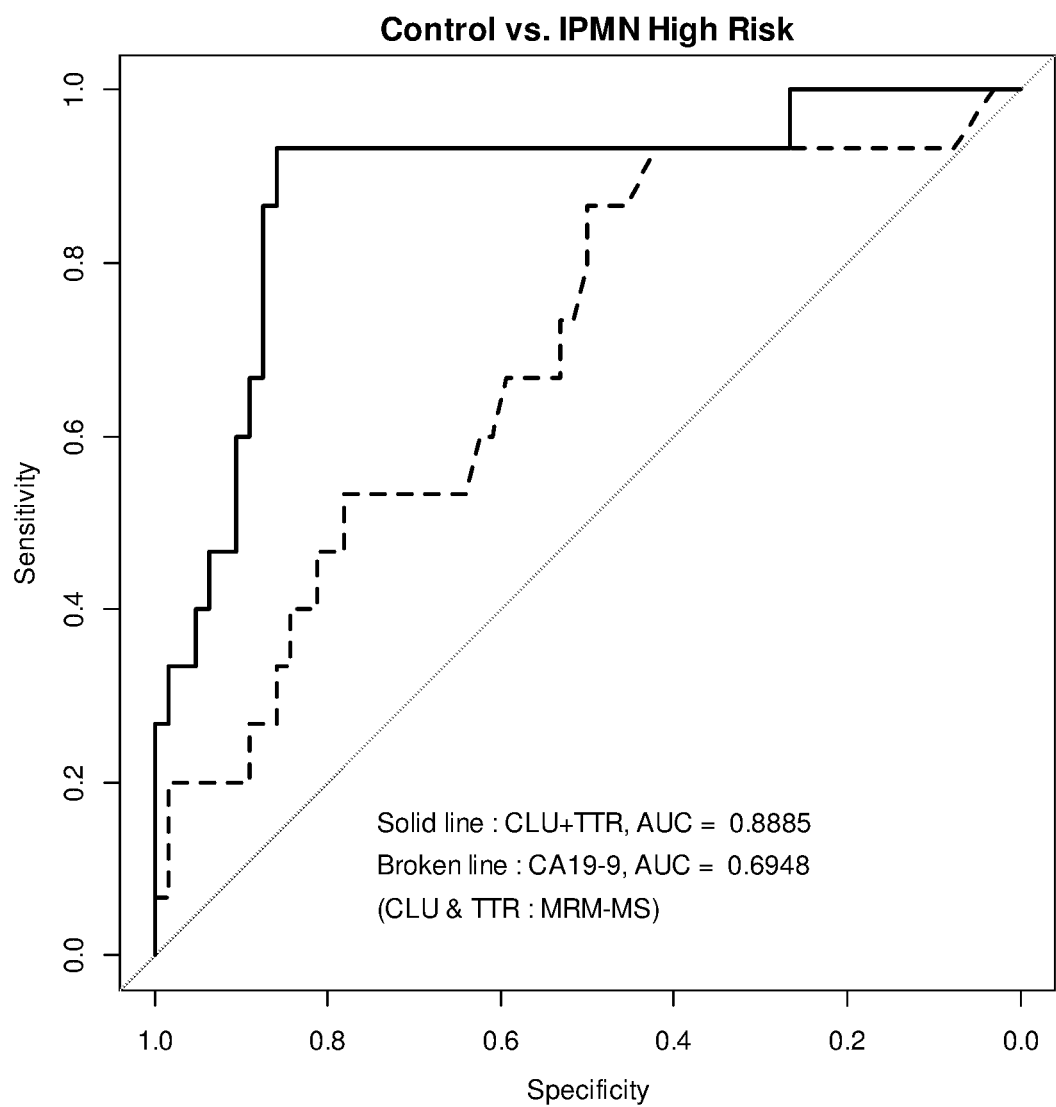

[Fig. 57]
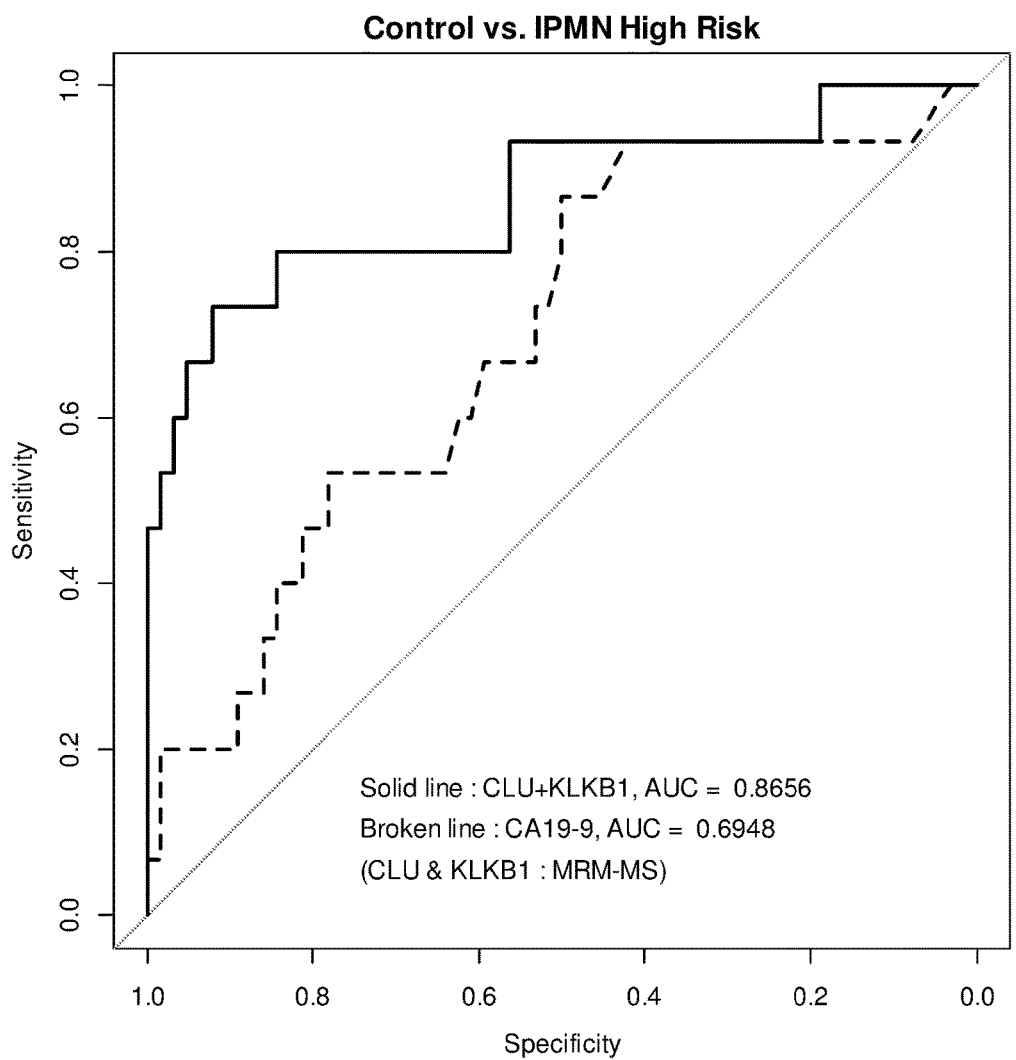

[Fig. 58]
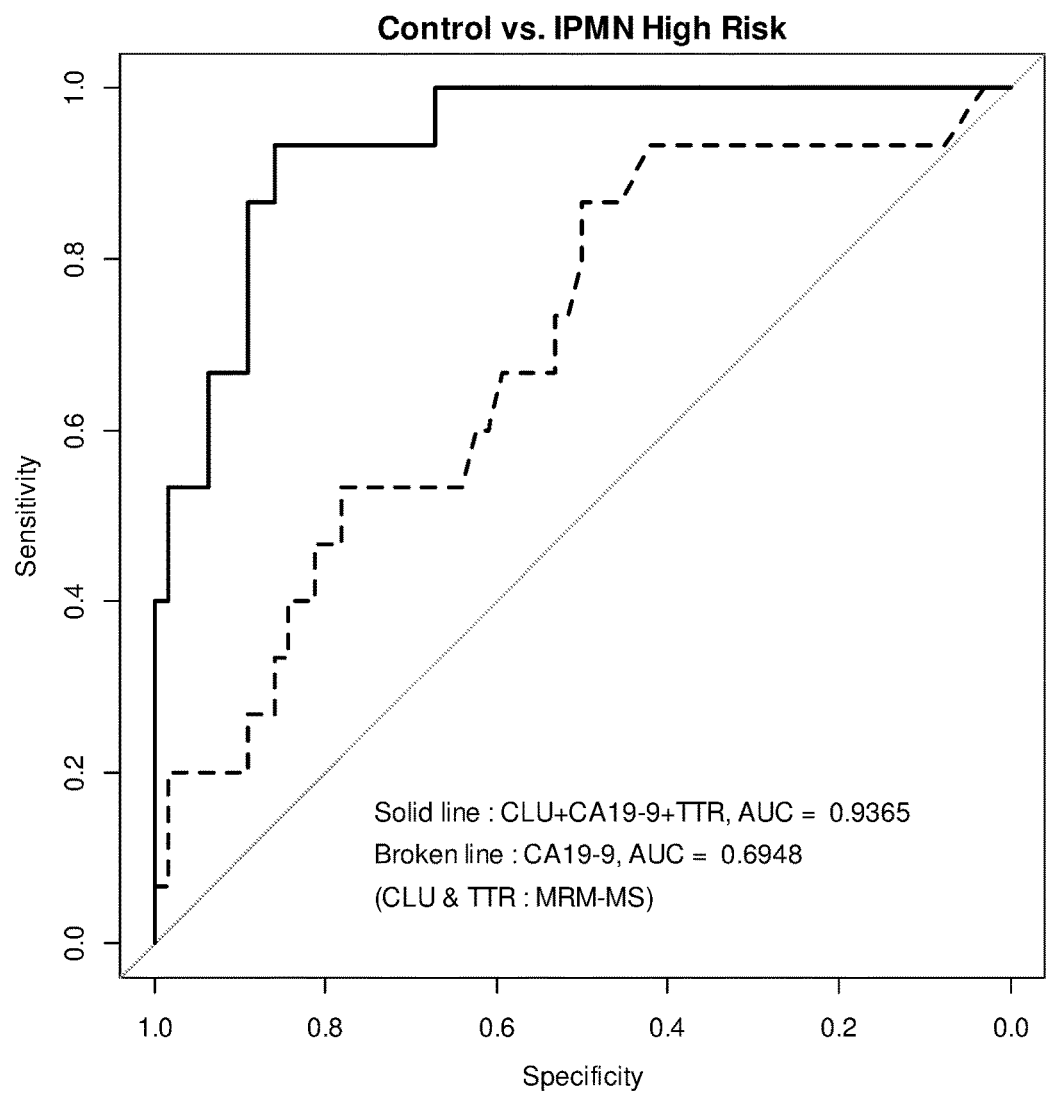

[Fig. 59]
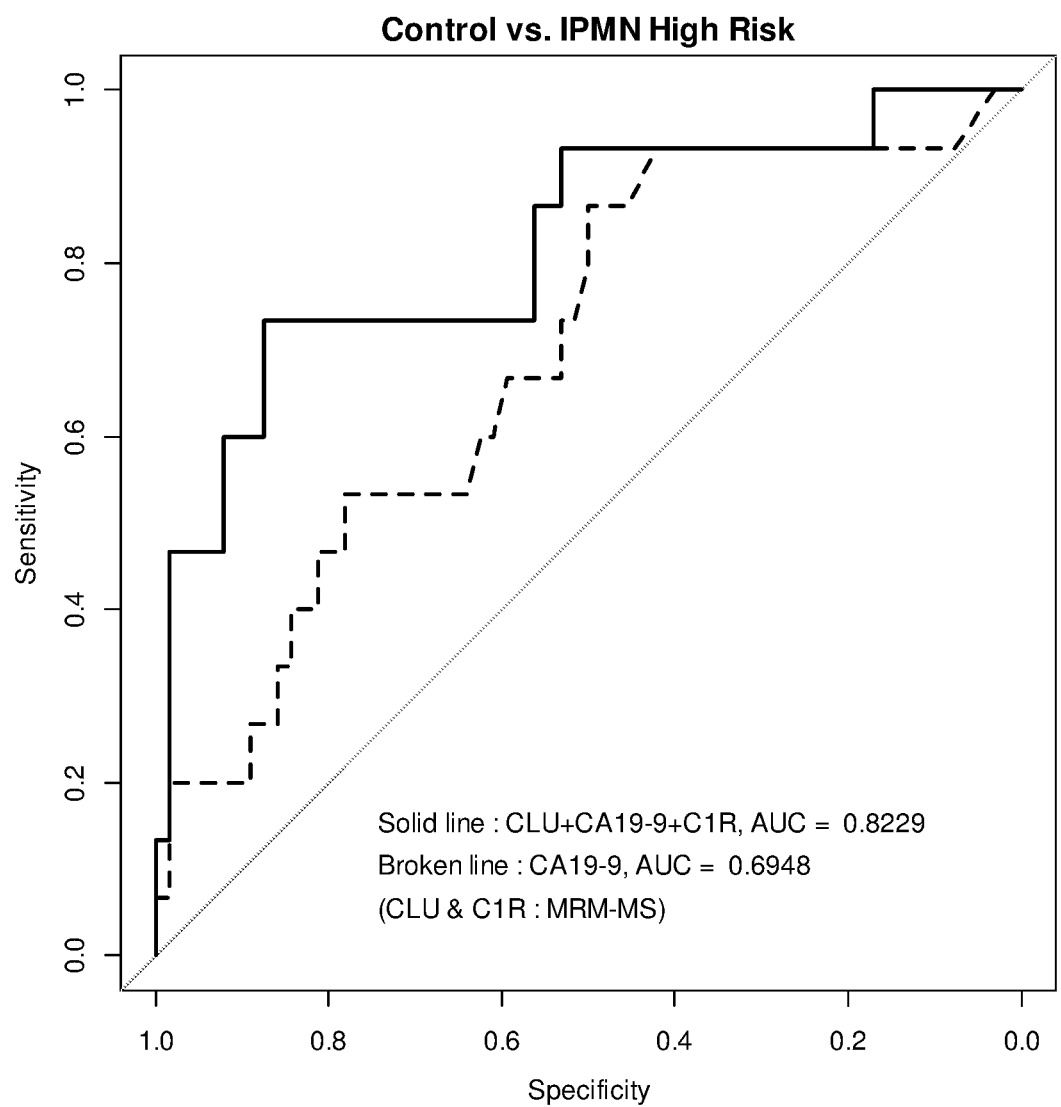

[Fig. 60]
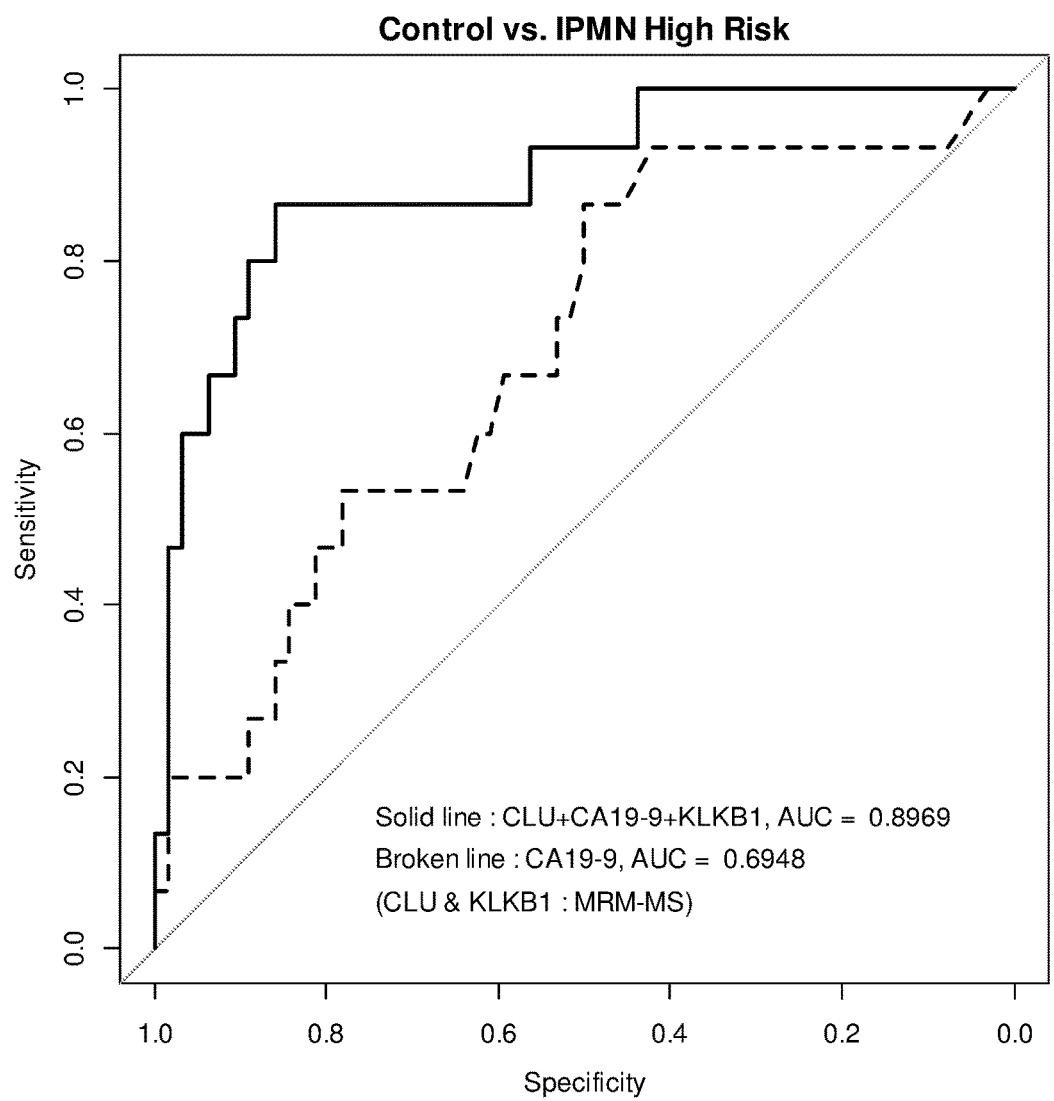

[Fig. 61]
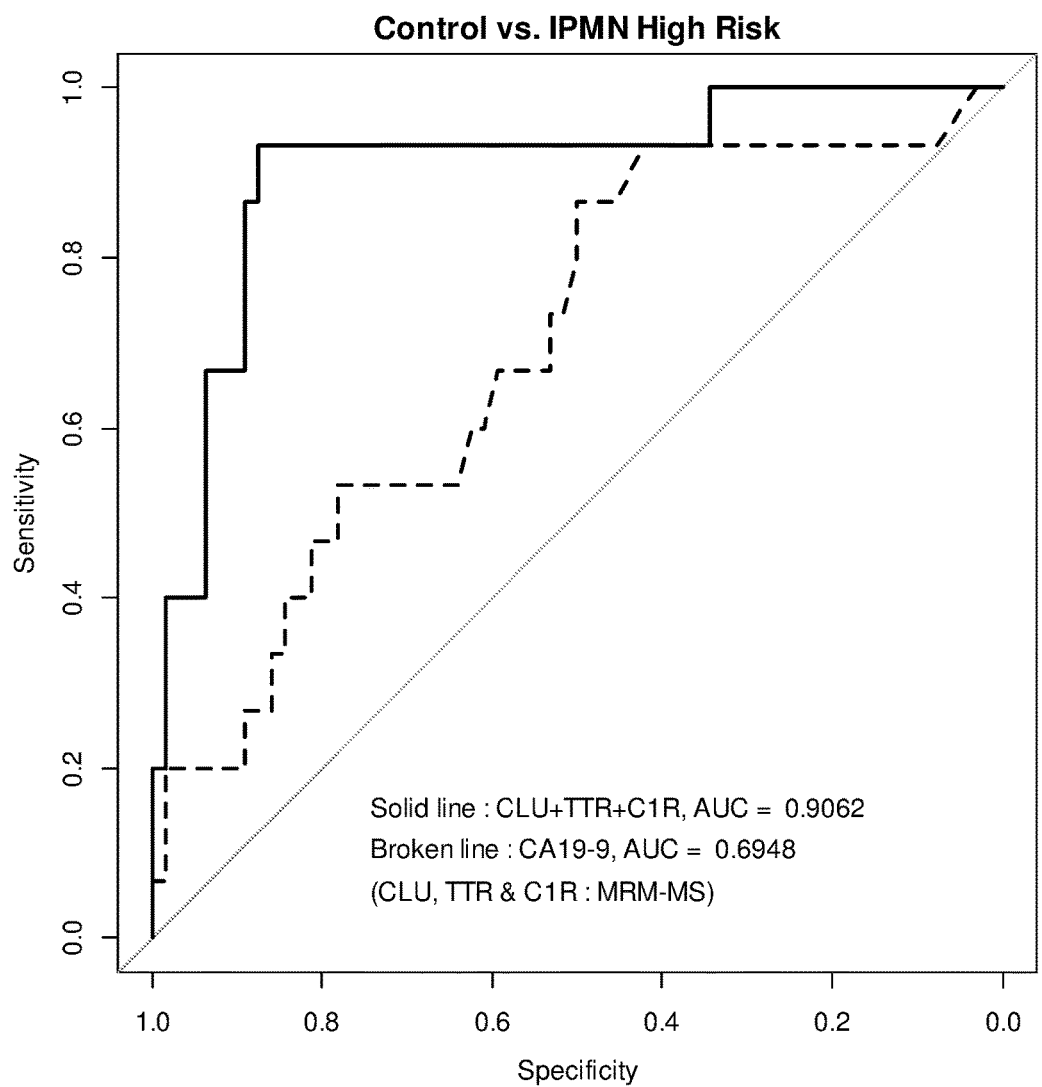

[Fig. 62]
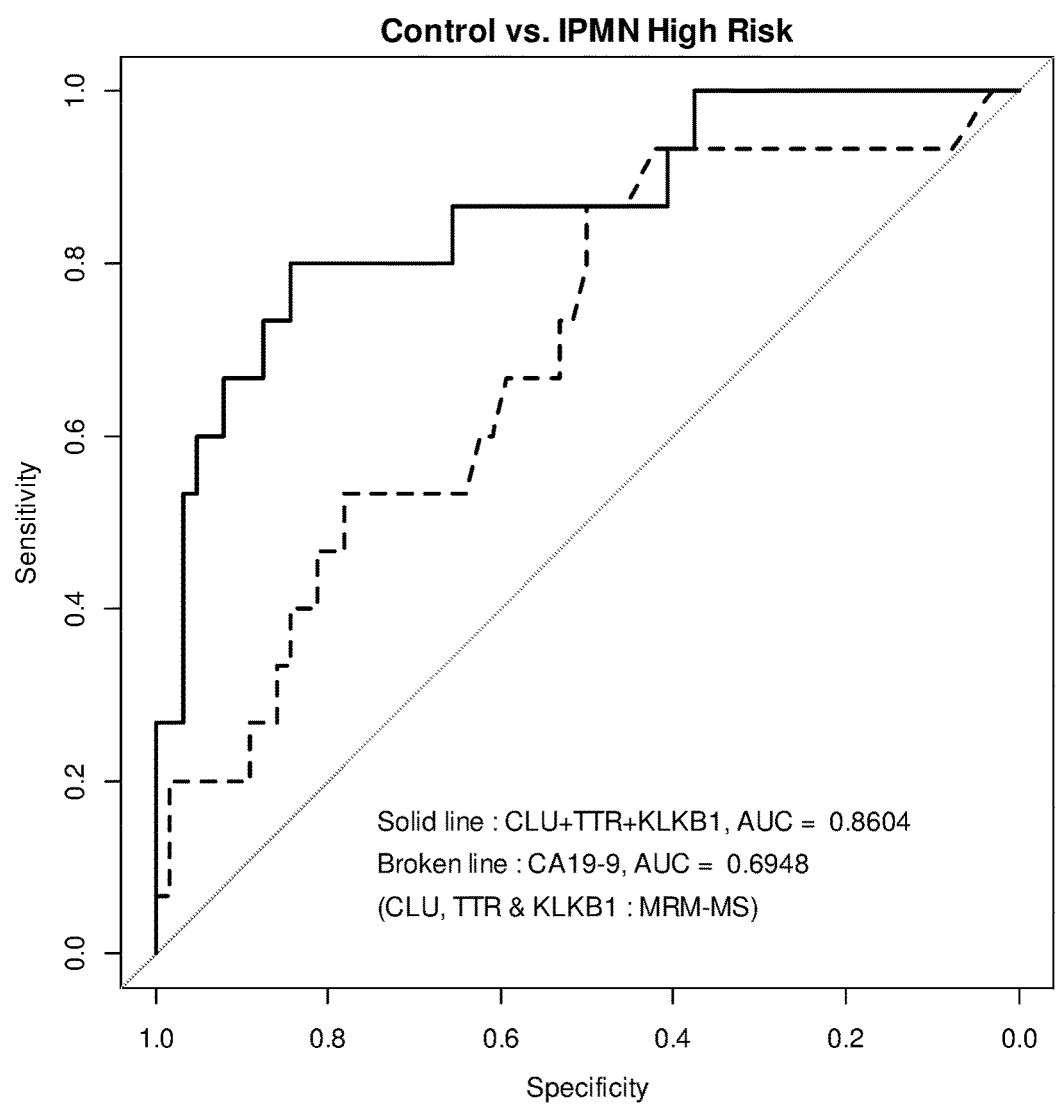

[Fig. 63]
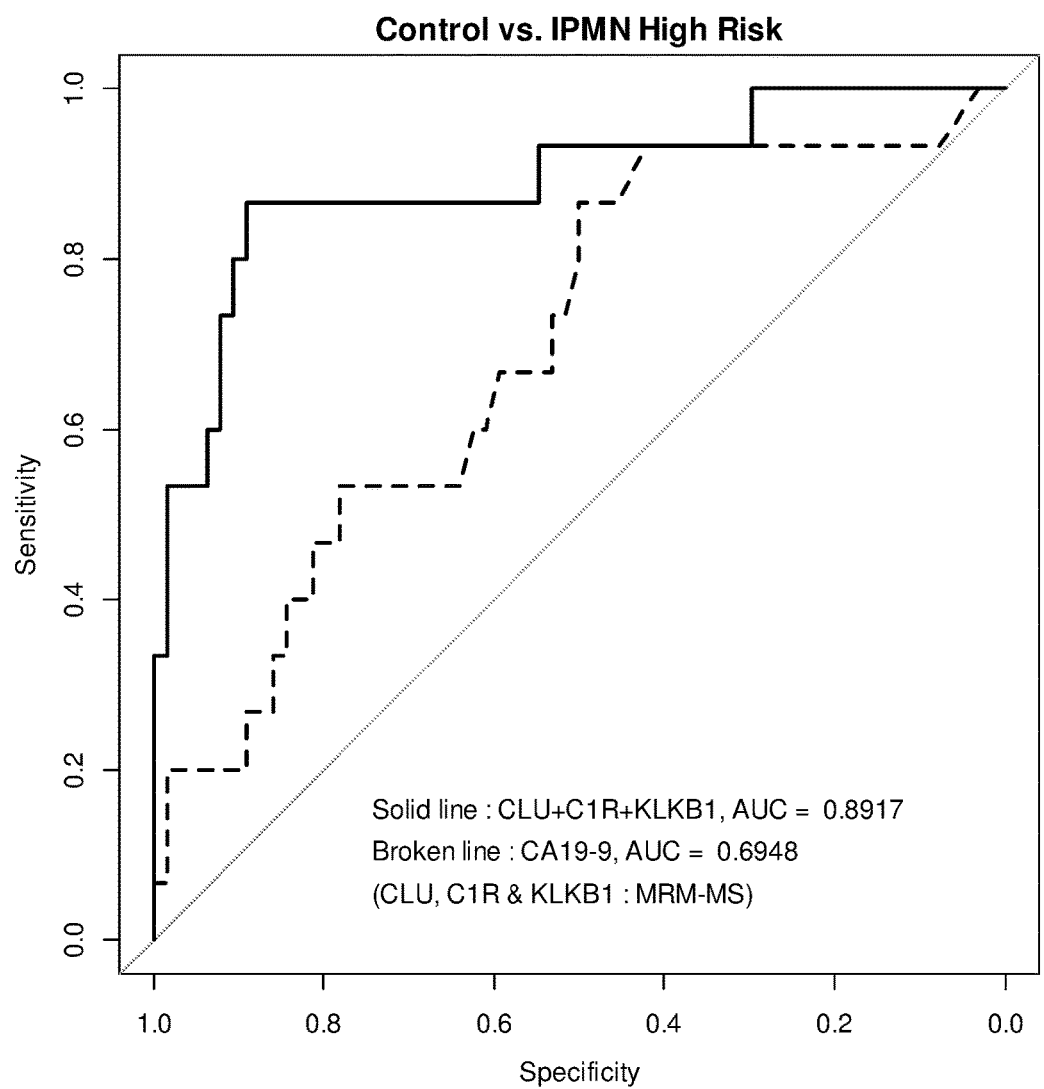

[Fig. 64]
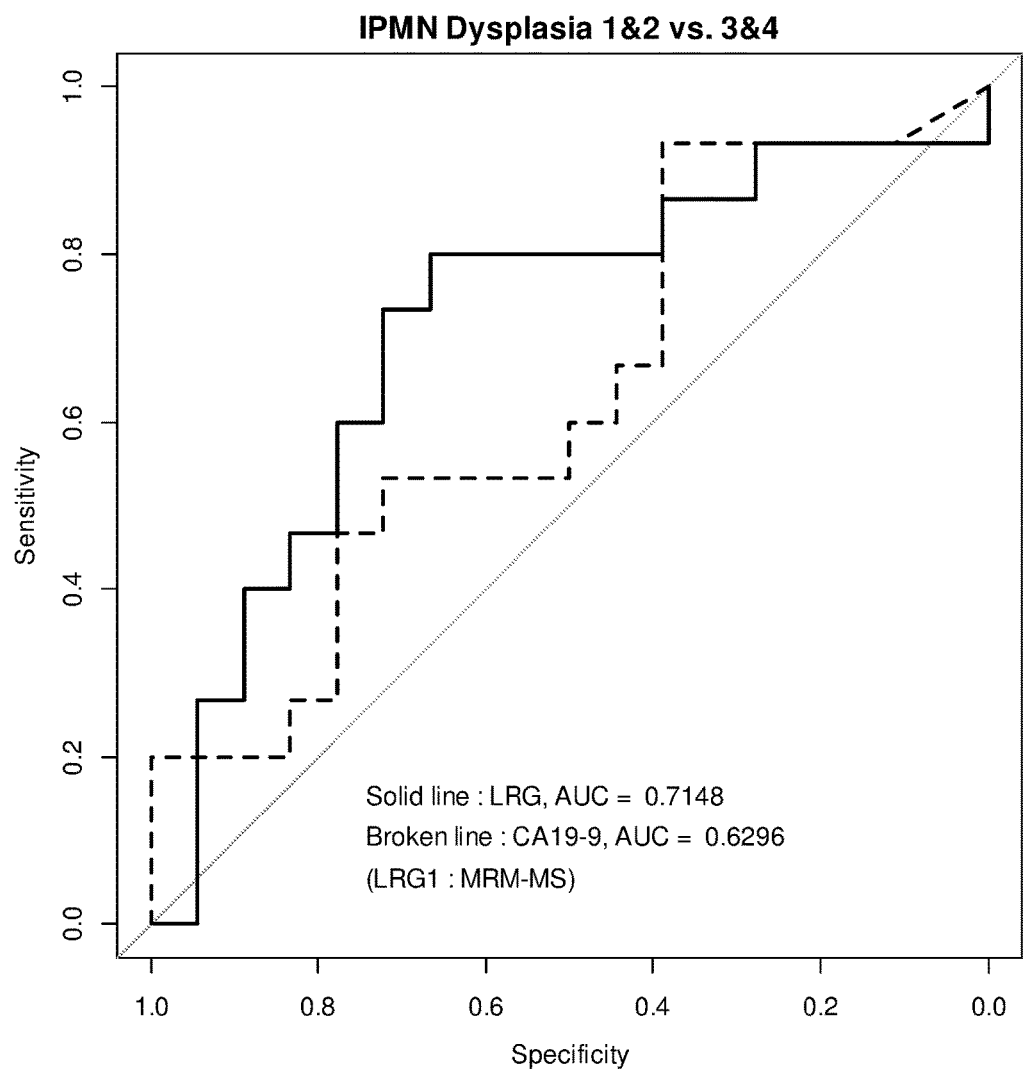

【Fig. 65】
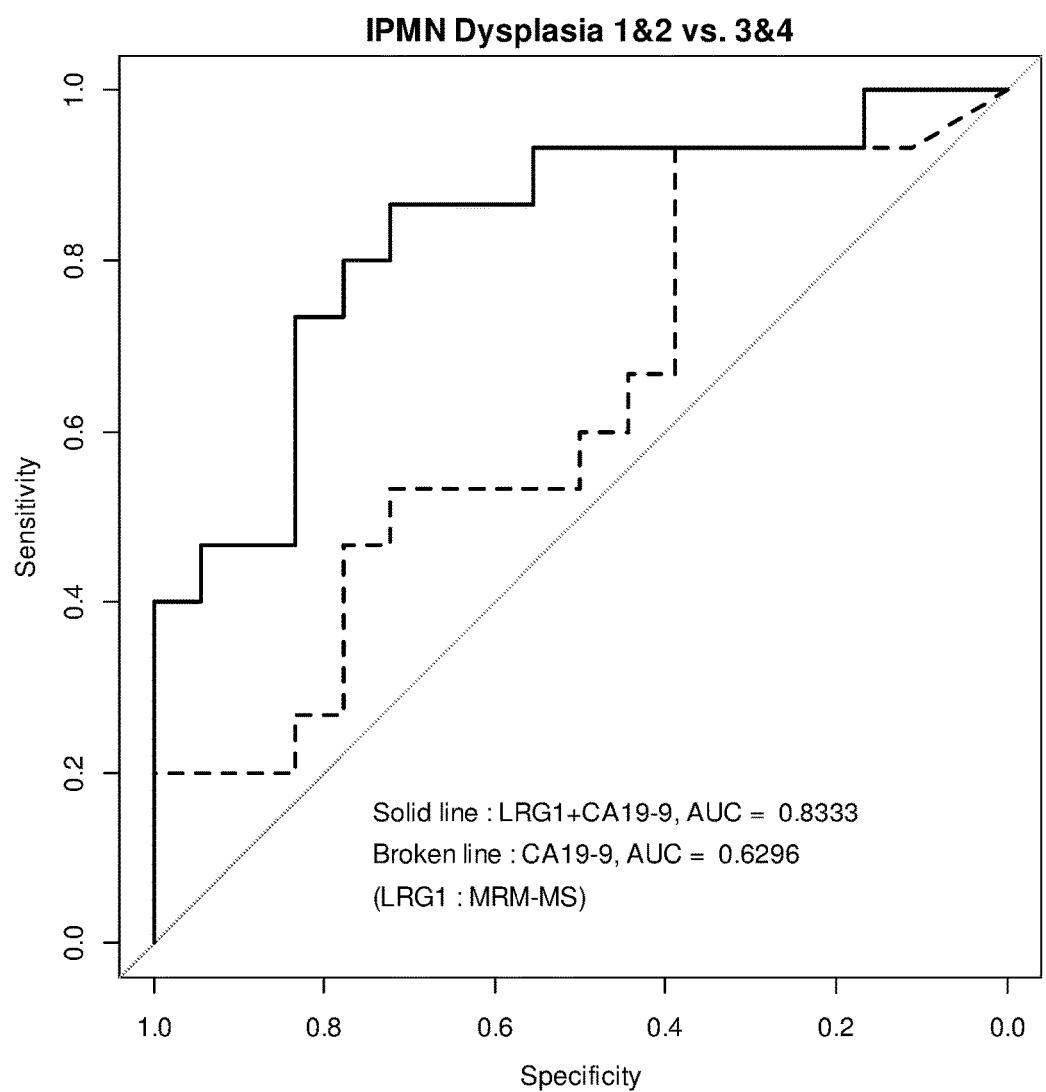

【Fig. 66】
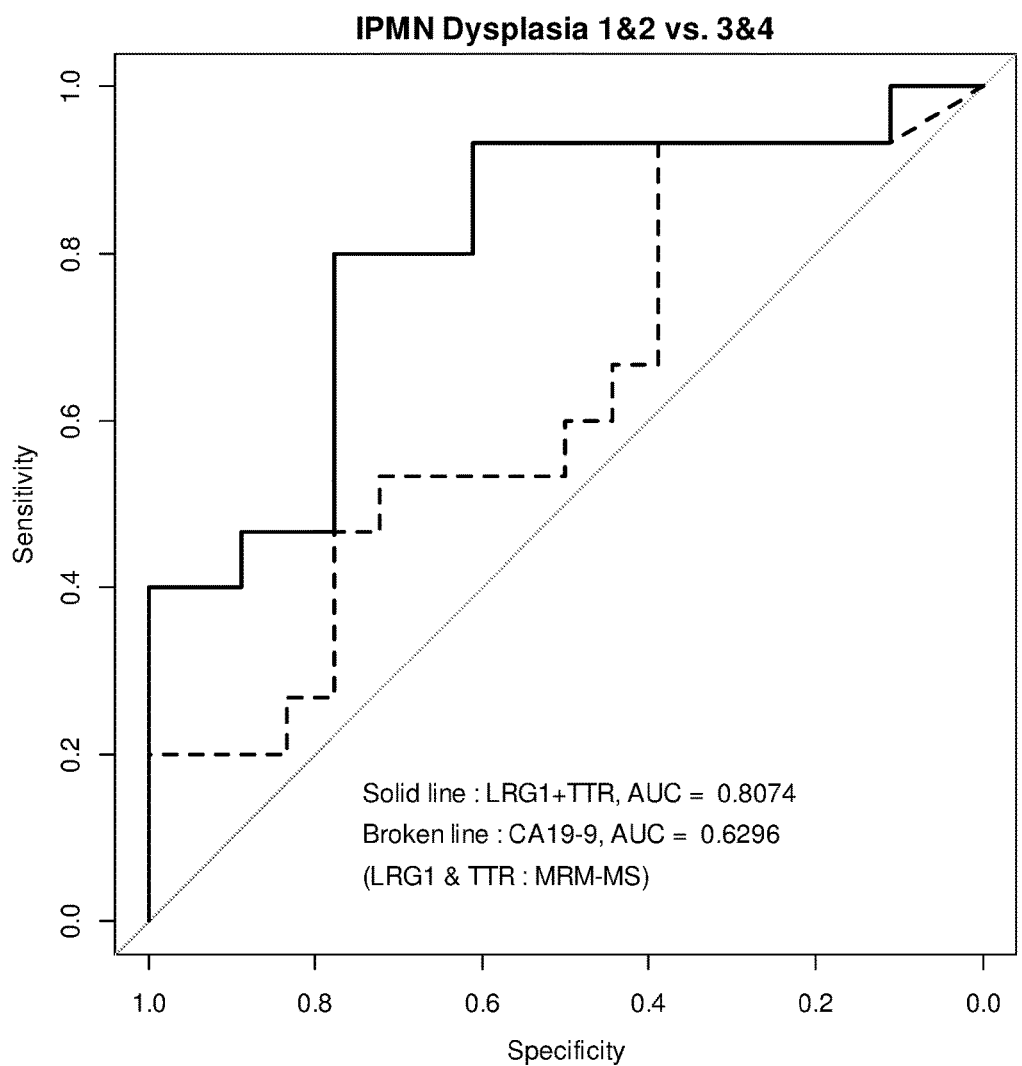

[Fig. 67]
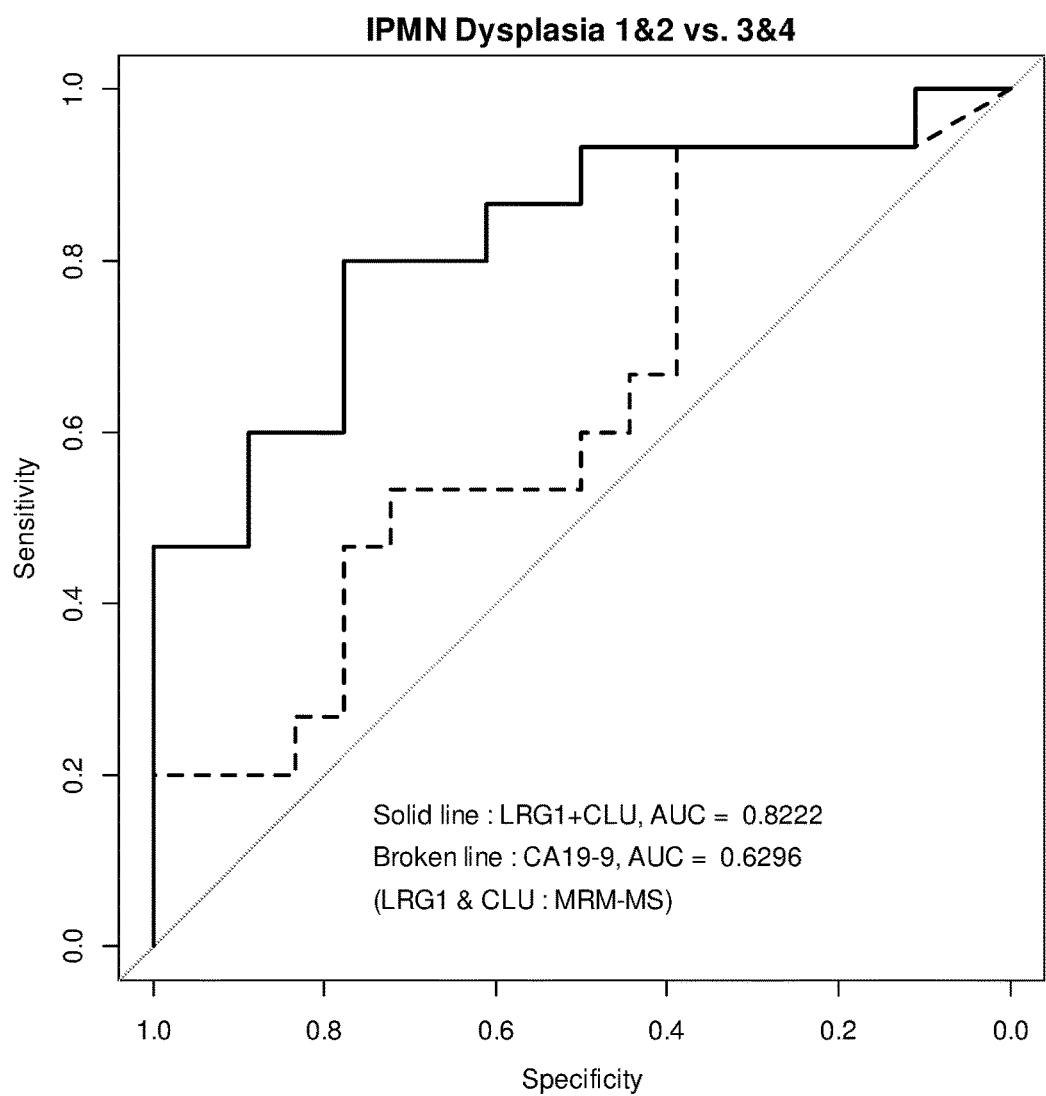

【Fig. 68】
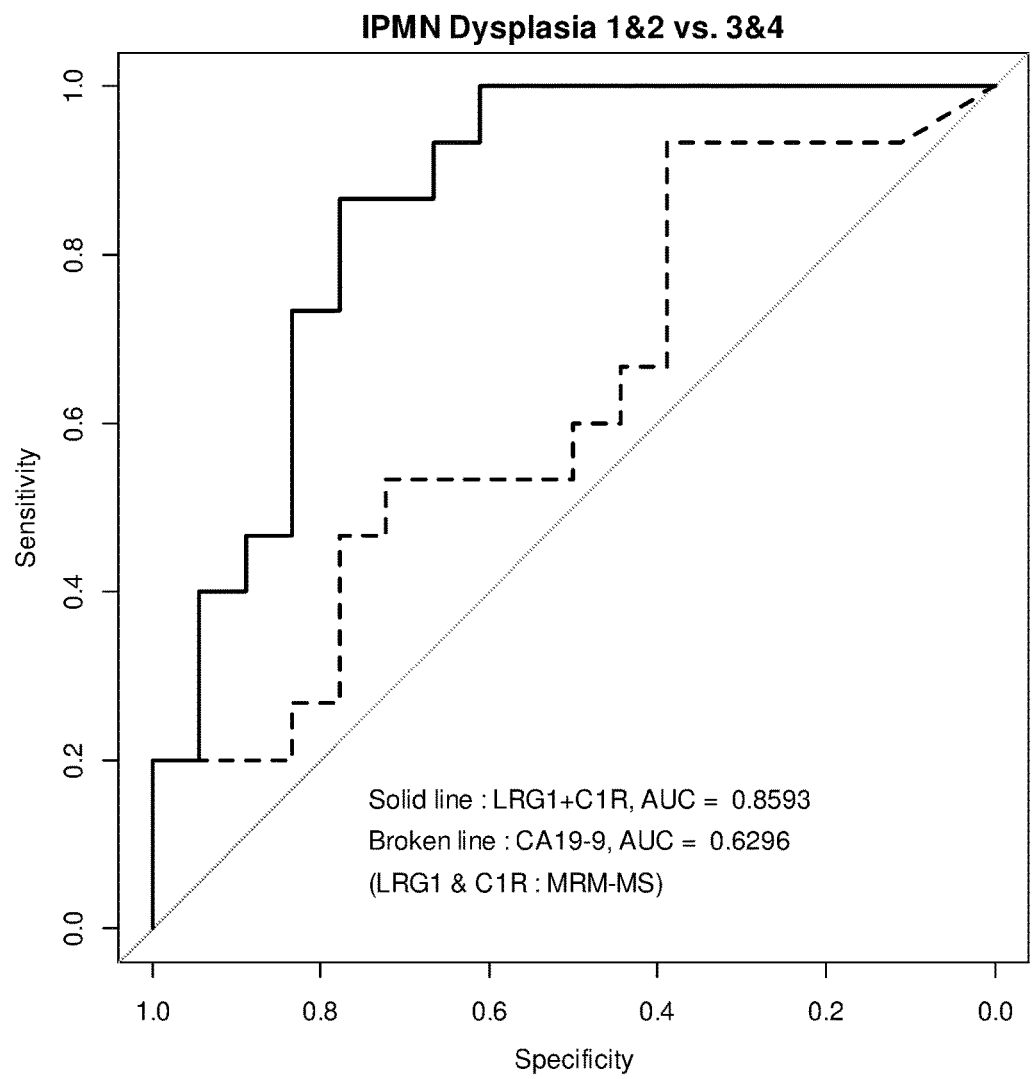

[Fig. 69]
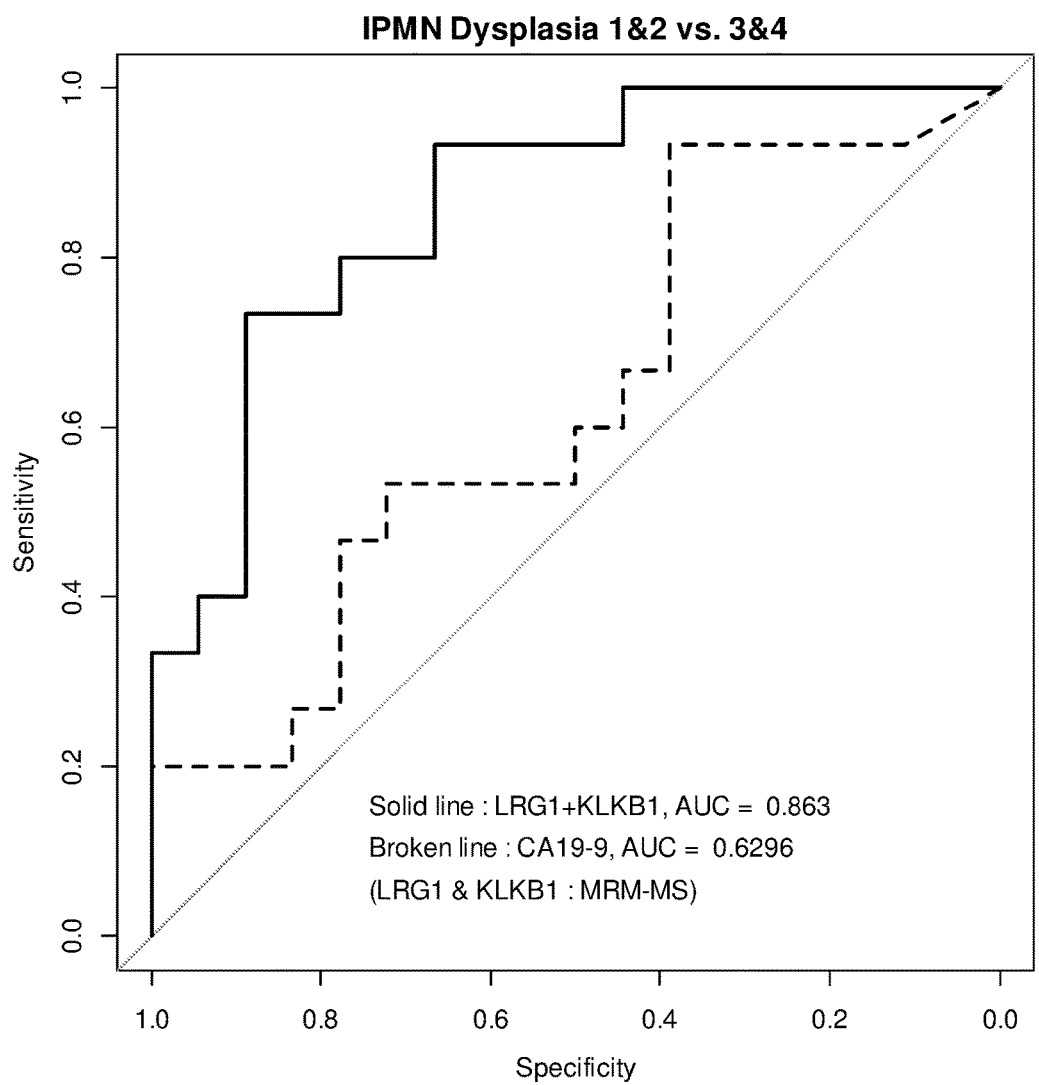

[Fig. 70]
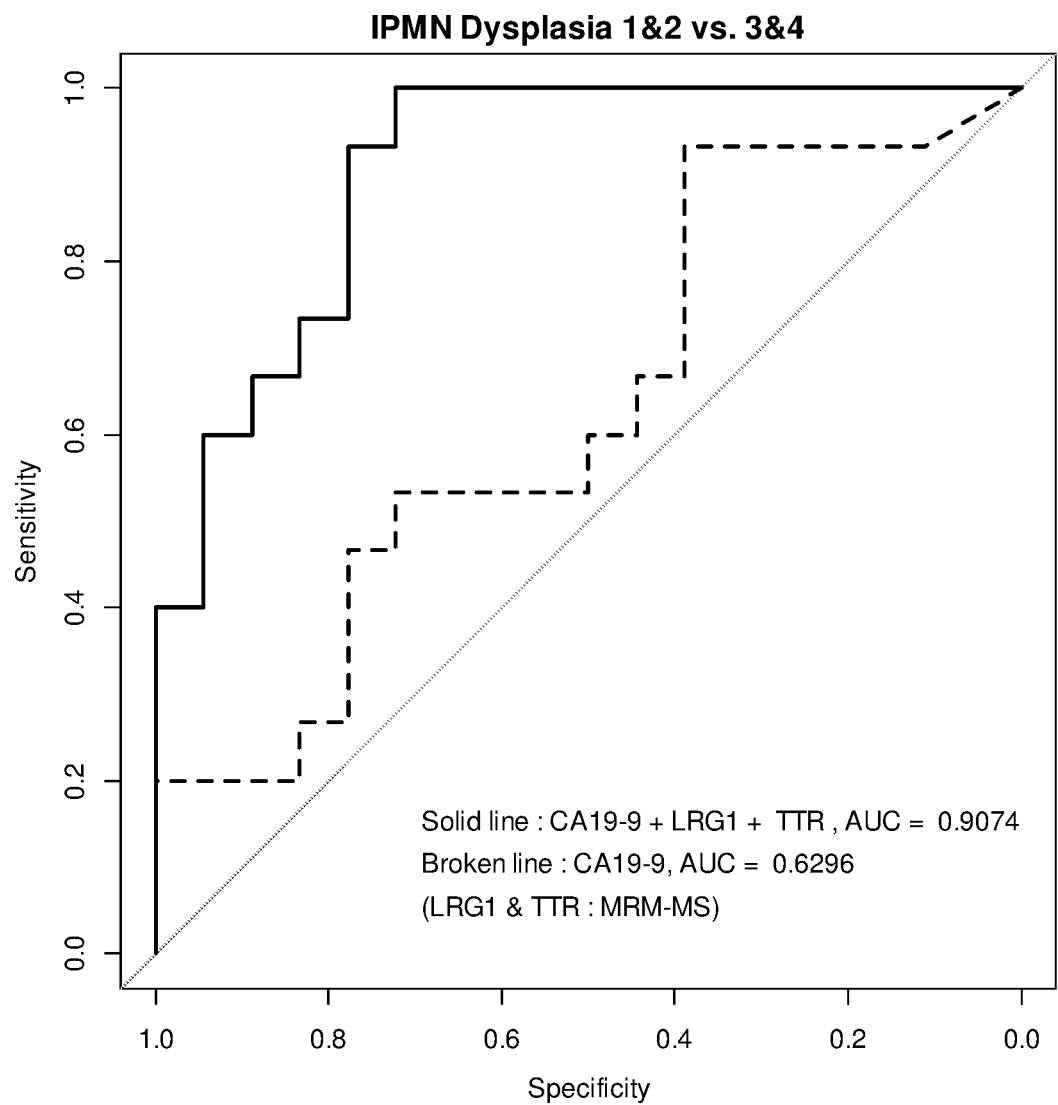

[Fig. 71]
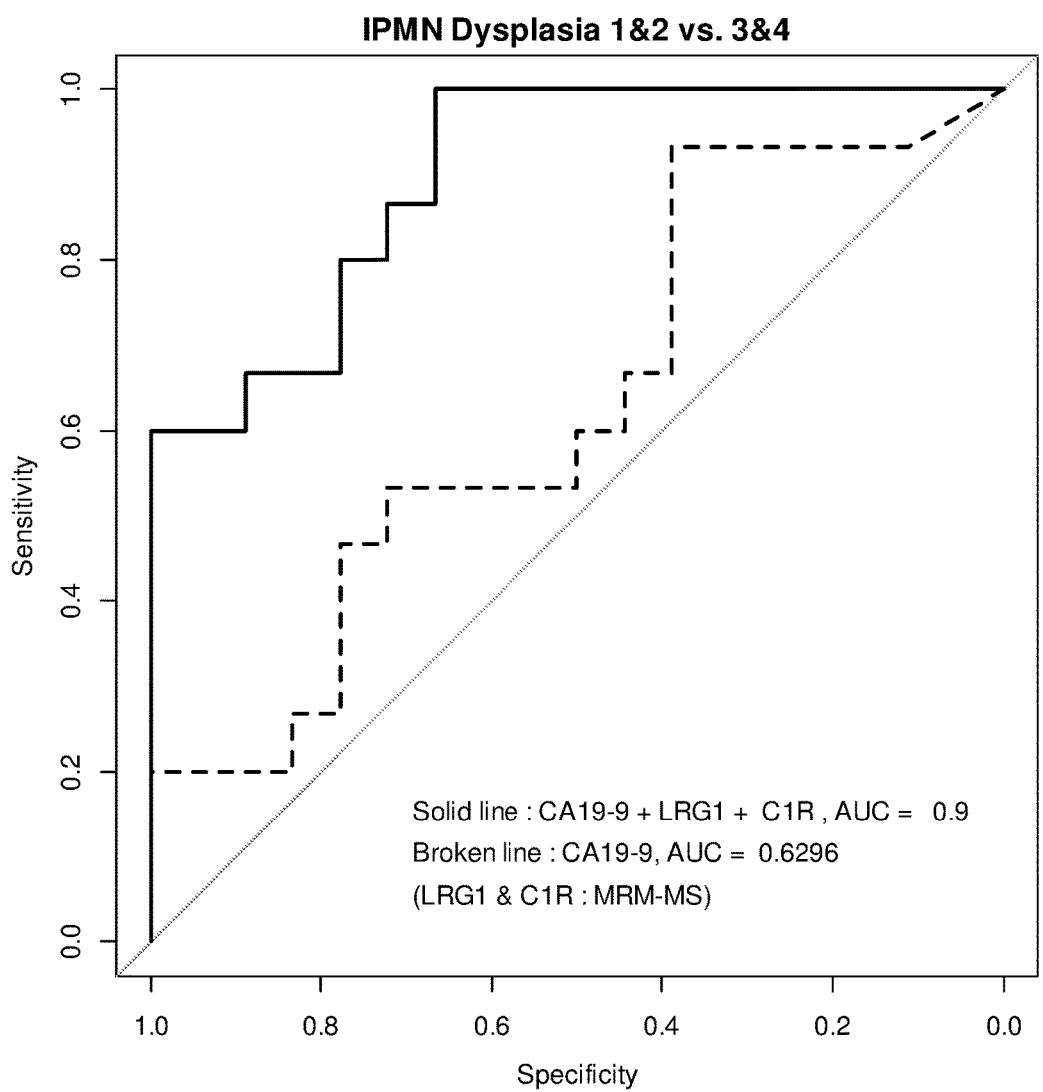

[Fig. 72]
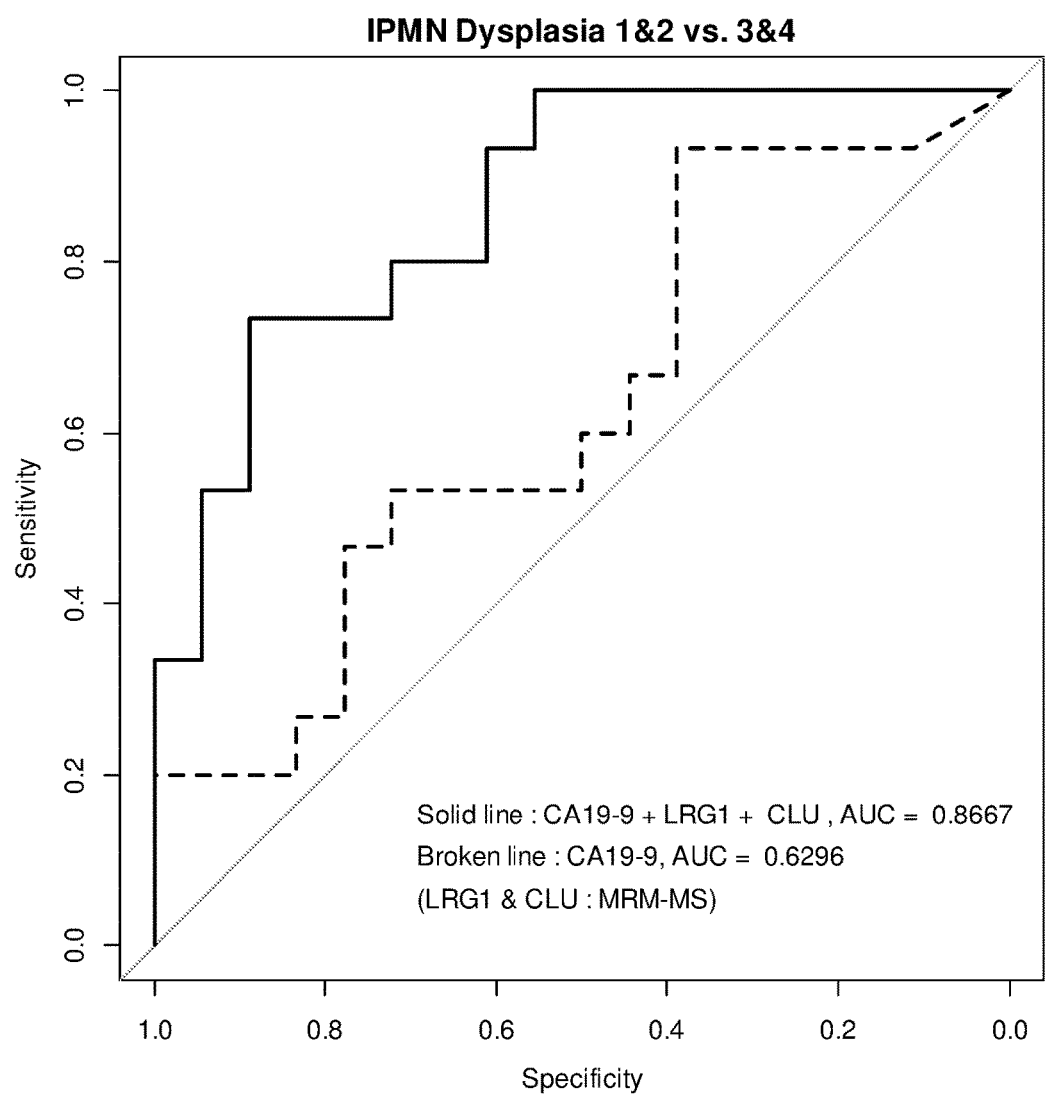

[Fig. 73]
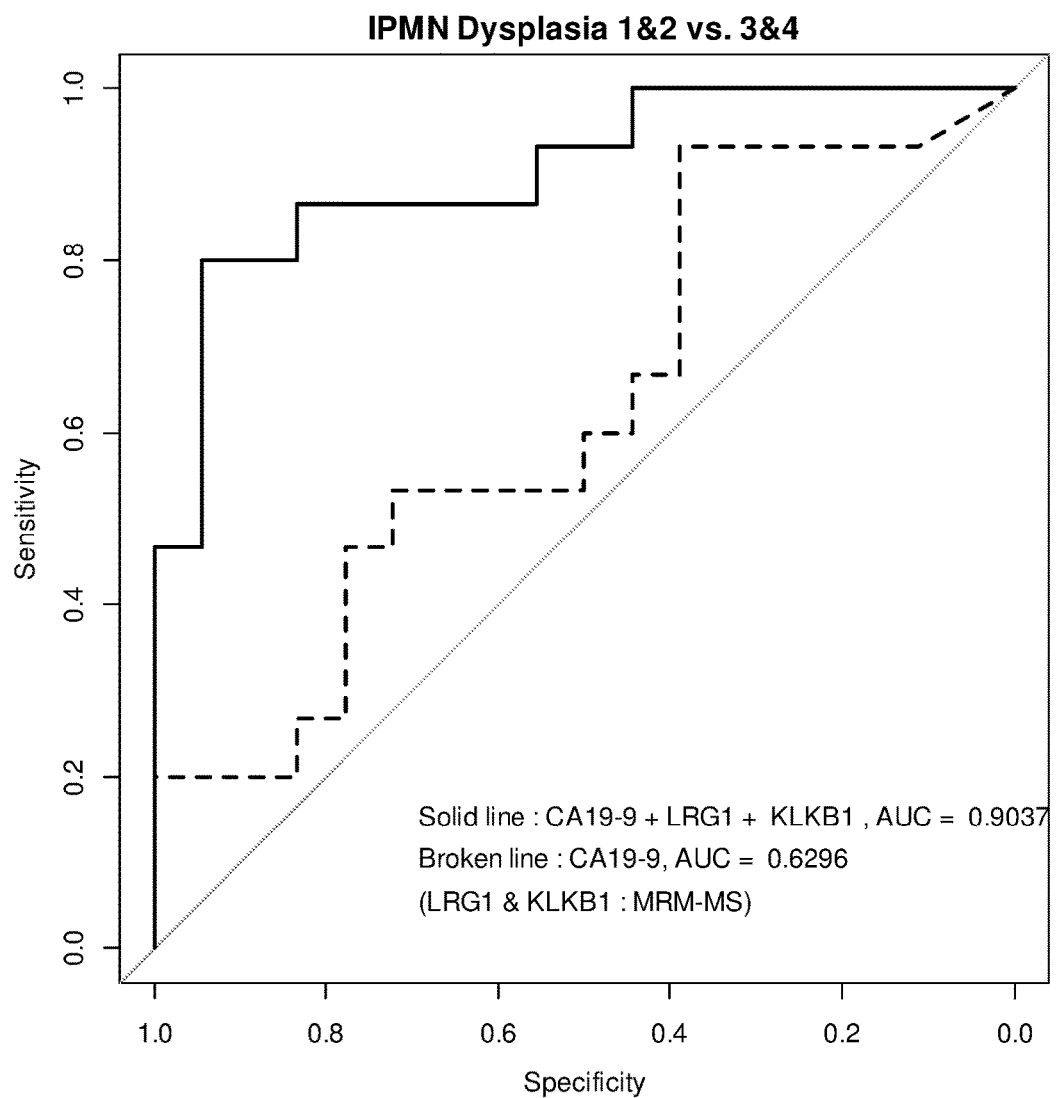

[Fig. 74]
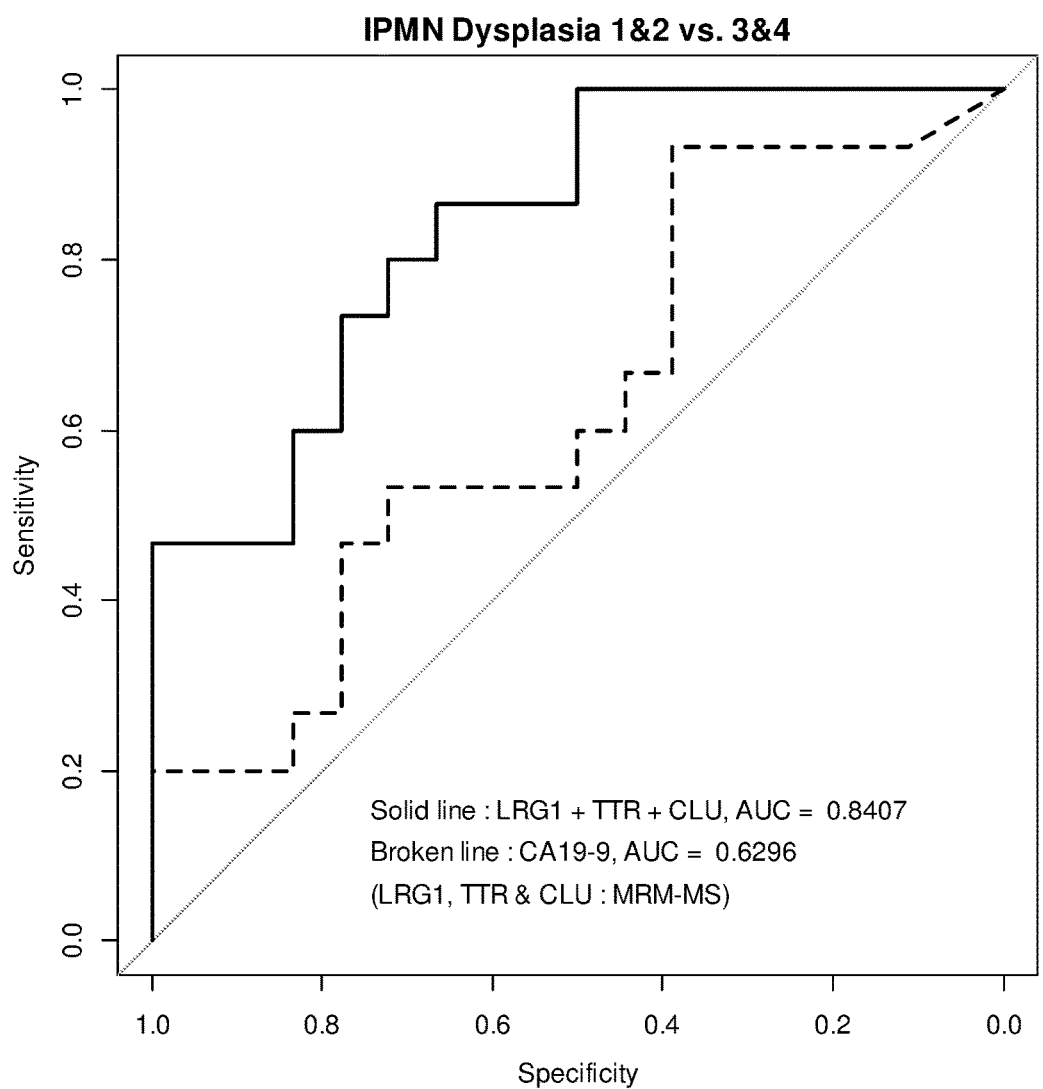

[Fig. 75]
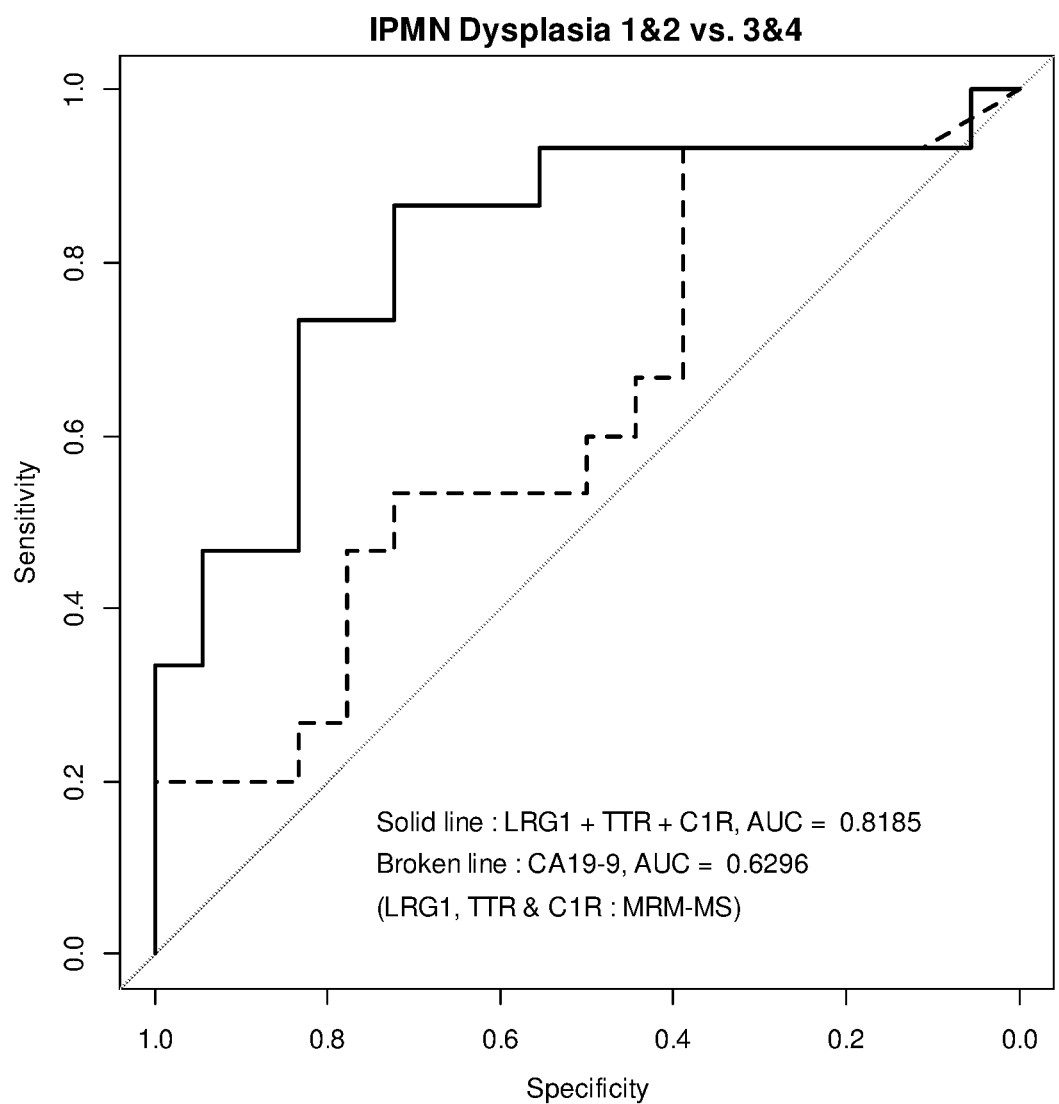

[Fig. 76]
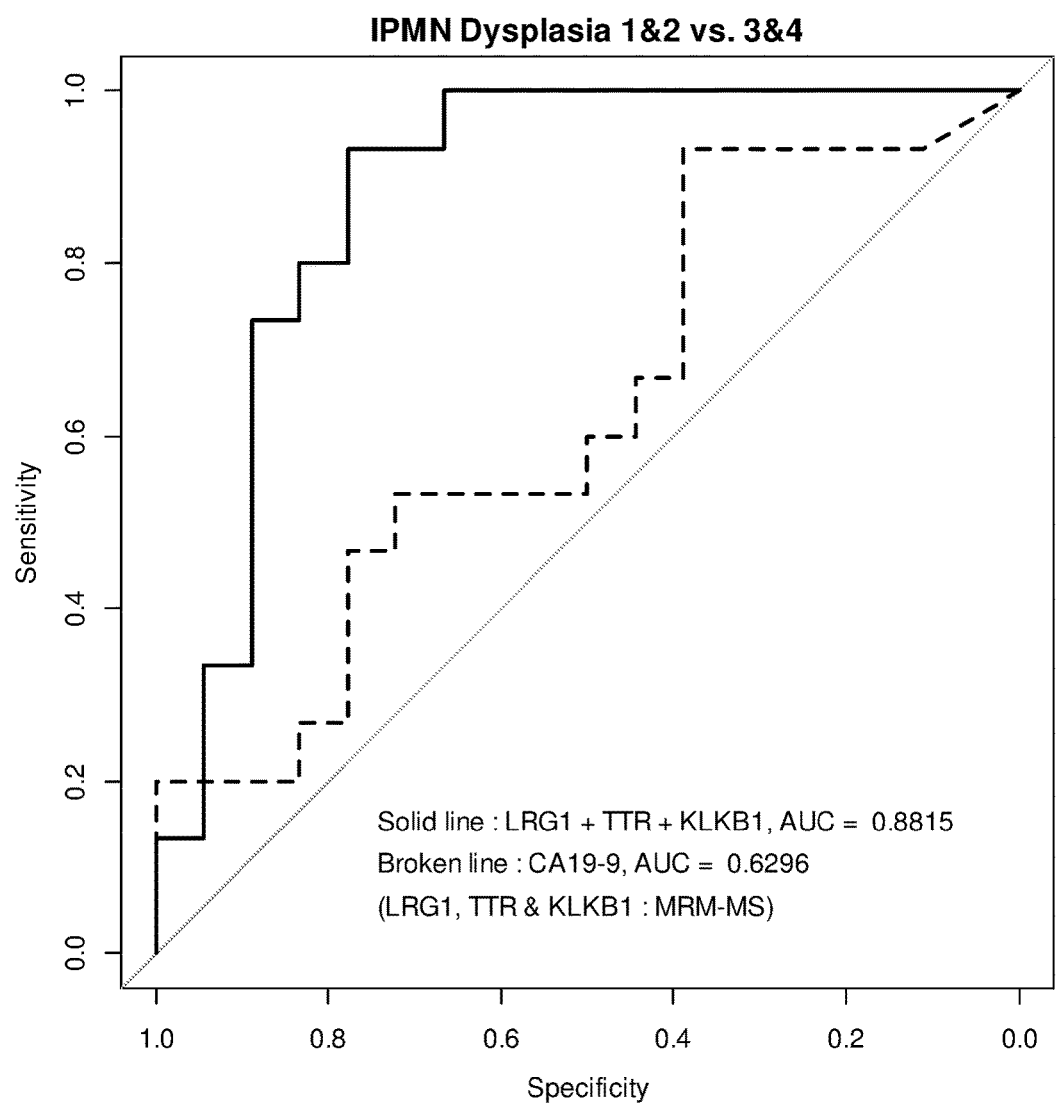

[Fig. 77]
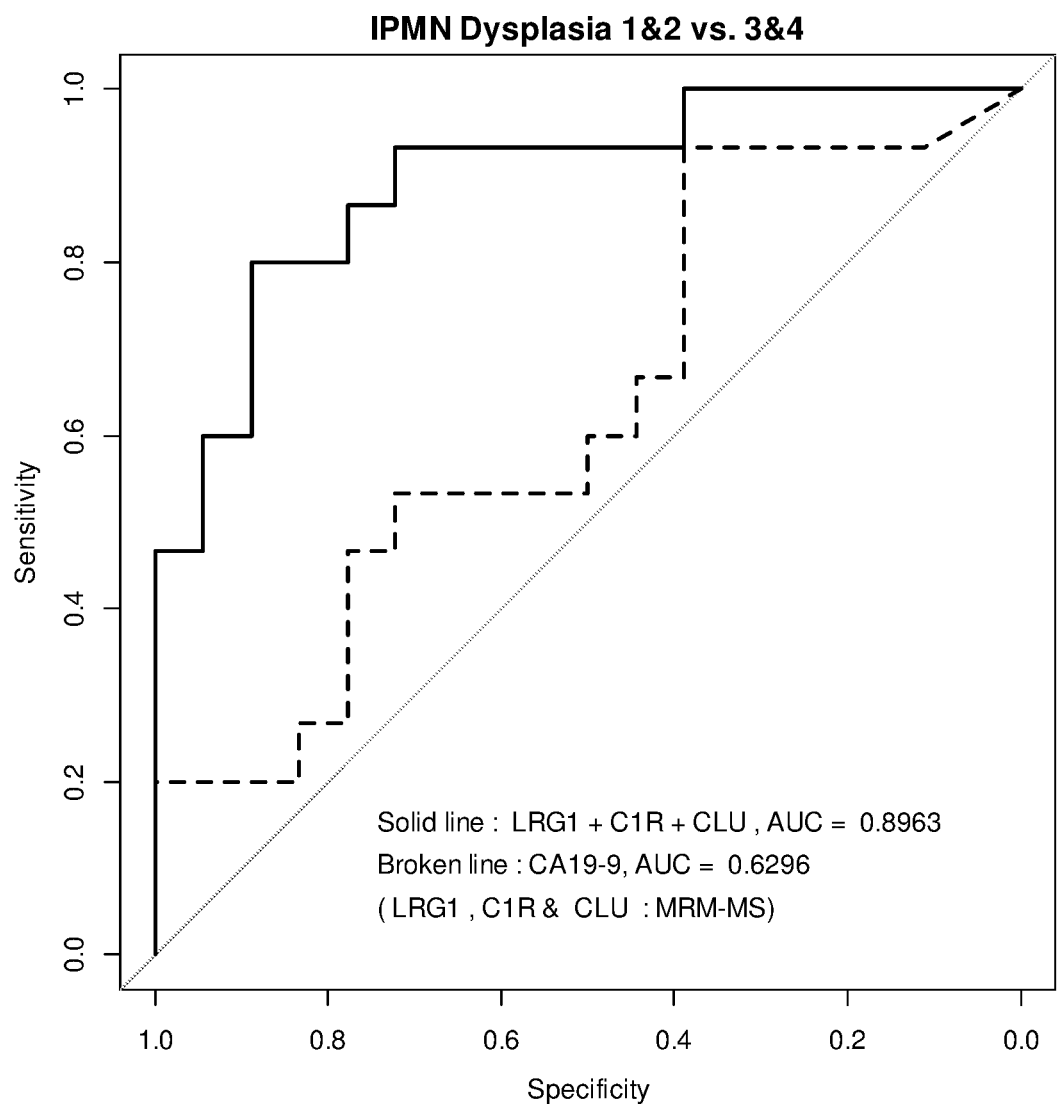

[Fig. 78]
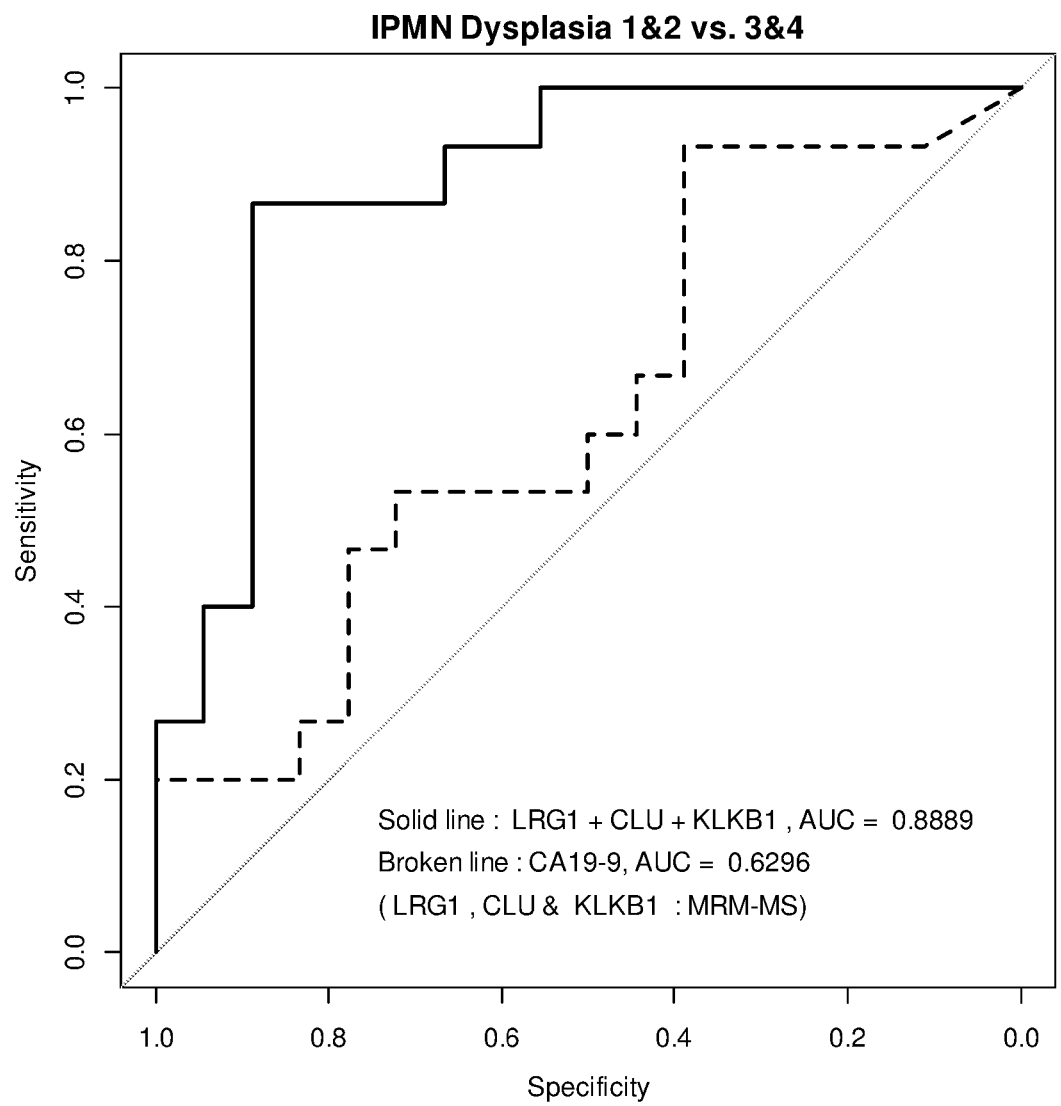

[Fig. 79]
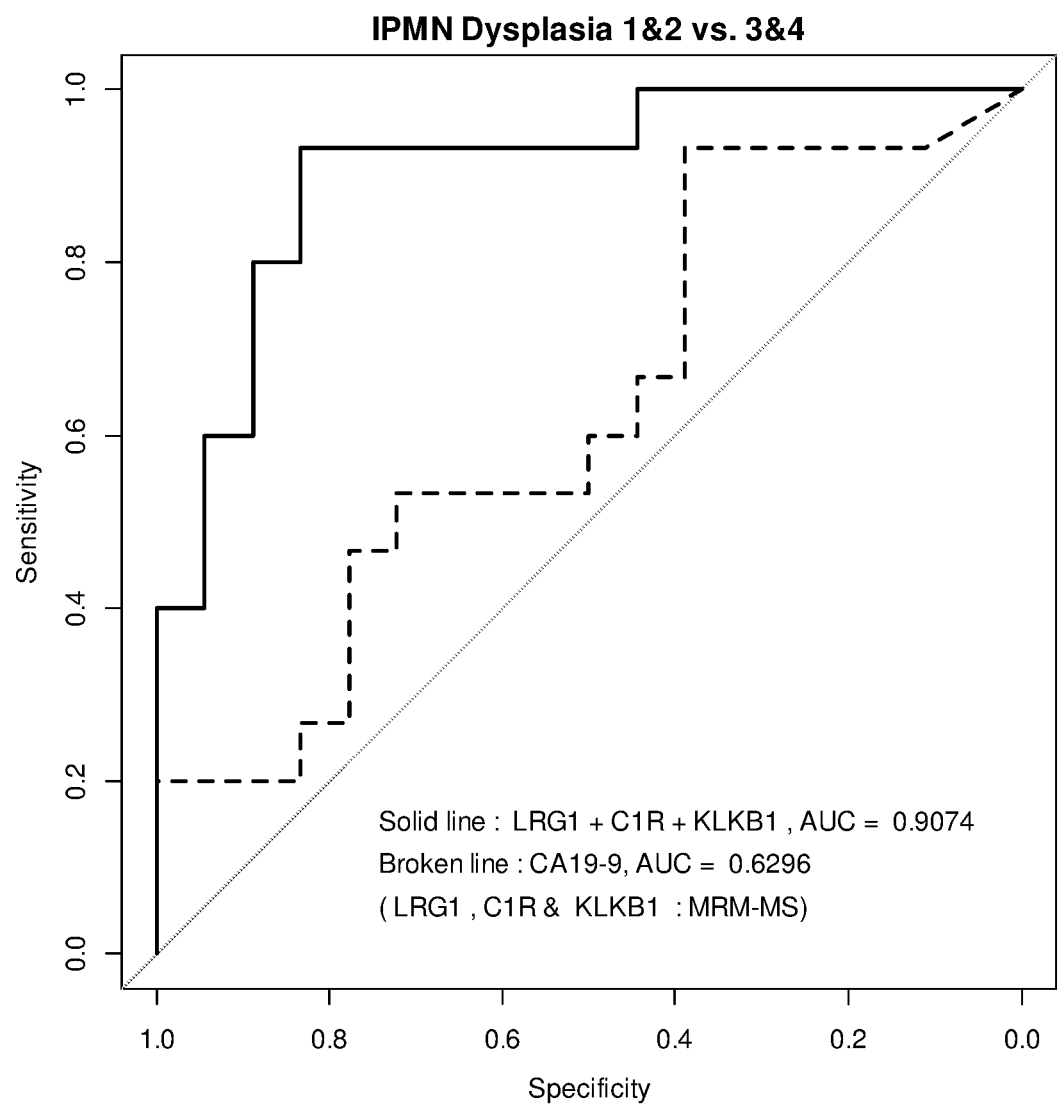

[Fig. 80]
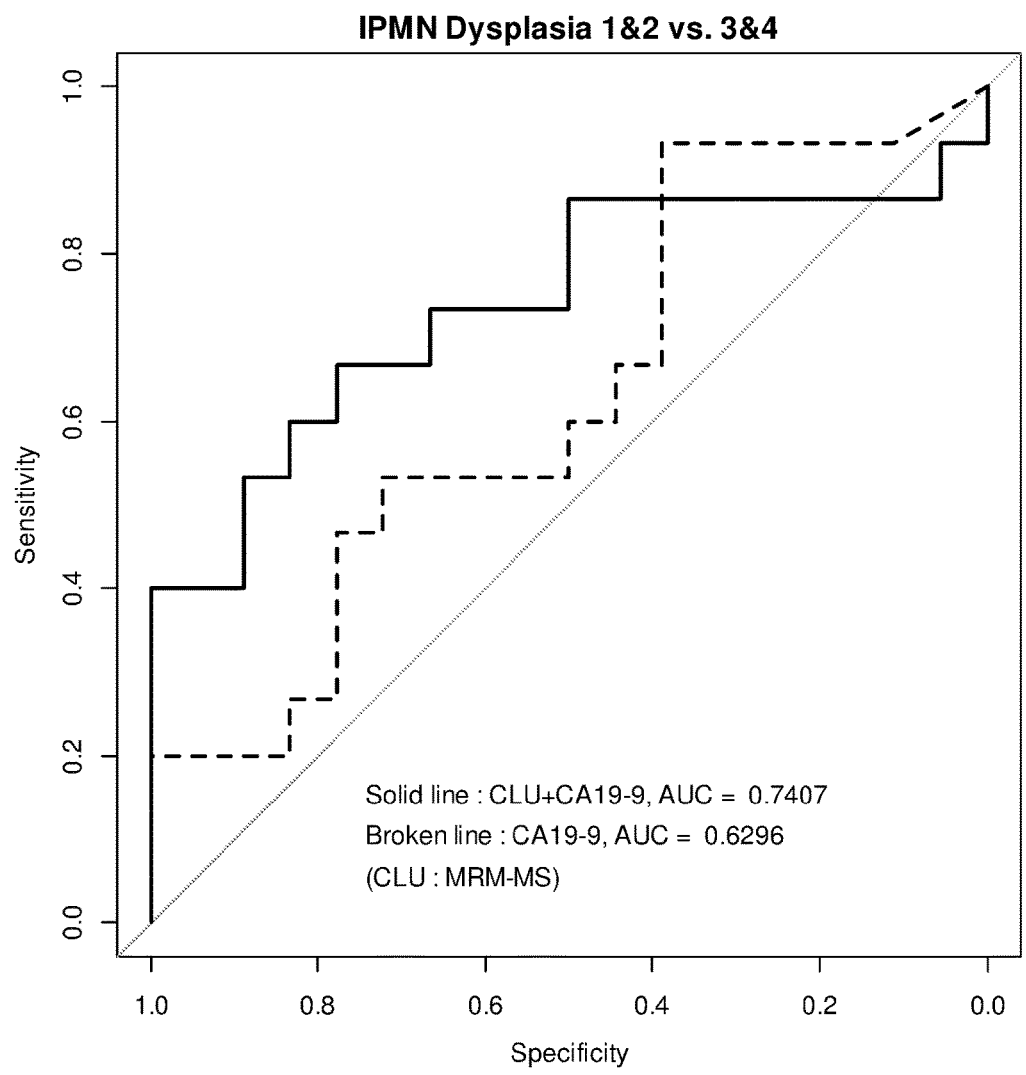

[Fig. 81]
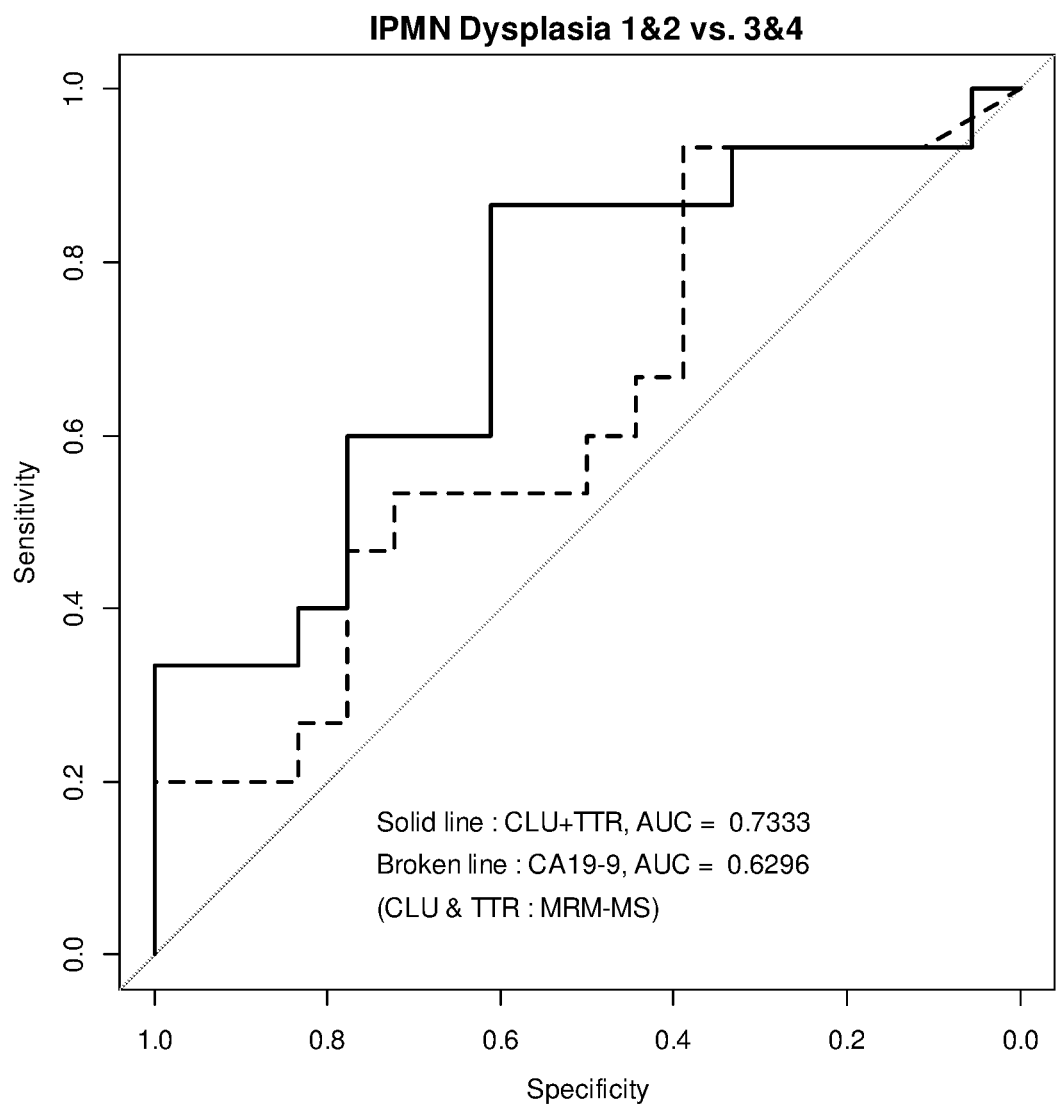

[Fig. 82]
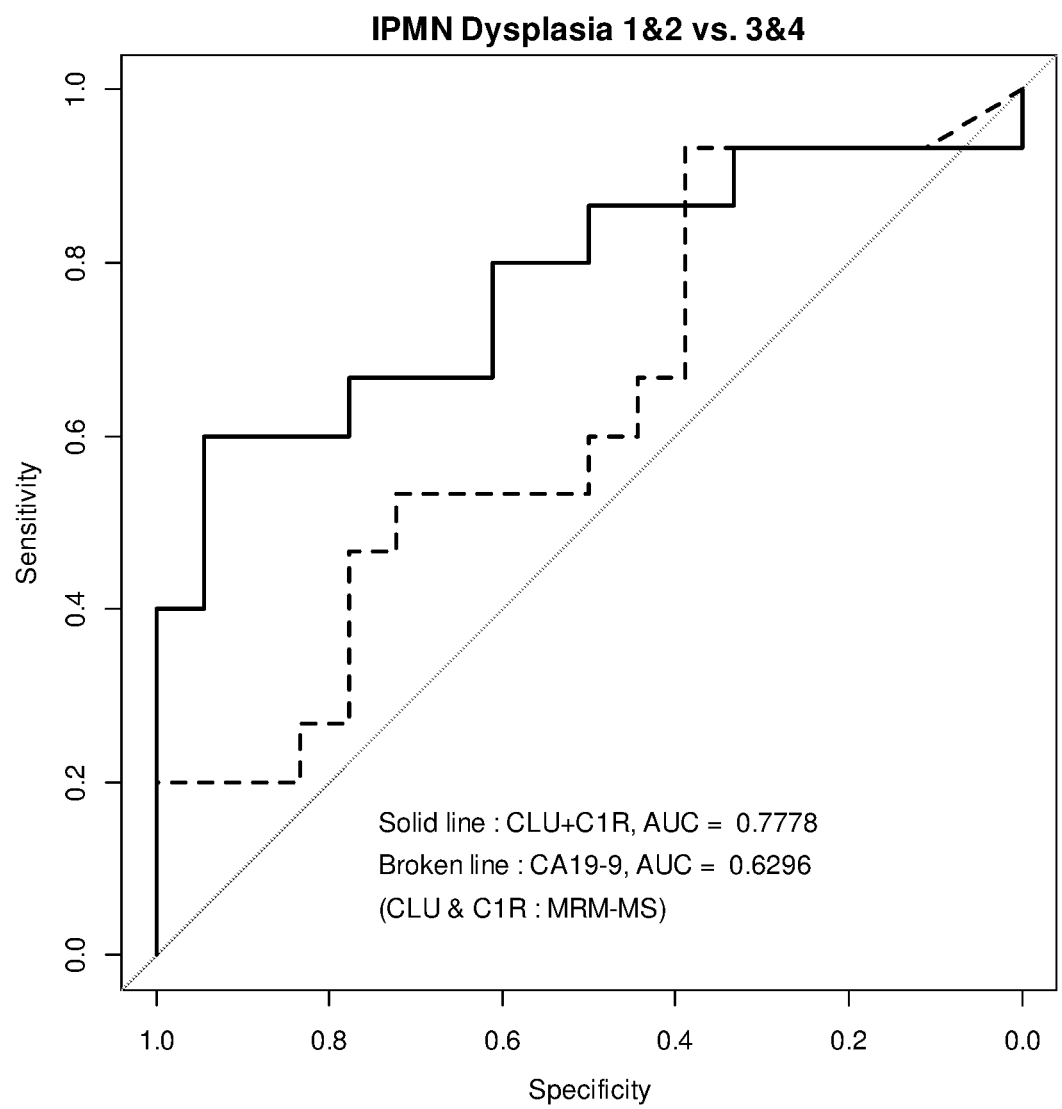

[Fig. 83]
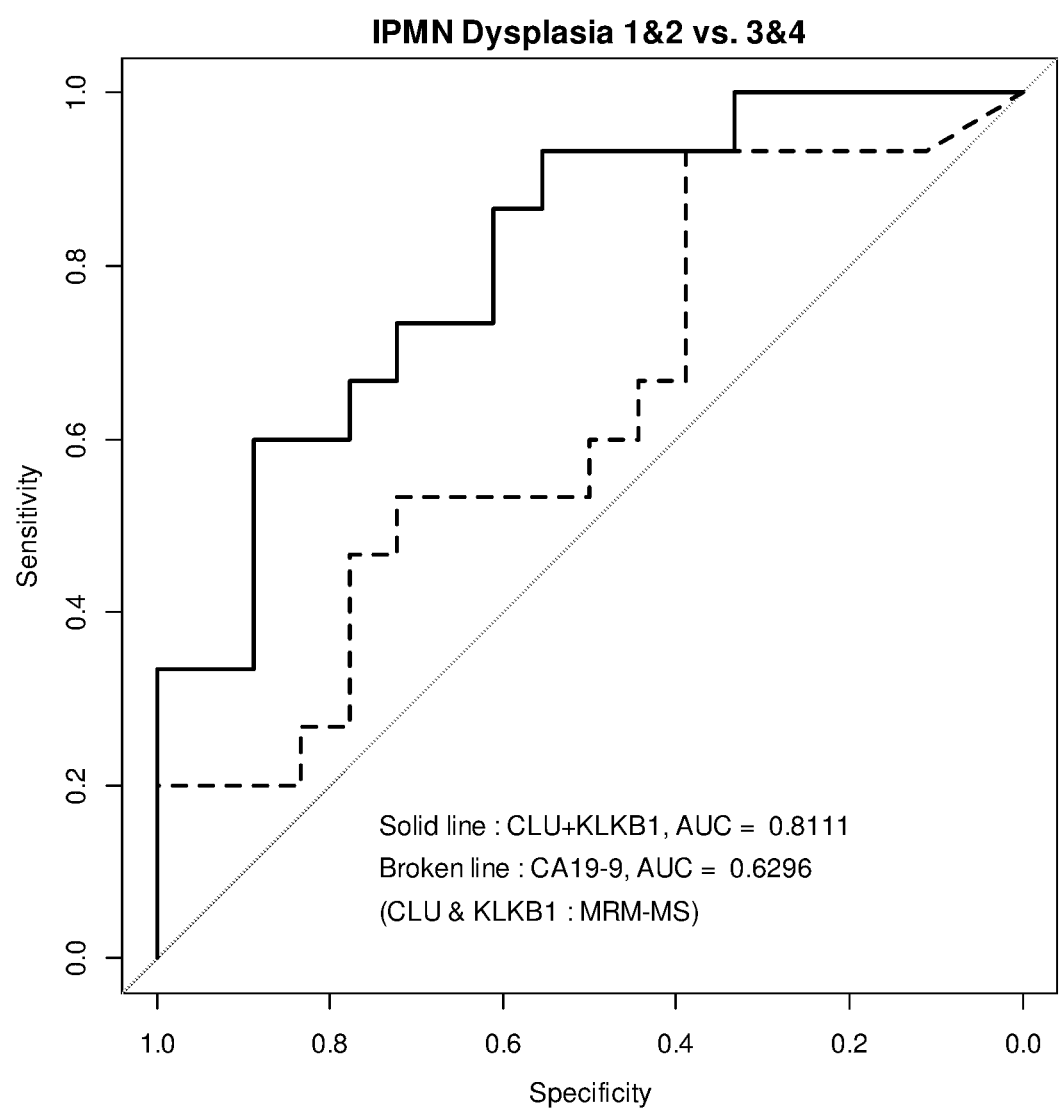

[Fig. 84]
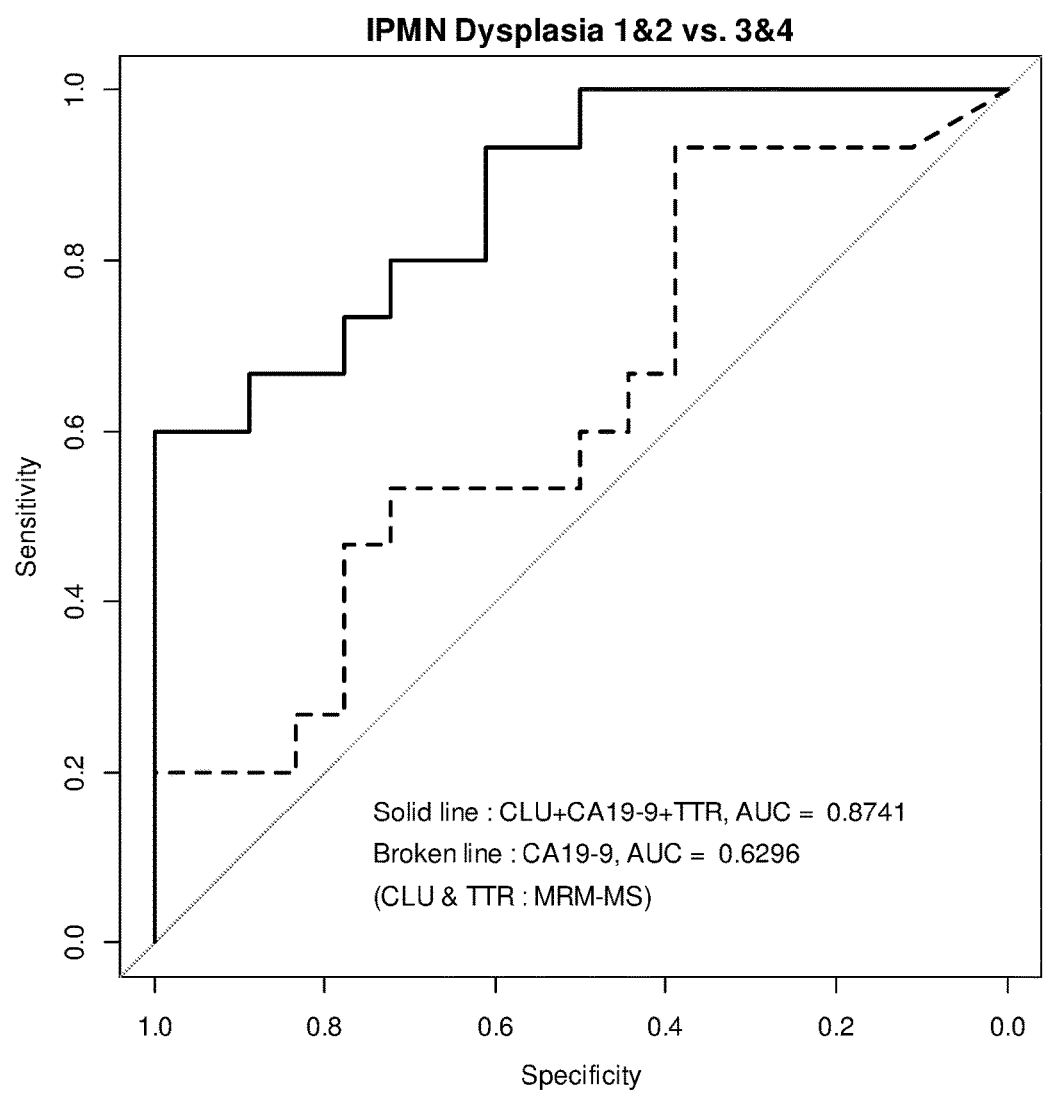

【Fig. 85】
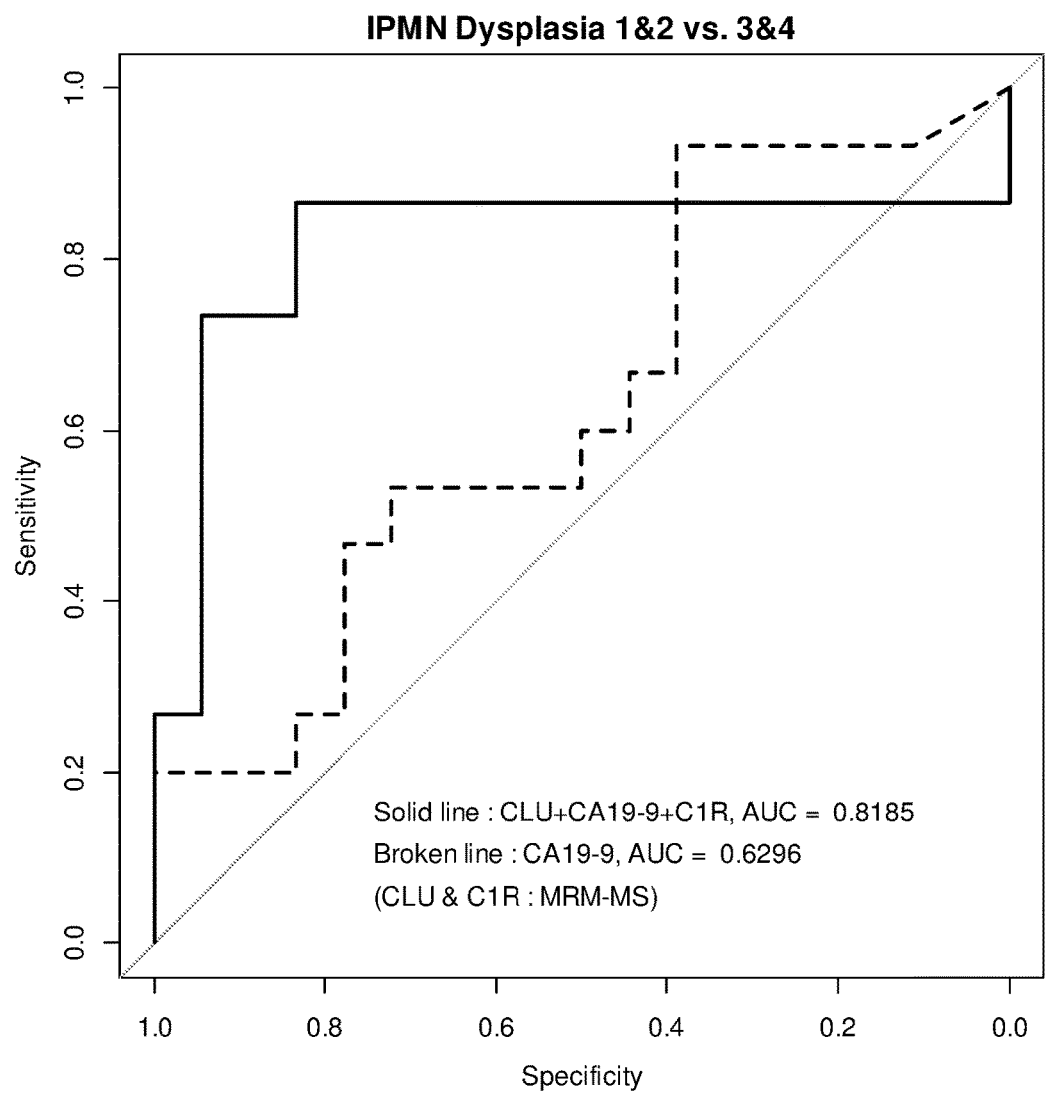

[Fig. 86]
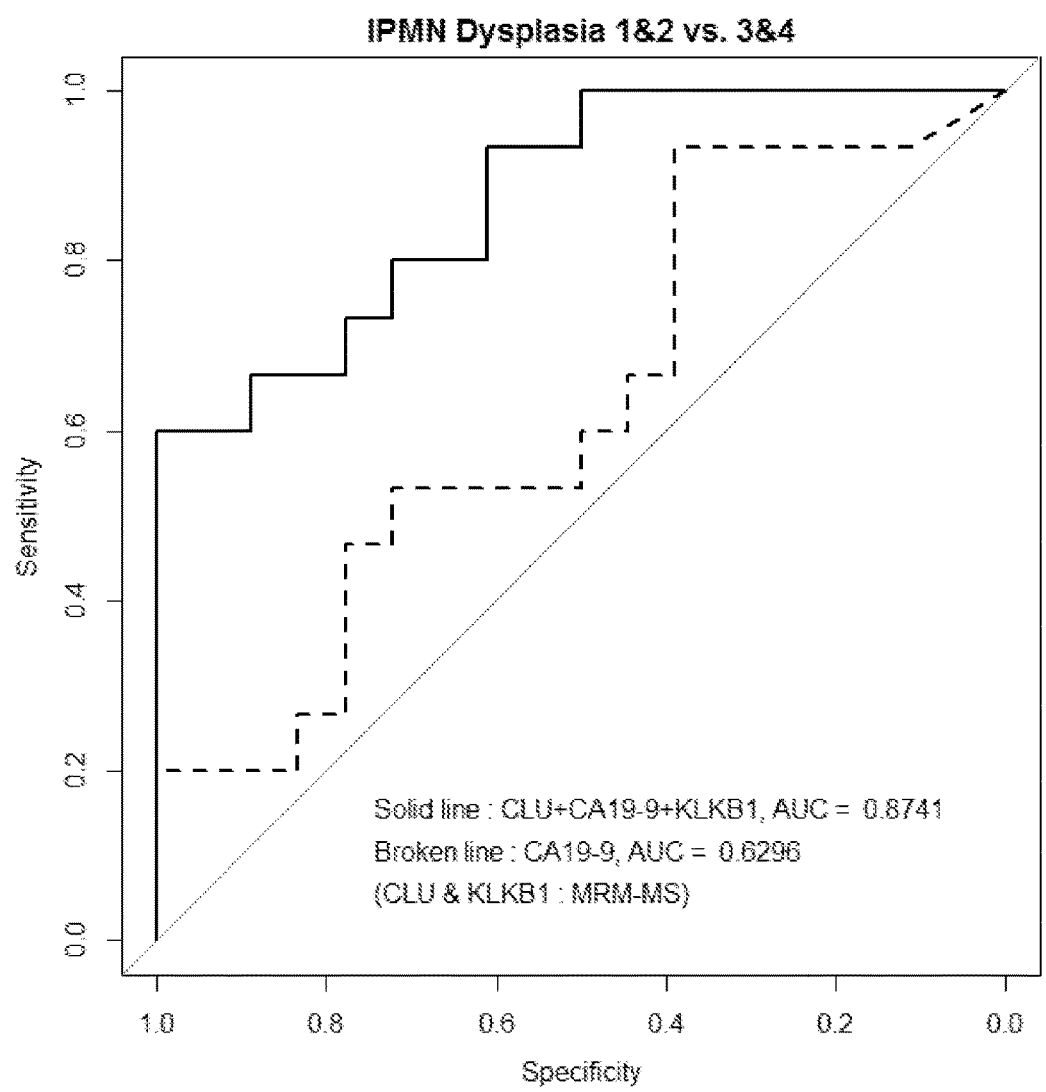

[Fig. 87]
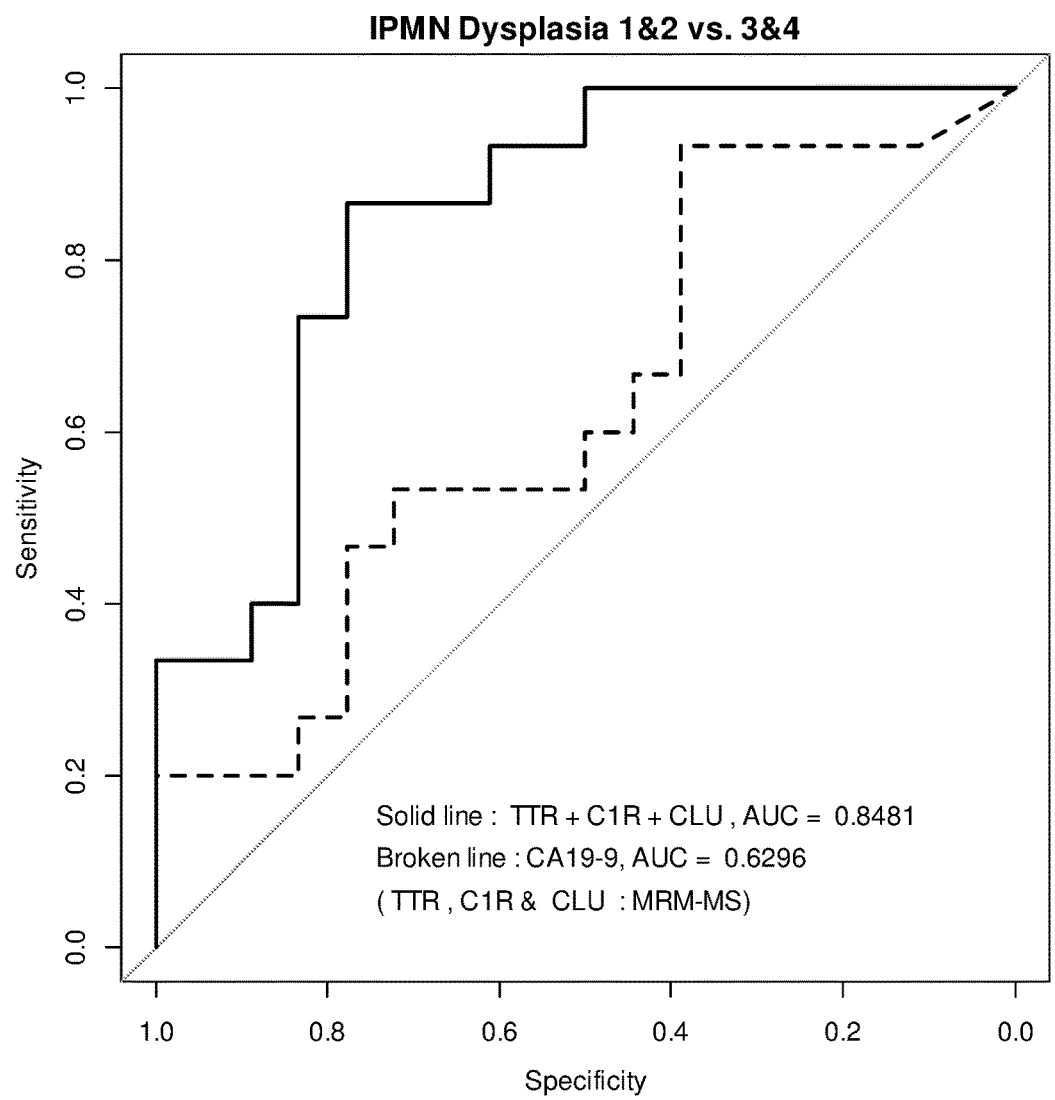

[Fig. 88]
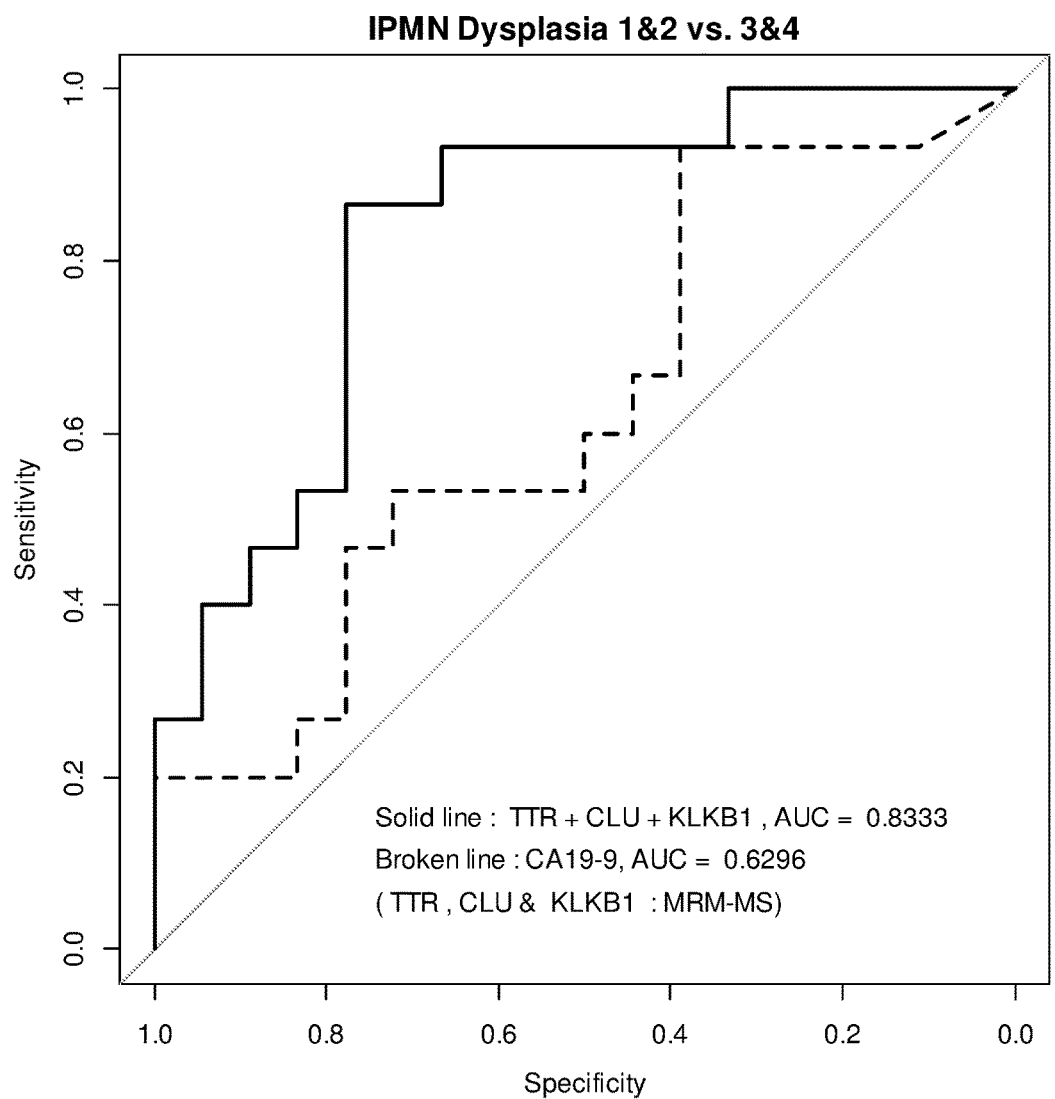

[Fig. 89]
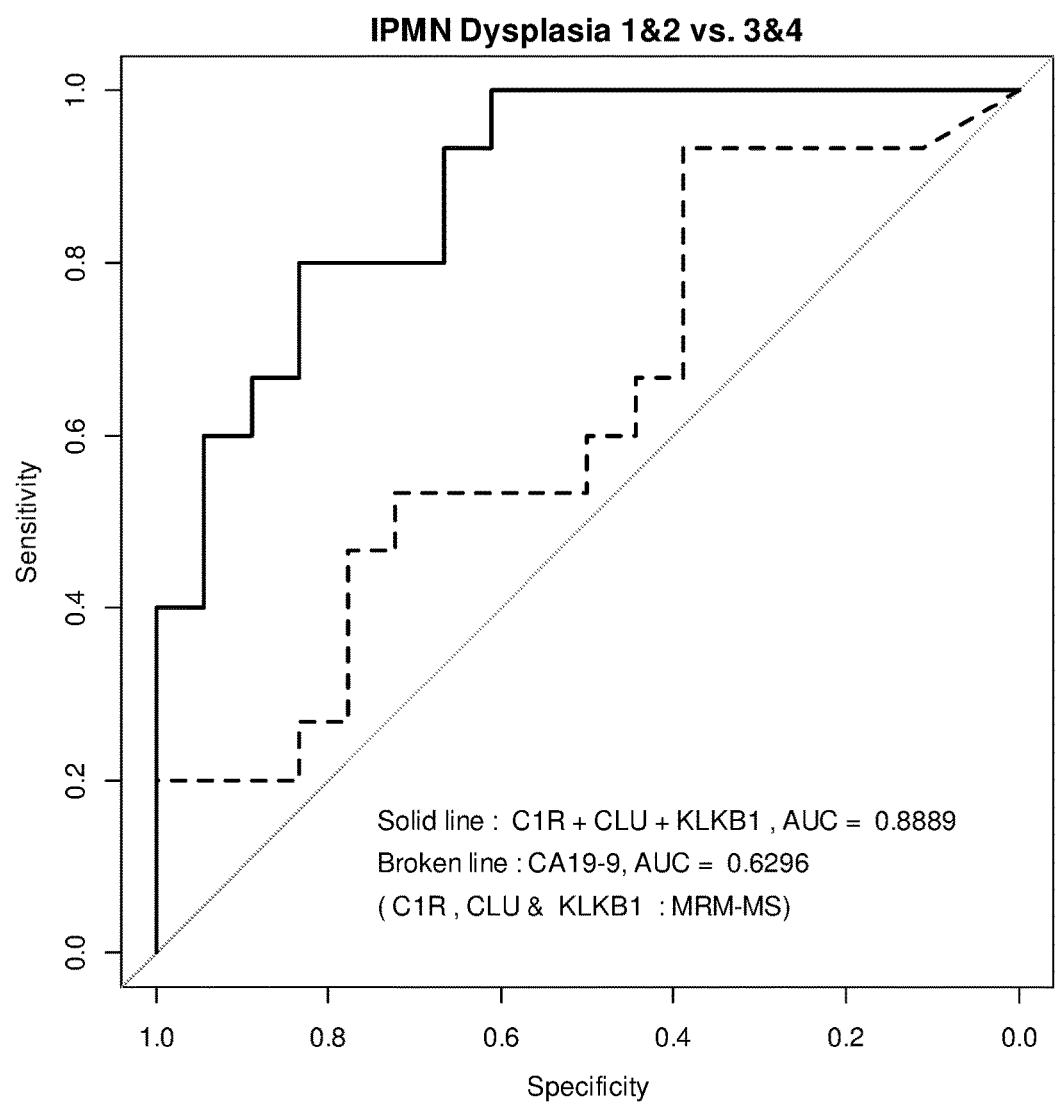

[Fig. 90]
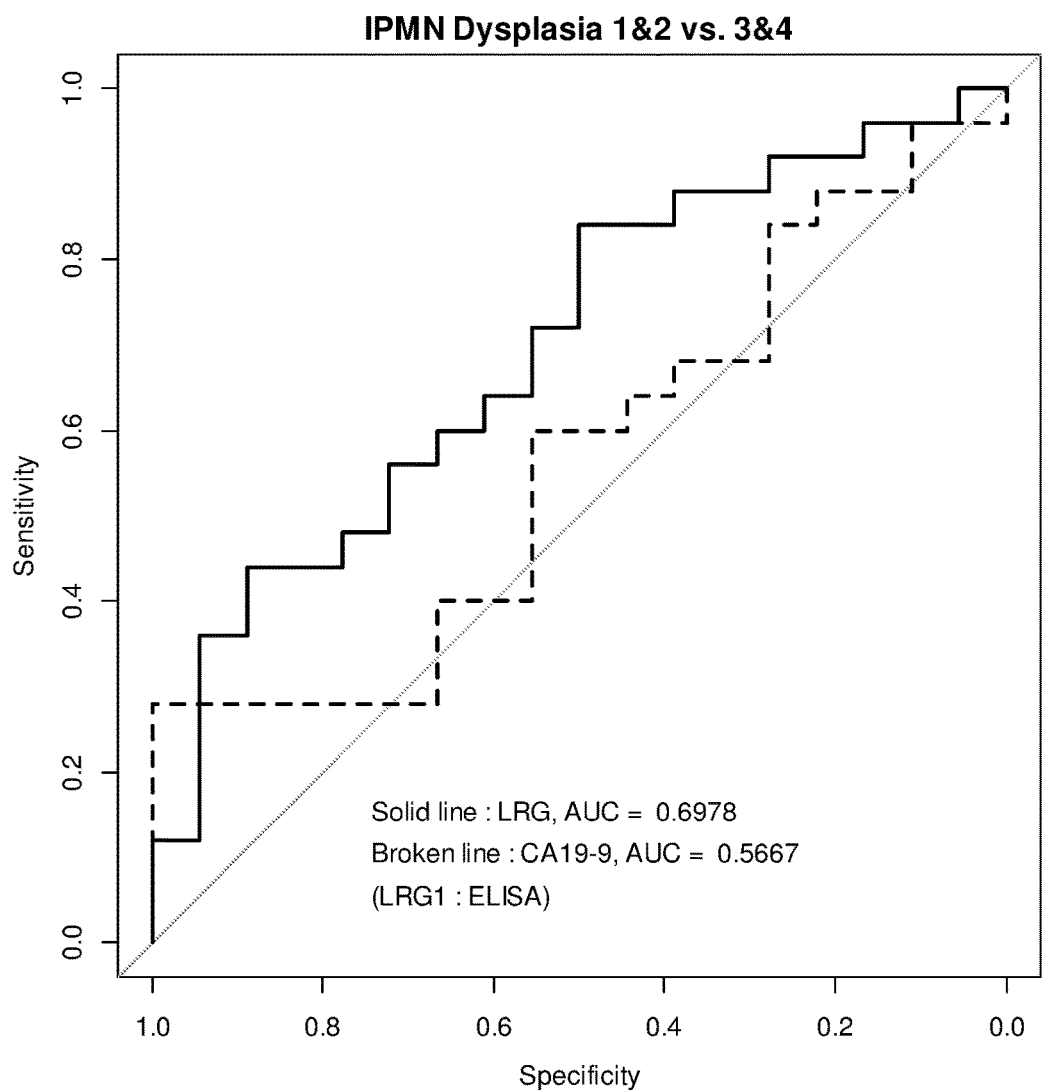

【Fig. 91】
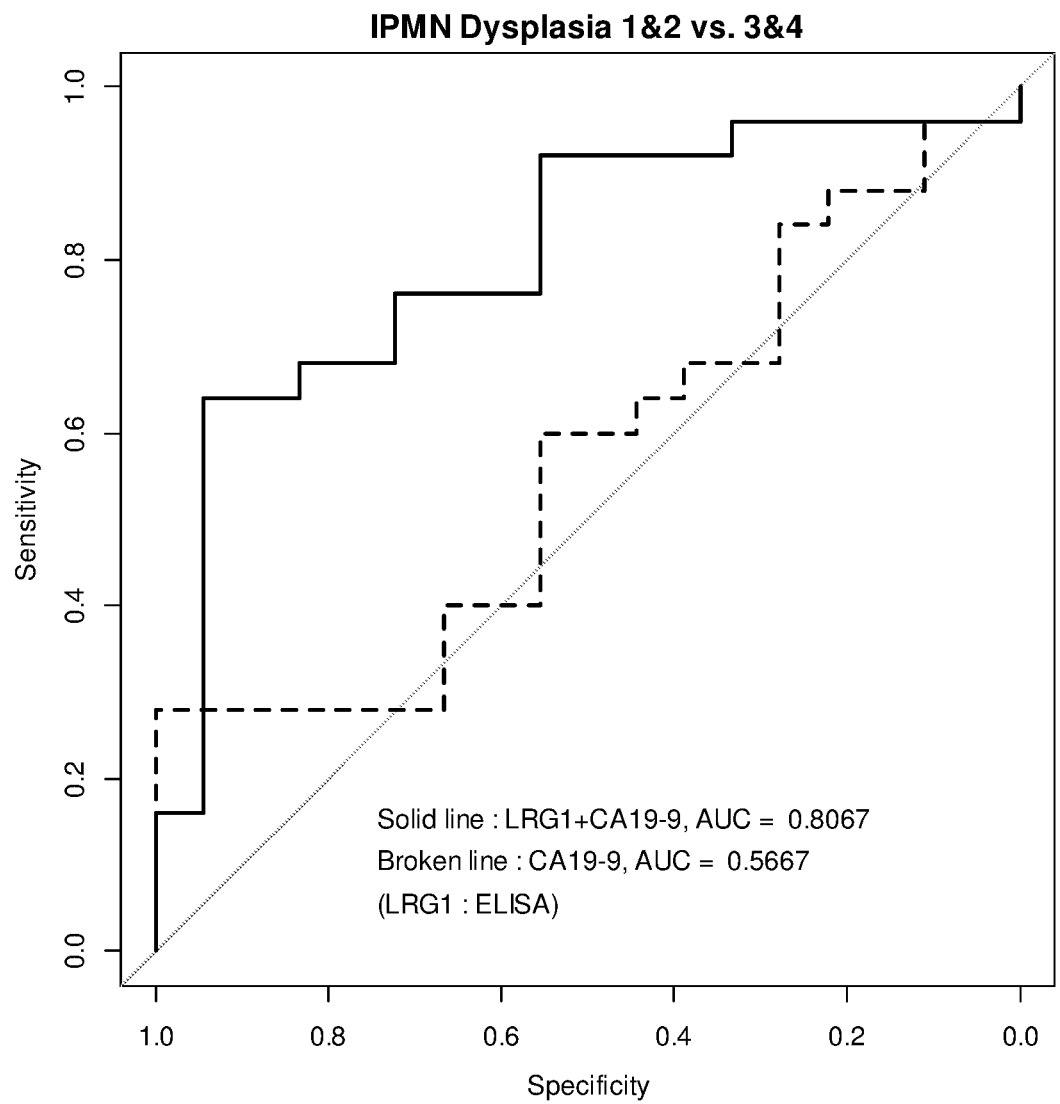

[Fig. 92]
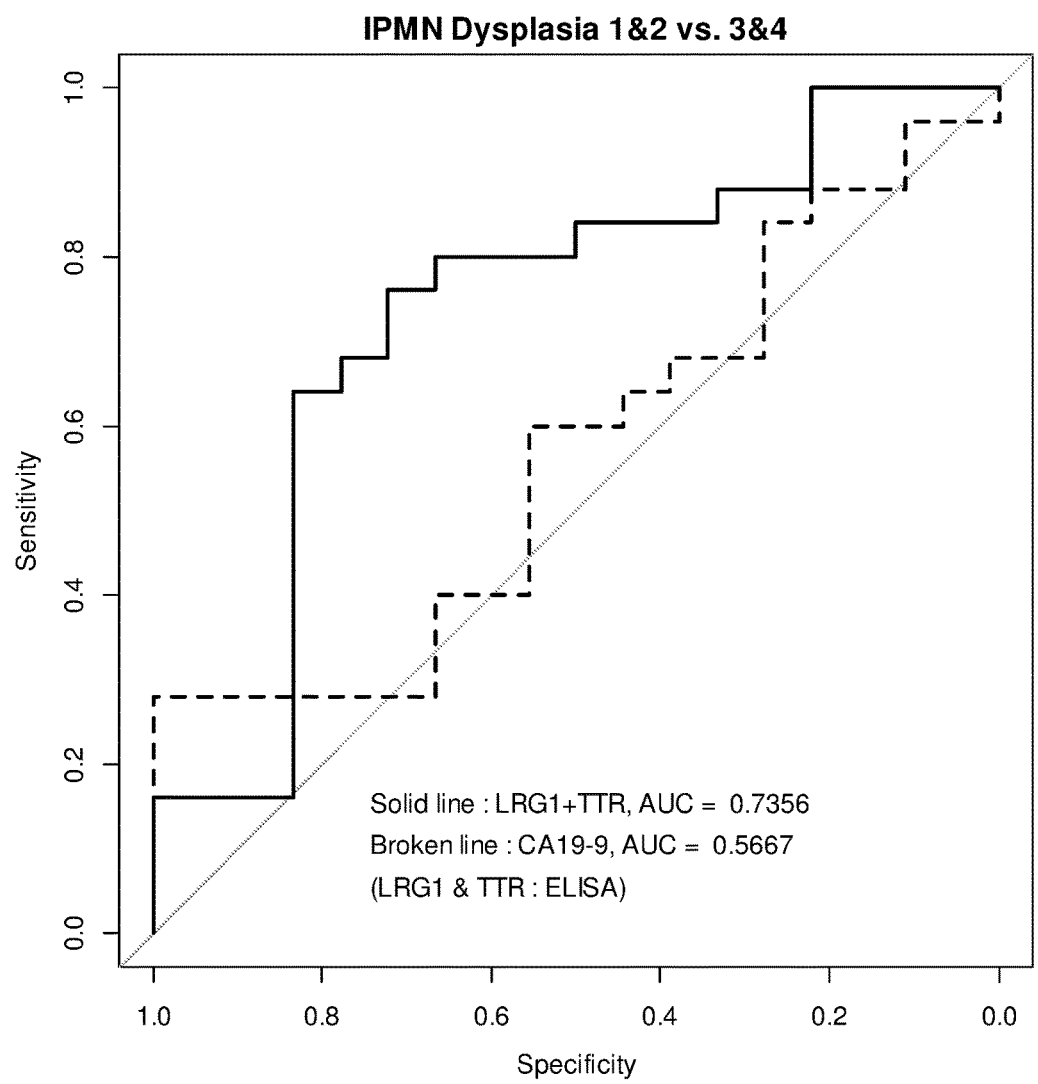

[Fig. 93]
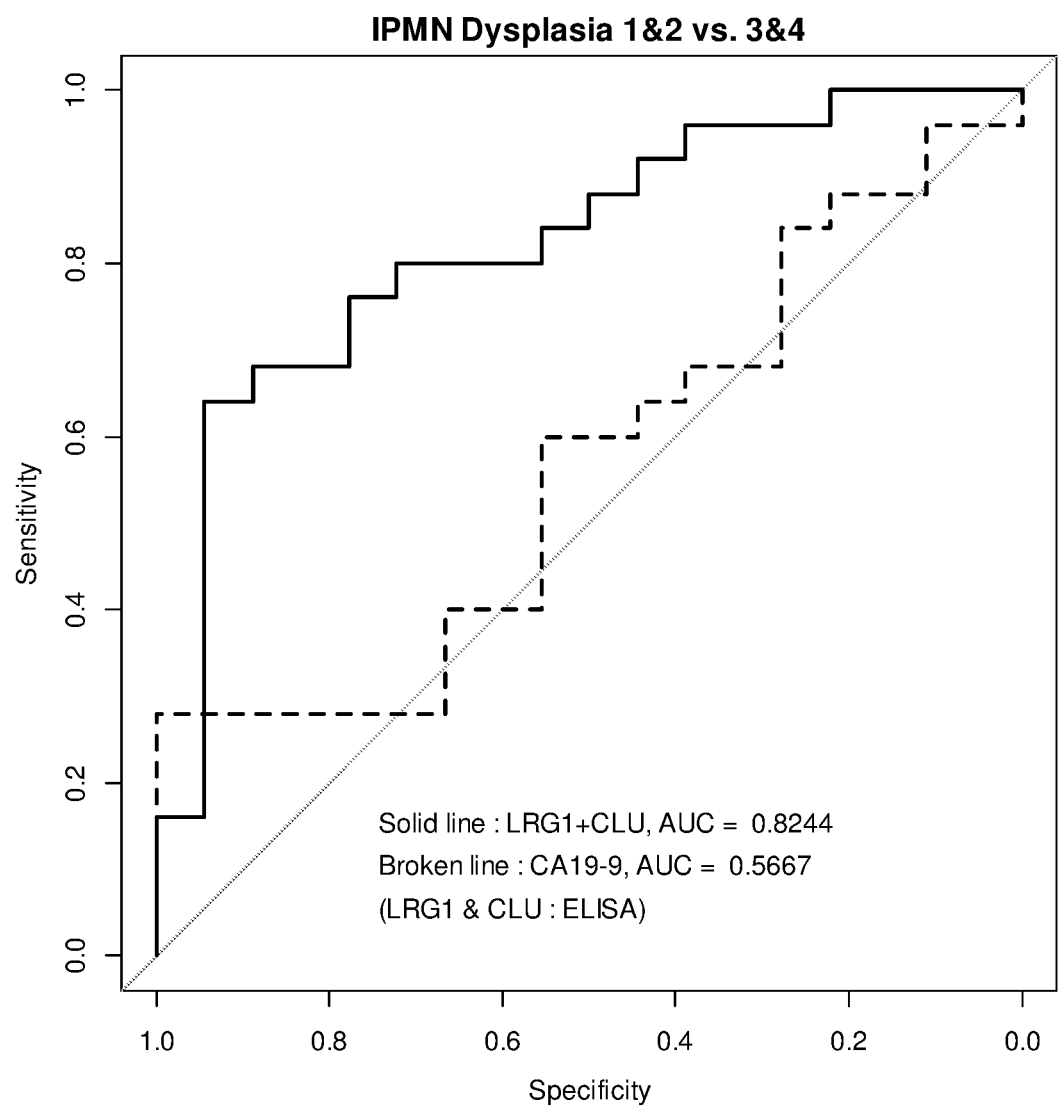

[Fig. 94]
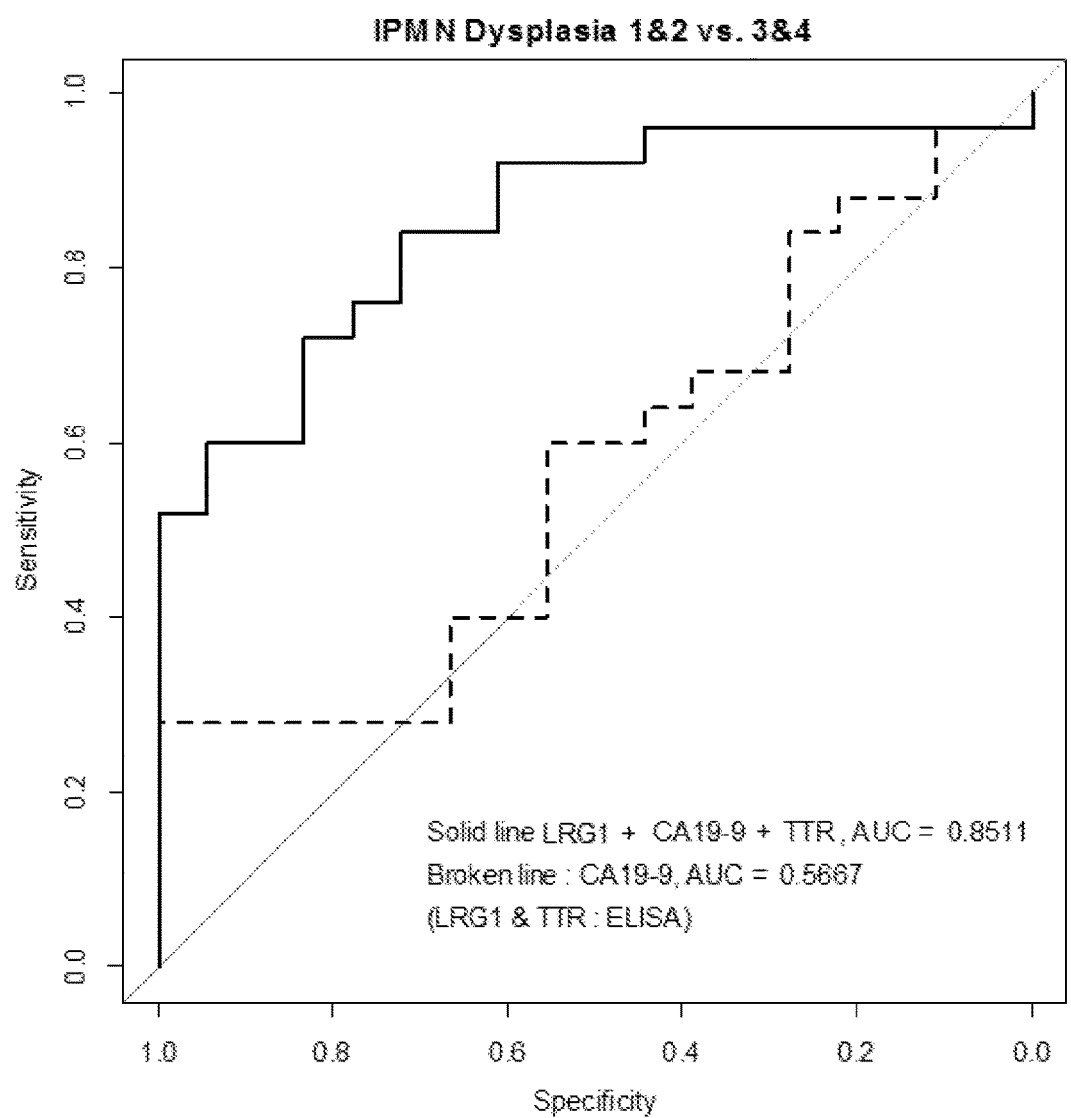

[Fig. 95]
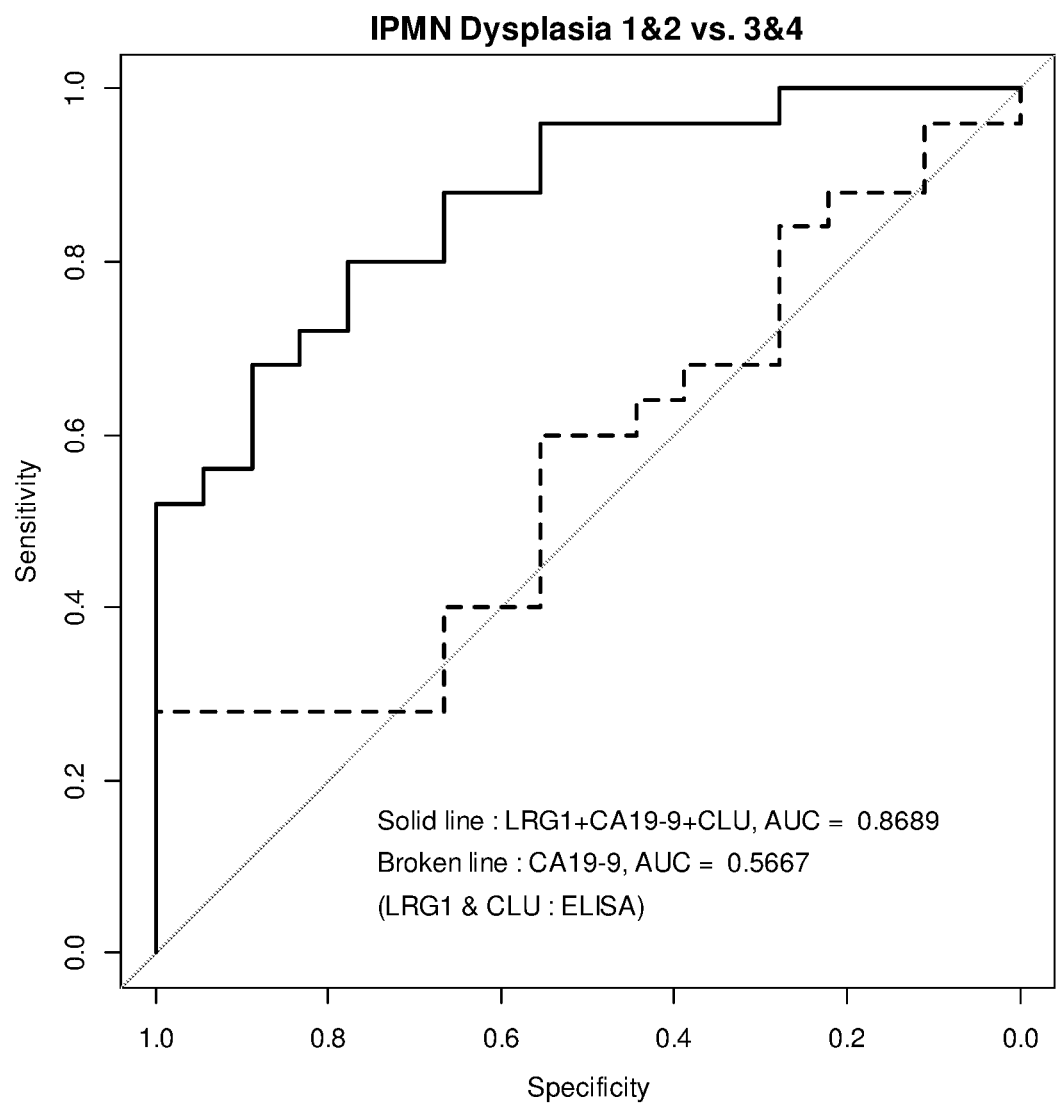

【Fig. 96】
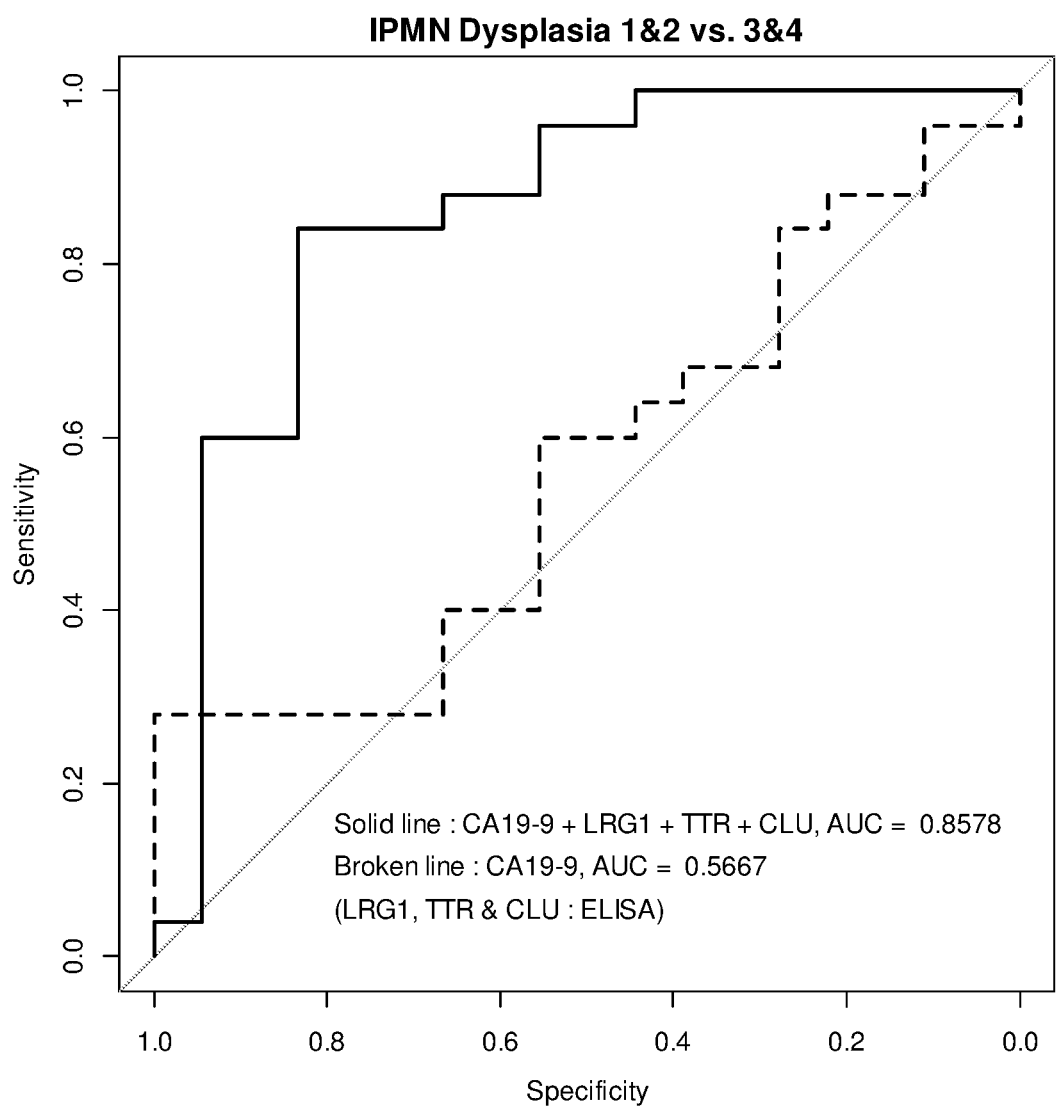

【Fig. 97】
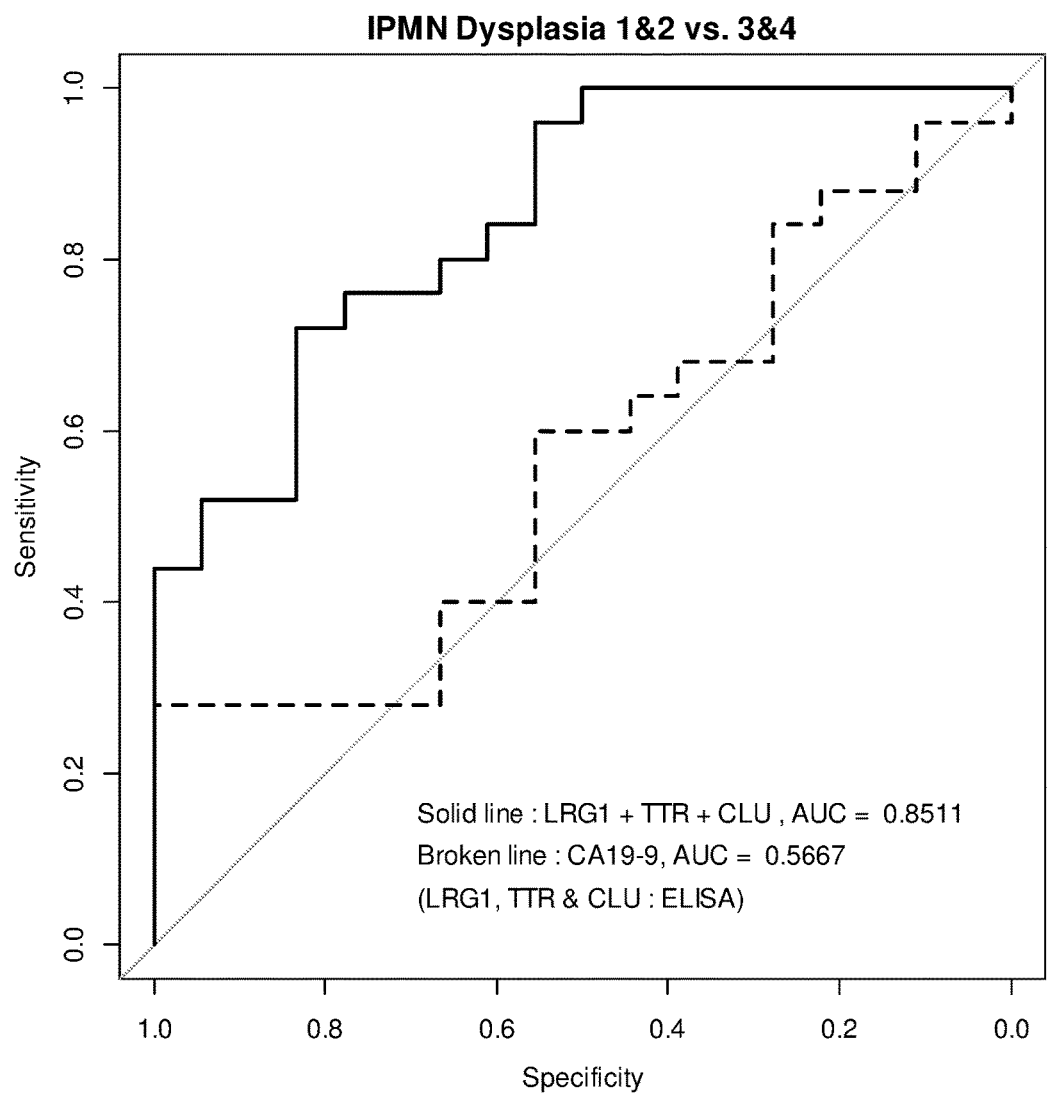

[Fig. 98]
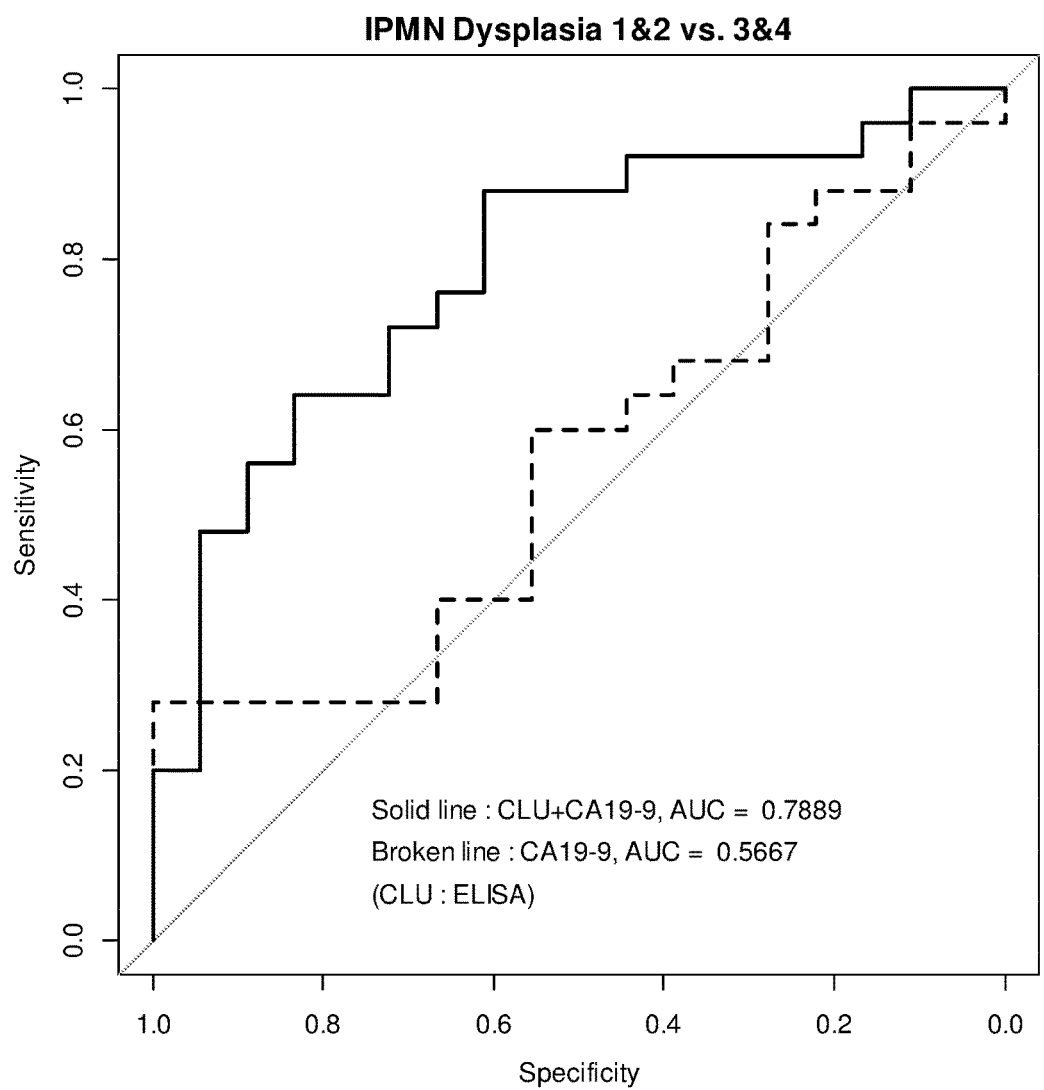

【Fig. 99】
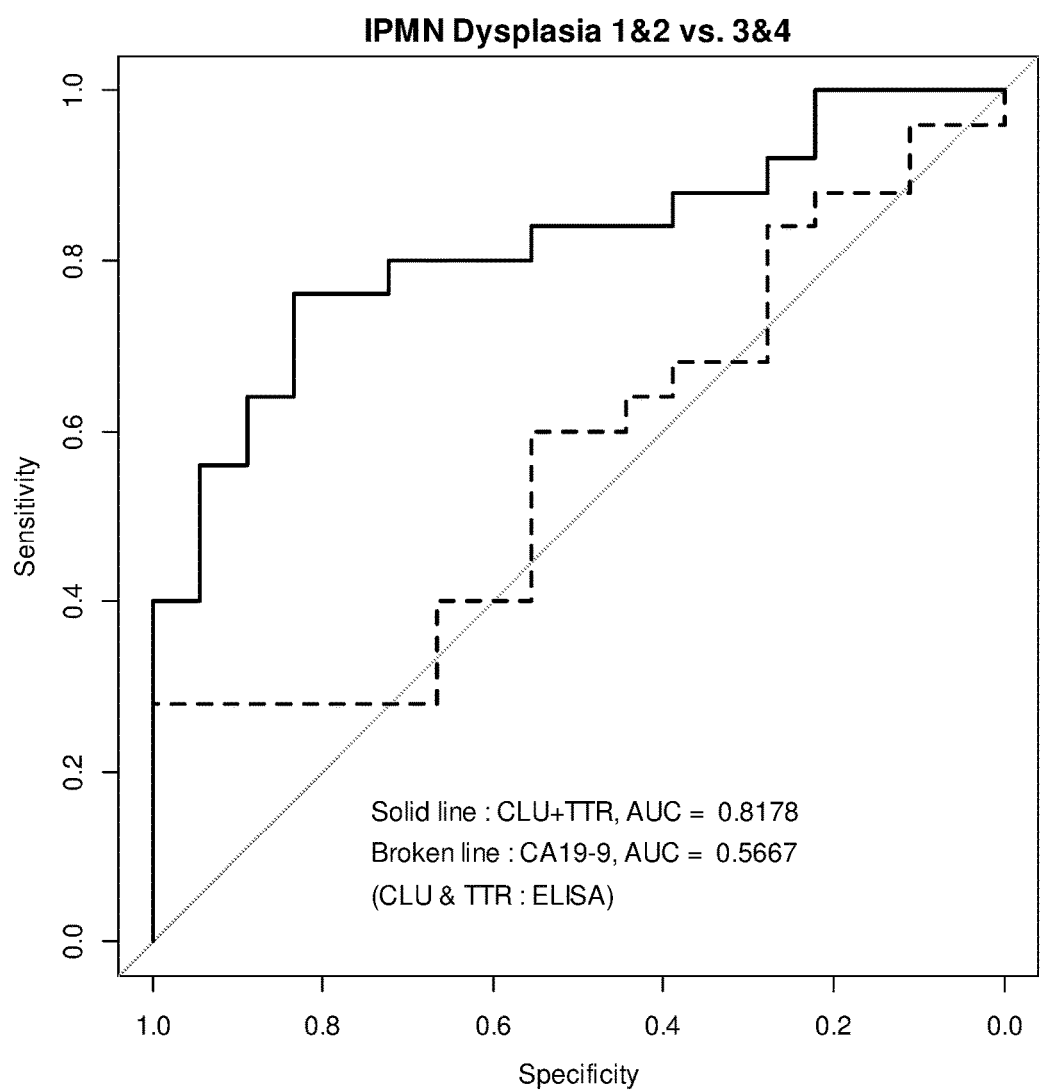

[Fig. 100]
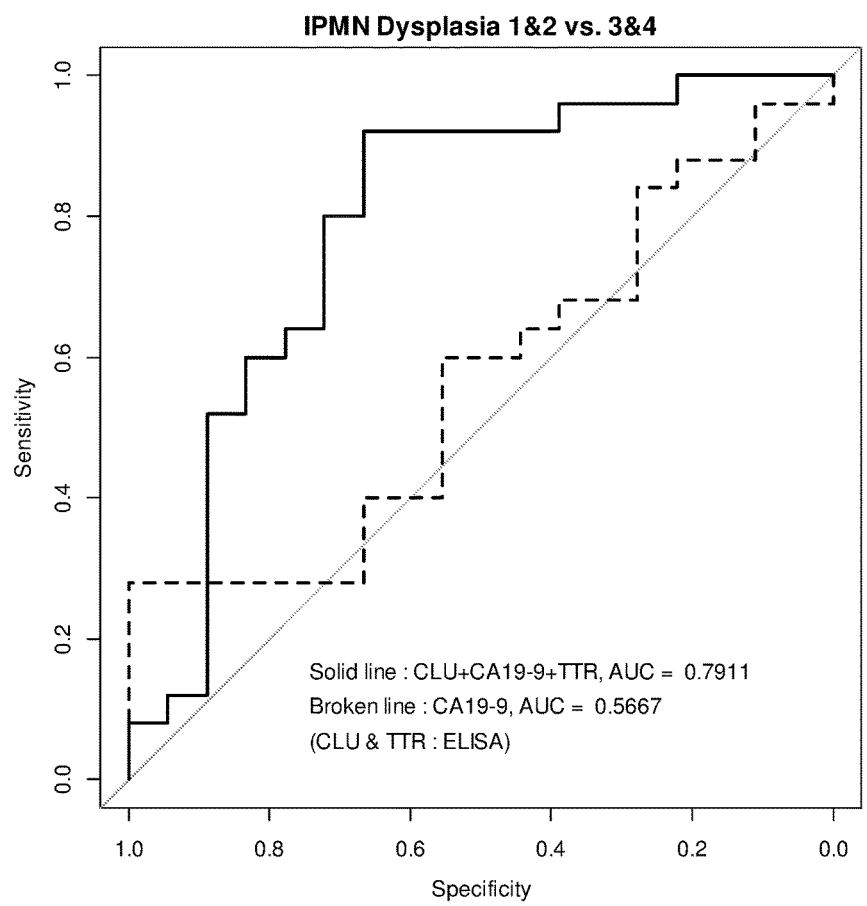

COMPOSITION FOR DIAGNOSING PANCREATIC CANCER AND METHOD FOR DIAGNOSING PANCREATIC CANCER USING THE SAME

CROSS-REFERENCES TO RELATED APPLICATION

This application is a Divisional Application of U.S. patent application Ser. No. 14/915,658, which was filed on Mar. 1, 2016, which is a National Stage application of PCT/KR2015/009827 filed on Sep. 18, 2015, which claims priority to Korean Patent Application No. Korean Patent Application Nos. 10-2014-0140695 filed on Oct. 17, 2014, Korean Patent Application No. 10-2014-0140714 filed on Oct. 17, 2014 and Korean Patent Application No. 10-2015-0092393 filed on Jun. 29, 2015, the contents of which are incorporated herein by reference.

TECHNICAL FIELD

The present disclosure relates to a composition and a kit for diagnosing pancreatic cancer, comprising an agent for measuring a protein or mRNA expression level of a certain marker gene available for determining the onset or the possibility of onset of pancreatic cancer, and a method for the diagnosis of pancreatic cancer using the composition or the kit.

BACKGROUND ART

Representative among main diseases of people these days is cancer. Studies on cancer are actively ongoing, particularly in the areas of high-prevalence cancers including lung cancer, liver cancer, stomach cancer, etc., but there are fewer studies being conducted on low-prevalence cancers including esophageal cancer, colorectal cancer, pancreatic cancer, etc.

In particular, pancreatic cancer usually does not cause recognizable symptoms in its early stages, and the disease is typically not diagnosed due to its minor symptoms such as pain, weight loss, etc., until it has spread beyond the pancreas itself to the whole body. Moreover, pancreatic cancer is generally poor in survival rate, and thus periodical diagnosis is very important. Clinical symptoms of pancreatic cancer are, in most part, slowly exposed, and patients with pancreatic cancer most commonly suffer from feebleness, anorexia, and weight loss. Found to have a five-year survival rate of 1-4% with a median survival time of 5 months, pancreatic cancer is very fatal and is the poorest in prognosis among human cancers. After diagnosis, it is found that 80-90% of people are impossible to treat by hopeful curative resection. This is one of the main reasons for the generally highly poor prognosis. Pancreatic cancer is predominantly treated with chemotherapy. Therefore, in comparison to other cancers, there is a desperate need for an early diagnosis method of pancreatic cancer.

Although known so far to be useful in treating pancreatic cancer, several anticancer agents including 5-fluorouracil, gemcitabine, and tarceva, exhibit very low curative effects and a reaction rate of only around 15% for cancer treatment. These situations suggest there is a pressing request for more effective early diagnosis and therapy for pancreatic cancer whereby the prognosis can be improved. In this context, appropriate diagnosis and therapy for a precursor lesion of pancreatic cancer, that is, a pre-stage of pancreatic cancer, is very important for the therapeutic result.

Diagnosis of pancreatic cancer or a precursor lesion thereof is determined upon hematologic examination (CA19-9), gastrointestinography and duodenography with X-ray contrast media, cholangiography through the skin and the liver, or endoscopic retrograde cholangiopancreatograhy. Many disease lesions can be detected by such methods, but currently, ultrasonography and computed tomography are the most preferred. More deliberate biopsy methods might result in relatively more accurate outcomes. The diagnosis methods described above are used because they are generally accurate; however, subjects are unwilling to undergo examination because such diagnosis methods are uncomfortable or painful. Hence, there is need for method of diagnosing pancreatic cancer or a precursor lesion thereof conveniently and rapidly.

Recently, extensive medical examination using imaging diagnosis technologies including abdominal ultrasound (US), computed tomography (CT), magnetic resonance imaging (MRI), and the like have been able to frequently discover malignant lesions at or around the pancreas, even though they tended to detect lesions in organs other than the pancreas. Lesions that appear as cysts as measured by imaging diagnosis are clinically important because they may cover various diseases from benign to premalignant and malignant lesions in terms of pathologic traits.

In spite of much advance in imaging diagnosis such as in CT, MRI, etc., it is still difficult to accurately discriminate cystic lesions of the pancreas having various pathologic traits from benign to premalignant and malignant lesions, prior to surgery. Hence, it is clinically important to determine whether a cystic lesion in the pancreas is a tumor lesion that is prone to malignant alteration, and whether it, if having potential for malignant alteration, remains premalignant or has already undergone malignancy.

Korean Patent No. 10-0819122 and Korean Patent Unexamined Application Publication No. 2012-0082372 disclose technologies using various pancreas cancer markers including matrilin, transthyretin, and stratifin. In addition, Korean Patent Unexamined Application Publication No. 2009-0003308 describes diagnosis of pancreatic cancer through the detection of an expression level of REG4 in a blood sample from a subject. Korean Patent Unexamined Application Publication No. 2012-0009781 describes an analysis method for measuring an XIST RNA expression level in a cancer tissue from a subject, whereby information on the onset of pancreatic cancer in the subject can be provided. Korean Patent Unexamined Application Publication No. 2007-0119250 discloses a family of new LBFL313 genes that are expressed in different patterns between normal pancreatic tissues and pancreatic cancer tissues. U. S. Patent Application No. 2011/0294136A1 discloses a diagnosis method of pancreatic cancer using biomarkers including keratin 8 protein. However, diagnostic efficiency and accuracy greatly differ from one marker to another. Therefore, there is a pressing need for an excellently efficient marker and a diagnosis method using the same.

DISCLOSURE

Technical Problem

It is an object of the present disclosure to provide a diagnostic marker of pancreatic cancer with which the onset, the possibility of onset, or the risk of pancreatic cancer can be conveniently diagnosed in an early stage.

It is another object of the present disclosure to provide a diagnostic composition of pancreatic cancer with which the onset, the possibility of onset, or the risk of pancreatic cancer can be conveniently diagnosed in an early stage.

It is a further object of the present disclosure to provide a kit for diagnosing pancreatic cancer, comprising the composition.

It is a still further object of the present disclosure to provide a method for diagnosing pancreatic cancer or for providing information on a diagnosis result of pancreatic cancer, using the diagnosis composition or kit.

It is still another object of the present disclosure to provide a method for determining the presence or malignancy of pancreatic cancer in a subject, using the diagnosis composition or kit.

It is an additional object of the present disclosure to provide use of the diagnostic marker in diagnosing the onset, the possibility of onset, or the risk of pancreatic cancer in an early stage.

Technical Solution

To accomplish the above objects, the present disclosure provides a composition for diagnosing pancreatic cancer or a precursor lesion thereof, comprising an agent for measuring a protein or mRNA expression level of a certain diagnostic marker gene of pancreatic cancer, a kit for diagnosing pancreatic cancer, comprising the composition, and a method for determining the presence or malignancy of pancreatic cancer in a pancreatic cancer patient or in a subject suspected of having pancreatic cancer. The composition or the kit may further comprise an additional ingredient, solution or device suitable for the analysis.

In some embodiments of the present disclosure, the diagnosis of pancreatic cancer is to selectively discriminate pancreatic cancer from a normal group, to selectively detect pancreatic cancer among various cancers, or to diagnose pancreatic cancer in a subject with a CA19-9 level of less than 37 U/ml. In detail, the composition or kit for diagnosing pancreatic cancer can be used for detecting or discriminating a pancreatic cancer patient group from a normal group, diagnosing pancreatic cancer (PDAC) in Stage 1 or 2, which is difficult to detect with conventional methods, selectively discriminating pancreatic cancer from various different cancers such as breast cancer, colorectal cancer and/or thyroid cancer, or various pancreatic diseases other than cancer, such as pancreatitis and cholecystitis, or diagnosing pancreatic cancer even in a subject with a CA19-9 level of less than 37 U/ml against a normal subject with a CA19-9 level of less than 36 U/ml or a patient with pancreatic disorder such as pancreatitis or cholecystitis.

The marker gene may be a combination of three or more marker genes. The combination may comprise:

(a) CA19-9(carbohydrate antigen 19-9);

(b) LRG1(Leucine-rich alpha-2-glycoprotein 1, LRG1); and (c) at least one selected from the group consisting of TTR (Transthyretin, ATTR, Prealbumin, TBPA), C1R (Complement C1r subcomponent precursor), CLU (Clusterin preproprotein), and KLKB1 (Plasma Kallikrein protein)

In accordance with some embodiments thereof, the present disclosure provides a kit for diagnosing pancreatic cancer, comprising the composition for diagnosing pancreatic cancer.

In accordance with some embodiments thereof, the present disclosure provide a method for diagnosing pancreatic cancer in a subject or for providing information on a diagnosis result of pancreatic cancer, comprising:

acquiring a sample from a subject to be diagnosed for the onset of pancreatic cancer;

measuring respective protein or mRNA expression levels of pancreatic cancer markers comprising (a) CA19-9, (b) LRG1, and (c) at least one marker selected from the group consisting of TTR, C1R, CLU, and KLKB1;

comparing the expression levels of the pancreatic cancer markers with those of corresponding normal controls, respectively; and determining the onset or the possibility of onset of pancreatic cancer in the subject, based on the comparison result.

In the determining step, the condition for determining that pancreatic cancer would be highly prone to occurring is as follows: a subject to be examined for the onset of pancreatic cancer is higher than a normal control in terms of the protein expression level of CA19-9 or the mRNA expression level of a gene coding for CA19-9; in terms of the protein expression level of LRG1 or the mRNA expression level of a gene coding for LRG1; and lower in terms of the protein expression level of TTR or the mRNA expression level of a gene coding for TTR, higher in terms of the protein expression level of C1R or the mRNA expression level of a gene coding for C1R, lower in terms of the protein expression level of CLU or the mRNA expression level of a gene coding for CLU, or lower in terms of the protein expression level of KLKB1 or the mRNA expression level of a gene coding for KLKB1.

In accordance with some embodiments thereof, the present disclosure provides a composition for selectively diagnosing high-risk IPMN, comprising an agent for measuring an expression level of an IPMN marker comprising LRG1 (Leucine-rich alpha-2-glycoportein 1, LRG1). The IPMN marker may further comprise at least one selected from the group consisting of CA19-9 (carbohydrate antigen 19-9), TTR, C1R, CLU, and KLKB1. For example, the IPMN marker may be a combination of LRG1 and at least one selected from the group consisting of TTR, C1R, CLU, and KLKB1, or a combination of LRG1 and at least two selected from the group consisting of TTR, C1R, CLU, and KLKB1.

In particular embodiments thereof, the present disclosure provides a composition for selectively diagnosing high-risk IPMN, comprising an agent for measuring expression levels of IPMN marker proteins comprising CLU (Clusterin preproprotein) and at least one selected from LRG1 (Leucine-rich alpha-2-glycoprotein 1, LRG1), CA19-9 (carbohydrate antigen 19-9), TTR (Transthyretin, ATTR, Prealbumin, TBPA), C1R (Complement C1r subcomponent precursor), and KLKB1(Plasma Kallikrein protein), or mRNA expression levels of genes encoding the proteins. For example, the IPMN marker is a combination of CLU and at least one selected from the group consisting of LRG1, CA19-9, TTR, C1R, and KLKB1, or a combination of LRG1 and at least two selected from the group consisting of LRG1, CA19-9, TTR, C1R, and KLKB1.

In some embodiments thereof, the present disclosure provides a method for diagnosing high-risk IPMN, comprising:

measuring expression levels of IPMN marker proteins, or mRNA expression levels of genes encoding the marker proteins in a sample from a subject, comparing the measured expression levels of each of the markers between the sample from the subject and a sample from a control; and determining onset risk of high-risk IPMN in the subject on the basis of the comparison result of the expression levels.

Advantageous Effects

As described hitherto, diagnostic markers of pancreatic cancer in accordance with the present disclosure are useful for predicting or diagnosing the onset, the possibility of onset, and the severity of pancreatic cancer in an early stage. The markers are also applied to a study on the tumorigenesis of pancreatic cancer. In addition, the diagnosis method of the present invention allows for the convenient detection of pancreatic cancer in a non-invasive manner in a sample such as blood.

DESCRIPTION OF DRAWINGS

FIG. 1 is a graph showing expression levels of the CA19-9 protein in a control and a pancreatic patient group, as measured by chemiluminescence enzyme immunoassay (CLEIA).

FIG. 2 is a graph showing expression levels of the LRG1 protein in a control and a pancreatic patient group, as measured by MRM assay.

FIG. 3 is a graph showing expression levels of the TTR protein in a control and a pancreatic patient group, as measured by MRM assay.

FIG. 4 is a graph showing expression levels of the C1R protein in a control and a pancreatic patient group, as measured by MRM assay.

FIG. 5 is a graph showing expression levels of the CLU protein in a control and a pancreatic patient group, as measured by MRM assay.

FIG. 6 is a graph showing expression levels of the KLKB1 protein in a control and a pancreatic patient group, as measured by MRM assay.

FIG. 7 is a graph showing expression levels of the LRG1 protein in a control and a pancreatic patient group, as measured by ELISA.

FIG. 8 is a graph showing expression levels of the TTR protein in a control and a pancreatic patient group, as measured by ELISA.

FIG. 9 is a graph showing expression levels of the CLU protein in a control and a pancreatic patient group, as measured by ELISA.

FIG. 10 is a graph showing expression levels of the TTR protein in a control and a pancreatic patient group, as measured by immunoturbidimetric assay.

FIG. 11 shows the performance (AUC and detection sensitivity) of a combination of the three markers CA19-9, LRG1, and TTR for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to MRM quantitative analysis.

FIG. 12 shows the performance (AUC and detection sensitivity) of a combination of the three markers CA19-9, LRG1, and TTR for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to MRM quantitative analysis.

FIG. 13 shows the diagnosis performance (AUC and detection sensitivity) for discriminating pancreatic cancer from other cancers of a combination of the three markers CA19-9, LRG1, and TTR for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to MRM quantitative analysis.

FIG. 14 shows the performance (AUC and detection sensitivity) of a combination of the three markers CA19-9, LRG1, and TTR for diagnosing pancreatic cancer in a subject with a CA19-9 level of less than 37 U/ml in comparison with CA19-9 alone and a combination of the two markers CA19-9 and hereTTR. The CA19-9 protein was quantitatively analyzed by chemiluminescence enzyme immunoassay (CLEIA) whereas LRG1 and TTR were subjected to MRM quantitative analysis.

FIG. 15 shows the performance (AUC and detection sensitivity) of a combination of the three markers CA19-9, LRG1, and TTR for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to ELISA.

FIG. 16 shows the performance (AUC and detection sensitivity) of a combination of the three markers CA19-9, LRG1, and TTR for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to ELISA.

FIG. 17 shows the diagnosis performance (AUC and detection sensitivity) of a combination of the three markers CA19-9, LRG1, and TTR for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to ELISA.

FIG. 18 shows the performance (AUC and detection sensitivity) of a combination of the three markers CA19-9, LRG1, and TTR for diagnosing pancreatic cancer in a subject with a CA19-9 level of less than 37 U/ml in comparison with CA19-9 alone and a combination of the two markers CA19-9 and TTR. The CA19-9 protein was quantitatively analyzed by chemiluminescence enzyme immunoassay (CLEIA) whereas LRG1 and TTR were subjected to ELISA.

FIG. 19 shows the performance (AUC and detection sensitivity) of a combination of the three markers CA19-9, LRG1, and TTR for diagnosing pancreatic cancer in comparison with CA19-9 alone and a combination of the two markers CA19-9 and TTR. The CA19-9 protein, the LRG1 protein, and the TTR protein were quantitatively analyzed by chemiluminescence enzyme immunoassay(CLEIA), ELISA, and immunoturbidimetric assay, respectively.

FIG. 20 shows the performance (AUC and detection sensitivity) of a combination of the three markers CA19-9, LRG1, and TTR for diagnosing early stage pancreatic cancer in comparison with CA19-9 alone and a combination of the two markers CA19-9 and TTR. The CA19-9 protein, the LRG1 protein, and the TTR protein were quantitatively analyzed by chemiluminescence enzyme immunoassay (CLEIA), ELISA, and immunoturbidimetric assay, respectively.

FIG. 21 shows the diagnosis performance (AUC and detection sensitivity) of a combination of the three markers CA19-9, LRG1, and TTR for discriminating pancreatic cancer from other cancers in comparison with CA19-9 alone and a combination of the two markers CA19-9 and TTR. The CA19-9 protein, the LRG1 protein, and the TTR protein were quantitatively analyzed by chemiluminescence enzyme immunoassay(CLEIA), ELISA, and immunoturbidimetric assay, respectively.

FIG. 22 shows the performance (AUC and detection sensitivity) of a combination of the three markers CA19-9, LRG1, and TTR for diagnosing pancreatic cancer in a subject with a CA19-9 level of less than 37 U/ml in comparison with CA19-9 alone and a combination of the two markers CA19-9 and TTR. The CA19-9 protein, the LRG1 protein, and the TTR protein were quantitatively analyzed by chemiluminescence enzyme immunoassay (CLEIA), ELISA, and immunoturbidimetric assay, respectively.

FIG. 23 shows the performance (AUC and detection sensitivity) of a combination of the three markers CA19-9, LRG1, and C1R for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and C1R were subjected to MRM quantitative analysis.

FIG. 24 shows the performance (AUC and detection sensitivity) of a combination of the three markers CA19-9, LRG1, and C1R for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and C1R were subjected to MRM quantitative analysis.

FIG. 25 shows the diagnosis performance (AUC and detection sensitivity) of a combination of the three markers CA19-9, LRG1, and C1R for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and C1R were subjected to MRM quantitative analysis.

FIG. 26 shows the performance (AUC and detection sensitivity) of a combination of the three markers CA19-9, LRG1, and C1R for diagnosing pancreatic cancer in a subject with a CA19-9 level of less than 37 U/ml in comparison with CA19-9 alone and a combination of the two markers CA19-9 and TTR. The CA19-9 protein was quantitatively analyzed by chemiluminescence enzyme immunoassay (CLEIA) whereas LRG1 and C1R were subjected to MRM quantitative analysis.

FIG. 27 shows the performance (AUC and detection sensitivity) of a combination of the three markers CA19-9, LRG1, and CLU for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to MRM quantitative analysis.

FIG. 28 shows the performance (AUC and detection sensitivity) of a combination of the three markers CA19-9, LRG1, and CLU for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to MRM quantitative analysis.

FIG. 29 shows the diagnosis performance (AUC and detection sensitivity) of a combination of the three markers CA19-9, LRG1, and CLU for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to MRM quantitative analysis.

FIG. 30 shows the performance (AUC and detection sensitivity) of a combination of the three markers CA19-9, LRG1, and CLU for diagnosing pancreatic cancer in a subject with a CA19-9 level of less than 37 U/ml in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to MRM quantitative analysis.

FIG. 31 shows the performance (AUC and detection sensitivity) of a combination of the three markers CA19-9, LRG1, and CLU for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to ELISA.

FIG. 32 shows the performance (AUC and detection sensitivity) of a combination of the three markers CA19-9, LRG1, and CLU for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to ELISA.

FIG. 33 shows the diagnosis performance (AUC and detection sensitivity) of a combination of the three markers CA19-9, LRG1, and CLU for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to ELISA.

FIG. 34 shows the performance (AUC and detection sensitivity) of a combination of the three markers CA19-9, LRG1, and CLU for diagnosing pancreatic cancer in a subject with a CA19-9 level of less than 37 U/ml in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to ELISA.

FIG. 35 shows the performance (AUC and detection sensitivity) of a combination of the three markers CA19-9, LRG1, and KLKB1 for diagnosing pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and KLKB1 were subjected to MRM quantitative analysis.

FIG. 36 shows the performance (AUC and detection sensitivity) of a combination of the three markers CA19-9, LRG1, and KLKB1 for diagnosing early stage pancreatic cancer in comparison with CA19-9 alone and a combination of the two markers CA19-9 and TTR. The CA19-9 protein was quantitatively analyzed by chemiluminescence enzyme immunoassay (CLEIA) whereas LRG1 and KLKB1 were subjected to MRM quantitative analysis.

FIG. 37 shows the diagnosis performance (AUC and detection sensitivity) of a combination of the three markers CA19-9, LRG1, and KLKB1 for discriminating pancreatic cancer from other cancers in comparison with CA19-9 alone and a combination of the two markers CA19-9 and TTR. The CA19-9 protein was quantitatively analyzed by chemiluminescence enzyme immunoassay (CLEIA) whereas LRG1 and KLKB1 were subjected to MRM quantitative analysis.

FIG. 38 shows the performance (AUC and detection sensitivity) of a combination of the three markers CA19-9, LRG1, and KLKB1 for diagnosing pancreatic cancer in a subject with a CA19-9 level of less than 37 U/ml in comparison with CA19-9 alone and a combination of the two markers CA19-9 and TTR. The CA19-9 protein was quantitatively analyzed by chemiluminescence enzyme immunoassay (CLEIA) whereas LRG1 and CLU were subjected to MRM quantitative analysis.

FIG. 39 shows the performance (AUC and detection sensitivity) of LRG1 for diagnosing high-risk IPMN in comparison with CA19-9 alone. The CA19-9 protein was quantitatively analyzed by chemiluminescence enzyme immunoassay (CLEIA) whereas LRG1 was subjected to MRM quantitative analysis.

FIGS. 40 to 44 show the performance (AUC and detection sensitivity) of a combination of two proteins (LRG1+CA19-9), (LRG1+TTR), (LRG1+CLU), (LRG1+C1R), or (LRG1+KLKB1) for diagnosing high-risk IPMN in comparison with CA19-9 alone. The CA19-9 protein was quantitatively analyzed by chemiluminescence enzyme immunoassay (CLEIA) whereas LRG1, TTR, CLU, C1R and KLKB1 were subjected to MRM quantitative analysis.

FIGS. 45 to 48 show the performance (AUC and detection sensitivity) of a combination of three proteins (LRG1+CA19-9+TTR), (LRG1+CA19-9+CLU), (LRG1+CA19-9+C1R), or (LRG1+CA19-9+KLKB1) for diagnosing high-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIGS. 49 to 54 show the performance (AUC and detection sensitivity) of a combination of three proteins (LRG1+TTR+CLU), (LRG1+TTR+C1R), (LRG1+TTR+KLKB1), (LRG1+CLU+C1R), (LRG1+CLU+KLKB1), or (LRG1+C1R+KLKB1) for diagnosing high-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIG. 55 to FIG. 57 show the performance (AUC and detection sensitivity) of a combination of two proteins (CLU+CA19-9), (CLU+TTR), or (CLU+KLKB1) for diagnosing high-risk IPMN in comparison with CA19-9 alone. The CA19-9 protein was quantitatively analyzed by chemiluminescence enzyme immunoassay (CLEIA) whereas TTR, CLU, C1R, and KLKB1 were subjected to MRM quantitative analysis.

FIGS. 58 to 63 show the performance (AUC and detection sensitivity) of a combination of three proteins (CLU+CA19-9+TTR), (CLU+CA19-9+C1R), (CLU+CA19-9+KLKB1), (CLU+TTR+C1R), (CLU+TTR+KLKB1), or (CLU+C1R+KLKB1) for diagnosing high-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIG. 64 shows the performance (AUC and detection sensitivity) of LRG1 for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1 was subjected to MRM quantitative analysis.

FIGS. 65 to 69 show the performance (AUC and detection sensitivity) of a combination of two proteins (LRG1+CA19-9), (LRG1+TTR), (LRG1+CLU), (LRG1+C1R), or (LRG1+KLKB1) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIGS. 70 to 73 show the performance (AUC and detection sensitivity) of a combination of three proteins (CA19-9+LRG1+TTR), (CA19-9+LRG1+C1R), (CA19-9+LRG1+CLU), or (CA19-9+LRG1+KLKB1) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIGS. 74 to 79 show the performance (AUC and detection sensitivity) of a combination of three proteins (LRG1+TTR+CLU), (LRG1+TTR+C1R), (LRG1+TTR+KLKB1), (LRG1+CLU+C1R), (LRG1+CLU+KLKB1), or (LRG1+C1R+KLKB1) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIGS. 80 to 83 show the performance (AUC and detection sensitivity) of a combination of two proteins (CLU+CA19-9), (CLU+TTR), (CLU+C1R), or (CLU+KLKB1) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIGS. 84 to 89 show the performance (AUC and detection sensitivity) of a combination of three proteins (CLU+CA19-9+TTR), (CLU+CA19-9+C1R), (CLU+CA19-9+KLKB1), (CLU+TTR+C1R), (CLU+TTR+KLKB1), or (CLU+C1R+KLKB1) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to MRM quantitative analysis.

FIG. 90 shows the performance (AUC and detection sensitivity) of LRG1 for discriminating high-risk IPMN from low-risk IPMN in comparison with CA19-9 alone. The CA19-9 protein was quantitatively analyzed by chemiluminescence enzyme immunoassay (CLEIA) whereas LRG1 was subjected to ELISA.

FIGS. 91 to 93 show the performance (AUC and detection sensitivity) of a combination of two proteins (LRG1+CA19-9), (LRG1+TTR), or (LRG1+CLU) for diagnosing high-risk IPMN in discrimination from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to ELISA.

FIGS. 94 to 97 show the performance (AUC and detection sensitivity) of (LRG1+CA19-9+TTR), (LRG1+CA19-9+CLU), (LRG1+CA19-9+TTR+CLU), or (LRG1+TTR+

CLU) combination markers for discriminating high-risk IPMN from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to ELISA.

FIGS. 98 to 100 show the performance (AUC and detection sensitivity) of (CLU+CA19-9), (CLU+TTR), or (CLU+CA19-9+TTR) combination markers for discriminating high-risk IPMN from low-risk IPMN in comparison with CA19-9 alone. The CA19-9 protein was quantitatively analyzed by chemiluminescence enzyme immunoassay (CLEIA) whereas LRG1, TTR, CLU, C1R, and KLKB1 were subjected to ELISA.

MODE FOR INVENTION

The term "pancreatic cancer", as used herein, means cancer (carcinoma) or malignant tumors that arise from cells in the pancreas. There are various kinds of pancreatic tumors from a benign tumor that can be cured by surgical ablation to a malignant tumor that has very poor prognosis. Included within the scope of pancreatic tumors are benign tumors, malignant tumors, and benign tumors that transform into malignant tumors. As for a malignant tumor of the pancreas, 90% of such tumors are pancreatic ductal adenocarcinomas (PDAC). Thus, pancreatic ductal adenocarcinoma is referred to, in a narrow sense, as pancreatic cancer. Other examples of pancreatic cancer include neuroendocrine tumors and acinar cell tumors. In addition, pancreatic tumors may be in the form of cystic tumor as representatively exemplified by serous cystic neoplasm, mucinous cystic neoplasm, intraductal papillary mucinous neoplasm (IPMN), and solid pseudopapillary tumor.

Particularly, pancreatic cancer may be pancreatic ductal adenocarcinoma or IPMN. Pancreatic ductal adenocarcinoma may occur due to various causes. For example, pancreatic ductal adenocarcinoma may be derived from IPMN or may occur irrespectively IPMN. Alternatively, it may be exclusive of IPMN-derived pancreatic ductal adenocarcinoma.

According to the tumor classification of the WHO, IPMN is defined as tumors (neoplasms) into which epithelial cells grow in a papillary form within the main pancreatic ducts or their branches, characterized by the production of thick fluid by the tumor cells and by the expansion of the pancreatic duct to a cyst.

IPMN has morphological traits including the diffuse dilatation of the main pancreatic duct, the atypical filling defect of mucous fluid or tumor mass, the cystic dilatation of branches of the pancreatic duct, the dilatation of the pailla orifice, and the extensive mucin oozing through the orifice of papilla. Histologically, IPMN is characterized by the papillary proliferations of mucin-producing epithelial cells within the pancreatic duct, and exhibits a broad spectrum of diseases from benign to malignant tumors. According to the site of tumor and the range of lesion, IPMN can be divided into three clinically distinct subtypes: the main duct type, the branch duct type, and the mixed type.

Factors of determining the prognosis of IPMN include invasivenss, lymph node metastasis, vascular invasion, histological findings, and histological findings on resection margin. Inter alia, the most important is invasiveness. IPMN is a curable disease before the occurrence of invasive cancer, but recurs at a rate of as high as 50-90% in remaining pancreas or extra-pancreatic tissues after the appearance of invasion. Since IPMN is likely to recur in the remaining pancreas even after curative resection, it needs to be traced for a long term, with intermittent proper treatments taken for increasing a survival rate.

Hence, malignancy assessment of IPMN is very important for determining subsequent prognosis and treatment methods. Typically, the malignancy of IPMN is divided by post-operative microscopic tissue examination into low, intermediate, high grade dysplasia, and IPMN associated with an invasive carcinoma in an ascending order. The invasive carcinoma with invasion into neighboring stroma may be in the form of ductal adenocarcinoma or mucinous noncystic carcinoma (colloid carcinoma), which are the most common form in pancreatic cancer.

In the present disclosure, a method, a composition, and a kit are provided for discriminating IPMN into high-grade dysplasia and invasive type as malignant subtype or high-risk IPMN, and low and intermediate glade dysplasia as low-risk IPMN. The pancreatic cancer-associated markers according to the present disclosure can be useful for discriminating high-risk IPMN from low-risk IPMN.

Also, the present disclosure addresses a kit for diagnosing pancreatic cancer, comprising the diagnosis composition of pancreatic cancer. Particularly, the kit may be an RT-PCR, a DNA chip kit, an ELISA kit, a protein chip kit, a rapid kit, or an MRM (multiple reaction monitoring) kit.

As used herein, the term "diagnosis" is intended to encompass determining the susceptibility of a subject to a certain disease or disorder, determining whether a subject is affected with a certain or disorder, determining the prognosis of a subject affected with a certain or disorder (e.g., identifying pre-metastatic or metastatic states of cancer, determining cancer stages or the responsiveness of cancer to treatment), or therametrics (e.g., monitoring the state of a subject to provide information on therapeutic efficacy). Particularly, the diagnosis, as used herein, means the determination of the onset or the possibility of onset (risk) of pancreatic cancer.

The term "marker", "biomarker", or "diagnostic marker", as used herein, means a label that allows for discrimination between normal and ill states or which enables therapeutic outputs to be predicted or objectively measured. In particular, in the context of relevance to pancreatic cancer, a marker means an organic biomolecule, such as a polypeptide or nucleic acid (e.g., mRNA, etc.), a lipid, a glycolipid, a glycoprotein, a sugar (monosaccharide, disaccharide, oligosaccharide, and the like), etc., which significantly increases or decreases in protein or gene expression level in a subject with pancreatic cancer or at risk of the onset of pancreatic cancer, compared to a normal control (subjects without pancreatic cancer).

The present disclosure addresses a composition for diagnosing pancreatic cancer, comprising: (a) an agent for measuring a protein or mRNA expression level of CA19-9 (carbohydrate antigen 19-9), (2) an agent for measuring a protein or mRNA expression level of LRG1 (Leucine-rich alpha-2-glycoprotein 1), and (3) an agent for measuring a protein or mRNA expression level of at least one marker selected from TTR (Transthyretin, ATTR, Prealbumin, TBPA); C1R (Complement C1r subcomponent precursor), CLU (Clusterin preproprotein), and KLKB1 (Plasma Kallikrein protein).

Taking advantage of a combination of at least three different marker genes, e.g., (a) CA19-9; (b) LRG1; and (c) at least one selected from among TTR, C1R, CLU, and KLKB1, the present disclosure can effectively determine the onset or the possibility of onset of pancreatic cancer in a subject.

The CA19-9 protein available as a diagnostic marker for pancreatic cancer in the present disclosure is conventionally used as a tumor marker in determining the prognosis of cancer of the digestive system.

As another diagnostic marker for pancreatic cancer useful in the present disclosure, the LRG1 protein is involved in angiogenesis with relevance to the onset of endometrial cancer and lung cancer. LRG1 may be NCBI Accession #NP_443204.1.

A further diagnostic marker for pancreatic cancer available in the present disclosure may be at least one selected from the group consisting of TTR, C1R, CLU, and KLKB1. TTR is a serum protein with a homotetrametic structure, each subunit consisting of 127 amino acid residues, and functions as a cerebrospinal fluid carrier of a thyroid hormone. The protein has relevance to the onset of Alzheimer's disease, breast cancer, ovarian cancer, and stomach cancer. C1R, the first found among the complements of the complement system, is in part responsible for body immunity, and has relevance to the onset of Alzheimer's disease and kidney cancer. CLU serves to block protein coagulation in blood, and is related to Alzheimer's disease and lung cancer. KLKB1 is involved in blood coagulation, and has relevance to hypertension and lung cancer.

In particular some embodiments of the present disclosure, TTR may be NCBI Accession #NP_000362.1, C1R may be NCBI Accession #NP_001724.3, CLU may be NCBI Accession #NP_001822.3, and KLKB1 may be NCBI Accession #NP_000883.2.

The present inventors analyzed serum samples from patients with pancreatic ductal adenocarcinoma (PDAC), intraductal papillary mucinous neoplasm (IPMN), or chronic cholecystitis, in comparison with serum samples from healthy controls, in such a manner as is suggested in Table 1, and finally established the effectiveness of a combination of CA19-9, LRG1, and at least one of TTR, C1R, CLU, and KLKB1.

TABLE 1

| Procedure | Method | # |
|---|---|---|
| Candidate for diagnostic marker for pancreatic cancer | Data mining Microarray analysis | 1,000 |
| Candidate to which MRM-MS is applicable | MRM-MS | 246 |
| Candidate with high diagnosis performance upon application alone | AUC >0.6 based on single markers alone. | 143 |
| Candidate to which SIS is applicable | MRM-MS using SIS | 54 |
| Final candidate | a combination of markers with performance maintained under various conditions, selected from 1~4 combinations. | 4 |

As used herein, the term "measuring a protein expression level" in the context of pancreatic cancer means detecting and identifying the presence and expression level of a diagnostic marker (protein) for pancreatic cancer or a gene coding therefor in a biological sample.

Examples of methods for use in measuring or comparatively analyzing the protein includes, but are not limited to, protein chip assay, immunoassay, ligand binding assay, MALDI-TOF(Matrix Assisted Laser Desorption/Ionization Time of Flight Mass Spectrometry), SELDI-TOF(Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

In the composition for diagnosing pancreatic cancer in accordance with the present disclosure, an agent for measuring a protein expression level of CA19-9, LRG1, TTR, C1R, CLU, or KLKB1 may comprise an antibody, an oligopeptide, a ligand, a PNA (peptide nucleic acid) or an aptamer that can specifically bind to the protein CA19-9, LRG1, TTR, C1R, CLU or KLKB1

As used herein, the term "antibody" refers to a substance that specifically binds to an antigen to provoke an antigen-antibody reaction. For the purpose of the present disclosure, the term "antibody" means an antibody that specifically binds to the CA19-9 protein, the LRG1 protein, the TTR protein, the C1R protein, the CLU protein or the KLKB1 protein. Falling within the scope of the antibody of the present disclosure are polyclonal antibodies, monoclonal antibodies, and recombinant antibodies. These antibodies can be easily prepared using a technique well known in the art. For example, a polyclonal antibody can be produced by injecting a pancreatic cancer marker as an antigen into an animal and obtaining a serum containing antibodies from the animal as well known in the art. Polyclonal antibodies may be prepared using any animal such as a goat, a rabbit, a sheep, a monkey, a horse, a pig, a cow, a dog, etc. Monoclonal antibodies can be obtained by the hybridoma method (Kohler and Milstein (1976) European Journal of Immunology 6:511-519), or a phage antibody library technique (Clackson et al, Nature, 352:624-628, 1991; Marks et al, J. Mol. Biol., 222:58, 1-597, 1991). The antibodies may be isolated and purified using gel electrophoresis, dialysis, salt precipitation, ion exchange chromatography, affinity chromatography, etc. In addition, the antibody useful in the present disclosure may be a complete antibody consisting of two full-length light chains and two full-length heavy chains, or a functional fragment of a complete antibody molecule. The term "functional fragment" of an antibody molecule means a fragment retaining an antigen-binding function, as exemplified by Fab, F(ab'), F(ab')$_2$, and Fv.

As used herein, the term "PNA (Peptide Nucleic Acid)" refers to an artificially synthesized polymer similar to DNA or RNA, first introduced by professors Nielsen, Egholm, Berg, and Buchardt (Univ. Copenhagen, Denmark) in 1991. DNA has a phosphoric acid-ribose sugar backbone whereas PNA's backbone is composed of repeating N-(2-aminoethyl)-glycine units linked by peptide bonds. Thanks to this structure, PNA significantly increases in binding affinity and stability for DNA or RNA, and thus is effectively used in molecular biology studies, diagnosis, and antisense therapy. For details of PNA, reference may be made to the document [Nielsen P E, Egholm M, Berg R H, Buchardt O (December 1991). "Sequence-selective recognition of DNA by strand displacement with a thymine-substituted polyamide". Science 254 (5037): 1497-500].

As used herein, "aptamers" are oligonucleotide or peptide molecules that bind to a specific target molecule. With regard to details of aptamers, reference may be made to documents [Bock L C et al., Nature 355(6360):5646(1992); Hoppe-Seyler F, Butz K "Peptide aptamers: powerful new tools for molecular medicine". J Mol Med. 78(8):42630 (2000); Cohen B A, Colas P, Brent R. "An artificial cell-cycle inhibitor isolated from a combinatorial library". Proc Natl Acad Sci USA. 95(24): 142727(1998)].

The term "measuring an mRNA expression level", as used herein, in the context of pancreatic cancer means detecting and identifying the presence and expression level of an mRNA of a gene coding for a diagnostic marker (protein) in a biological sample.

Examples of analysis methods available for the measurement of mRNA expression levels in the present disclosure include reverse-transcription polymerase chain reaction (RT-PCR), competitive RT-PCR, real-time RT-PCR, RNase protection assay (RPA), Northern blotting, and DNA chip, but are not limited thereto.

In the composition for diagnosing pancreatic cancer according to the present disclosure, the agent for measuring an mRNA expression level of a gene coding for CA19-9, LRG1, TTR, C1R, CLU or KLKB1 comprises a primer, probe, or antisense nucleotide that specifically binds to an mRNA of a gene encoding CA19-9, LRG1, TTR, C1R, CLU, or KLKB1. Information on CA19-9, LRG1, TTR, C1R, CLU, and KLKB1 proteins may be obtained from UniProt, and a person skilled in the art can design a primer, probe, or antisense nucleotide that specifically binds to an mRNA of a gene encoding the protein, based on the information.

As used herein, the term "primer" is a strand of short nucleic acid sequences that recognizes target gene sequences, and includes a pair of forward and reverse primers. Particularly, it includes a pair of primers providing analysis results of specificity and sensitivity. A primer is regarded as providing high specificity when it is used to amplify a target gene sequence, but does not cause the amplification of non-target sequences that are inconsistent therewith or complementary thereto.

The term "probe", as used herein, refers to a substance that specifically binds to a target to be detected in a sample. Through the binding, the probe can ascertain the presence of the target in the sample. So long as it is typically used in the art, any probe may be available in the present disclosure. Particularly, the probe may be a PNA (peptide nucleic acid), an LNA (locked nucleic acid), a peptide, a polypeptide, a protein, an RNA, or a DNA, with the most preference for PNA. In detail, the probe is a biomaterial that may be of organism origin or may be synthesized ex vivo, or a mimic thereof. For example, the probe may be an enzyme, a protein, an antibody, a microbe, an animal or plant cell or organ, a neuron, a DNA, or an RNA. The DNA may include cDNA, genomic DNA, and oligonucleotide. Also, within the scope of the RNA, genomic RNA, mRNA, and oligonucleotide may fall. Examples of the protein include an antibody, an antigen, an enzyme, and a peptide.

As used herein, the term "antisense oligomer" refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The oligomer may have exact or near sequence complementarity to the target sequence.

Further, the present disclosure addresses a kit for diagnosing pancreatic cancer, comprising the composition for the diagnosis of pancreatic cancer. For example, the kit may be an RT-PCR kit, a DNA chip kit, an ELISA kit, a protein chip kit, a rapid kit, or an MRM (multiple reaction monitoring) kit.

Employing a combination of pancreatic markers comprising CA19-9, LRG1, and at least one selected from the group consisting of TTR, C1R, CLU, and KLKB1, the composition for diagnosing pancreatic cancer or the kit comprising the same in accordance with the present disclosure is far superior in diagnostic performance to compositions or kits that use the two markers CA19-9 and LRG1.

The kit for diagnosing pancreatic cancer may further comprise at least one additional elemental composition, solution, or device suitable for the analysis.

For example, the diagnostic kit may further comprise an element necessary for a reverse transcription polymerase chain reaction. A RT-PCR kit comprises a pair of primers specific for a gene encoding a marker protein. Each primer is a nucleotide having a sequence specific for a nucleic acid sequence of the gene, and may have a length of about 7 to 50 bp, and more particularly about 10 to 30 bp. Further, the kit may further comprise a primer specific for a nucleic acid sequence of a control gene. In addition, the RT-PCR kit may comprise a test tube or a suitable vessel, a reaction buffer (various pH values and magnesium concentrations), deoxynucleotides (dNTPs), enzymes such as Taq-polymerase and reverse transcriptase, a DNase inhibitor, an RNase inhibitor, DEPC-water, and sterile water.

Further, the diagnostic kit of the present disclosure may comprise an element necessary for operating a DNA chip. The DNA chip kit may comprise a substrate to which a gene or a cDNA or oligonucleotide corresponding to a fragment thereof is bound, and reagents, agents, and enzymes for constructing a fluorescence-labeled probe. In addition, the substrate may comprise a control gene or a cDNA or oligonucleotide corresponding to a fragment thereof.

In some embodiments, the diagnostic kit of the present disclosure may comprise an element necessary for performing ELISA. The ELISA kit may comprise antibodies specific for the proteins. The antibodies have high selectivity and affinity for the marker proteins, with no cross-reactivity to other proteins, and may be monoclonal antibodies, polyclonal antibodies, or recombinant antibodies. Further, the ELISA kit may comprise an antibody specific for a control protein. In addition, the ELISA kit may further comprise a reagent capable of detecting the bound antibody, for example, a labeled secondary antibody, chromophores, an enzyme (e.g., conjugated with an antibody), and a substrate thereof or an material capable of binding to the antibody.

In some embodiments, the composition for diagnosing pancreatic cancer in accordance with the present disclosure or the diagnostic kit comprising the composition in accordance with the present disclosure may be used to discriminate a normal subject from a patient with pancreatic cancer of an early stage (stage 1 or 2) as well as from a patient with severe pancreatic cancer.

Therefore, the present disclosure provides a composition for diagnosing pancreatic cancer of stage 1 or 2, comprising (a) an agent for measuring an expression level of CA19-9, (b) an agent for measuring an expression level of LRG1, and (c) an agent for measuring an expression level of at least one selected from the group consisting of TTR, C1R, CLU, and KLKB1.

In addition, the composition for diagnosing pancreatic cancer in accordance with the present disclosure or the diagnostic kit comprising the composition in accordance with the present disclosure may be used to selectively discriminate a patient with pancreatic cancer from a patient with a different cancer as well as from a normal subject. Therefore, the present disclosure provides a composition for discriminating pancreatic cancer from other cancers, comprising (a) an agent for measuring an expression level of CA19-9, (b) an agent for measuring an expression level of LRG1, and (c) an agent for measuring an expression level of at least one selected from the group consisting of TTR, C1R, CLU, and KLKB1.

Moreover, the present disclosure addresses a method for diagnosing pancreatic cancer in a subject or for providing information on a diagnosis result of pancreatic cancer, using the diagnostic composition or kit of pancreatic cancer according to the present disclosure. The method comprises the following steps:

acquiring a sample from a subject to be diagnosed for the onset of pancreatic cancer;

measuring respective protein or mRNA expression levels of pancreatic cancer markers comprising (a) CA19-9, (b) LRG1, and (c) at least one marker selected from the group consisting of TTR, C1R, CLU, and KLKB1;

comparing the expression levels of the pancreatic cancer markers comprising (a) CA19-9, (b) LRG1, and (c) at least one marker selected from the group consisting of TTR, C1R, CLU, and KLKB1 with those of corresponding normal controls, respectively; and determining the onset or the possibility of onset of pancreatic cancer in the subject, based on the comparison result.

The term "subject", as used in the context of the method for diagnosing pancreatic cancer or for providing diagnostic information on pancreatic cancer, refers to a subject to be examined for the onset of pancreatic cancer, including a pancreatic cancer patient, a subject suspected of having pancreatic cancer, and a normal subject free of pancreatic cancer. For example, a healthy subject that is to be under medical examination for PDAC, with no clinical determination history of pancreatic cancer, or a subject which is under a periodical examination because of the past history of pancreatic cancer in spite of the resection of the tumor falls within the scope of the subject. The subject may be a mammal in one embodiment, and a human in another embodiment.

In the step of determining the onset or the possibility of onset of pancreatic cancer in the subject, based on the comparison result, the condition for determining that pancreatic cancer would be highly prone to occurring is as follows: a subject to be examined for the onset of pancreatic cancer is higher than a normal control in terms of the protein expression level of CA19-9 or the mRNA expression level of a gene coding for CA19-9; in terms of the protein expression level of LRG1 or the mRNA expression level of a gene coding for LRG1; and lower in terms of the protein expression level of TTR or the mRNA expression level of a gene coding for TTR, higher in terms of the protein expression level of C1R or the mRNA expression level of a gene coding for C1R, lower in terms of the protein expression level of CLU or the mRNA expression level of a gene coding for CLU, or lower in terms of the protein expression level of KLKB1 or the mRNA expression level of a gene coding for KLKB1.

The term "sample", as used in conjunction with the method, refers to a biological sample that differs in protein or gene expression level, with the onset of pancreatic cancer, and examples of which include a tissue, a cell, a serum, a plasma, saliva, cerebrospinal fluid, and urine, with preference for blood, serum, or plasma.

Because pancreatic cancer patients increase in the expression level of CA19-9 and LRG1 proteins or in the expression level of mRNAs of genes encoding the proteins, decrease in the expression level of TTR, CLU, and KLKB1 proteins or in the expression level of mRNAs of genes encoding the proteins, and also increase in the expression level of C1R protein or in the expression level of mRNAs of genes encoding the protein, compared to a normal control, the possibility of onset of pancreatic cancer can be determined by measuring respective protein expression levels of pancreatic cancer markers comprising (a) CA19-9, (b) LRG1, and (c) at least one marker selected from the group consisting of TTR, C1R, CLU, and KLKB1, or mRNA expression levels of genes encoding the proteins.

For example, when a subject is measured to have a higher protein or mRNA expression level of CA19-9 and LRG1 and a lower protein or mRNA expression level of TRR than a normal control, the subject may be determined to have high possibility of onset of pancreatic cancer.

The expression or phrase "a subject to be examined for the onset of pancreatic cancer is higher than a normal control in terms of the protein expression level of CA19-9 or the mRNA expression level of a gene coding for CA19-9" means that the protein expression level of CA19-9 protein or the mRNA expression level of a gene coding therefor in a subject to be examined for the onset of pancreatic cancer is 1.0-, 1.5-, 2-, 3-, 5-, or 10-fold higher than that in a normal control, as measured by various methods. This meaning is true of the protein level of LRG1 or C1R or the mRNA expression level of a gene encoding the protein.

The expression or phrase "a subject to be examined for the onset of pancreatic cancer is lower than a normal control in terms of the protein expression level of TTR or the mRNA expression level of a gene coding for CA19-9" means that the protein expression level of TTR protein or the mRNA expression level of a gene coding therefor in a subject to be examined for the onset of pancreatic cancer is 0.1-, 0.2-, 0.3-, 0.5- or 1-fold lower than that in a normal control, as measured by various methods. This meaning is true of the protein level of CLU or KLKB1 or the mRNA expression level of a gene encoding the protein.

In some embodiments, "determining that pancreatic cancer would be highly prone to occurring" may be decided according to a pancreatic cancer diagnosis formula, as exemplified by the following Formula 1.

$$f(x) = \text{sgn}\left(\sum_{i=1}^{n} \alpha_i y_i \langle x, x_i \rangle + b\right)$$ [Formula 1]

wherein, x is an expression level measurement of a diagnostic marker for pancreatic cancer, $\alpha_i$ is a Lagrange multiplier in SVM, $y_i$ is a separator of normal group/pancreatic cancer group, $x_i$ is a reference measurement, and b is a correction value.

The function is derived from SVM (Support Vector Machine). SVMs are algorithms designed to estimate a function that meets a given condition on the basis of the Lagrangian optimization theory. Of them, a case where classification analysis is applied using a maximum margin classifier is called SVC (Support Vector Classification). When relative MRM measurements of CA19-9, LRG1, and any one of TTR, C1R, CLU, and KLKB1 are applied to the function, a function value of 1 leads to diagnosing a high likelihood of the onset of pancreatic cancer whereas a functional value of −1 accounts for a normal state.

According to the method of the present disclosure, the possibility of onset of pancreatic cancer can be readily determined on the basis of results obtained by applying protein or mRNA expression levels of CA19-9, LRG1, and any one of TTR, C1R, CLU, and KLKB1 to the pancreatic cancer diagnosis formula.

The diagnosis function, although constructed with SVM, may be made with various types of discriminative analysis including machine learning such as Neural Network, Random Forest, etc.

In addition, the present disclosure provides a method for diagnosing pancreatic cancer, comprising (a) acquiring a sample from a subject to be diagnosed for the onset of pancreatic cancer; (b) measuring a protein expression level of CA19-9 or an mRNA expression level of a gene encoding the CA19-9 protein, and a protein expression level of LRG1 or an mRNA expression level of a gene encoding the LRG1 protein in the sample; (c) measuring a protein expression level of at least one selected from the group consisting of TTR, C1R, CLU, and KLKB1, or an mRNA expression level of a gene encoding the protein in the sample; and (d) determining the possibility of onset of pancreatic cancer by applying the measurements of steps (b) and (c) to the following Formula 1:

$$f(x) = \text{sgn}\left(\sum_{i=1}^{n} \alpha_i y_i \langle x, x_i \rangle + b\right) \quad \text{[Formula 1]}$$

wherein x is an expression level measurement of CA19-9, LRG1, and any one of TTR, C1R, CLU, and KLKB1, a diagnostic marker for pancreatic cancer, $\alpha_i$ is a Lagrange multiplier in SVM, $y_i$ is a separator of normal group/pancreatic cancer group, $x_i$ is a reference measurement, and b is a correction value.

In the method of the present disclosure, the protein expression levels can be measured and compared using respective antibodies specifically binding to corresponding proteins. The antibody is allowed to form an antigen-antibody complex with a corresponding protein in a biological sample, and the complex is detected.

As used herein, the term "antigen-antibody complex" means a complex in which an antigen is bound with an antibody recognizing the antigen and which is used to determine the presence or absence of a corresponding gene in a biological sample. The detection of the antigen-antibody complex can be achieved using a method well known in the art, such as a spectrometric method, a photochemical method, a biochemical method, an immunochemical method, an electrical method, a photochemical method, a chemical method, etc.

For the purpose of the present disclosure, the measurement or comparison of protein expression may be achieved using a method well known in the art, examples of which include, but are not limited to, protein chip assay, immunoassay, ligand binding assay, MALDI-TOF (Matrix Assisted Laser Desorption/Ionization Time of Flight Mass Spectrometry), SELDI-TOF (Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

In the present disclosure, LC-MRM may be used to measure and compare expression levels of CA19-9, LRG1, C1R, CLU, and KLKB1 proteins.

Briefly, proteins of target in a biological sample can be separated by LC using an LC analysis column while with a solution containing, by volume, 95% of distilled water, 5% of acetonitrile, and 0.1% of formic acid, and a solution containing, by volume, 5% of distilled water, 95% of acetonitrile, and 0.1% of formic acid are used with a concentration gradient from 95:5 to 15:85. Since a resolution for certain materials may vary depending on the mix ratio of the solutions, concentration gradients are set. The gradient range is optimal for separating various proteins concomitantly. First, a column is equilibrated for 10 min with Sol A (95% distilled water, 5% acetonitrile, 0.1% formic acid), followed by eluting peptides with Sol B (5% distilled water, 95% acetonitrile, 0.1% formic acid) at a concentration gradient from 5% to 85% for 50 min and at a concentration of 85% for 5 min For mass analysis, MRM (multiple reaction monitoring) is performed in the MS/MS mode. SIM (Selected Ion Monitoring) takes advantage of ions formed upon collision onto an ion source of a mass spectrometer whereas MRM utilizes ions produced after specific ions are selected among from the ions broken already and then again collided against a source of a different MS in tandem. SIM is problematic in that the selected quantitative ions may interfere with quantitative analysis if they are the same as is detected in serum. On the other hand, when ions, although having the same mass, are collided once more, they are different in molecular structure from those that are not collided, exhibiting a distinct feature. Thus, the use of such ions removes the noise peaks in the background, so that MRM allows for even clearer base lines. In addition, a stable isotope standard (SIS) peptide is synthesized and measured in comparison with a target peptide, thereby enabling the accurate analysis of desired materials at the same time with higher sensitivity.

Using the above analysis methods, protein levels can be compared between a normal control and a subject suspected of the onset of pancreatic cancer, and a significant increase in the protein expression level of pancreatic cancer markers is assessed to determine the possibility of onset of pancreatic cancer.

An assay available for the measurement and comparison of mRNA expression levels of respective genes coding for CA19-9, LRG1, C1R, CLU, and KLKB1 proteins includes, but is not limited to, RT-PCR, competitive RT-PCR, real-time RT-PCR, RNase protection assay, Northern blotting, and DNA chip. Using the assay methods, mRNA expression levels of the pancreatic cancer markers can be measured in a subject of suspect in comparison with a normal control to diagnose or predict the onset likelihood of pancreatic cancer.

Also, the present disclosure addresses a method for providing information for diagnosis of pancreatic cancer, comprising: (a) acquiring a sample from a subject to be diagnosed for the onset of pancreatic cancer; (b) measuring a protein expression level of CA19-9 or an mRNA expression level of a gene encoding the CA19-9 protein, and a protein expression level of LRG1 or an mRNA expression level of a gene encoding the LRG1 protein in the sample; (c) measuring a protein expression level of at least one selected from the group consisting of TTR, C1R, CLU, and KLKB1 or an mRNA expression level of a gene encoding the protein in the sample; (d) comparing the protein expression level of CA19-9 or the mRNA expression level of a gene encoding the CA19-9 protein, and the protein expression level of LRG1 or the mRNA expression level of a gene encoding the LRG1 protein in the sample with those in a normal control; and (e) comparing the protein expression level of at least one selected from the group consisting of TTR, C1R, CLU, and KLKB1 or an mRNA expression level of a gene encoding the protein in the sample with that in the normal control.

In the marker, the composition, the kit, and the method for diagnosing pancreatic cancer in accordance with the present disclosure, the pancreatic cancer may be IPMN, particularly high-risk IPMN. The composition can allow for the discrimination of high-risk IPMN from low-risk IPMN or for the selective diagnosis of high-risk IPMN in distinction from a normal group, patients with pancreatic diseases other than IPMN or pancreatic ductal adenocarcinoma, or a control with low-risk IPMN. The high-risk IPMN may include high-grade dysplasia and invasive type IPMN. Also, the high-risk IPMN may include IPMN-derived pancreatic ductal adenocarcinoma.

In some embodiments, the present disclosure addresses a composition for the selective diagnosis of high-risk IPMN, comprising an agent for measuring an expression level of an IPMN (intraductal papillary mucinous neoplasm) marker comprising LRG1 (leucine-rich alpha-2-glycoprotein 1), or an mRNA expression level of a gene encoding the marker. The IPMN marker may further comprise at least one marker selected from the group consisting of CA19-9 (carbohydrate antigen 19-9), TTR, C1R, CLU, and KLKB1. For example, the IPMN may be a combination of LRG1 in combination with one selected from the group consisting of TTR, C1R, CLU, and KLKB1, or in combination with two selected from the group consisting of TTR, C1R, CLU, and KLKB1.

According to some embodiments, the present disclosure addresses a composition for the selective diagnosis of high-risk IPMN, comprising an agent for measuring respective expression levels of IPMN marker proteins comprising CLU (Clusterin preproprotein); and at least one selected from the group consisting of LRG1 (Leucine-rich alpha-2-glycoprotein 1, LRG1), CA19-9 (carbohydrate antigen 19-9), TTR (Transthyretin, ATTR, Prealbumin, TBPA), C1R (Complement C1r subcomponent precursor), and KLKB1 (Plasma Kallikrein protein), or respective mRNA expression levels of genes encoding the IPMN marker proteins.

According to some embodiments, the present disclosure addresses a method for diagnosing high-risk IPMN, comprising:

measuring respective expression levels of the IPMN marker proteins or respective mRNA expression levels of genes encoding the proteins in a sample from a subject, comparing the expression level measurements with those of control markers, and determining onset probability of high-risk IPMN in the subject, based on the comparison result of the marker expression levels.

Prior to the measuring step, the method may further comprise examining whether the subject has IPMN. This examination may be conducted by imaging diagnosis or biopsy, or using a genetic marker. By way of example, the imaging diagnosis includes, but is not limited to, abdominal ultrasound, computed tomography (CT), endoscopic retrograde cholangiopancreatography (ERCP), magnetic resonance cholangiopancreatography (MRCP), and endoscopic ultrasonography (EUS). The biomarker useful in the examination may be CA-19-9, which is well known as a diagnostic marker for pancreatic cancer. The biopsy may be FNA (fine needle aspiration) biopsy.

When the control is a normal group, a patient with a pancreatic disease other than IPMN or pancreatic ductal adenocarcinoma, or a patient with low-risk IPMN, high-risk IPMN can be diagnosed in discrimination from a normal state and various other pancreatic diseases, using the IPMN marker. In addition, when the control is a low-risk IPMN patient, high-risk IPMN can be selectively diagnosed in discrimination from low-risk IPMN.

The method may further comprise conducting a treatment measure, such as surgical resection, drug administration, etc., when the subject is determined to have high-risk IPMN.

The method may further comprise conducting a treatment measure, such as drug administration, prognosis monitoring, etc., when the subject is determined to have low-risk IPMN.

Details of the IMPN markers, measurement of expression levels, and determination are as described above.

A better understanding of the present invention may be obtained through the following examples that are set forth to illustrate, but are not to be construed as limiting the present invention.

EXAMPLE 1

Preparation of Experimental Sample

To excavate a protein combination useful in diagnosing pancreatic cancer, samples were obtained from patient groups with pancreatic cancer, other cancers, pancreatitis, or cholecystitis in 5 hospitals, under the consent of the patients, and from a normal group, as shown in Tables 2 and 3.

For Test 1 of discriminating PDAC, normal, pancreatitis, and cholecystitis groups were used as controls while patients with pancreatic cancer (PDAC) was grouped.

Test 2 for discriminating PDAC in an early stage was conducted with samples from pancreatic cancer (PDAC) patients of stage 1 or 2 while normal persons and patients with pancreatitis or cholecystitis are used controls.

Test 3 was designed for cancer/pancreatic selection. In this regard, an experiment group consisted of pancreatic cancer samples while a control contained samples of other cancers, that is, 54 cases of breast cancer, 45 cases of colorectal cancer, and 53 cases of thyroid cancer.

In Test 4, PDAC was discriminated under the condition where CA19-9 cannot clinically function. A control was comprised of normal, pancreatitis, and cholecystitis groups with a CA19-9 level of less than 37 U/ml while a pancreatic cancer (PDAC) group with a CA19-9 level of less than 37 U/ml was used as an experimental group.

TABLE 2

| Classification | Pancreatic cancer (1/2/3/4 phase) | training sets * | Test 1 | Test 2 | Test 3 | Test 4 |
|---|---|---|---|---|---|---|
| sum | 396 (20/228/31/117) | 316 (16/182/25/93) | 80 (4/46/6/24) | 50 (4/46/0/0) | 80 (4/46/6/24) | 29 (3/21/1/4) |
| AMC | 75 (10/63/1/1) | 60 (8/50/1/1) | 15 (2/13/0/0) | 15 (2/13/0/0) | 15 (2/13/0/0) | 10 (2/8/0/0) |
| NCC | 128 (3/27/25/73) | 102 (2/22/20/58) | 26 (1/5/5/15) | 6 (1/5/0/0) | 26 (1/5/5/15) | 7 (1/3/1/2) |

TABLE 2-continued

| Classification | Pancreatic cancer (1/2/3/4 phase) | training sets * | Test 1 | Test 2 | Test 3 | Test 4 |
|---|---|---|---|---|---|---|
| SMC | 96 (1/50/2/43) | 76 (1/40/1/34) | 19 (0/10/1/9) | 10 (0/10/0/0) | 19 (0/10/1/9) | 5 (0/3/0/2) |
| SNUH | 50 (3/45/2/0) | 40 (2/36/2/0) | 10 (1/9/0/0) | 10 (1/9/0/0) | 10 (1/9/0/0) | 1 (0/1/0/0) |
| YMC | 47 (3/43/1/0) | 38 (3/34/1/0) | 9 (0/9/0/0) | 9 (0/9/0/0) | 9 (0/9/0/0) | 6 (0/6/0/0) |

TABLE 3

| Classification | Organization | sum | training sets* | Test 1 | Test 2 | Test 3 | Test 4 |
|---|---|---|---|---|---|---|---|
| Other cancer | SMC | 149 | 0 | 0 | 0 | 149 | 0 |
| pancreatitis | AMC | 47 | 33 | 14 | 14 | 0 | 14 |
| | SMC | 30 | 26 | 4 | 4 | 0 | 4 |
| | SNUH | 5 | 4 | 1 | 1 | 0 | 1 |
| | YMC | 27 | 25 | 2 | 2 | 0 | 2 |
| | sum | 109 | 88 | 21 | 21 | 0 | 21 |
| cholecystitis | SNUH | 48 | 40 | 8 | 8 | 0 | 8 |
| Normal | SNUH | 300 | 240 | 60 | 60 | 0 | 60 |

AMC: Asan Medical Center
NCC: National Cancer Center
SMC: Samsung Medical Center
SNUH: Seoul National University Hospital
YMC: Yonsei Medical Center
*all tests were performed with the classifiers deducted from the training sets.

EXAMPLE 2

Excavation and Performance Analysis of Pancreatic Cancer Diagnostic Maker by MRM-MS <2-1> Pretreatment of Blood Sample Of 40 μl of each blood sample, the most abundant 7 proteins were depleted using a depletion column, and the residue was concentrated through a 3 kDa filter. The concentrate was quantified by BCA. A plasma corresponding to 200 μg was taken from the concentrate, denatured with 6 M urea, and reduced and alkylated with 20 mM DTT and 50 mM iodoacetic acid. The proteins were decomposed into peptides by treatment with trypsin at a ratio of 50:1 (protain:trypsin, w/w) at 37° C. for 16 hrs, and the peptides were desalted using a C18 OASIS column (Waters, USA) and lyophilized. The lyophilizate was dissolved in solution A (98% distilled water, 2% acetonitrile, 0.1% formic acid) before MRM analysis.

<2-2> Transition Selection

For MRM analysis, selection was made of a peptide that had a charge-to-mass (m/z) characteristic of a certain protein (Q1). Further, among various fragmentation ions generated from the peptide by electric collision, those with m/z characteristic of a certain protein were selected (Q3). A combination of Q1 and Q3 in which ions characteristic of a certain protein were combined was designated transition. Signals obtained by sequentially passing the characteristic ions in Q1 and Q3 through a high-resolution (triple-quadrupole) mass spectrometer were reduced into quantitative information for quantitative analysis. Using the software SKYLine developed by MacCoss's research team, University of Washington School of Medicine, Seattle, Wash., USA, up to 10 peptides per one protein were selected with regard to peptides provided with ms/ms on the basis of the peptide tandem mass spectra of the NIST (National Institute of Standards and Technology). The peptides were at least 7 amino acids to up to 24 amino acids in length.

From a total of peptides that can be produced by trypsinization, however, peptides having the following amino acids or motifs were excluded due to poor signal conditions:

ⓐ when methionine is present in a peptide of interest, it is prone to oxidation by ROS (reactive oxygen species) in vivo, thereby increasing the mass by 32 Da;

ⓑ when histidine is present in a peptide of interest, the positive charge of the R-group may alter the charge state of the peptide of interest.

ⓒ an N×S/T motif present in a peptide of interest may undergo N-glycosylation, resulting in a shift of mass value;

ⓓ when a proline residue is present just after an R or K residue in a peptide of interest, missed cleavage may occur at the R or K site, which can be cleaved by trypsin.

For a precursor charge, a peptide with a charge of +2 was selected while a charge of +1 was used as an ion charge, with a y-ion type. Distinct transitions and peptides were selected using Protein Blast P and Skyline. Finally, the transitions that fell within an expected retention time (RT) scope were used. For RT expectation, MRM analysis of 600 SIS peptides was conducted, and a calibration curve was made based on the analysis result using a hydrophobicity scale and an RT chromatogram.

<2-3> LC and MRM

For LC analysis, 1260-capillary LC of Agilent Technologies was employed, with a capillary RR 0.5×150 3.5 um column for peptide separation. A sample was injected in an amount of 5 μl, with a flow rate of 20 μl/min. First, the column was equilibrated with Sol A(by volume, 95% distilled water, 5% acetonitrile, 0.1% formic acid) for 10 min, after which peptides were eluted with Sol B (by volume, 5% distilled water, 95% acetonitrile, 0.1% formic acid) at a concentration gradient from 5% to 85% for 50 min and at a concentration of 85% for 5 min.

Using the mass spectrometer triple quadrupole 6490-QQQ of Agilent Technologies, transitions for the selected proteins were monitored in an MRM mode. To compensate for deviations between batches, 5 fmol beta-galactosidase peptide (GDFQFNISR[C13N15], 547.3/646.4) with which each sample was spiked was monitored simultaneously.

<2-4> Quantitative Analysis of Data

For quantitative analysis, the internal standard beta-galatosidase peptide (GDFQFNISR[C13N15], 547.3/646.4 m/z) was diluted to 0.09, 0.27, 0.82, 2.5, 7.4, 22.2, 66.7, and 200 fmol, and the matrix was supplemented with 10 μg of plasma as in the condition for target peptide analysis. Analysis was also done in the absence of the internal standard peptide with the aim of ascertaining endogenous signals. MRM quantification was repeated three time at all 9 concentration points to construct a standard curve.

For the result of MRM of each individual, the extract ion chromatography (XIC) of the corresponding MRM transition was produced using SKYLine (MacCoss Lab, ver1.4.1), and the peak area of each transition was calculated and plotted with time. In addition, a stable isotope standard (SIS) peptide was synthesized and measured. The XIC peak area of each transition was normalized with the XIC peak area of the standard, and on the basis of the normalization, quantitative analysis was performed for each protein.

Based on the results of the MRM analysis, proteins in the four marker combinations deduced by the method of Table 1 were shown to have the following expression patterns in the pancreatic cancer patient group.

As can be seen in FIGS. 1 and 2, the expression levels of CA19-9 and LRG1 were significantly increased in the pancreatic cancer patient group, compared to the normal group, and thus CA19-9 and LRG1 were selected as makers for the diagnosis of pancreatic cancer.

As shown in FIGS. 3 to 6, the pancreatic cancer patient group specifically decreased in the expression levels of TTR, CLU and KLKB1, and increased in the expression level of C1R, compared to the normal group.

EXAMPLE 3

Excavation and Performance Analysis of Protein Combination for Diagnosis of Pancreatic Cancer by ELISA Expression levels of LRG1, TTR and CLU were measured in both the pancreatic cancer patient group and the normal group by ELISA. According to the manufacturers' instructions, the hLRG1 ELISA of IBL was used for LRG1, the prealbumin ELISA kit of AssayPro was used for TTR, and the Human Clusterin Quantikine kit of R&D Systems was used for CLU.

Briefly, the ELISA kit and the sample were left at room temperature, and then the sample was diluted with the dilution buffer (LRG1: 1,000-fold; TTR: 80,000-fold; CLU: 2,091-fold). Each of the standard, the control, and the sample was plated in an amount of 50 μl per well, and then incubated at room temperature for 2 hrs with a cover sealer applied to each well. The wells were washed with distilled water after removal of the solution therefrom. This procedure was repeated four times. Subsequently, 200 μl of a conjugate was added to each well, and incubated at room temperature for 2 hrs, with a fresh cover sealer applied to each well. The wells were washed with distilled water. These procedures were repeated again four times. Then, 200 μl of a substrate solution was added to each well, and incubated at room temperature for 30 min. After the addition of 50 μl of a stop solution to each well, absorbance at 540 nm or 570 nm was read to calculate concentrations.

ELISA analysis results are given in FIGS. 7 and 9. Consistent with the results of MRM-MS in Example 2, the pancreatic cancer patient group was observed to increase specifically in the protein expression level of LRG1 and decrease specifically in the protein expression level of TTR and CLU, compared to the normal group.

EXAMPLE 4

Excavation and Performance Analysis of Pancreatic Cancer by Immunoturbidimetric Assay Protein expression levels of TTR were measured in the pancreatic cancer group and the normal group by immunoturbidimetric assay. Using the COBAS INTEGRA 800 Prealbumin of Roche Diagnostics, immunoturbidimetric assay was preformed according to the manufacturer's instruction.

Briefly, the instrument and the sample were left at room temperature before start of the experiment. Then, the sample was added in an amount of 50 μl to each well, and four-fold diluted with the exclusive dilution solution. The diluted sample was fed in an amount of 200 μl to the instrument, and concentration outputs from the instrument were taken as results.

Consistent with the results of MRM-MS and ELISA in Examples 2 and 3, the results of the immunoturbidimetric assay showed that the protein expression level of TTR was decreased specifically in the pancreatic cancer patient group, compared to the normal group, as understood in FIG. 10.

EXAMPLE 5

Assay for Diagnostic Performance of Marker Combination of CA19-9, LRG1 and TTR by MRM-MS <5-1> Diagnostic Performance of a Marker Combination of CA19-9, LRG1, and TTR for PDAC Discrimination Using the MRM-MS method of Example 2, the marker combination of CA19-9, LRG1, and TTR was assayed for diagnostic performance for pancreatic cancer discrimination. The CA19-9 protein was quantitatively analyzed by chemiluminescence enzyme immunoassay (CLEIA) using the COBAS Elecsys CA 19-9 instrument of Roche Diagnostics whereas LRG1 and TTR were subjected to MRM quantitative analysis.

When using a pancreatic cancer diagnosis function, the diagnostic performance of a combination of CA19-9, LRG1, and TTR for pancreatic cancer was expressed in AUC and $Sn|_{Sp=0.9}$ of an ROC curve. An ROC curve expresses relationship between sensitivity and specificity on a 2D plane. A greater area under curve (AUC; 0≤AUC≤1) represents more correct information. $Sn|_{Sp=0.9}$ is a sensitivity value at a specificity of 0.9, showing detection sensitivity. A higher value of $Sn|_{Sp=0.9}$ provides more correct information.

Measurements of AUC and $Sn|_{Sp=0.9}$ are given in Table 4 and FIG. 11.

TABLE 4

| Marker combination | AUC | Sn\|Sp = 0.9 |
|---|---|---|
| CA19-9 + LRG1 + TTR | 0.9312 | 0.8250 |
| CA19-9 + LRG1 | 0.9305 | 0.8125 |
| CA19-9 + TTR | 0.8823 | 0.7125 |

TABLE 4-continued

| Marker combination | AUC | Sn\|Sp = 0.9 |
|---|---|---|
| LRG1 + TTR | 0.8027 | 0.5375 |
| CA19-9 | 0.8259 | 0.7250 |
| LRG1 | 0.7104 | 0.4375 |
| TTR | 0.6573 | 0.1375 |

As can be seen in Table 4 and FIG. 11, the combination of CA19-9, LRG1, and TTR in accordance with the present disclosure was observed to have an AUC of 0.9312 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for pancreatic cancer than individual CA19-9, LRG1, and TTR, or a combination of any two thereof.

<5-2> Diagnostic Performance of a Marker Combination of CA19-9, LRG1 and TTR for Discrimination of Early Stage PDAC Using the MRM-MS method of Example 2, a maker combination of CA19-9, LRG1, and TTR was assayed for diagnostic performance for early stage pancreatic cancer. The CA19-9 protein was quantitatively analyzed by chemiluminescence enzyme immunoassay (CLEIA) whereas LRG1 and TTR were subjected to MRM quantitative analysis. Measurements of AUC and $Sn|_{Sp=0.9}$ are given in Table 5 and FIG. 12.

TABLE 5

| Test classification | Marker combination | AUC | $Sn|_{sp=0.9}$ |
|---|---|---|---|
| 5-2 | CA19-9 + LRG1 + TTR | 0.9070 | 0.7600 |
|  | CA19-9 + TTR | 0.8440 | 0.6400 |
|  | CA19-9 | 0.7924 | 0.6400 |
| 5-3 | CA19-9 + LRG1 + TTR | 0.8994 | 0.8250 |
|  | CA19-9 + TTR | 0.8494 | 0.7125 |
|  | CA19-9 | 0.7964 | 0.6875 |
| 5-4 | CA19-9 + LRG1 + TTR | 0.8295 | 0.5172 |
|  | CA19-9 + TTR | 0.6753 | 0.2069 |
|  | CA19-9 | 0.5198 | 0.2414 |

As can be seen in Table 5 and FIG. 12, the combination of CA19-9, LRG1, and TTR in accordance with the present disclosure was observed to have an AUC of 0.9070 and an $Sn|_{Sp=0.9}$ of 0.7600, indicating that the combination exhibits excellent performance as a diagnostic marker for pancreatic cancer. Particularly, a combination of CA19-9, LRG1, and TTR was observed to have higher diagnostic performance for pancreatic cancer than the commercially available diagnostic marker CA19-9 alone.

<5-3> Diagnostic Performance of a Marker Combination of CA19-9, LRG1, and TTR for Cancer/Pancreatic Cancer Discrimination Using the MRM-MS method of Example 2, a maker combination of CA19-9, LRG1, and TTR was assayed for diagnostic performance for discrimination between cancer and pancreatic cancer. The CA19-9 protein was quantitatively analyzed by chemiluminescence enzyme immunoassay (CLEIA) whereas LRG1 and TTR were subjected to MRM quantitative analysis. Measurements of AUC and $Sn|_{Sp=0.9}$ are given in Table 5 and FIG. 13.

As can be seen in Table 5 and FIG. 13, the combination of CA19-9, LRG1, and TTR in accordance with the present disclosure was observed to have an AUC of 0.8994 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<5-4> Diagnostic Performance of a Marker Combination of CA19-9, LRG1, and TTR for PDAC Discrimination in Test Group with CA19-9<37 U/ml Using the MRM-MS method of Example 2, the marker combination of CA19-9, LRG1, and TTR was assayed for diagnostic performance for pancreatic cancer discrimination in a group with CA19-9<37 U/ml. In most clinical cases, a subject is determined to have pancreatic cancer when CA19-9 is measured to be 37 U/ml or higher. Hence, CA19-9 cannot function as a diagnostic marker for pancreatic cancer in a subject with CA19-9<37 U/ml. The CA19-9 protein was quantitatively analyzed by chemiluminescence enzyme immunoassay (CLEIA) using the COBAS Elecsys CA 19-9 instrument of Roche Diagnostics whereas LRG1 and TTR were subjected to MRM quantitative analysis.

When using a pancreatic cancer diagnosis function, the diagnostic performance of a combination of CA19-9, LRG1, and TTR for pancreatic cancer was expressed in AUC and $Sn|_{Sp=0.9}$ of an ROC curve. An ROC curve expresses relationship between sensitivity and specificity on a 2D plane. A greater area under curve (AUC; 0≤AUC≤1) represents more correct information. $Sn|_{Sp=0.9}$ is a sensitivity value at a specificity of 0.9, showing detection sensitivity. A higher value of $Sn|_{Sp=0.9}$ provides more correct information. Measurements of AUC and $Sn|_{Sp=0.9}$ are given in Table 5 and FIG. 14.

As can be seen in Table 5 and FIG. 14, the combination of CA19-9, LRG1, and TTR in accordance with the present disclosure was observed to have an AUC of 0.8295 and an $Sn|_{Sp=0.9}$ of 0.5172, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

Example 6

Assay for Diagnostic Performance of Marker Combination of CA19-9, LRG1, and TTR by ELISA Examination was made to see whether ELISA would reproduce results of the MRM-MS assay of the marker combination of CA19-9, LRG1, and TTR for pancreatic cancer discrimination in Example 5. The excellent diagnostic performance of the combination of CA19-9, LRG1, and TTR for pancreatic cancer was also confirmed as assayed by ELISA.

<6-1> Diagnostic Performance of a Marker Combination of CA19-9, LRG1, and TTR for PDAC Discrimination Using the ELISA method of Example 3, the marker combination of CA19-9, LRG1, and TTR was assayed for diagnostic performance for pancreatic cancer discrimination. The CA19-9 protein was quantitatively analyzed by chemiluminescence enzyme immunoassay (CLEIA) whereas LRG1 and TTR were subjected to ELISA.

Measurements of AUC and $Sn|_{Sp=0.9}$ are given in Table 6 and FIG. 15.

TABLE 6

| Test classification | Marker combination | AUC | $Sn|_{Sp=0.9}$ |
|---|---|---|---|
| 6-1 | CA19-9 + LRG1 + TTR | 0.9315 | 0.8250 |
|  | CA19-9 + TTR | 0.9060 | 0.7750 |
|  | CA19-9 | 0.8259 | 0.7250 |
| 6-2 | CA19-9 + LRG1 + TTR | 0.9144 | 0.7800 |
|  | CA19-9 + TTR | 0.8937 | 0.7400 |
|  | CA19-9 | 0.7924 | 0.6400 |
| 6-3 | CA19-9 + LRG1 + TTR | 0.8981 | 0.8250 |
|  | CA19-9 + TTR | 0.8488 | 0.7750 |
|  | CA19-9 | 0.7964 | 0.6875 |
| 6-4 | CA19-9 + LRG1 + TTR | 0.8287 | 0.5172 |
|  | CA19-9 + TTR | 0.7408 | 0.3793 |
|  | CA19-9 | 0.5198 | 0.2414 |

As can be seen in Table 6 and FIG. 15, the combination of CA19-9, LRG1, and TTR in accordance with the present disclosure was observed to have an AUC of 0.9315 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<6-2> Diagnostic Performance of Marker Combination of CA19-9, LRG1, and TTR for Discrimination of Early Stage PDAC Using the ELISA of Example 3, a maker combination of CA19-9, LRG1, and TTR was assayed for diagnostic performance for early stage pancreatic cancer. The CA19-9 protein was quantitatively analyzed by chemiluminescence enzyme immunoassay (CLEIA) whereas LRG1 and TTR were subjected to ELISA analysis. Measurements of AUC and $Sn|_{Sp=0.9}$ are given in Table 6 and FIG. 16.

As can be seen in Table 6 and FIG. 16, the combination of CA19-9, LRG1, and TTR in accordance with the present disclosure was observed to have an AUC of 0.9144 and an $Sn|_{Sp=0.9}$ of 0.7800, indicating that the combination exhibits excellent performance as a diagnostic marker for pancreatic cancer. Particularly, a combination of CA19-9, LRG1, and TTR was observed to have higher diagnostic performance for pancreatic cancer than the commercially available diagnostic marker CA19-9 alone.

<6-3> Diagnostic Performance of Marker Combination of CA19-9, LRG1, and TTR for Cancer/Pancreatic Cancer Discrimination Using the ELISA of Example 3, a maker combination of CA19-9, LRG1, and TTR was assayed for diagnostic performance for discrimination between cancer and pancreatic cancer. The CA19-9 protein was quantitatively analyzed by chemiluminescence enzyme immunoassay (CLEIA) whereas LRG1 and TTR were subjected to ELISA analysis. Measurements of AUC and $Sn|_{Sp=0.9}$ are given in Table 6 and FIG. 17.

As can be seen in Table 6 and FIG. 17, the combination of CA19-9, LRG1, and TTR in accordance with the present disclosure was observed to have an AUC of 0.8981 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<6-4> Diagnostic Performance of a Marker Combination of CA19-9, LRG1, and TTR for PDAC Discrimination in Test Group with CA19-9<37 U/ml Using the ELISA of Example 3, the marker combination of CA19-9, LRG1, and TTR was assayed for diagnostic performance for pancreatic cancer discrimination in a group with CA19-9<37 U/ml. In most clinical cases, a subject is determined to have pancreatic cancer when CA19-9 is measured to be 37 U/ml or higher. Hence, CA19-9 cannot function as a diagnostic marker for pancreatic cancer in a subject with CA19-9<37 U/ml. The CA19-9 protein was quantitatively analyzed by chemiluminescence enzyme immunoassay (CLEIA) whereas LRG1 and TTR were subjected to ELISA. Measurements of AUC and $Sn|_{Sp=0.9}$ are given in Table 6 and FIG. 18.

As can be seen in Table 6 and FIG. 18, the combination of CA19-9, LRG1, and TTR in accordance with the present disclosure was observed to have an AUC of 0.8287 and an $Sn|_{Sp=0.9}$ of 0.5172, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

EXAMPLE 7

Immunoturbidimetric Assay for Diagnostic Performance of Marker Combination of CA19-9, LRG1, and TTR Examination was made to see whether immunoturbidimetric assay would reproduce results of the MRM-MS assay of the marker combination of CA19-9, LRG1, and TTR for pancreatic cancer discrimination in Example 5. The diagnostic performance of the combination of CA19-9, LRG1, and TTR for pancreatic cancer was also confirmed as measured by immunoturbidimetric assay.

<7-1> Diagnostic Performance of a Marker Combination of CA19-9, LRG1, and TTR for PDAC Discrimination Using the immunoturbidimetric assay of Example 4, the marker combination of CA19-9, LRG1, and TTR was assayed for diagnostic performance for pancreatic cancer discrimination. Analysis was performed on the CA19-9 protein by chemiluminescence enzyme immunoassay (CLEIA), on the LRG1 protein by ELISA, and on TTR by immunoturbidimetric assay. Measurements of AUC and $Sn|_{Sp=0.9}$ are given in Table 7 and FIG. 19.

TABLE 7

| Test classification | Marker combination | AUC | $Sn|_{Sp=0.9}$ |
|---|---|---|---|
| 7-1 | CA19-9 + LRG1 + TTR | 0.9402 | 0.8250 |
|  | CA19-9 + TTR | 0.9001 | 0.7500 |
|  | CA19-9 | 0.8259 | 0.7250 |
| 7-2 | CA19-9 + LRG1 + TTR | 0.9146 | 0.7600 |
|  | CA19-9 + TTR | 0.8678 | 0.6800 |
|  | CA19-9 | 0.7924 | 0.6400 |
| 7-3 | CA19-9 + LRG1 + TTR | 0.8965 | 0.8250 |
|  | CA19-9 + TTR | 0.8367 | 0.7500 |
|  | CA19-9 | 0.7964 | 0.6875 |
| 7-4 | CA19-9 + LRG1 + TTR | 0.8439 | 0.5172 |
|  | CA19-9 + TTR | 0.7255 | 0.3103 |
|  | CA19-9 | 0.5198 | 0.2414 |

As can be seen in Table 7 and FIG. 19, the combination of CA19-9, LRG1, and TTR in accordance with the present disclosure was observed to have an AUC of 0.9402 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<7-2> Diagnostic Performance of Marker Combination of CA19-9, LRG1, and TTR for Discrimination of Early Stage PDAC Using the immunoturbidimetric assay of Example 4, a maker combination of CA19-9, LRG1, and TTR was assayed for diagnostic performance for early stage pancreatic cancer. Analysis was performed on the CA19-9 protein by chemiluminescence enzyme immunoassay (CLEIA), on the LRG1 protein by ELISA, and on TTR by immunoturbidimetric assay. Measurements of AUC and $Sn|_{Sp=0.9}$ are given in Table 7 and FIG. 20.

As can be seen in Table 7 and FIG. 20, the combination of CA19-9, LRG1, and TTR in accordance with the present disclosure was observed to have an AUC of 0.9146 and an $Sn|_{Sp=0.9}$ of 0.7600, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<6-3> Diagnostic Performance of Marker Combination of CA19-9, LRG1, and TTR for Cancer/Pancreatic Cancer Discrimination Using the immunoturbidimetric assay of Example 4, a maker combination of CA19-9, LRG1, and TTR was assayed for diagnostic performance for discrimination between cancer and pancreatic cancer. Analysis was performed on the CA19-9 protein by chemiluminescence enzyme immunoassay (CLEIA), on the LRG1 protein by ELISA, and on TTR by immunoturbidimetric assay. Measurements of AUC and $Sn|_{Sp=0.9}$ are given in Table 7 and FIG. 21.

As can be seen in Table 7 and FIG. 21, the combination of CA19-9, LRG1, and TTR in accordance with the present disclosure was observed to have an AUC of 0.8965 and an $Sn|_{Sp=0.9}$ of 0.8250, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<7-4> Diagnostic Performance of Marker Combination of CA19-9, LRG1, and TTR for PDAC Discrimination in Test Group with CA19-9<37 U/ml Using the immunoturbidimetric assay of Example 4, the marker combination of CA19-9, LRG1 and TTR was assayed for diagnostic performance for pancreatic cancer discrimination in a group with CA19-9<37 U/ml. In most clinical cases, a subject is determined to have pancreatic cancer when CA19-9 is measured to be 37 U/ml or higher. Hence, CA19-9 cannot function as a diagnostic marker for pancreatic cancer in a subject with CA19-9<37 U/ml. Analysis was performed on the CA19-9 protein by chemiluminescence enzyme immunoassay (CLEIA), on the LRG1 protein by ELISA, and on TTR by immunoturbidimetric assay. Measurements of AUC and $Sn|_{Sp=0.9}$ are given in Table 7 and FIG. 22.

As can be seen in Table 7 and FIG. 22, the combination of CA19-9, LRG1, and TTR in accordance with the present disclosure was observed to have an AUC of 0.8439 and an $Sn|_{Sp=0.9}$ of 0.5172, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

EXAMPLE 8

Assay for Diagnostic Performance of Marker Combination of CA19-9, LRG1, and C1R by MRM-MS <8-1> Diagnostic Performance of a Marker Combination of CA19-9, LRG1, and C1R for PDAC Discrimination Using the MRM-MS method of Example 2, the marker combination of CA19-9, LRG1, and C1R was assayed for diagnostic performance for pancreatic cancer discrimination. The CA19-9 protein was quantitatively analyzed by chemiluminescence enzyme immunoassay (CLEIA) using the COBAS Elecsys CA 19-9 instrument of Roche Diagnostics whereas LRG1 and C1R were subjected to MRM quantitative analysis. Measurements of AUC and $Sn|_{Sp=0.9}$ are given in Table 8 and FIG. 23.

TABLE 8

| Marker combination | AUC | $Sn|_{Sp=0.9}$ |
|---|---|---|
| CA19-9 + LRG1 + C1R | 0.9296 | 0.8375 |
| CA19-9 + TTR | 0.8823 | 0.7125 |
| CA19-9 | 0.8259 | 0.7250 |

As can be seen in Table 8 and FIG. 23, the combination of CA19-9, LRG1, and C1R in accordance with the present disclosure was observed to have an AUC of 0.9296 and an $Sn|_{Sp=0.9}$ of 0.8375, indicating that the combination exhibits excellent performance as a diagnostic marker for pancreatic cancer. Particularly, a combination of CA19-9, LRG1, and C1R was observed to have higher diagnostic performance for pancreatic cancer than individual CA19-9, LRG1, and C1R, or a combination of any two thereof.

<8-2> Diagnostic Performance of a Marker Combination of CA19-9, LRG1, and C1R for Discrimination of Early Stage PDAC Using the MRM-MS method of Example 2, a maker combination of CA19-9, LRG1, and C1R was assayed for diagnostic performance for pancreatic cancer of early stage. The CA19-9 protein was quantitatively analyzed by chemiluminescence enzyme immunoassay (CLEIA) whereas LRG1 and C1R were subjected to MRM quantitative analysis. Measurements of AUC and $Sn|_{Sp=0.9}$ are given in Table 9 and FIG. 24.

TABLE 9

| Marker combination | AUC | $Sn|_{Sp=0.9}$ |
|---|---|---|
| CA19-9 + LRG1 + C1R | 0.9097 | 0.7800 |
| CA19-9 + LRG1 | 0.9094 | 0.7400 |
| CA19-9 + C1R | 0.8658 | 0.6600 |
| LRG1 + C1R | 0.7297 | 0.3800 |
| CA19-9 | 0.7924 | 0.6400 |
| LRG1 | 0.6362 | 0.3800 |
| C1R | 0.5137 | 0.1400 |

As can be seen in Table 9 and FIG. 24, the combination of CA19-9, LRG1, and C1R in accordance with the present disclosure was observed to have an AUC of 0.9097 and an $Sn|_{Sp=0.9}$ of 0.7800, indicating that the combination exhibits excellent performance as a diagnostic marker for pancreatic cancer. Particularly, a combination of CA19-9, LRG1, and C1R was observed to have higher diagnostic performance for early stage pancreatic cancer than the commercially available diagnostic marker CA19-9 alone.

<8-3> Diagnostic Performance of a Marker Combination of CA19-9, LRG1, and C1R for Cancer/Pancreatic Cancer Discrimination Using the MRM-MS method of Example 2, a maker combination of CA19-9, LRG1, and C1R was assayed for diagnostic performance for discrimination between cancer and pancreatic cancer. The CA19-9 protein was quantitatively analyzed by chemiluminescence enzyme immunoassay (CLEIA) whereas LRG1 and C1R were subjected to MRM quantitative analysis. Measurements of AUC and $Sn|_{Sp=0.9}$ are given in Table 10 and FIG. 25.

TABLE 10

| Test classification | Marker combination | AUC | Sn\|Sp = 0.9 |
|---|---|---|---|
| 8-3 | CA19-9 + LRG1 + C1R | 0.9088 | 0.8375 |
|  | CA19-9 + TTR | 0.8494 | 0.7125 |
|  | CA19-9 | 0.7964 | 0.6875 |
| 8-4 | CA19-9 + LRG1 + C1R | 0.8160 | 0.5517 |
|  | CA19-9 + TTR | 0.6753 | 0.2069 |
|  | CA19-9 | 0.5198 | 0.2414 |

As can be seen in Table 10 and FIG. 25, the combination of CA19-9, LRG1, and C1R in accordance with the present disclosure was observed to have an AUC of 0.9088 and an $Sn|_{Sp=0.9}$ of 0.8375, indicating that the combination exhibits excellent performance as a diagnostic marker for pancreatic cancer. Particularly, a combination of CA19-9, LRG1, and C1R was observed to have higher diagnostic performance for discrimination between cancer and pancreatic cancer than the commercially available diagnostic marker CA19-9 alone.

<8-4> Diagnostic Performance of a Marker Combination of CA19-9, LRG1, and C1R for PDAC Discrimination in Test Group with CA19-9<37 U/ml Using the MRM-MS method of Example 2, the marker combination of CA19-9, LRG1, and C1R was assayed for diagnostic performance for pancreatic cancer discrimination in a group with CA19-9<37 U/ml. The CA19-9 protein was quantitatively analyzed by chemiluminescence enzyme immunoassay (CLEIA) whereas LRG1 and C1R were subjected to MRM quantitative analysis. Measurements of AUC and $Sn|_{Sp=0.9}$ are given in Table 10 and FIG. 26.

As can be seen in Table 10 and FIG. 26, the combination of CA19-9, LRG1, and C1R in accordance with the present disclosure was observed to have an AUC of 0.8160 and an $Sn|_{Sp=0.9}$ of 0.5517, indicating that the combination exhibits excellent performance as a diagnostic marker for pancreatic cancer. Particularly, a combination of CA19-9, LRG1, and C1R was observed to have higher diagnostic performance for discrimination between cancer and pancreatic cancer than the commercially available diagnostic marker CA19-9 alone.

EXAMPLE 9

Assay for Diagnostic Performance of Marker Combination of CA19-9, LRG1, and CLU by MRM-MS <9-1> Diagnostic Performance of a Marker Combination of CA19-9, LRG1, and CLU for PDAC Discrimination Using the MRM-MS method of Example 2, the marker combination of CA19-9, LRG1 and CLU was assayed for diagnostic performance for pancreatic cancer discrimination. The CA19-9 protein was quantitatively analyzed by chemiluminescence enzyme immunoassay (CLEIA) whereas LRG1 and CLU were subjected to MRM quantitative analysis. Measurements of AUC and $Sn|_{Sp=0.9}$ are given in Table 11 and FIG. 27.

TABLE 11

| Marker combination | AUC | $Sn|_{Sp=0.9}$ |
|---|---|---|
| CA19-9 + LRG1 + CLU | 0.9338 | 0.8500 |
| CA19-9 + LRG1 | 0.9305 | 0.8125 |
| CA19-9 + CLU | 0.8662 | 0.7250 |
| LRG1 + CLU | 0.8004 | 0.6125 |
| CA19-9 | 0.8259 | 0.7250 |
| LRG1 | 0.7104 | 0.4375 |
| CLU | 0.6456 | 0.2250 |

As can be seen in Table 11 and FIG. 27, the combination of CA19-9, LRG1, and CLU in accordance with the present disclosure was observed to have an AUC of 0.9338 and an $Sn|_{Sp=0.9}$ of 0.8500, indicating that the combination exhibits excellent performance as a diagnostic marker for pancreatic cancer. Particularly, a combination of CA19-9, LRG1 and CLU was observed to have higher diagnostic performance for pancreatic cancer than individual CA19-9, LRG1, and CLU, or a combination of any two thereof.

<9-2> Diagnostic Performance of a Marker Combination of CA19-9, LRG1, and CLU for Discrimination of Early Stage PDAC Using the MRM-MS method of Example 2, a maker combination of CA19-9, LRG1, and CLU was assayed for diagnostic performance for early stage pancreatic cancer. The CA19-9 protein was quantitatively analyzed by chemiluminescence enzyme immunoassay (CLEIA) whereas LRG1 and CLU were subjected to MRM quantitative analysis. Measurements of AUC and $Sn|_{Sp=0.9}$ are given in Table 12 and FIG. 28.

TABLE 12

| Test classification | Maker combination | AUC | $Sn|_{Sp=0.9}$ |
|---|---|---|---|
| 9-2 | CA19-9 + LRG1 + CLU | 0.9027 | 0.7800 |
|  | CA19-9 + TTR | 0.8440 | 0.6400 |
|  | CA19-9 | 0.7924 | 0.6400 |
| 9-3 | CA19-9 + LRG1 + CLU | 0.9093 | 0.8500 |
|  | CA19-9 + TTR | 0.8494 | 0.7125 |
|  | CA19-9 | 0.7964 | 0.6875 |
| 9-4 | CA19-9 + LRG1 + CLU | 0.8384 | 0.5862 |
|  | CA19-9 + TTR | 0.6753 | 0.2069 |
|  | CA19-9 | 0.5198 | 0.2414 |

As can be seen in Table 12 and FIG. 28, the combination of CA19-9, LRG1, and CLU in accordance with the present disclosure was observed to have an AUC of 0.9027 and an $Sn|_{Sp=0.9}$ of 0.7800, indicating that the combination exhibits excellent performance as a diagnostic marker for pancreatic cancer. Particularly, a combination of CA19-9, LRG1 and CLU was observed to have higher diagnostic performance for early stage pancreatic cancer than the commercially available diagnostic marker CA19-9 alone.

<9-3> Diagnostic Performance of a Marker Combination of CA19-9, LRG1, and CLU for Cancer/Pancreatic Cancer Discrimination Using the MRM-MS method of Example 2, a maker combination of CA19-9, LRG1, and CLU was assayed for diagnostic performance for discrimination between cancer and pancreatic cancer. The CA19-9 protein was quantitatively analyzed by chemiluminescence enzyme immunoassay (CLEIA) whereas LRG1 and CLU were subjected to MRM quantitative analysis. Measurements of AUC and $Sn|_{Sp=0.9}$ are given in Table 12 and FIG. 29.

As can be seen in Table 12 and FIG. 29, the combination of CA19-9, LRG1, and CLU in accordance with the present disclosure was observed to have an AUC of 0.9093 and an $Sn|_{Sp=0.9}$ of 0.8500, indicating that the combination exhibits excellent performance as a diagnostic marker for pancreatic cancer. Particularly, a combination of CA19-9, LRG1, and CLU was observed to have higher diagnostic performance for discrimination between cancer and pancreatic cancer than the commercially available diagnostic marker CA19-9 alone.

<9-4> Diagnostic Performance of a Marker Combination of CA19-9, LRG1, and CLU for PDAC Discrimination in Test Group with CA19-9<37 U/ml Using the MRM-MS method of Example 2, the marker combination of CA19-9, LRG1, and CLU was assayed for diagnostic performance for pancreatic cancer discrimination in a group with CA19-9<37 U/ml. The CA19-9 protein was quantitatively analyzed by chemiluminescence enzyme immunoassay (CLEIA) whereas LRG1 and CLU were subjected to MRM quantitative analysis. Measurements of AUC and $Sn|_{Sp=0.9}$ are given in Table 12 and FIG. 30.

As can be seen in Table 12 and FIG. 30, the combination of CA19-9, LRG1, and CLU in accordance with the present disclosure was observed to have an AUC of 0.8384 and an $Sn|_{Sp=0.9}$ of 0.5862, indicating that the combination exhibits excellent performance as a diagnostic marker for pancreatic cancer. Particularly, a combination of CA19-9, LRG1 and CLU was observed to have higher diagnostic performance for discrimination between cancer and pancreatic cancer than the commercially available diagnostic marker CA19-9 alone.

EXAMPLE 10

Assay for Diagnostic Performance of Marker Combination of CA19-9, LRG1, and CLU by ELISA Examination was made to see whether ELISA would reproduce results of the MRM-MS assay of the marker combination of CA19-9, LRG1, and CLU for pancreatic cancer discrimination in Example 9. The excellent diagnostic performance of the combination of CA19-9, LRG1, and CLU for pancreatic cancer was also confirmed as assayed by ELISA.

<10-1> Diagnostic Performance of a Marker Combination of CA19-9, LRG1, and CLU for PDAC Discrimination Using the ELISA method of Example 3, the marker combination of CA19-9, LRG1, and CLU was assayed for diagnostic performance for pancreatic cancer discrimination. The CA19-9 protein was quantitatively analyzed by chemiluminescence enzyme immunoassay (CLEIA) whereas LRG1 and CLU were subjected to ELISA. Measurements of AUC and $Sn|_{Sp=0.9}$ are given in Table 13 and FIG. 31.

TABLE 13

| Marker | AUC | $Sn|_{Sp=0.9}$ |
|---|---|---|
| CA19-9 + LRG1 + CLU | 0.9399 | 0.8000 |
| CA19-9 + LRG1 | 0.9323 | 0.8000 |
| CA19-9 + CLU | 0.8980 | 0.8000 |
| LRG1 + CLU | 0.8607 | 0.5750 |
| CA19-9 | 0.8259 | 0.7250 |
| LRG1 | 0.8320 | 0.5750 |
| CLU | 0.7083 | 0.3000 |

As can be seen in Table 13 and FIG. 31, the combination of CA19-9, LRG1, and CLU in accordance with the present disclosure was observed to have an AUC of 0.9399 and an $Sn|_{Sp=0.9}$ of 0.8000, indicating that the combination exhibits excellent performance as a diagnostic marker for pancreatic cancer. Particularly, a combination of CA19-9, LRG1, and CLU was observed to have higher diagnostic performance for pancreatic cancer than individual CA19-9, LRG1, and CLU, or a combination of any two thereof.

<10-2> Diagnostic Performance of Marker Combination of CA19-9, LRG1, and CLU for Discrimination of Early Stage PDAC Using the ELISA of Example 3, a maker combination of CA19-9, LRG1, and CLU was assayed for diagnostic performance for early stage pancreatic cancer. The CA19-9 protein was quantitatively analyzed by chemiluminescence enzyme immunoassay (CLEIA) whereas LRG1 and CLU were subjected to ELISA analysis. Measurements of AUC and $Sn|_{Sp=0.9}$ are given in Table 14 and FIG. 32.

TABLE 14

| Test classification | Marker combination | AUC | $Sn|_{Sp=0.9}$ |
|---|---|---|---|
| 10-2 | CA19-9 + LRG1 + CLU | 0.9193 | 0.7000 |
|  | CA19-9 + TTR | 0.8937 | 0.7400 |
|  | CA19-9 | 0.7924 | 0.6400 |
| 10-3 | CA19-9 + LRG1 + CLU | 0.9079 | 0.8000 |
|  | CA19-9 + TTR | 0.8488 | 0.7750 |
|  | CA19-9 | 0.7964 | 0.6875 |
| 10-4 | CA19-9 + LRG1 + CLU | 0.8435 | 0.4828 |
|  | CA19-9 + TTR | 0.6753 | 0.2069 |
|  | CA19-9 | 0.5198 | 0.2414 |

As can be seen in Table 14 and FIG. 32, the combination of CA19-9, LRG1, and CLU in accordance with the present disclosure was observed to have an AUC of 0.9193 and an $Sn|_{Sp=0.9}$ of 0.6400, indicating that the combination exhibits excellent performance as a diagnostic marker for pancreatic cancer. Particularly, a combination of CA19-9, LRG1, and CLU was observed to have higher diagnostic performance for pancreatic cancer than the commercially available diagnostic marker CA19-9 alone.

<10-3> Diagnostic Performance of Marker Combination of CA19-9, LRG1, and CLU for Cancer/Pancreatic Cancer Discrimination Using the ELISA of Example 3, a maker combination of CA19-9, LRG1, and CLU was assayed for diagnostic performance for discrimination between cancer and pancreatic cancer. The CA19-9 protein was quantitatively analyzed by chemiluminescence enzyme immunoassay (CLEIA) whereas LRG1 and TTR were subjected to ELISA analysis. Measurements of AUC and $Sn|_{Sp=0.9}$ are given in Table 14 and FIG. 33.

As can be seen in Table 14 and FIG. 33, the combination of CA19-9, LRG1, and TTR in accordance with the present disclosure was observed to have an AUC of 0.9079 and an $Sn|_{Sp=0.9}$ of 0.8000, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

<10-4> Diagnostic Performance of a Marker Combination of CA19-9, LRG1, and CLU for PDAC Discrimination in Test Group with CA19-9<37 U/ml Using the ELISA of Example 3, the marker combination of CA19-9, LRG1, and CLU was assayed for diagnostic performance for pancreatic cancer discrimination in a group with CA19-9<37 U/ml. The CA19-9 protein was quantitatively analyzed by chemiluminescence enzyme immunoassay (CLEIA) whereas LRG1 and CLU were subjected to ELISA. Measurements of AUC and $Sn|_{Sp=0.9}$ are given in Table 14 and FIG. 34.

As can be seen in Table 14 and FIG. 34, the combination of CA19-9, LRG1, and CLU in accordance with the present disclosure was observed to have an AUC of 0.8435 and an $Sn|_{Sp=0.9}$ of 0.4828, indicating that the combination exhibits excellent performance as a diagnostic marker for pancreatic cancer. Particularly, a combination of CA19-9, LRG1, and TTR was observed to have higher diagnostic performance for discrimination between cancer and pancreatic cancer than the commercially available diagnostic marker CA19-9 alone.

EXAMPLE 11

Assay for Diagnostic Performance of Marker Combination of CA19-9, LRG1, and KLKB1 by MRM-MS <11-1> Diagnostic Performance of a Marker Combination of CA19-9, LRG1, and KLKB1 for PDAC Discrimination Using the MRM-MS method of Example 2, the marker combination of CA19-9, LRG1, and KLKB1 was assayed for diagnostic performance for pancreatic cancer discrimination. The CA19-9 protein was quantitatively analyzed by chemiluminescence enzyme immunoassay (CLEIA) whereas LRG1 and KLKB1 were subjected to MRM quantitative analysis. Measurements of AUC and $Sn|_{Sp=0.9}$ are given in Table 15 and FIG. 35.

TABLE 15

| Marker | AUC | Sn|Sp = 0.9 |
|---|---|---|
| CA19-9 + LRG1 + KLKB1 | 0.9382 | 0.8625 |
| CA19-9 + LRG1 | 0.9305 | 0.8125 |
| CA19-9 + KLKB1 | 0.8744 | 0.7250 |
| LRG1 + KLKB1 | 0.8608 | 0.7000 |
| CA19-9 | 0.8259 | 0.7250 |
| LRG1 | 0.7104 | 0.4375 |
| KLKB1 | 0.6076 | 0.1750 |

As can be seen in Table 15 and FIG. 35, the combination of CA19-9, LRG1, and KLKB1 in accordance with the present disclosure was observed to have an AUC of 0.9382 and an $Sn|_{Sp=0.9}$ of 0.8625, indicating that the combination exhibits excellent performance as a diagnostic marker for pancreatic cancer. Particularly, a combination of CA19-9, LRG1, and KLKB1 was observed to have higher diagnostic performance for pancreatic cancer than individual CA19-9, LRG1, and KLKB1, or a combination of any two thereof.

<11-2> Diagnostic Performance of a Marker Combination of CA19-9, LRG1, and KLKB1 for Discrimination of Early Stage PDAC Using the MRM-MS method of Example 2, a maker combination of CA19-9, LRG1, and KLKB1 was assayed for diagnostic performance for early stage pancreatic cancer. The CA19-9 protein was quantitatively analyzed by chemiluminescence enzyme immunoassay (CLEIA) whereas LRG1 and KLKB1 were subjected to MRM quantitative analysis. Measurements of AUC and $Sn|_{Sp=0.9}$ are given in Table 16 and FIG. 36.

TABLE 16

| Test classification | Marker | AUC | $Sn|_{Sp=0.9}$ |
|---|---|---|---|
| 11-2 | CA19-9 + LRG1 + KLKB1 | 0.9148 | 0.8000 |
|  | CA19-9 + TTR | 0.8440 | 0.6400 |
|  | CA19-9 | 0.7924 | 0.6400 |
| 11-3Table | CA19-9 + LRG1 + KLKB1 | 0.8924 | 0.8625 |
|  | CA19-9 + TTR | 0.8494 | 0.7125 |
|  | CA19-9 | 0.7924 | 0.6400 |
| 11-4 | CA19-9 + LRG1 + KLKB1 | 0.8349 | 0.6207 |
|  | CA19-9 + TTR | 0.6753 | 0.2069 |
|  | CA19-9 | 0.5198 | 0.2414 |

As can be seen in Table 16 and FIG. 36, the combination of CA19-9, LRG1, and KLKB1 in accordance with the present disclosure was observed to have an AUC of 0.9148 and an $Sn|_{Sp=0.9}$ of 0.8000, indicating that the combination exhibits excellent performance as a diagnostic marker for pancreatic cancer. Particularly, a combination of CA19-9, LRG1, and KLKB1 was observed to have higher diagnostic performance for early stage pancreatic cancer than the commercially available diagnostic marker CA19-9 alone.

<11-3> Diagnostic Performance of a Marker Combination of CA19-9, LRG1, and KLKB1 for Cancer/Pancreatic Cancer Discrimination Using the MRM-MS method of Example 2, a maker combination of CA19-9, LRG1, and KLKB1 was assayed for diagnostic performance for discrimination between cancer and pancreatic cancer. The CA19-9 protein was quantitatively analyzed by chemiluminescence enzyme immunoassay (CLEIA) whereas LRG1 and CLU were subjected to MRM quantitative analysis. Measurements of AUC and $Sn|_{Sp=0.9}$ are given in Table 16 and FIG. 37.

As can be seen in Table 16 and FIG. 37, the combination of CA19-9, LRG1, and KLKB1 in accordance with the present disclosure was observed to have an AUC of 0.8924 and an $Sn|_{Sp=0.9}$ of 0.8625, indicating that the combination exhibits excellent performance as a diagnostic marker for pancreatic cancer. Particularly, a combination of CA19-9, LRG1, and CLU was observed to have higher diagnostic performance for discrimination between cancer and pancreatic cancer than the commercially available diagnostic marker CA19-9 alone.

<11-4> Diagnostic Performance of a Marker Combination of CA19-9, LRG1, and KLKB1 for PDAC Discrimination in Test Group with CA19-9<37 U/ml Using the MRM-MS method of Example 2, the marker combination of CA19-9, LRG1, and KLKB1 was assayed for diagnostic performance for pancreatic cancer discrimination in a group with CA19-9<37 U/ml. The CA19-9 protein was quantitatively analyzed by chemiluminescence enzyme immunoassay (CLEIA) whereas LRG1 and KLKB1 were subjected to MRM quantitative analysis. Measurements of AUC and $\text{Sn}|_{Sp=0.9}$ are given in Table 16 and FIG. 38.

As can be seen in Table 16 and FIG. 38, the combination of CA19-9, LRG1, and KLKB1 in accordance with the present disclosure was observed to have an AUC of 0.8349 and an $\text{Sn}|_{Sp=0.9}$ of 0.6207, indicating that the combination exhibits excellent performance as a diagnostic marker for pancreatic cancer. Particularly, a combination of CA19-9, LRG1, and KLKB1 was observed to have higher diagnostic performance for discrimination between cancer and pancreatic cancer than the commercially available diagnostic marker CA19-9 alone.

EXAMPLE 12

Diagnosis of Pancreatic Cancer—Data Statistics

<12-1> CA19-9+LRG1+TTR

For statistical analysis, SVM (Support Vector Machine) was utilized. SVMs are algorithms designed to estimate a function that meets a given condition on the basis of the Lagrangian optimization theory. Of SVMs, a case where classification analysis is applied using a maximum margin classifier is called SVC (Support Vector Classification). In this Example, one of two sample groups was taken. The SVC in which a maximal difference exists between two sets (a normal set and a pancreatic cancer set) within the sample group was derived from machine learning and applied to the construction of the following pancreatic cancer diagnosis function.

$$f(x) = \text{sgn}\left(\sum_{i=1}^{n} \alpha_i y_i \langle x, x_i \rangle + b\right)$$

wherein, x is an expression level measurement of a diagnostic marker for pancreatic cancer, $\alpha_i$ is a Lagrange multiplier in SVM, $y_i$ is a separator of normal group/pancreatic cancer group, $x_i$ is a reference measurement, and b is a correction value.

The formula accounts for the onset of pancreatic cancer with a function value of 1 and a normal state with a function value of −1. Decision was made of the onset or the possibility of onset of pancreatic cancer using the function.

In detail, measurements of CA19-9, and MRM values of TTR and LRG1 were obtained from three normal persons as follows respectively: (7.4, 1.451, 3.2359), (6.3, 1.0718, 2.136), and (26.1, 1.2053, 3.1797). When these were applied to the formula, respective function values were calculated to be f(7.4, 1.451, 3.2359)=−1, f(6.3, 1.0718, 2.136)=−1, and f(26.1, 1.2053, 3.1797)=−1, indicating that the three persons were normal.

Separately, measurements of CA19-9, and MRM values of TTR and LRG1 were obtained from three pancreatic cancer patients as follows respectively: (45318, 4.898, 1.2514), (145, 2.4608, 1.6616), and (889, 2.5153, 1.5474). When these were applied to the formula, respective function values were calculated to be f(45318, 4.898, 1.2514)=1, f(145, 2.4608, 1.6616)=1, and f(889, 2.5153, 1.5474)=1, indicating that the three persons were affected with pancreatic cancer.

<12-2> CA19-9+LRG1+C1R

Decision was made of the onset or the possibility of onset of pancreatic cancer using Formula 1 based on SVM (Support Vector Machine) for statistical analysis.

Measurements of CA19-9, and MRM values of LRG1 and C1R were obtained from three normal persons as follows respectively: (7.4, 1.451, 1.0748), (6.3, 1.0718, 0.4531), and (26.1, 1.2053, 1.0929). When these were applied to the formula, respective function values were calculated to be f(7.4, 1.451, 1.0748)=−1, f(6.3, 1.0718, 0.4531)=−1, and f(26.1, 1.2053, 1.0929)=−1, indicating that the three persons were normal.

Separately, measurements of CA19-9, and MRM values of LRG1 and C1R were obtained from three pancreatic cancer patients as follows respectively: (45318, 4.893, 1.3742), (145, 2.4608, 1.483), and (889, 2.5153, 1.474). When these were applied to the formula, respective function values were calculated to be f(45318, 4.893, 1.3742)=1, f(145, 2.4608, 1.483)=1, and f(889, 2.5153, 1.474)=1, indicating that the three persons were affected with pancreatic cancer.

<12-3> CA19-9+LRG1+CLU

Decision was made of the onset or the possibility of onset of pancreatic cancer using Formula 1 based on SVM (Support Vector Machine) for statistical analysis. Measurements of CA19-9, and MRM values of LRG1 and CLU were obtained from three normal persons as follows respectively: (7.4, 1.451, 3.3803), (6.3, 1.0718, 3.1325), and (26.1, 1.2053, 2.8642). When these were applied to the formula, respective function values were calculated to be f(7.4, 1.451, 3.3803)=−1, f(6.3, 1.0718, 3.1325)=−1, and f(26.1, 1.2053, 2.8642)=−1, indicating that the three persons were normal.

Separately, measurements of CA19-9, and MRM values of LRG1 and CLU were obtained from three pancreatic cancer patients as follows respectively: (45318, 4.893, 1.6821), (145, 2.4608, 2.545), and (889, 2.5153, 1.5101) When these were applied to the formula, respective function values were calculated to be f(45318, 4.893, 1.6821)=1, f(145, 2.4608, 2.545)=1, and f(889, 2.5153, 1.5101)=1, indicating that the three persons were affected with pancreatic cancer.

<12-4> CA19-9+LRG1+KLKB1

Decision was made of the onset or the possibility of onset of pancreatic cancer using Formula 1 based on SVM (Support Vector Machine) for statistical analysis. Measurements of CA19-9, and MRM values of LRG1 and KLKB1 were obtained from three normal persons as follows respectively: (7.4, 1.451, 1.2801), (6.3, 1.0718, 0.961), and (26.1, 1.2053, 1.5657). When these were applied to the formula, respective function values were calculated to be f(7.4, 1.451, 1.2801)=−1, f(6.3, 1.0718, 0.961)=−1, and f(26.1, 1.2053, 1.5657)=−1, indicating that the three persons were normal.

Separately, measurements of CA19-9, and MRM values of LRG1 and KLKB1 were obtained from three pancreatic cancer patients as follows respectively: (45318, 4.893, 0.555), (145, 2.4608, 0.5347), and (889, 2.5153, 0.8084). When these were applied to the formula, respective function values were calculated to be f(45318, 4.893, 0.555)=1, f(145, 2.4608, 0.5347)=1, and f(889, 2.5153, 0.8084)=1, indicating that the three persons were affected with pancreatic cancer.

EXAMPLE 13

Diagnosis of Early Stage Pancreatic Cancer—Data Statistics

Decision was made of the onset of pancreatic cancer in an early stage using Formula 1 based on SVM (Support Vector Machine) for statistical analysis. Measurements of CA19-9, and MRM values of LRG1 and KLKB1 were obtained from three normal persons as follows respectively: (7.4, 1.451, 1.2801), (6.3, 1.0718, 0.961), and (26.1, 1.2053, 1.5657). When these were applied to the formula, respective function values were calculated to be f(7.4, 1.451, 1.2801)=−1, f(6.3, 1.0718, 0.961)=−1, and f(26.1, 1.2053, 1.5657)=−1, indicating that the three persons were normal.

Separately, measurements of CA19-9, and MRM values of LRG1 and KLKB1 were obtained from three pancreatic cancer patients in early stages as follows respectively: (154.52, 4.0994, 1.2722), (190.16, 4.5008, 0.7645), and (1052.8, 3.5696, 0.6775). When these were applied to the formula, respective function values were calculated to be f(154.52, 4.0994, 1.2722)=1, f(190.16, 4.5008, 0.7645)=1, and f(1052.8, 3.5696, 0.6775)=1, indicating that the three persons were pancreatic cancer patients in early stages.

EXAMPLE 14

Discriminative Diagnosis of Pancreatic Cancer from Other Cancer—Data Statistics Decision was made of the onset of pancreatic cancer in an early stage using Formula 1 based on SVM (Support Vector Machine) for statistical analysis. Measurements of CA19-9, and MRM values of LRG1 and KLKB1 were obtained from three patients with cancer other than pancreatic cancer as follows respectively: (8, 1.3985, 0.7085), (10.68, 0.9864, 0.776), and (7.32, 1.1431, 0.9214). When these were applied to the formula, respective function values were calculated to be f(8, 1.3985, 0.7085)=−1, f(10.68, 0.9864, 0.776)=−1, and f(7.32, 1.1431, 0.9214)=−1, whereby the three persons could be determined to be affected with cancer other than pancreatic cancer.

Separately, measurements of CA19-9, and MRM values of LRG1 and KLKB1 were obtained from three pancreatic cancer patients as follows respectively: (280.72, 4.0849, 0.9165), (4000, 5.7558, 0.7216), and (120.32, 6.2917, 0.555). When these were applied to the formula, respective function values were calculated to be f(154.52, 4.0994, 1.2722)=1, f(190.16, 4.5008, 0.7645)=1, and f(1052.8, 3.5696, 0.6775)=1, indicating that the three persons were affected with pancreatic cancer.

EXAMPLE 15

Preparation of Sample for Experiment

To effectively detect a malignant subtype of IPMN, consenting patients in the Seoul National University Hospital were divided into various groups including a normal group, a test group (high-risk group), etc., as shown in Table 17, below.

TABLE 17

| Classification | Group | Sample kind | Number of sample |
| --- | --- | --- | --- |
| Test 5 | Test group | High risk IPMN (High/Invasive) | 17 (8/9) |
|  | Control group | Poisitve IPMN (Low/Intermediate) | 16 (6/10) |
|  |  | cholecystitis | 22 |
|  |  | Normal | 24 |
|  |  | Sum | 79 |

TABLE 17-continued

| Classification | Group | Sample kind | Number of sample |
| --- | --- | --- | --- |
| Test 6 | High risk IPMN | High risk IPMN (High/Invasive) | 17 (8/9) |
|  | Low risk IPMN | Positive IPMN (Low/Intermediate) | 16 (6/10) |
|  |  | Sum | 33 |
| Test 7 | High risk IPMN | High risk IPMN (High/Invasive) | 25 (13/12) |
|  | Low risk IPMN | Positive IPMN (Low/Intermediate) | 18 (11/7) |
|  |  | Sum | 43 |

In Test 5, high-grade dysplasia and invasive type IPMN were used as a malignant (high-risk) subtype IPMN test group while normal persons, low dysplasia IPMN patients, intermediate dysplasia IPMN patients, and cholelithiasis patients with benign tumors were grouped into a control.

Test 6 for examining whether high-risk and low-risk groups can be discriminated from each other by the MMS assay was conducted with a malignant (high-risk) subtype IPMN test group consisting of high grade dysplasia and invasive type IPMN, and a low-risk group consisting of low dysplasia IPMN and intermediate dysplasia IPMN.

Test 7 for examining whether high-risk and low-risk groups can be discriminated from each other by the ELISA assay was conducted with a malignant (high-risk) subtype IPMN test group consisting of high grade dysplasia and invasive type IPMN, and a low-risk group consisting of low dysplasia IPMN and intermediate dysplasia IPMN. [Table 17]

EXAMPLE 16

Detection of High-Risk IPMN by MRM-MS

Using the MRM-MS method of Example 2, the markers of Table 32, below were assayed for diagnostic performance for high-risk IPMN discrimination. The CA19-9 protein was quantitatively analyzed by chemiluminescence enzyme immunoassay (CLEIA) using the COBAS Elecsys CA 19-9 instrument of Roche Diagnostics whereas LRG1 and TTR were subjected to MRM quantitative analysis.

When using a pancreatic cancer diagnosis function in the same manner as in the pancreatic cancer diagnosis function, the diagnostic performance of a combination of CA19-9, LRG1, and TTR for pancreatic cancer was expressed in AUC and $Sn|_{Sp=0.9}$ of an ROC curve. An ROC curve expresses relationship between sensitivity and specificity on a 2D plane. A greater area under curve (AUC; $0 \leq AUC \leq 1$) represents more correct information. $Sn|_{Sp=0.9}$ is a sensitivity value at a specificity of 0.9, showing detection sensitivity. A higher value of $Sn|_{Sp=0.9}$ provides more correct information.

Measurements of AUC and $Sn|_{Sp=0.9}$ are given in Table 18 and FIGS. 39 to 63.

TABLE 18

| Marker | AUC | Sn|Sp = 0.9 | Fig.# |
| --- | --- | --- | --- |
| CA19-9 | 0.6948 | 0.2000 | ** |
| LRG1 | 0.7375 | 0.4000 | 39 |
| LRG1 + CA19-9 | 0.8438 | 0.5333 | 40 |
| LRG1 + TTR | 0.9479 | 0.7333 | 41 |
| LRG1 + CLU | 0.8146 | 0.6000 | 42 |

TABLE 18-continued

| Marker | AUC | Sn\|Sp = 0.9 | Fig.# |
|---|---|---|---|
| LRG1 + C1R | 0.8448 | 0.7333 | 43 |
| LRG1 + KLKB1 | 0.8969 | 0.7333 | 44 |
| LRG1 + CA19-9 + TTR | 0.9500 | 0.9333 | 45 |
| LRG1 + CA19-9 + CLU | 0.9104 | 0.8667 | 46 |
| LRG1 + CA19-9 + C1R | 0.8708 | 0.6667 | 47 |
| LRG1 + CA19-9 + KLKB1 | 0.8938 | 0.8667 | 48 |
| LRG1 + TTR + CLU | 0.9653 | 0.8667 | 49 |
| LRG1 + TTR + C1R | 0.9542 | 0.7333 | 50 |
| LRG1 + TTR + KLKB1 | 0.9010 | 0.8000 | 51 |
| LRG1 + CLU + C1R | 0.9542 | 0.8000 | 52 |
| LRG1 + CLU + KLKB1 | 0.9031 | 0.8667 | 53 |
| LRG1 + C1R + KLKB1 | 0.8500 | 0.7333 | 54 |
| CLU + CA19-9 | 0.8479 | 0.7333 | 55 |
| CLU + TTR | 0.8885 | 0.6000 | 56 |
| CLU + KLKB1 | 0.8656 | 0.7333 | 57 |
| CLU + CA19-9 + TTR | 0.9365 | 0.6667 | 58 |
| CLU + CA19-9 + C1R | 0.8229 | 0.6000 | 59 |
| CLU + CA19-9 + KLKB1 | 0.8969 | 0.7333 | 60 |
| CLU + TTR + C1R | 0.9062 | 0.6667 | 61 |
| CLU + TTR + KLKB1 | 0.8604 | 0.6667 | 62 |
| CLU + C1R + KLKB1 | 0.8917 | 0.8000 | 63 |

As can be seen in Table 18 and FIGS. 39 to 63, individual markers or a combination of any two or more thereof according to the present disclosure was observed to have excellent performance of selectively diagnosing high-risk IPMN in discrimination from the control. Particularly, combinations of the markers according to the present disclosure were demonstrated to have higher diagnostic performance for high-risk IPMN than the commercially available diagnostic marker CA19-9 alone.

EXAMPLE 17

Selective Diagnosis Between High-Risk IPMN and Low-Risk IPMN by MRM-MS

To discriminate high-risk IPMN from low-risk IPMN, the test shown in Table 33 below was performed in the substantially same manner as in the MMS assay of Example 16. Measurements of AUC and $Sn|_{Sp=0.9}$ are given in Table 19 and FIGS. 64 to 89

TABLE 19

| 150 | AUC | $Sn|_{Sp=0.9}$ | Fig.# |
|---|---|---|---|
| CA19-9 | 0.6296 | 0.2000 | ** |
| LRG1 | 0.7148 | 0.2667 | 64 |
| LRG1 + CA19-9 | 0.8333 | 0.4667 | 65 |
| LRG1 + TTR | 0.8704 | 0.4000 | 66 |
| LRG1 + CLU | 0.8222 | 0.4667 | 67 |
| LRG1 + C1R | 0.8593 | 0.4000 | 68 |
| LRG1 + KLKB1 | 0.8630 | 0.4000 | 69 |
| CA19-9 + LRG1 + TTR | 0.9074 | 0.6000 | 70 |
| CA19-9 + LRG1 + C1R | 0.9000 | 0.6000 | 71 |
| CA19-9 + LRG1 + CLU | 0.8667 | 0.6000 | 72 |
| CA19-9 + LRG1 + KLKB1 | 0.9037 | 0.8000 | 73 |
| LRG1 + TTR + CLU | 0.8407 | 0.4667 | 74 |
| LRG1 + TTR + C1R | 0.8185 | 0.4667 | 75 |
| LRG1 + TTR + KLKB1 | 0.8815 | 0.3333 | 76 |
| LRG1 + CLU + C1R | 0.8963 | 0.6000 | 77 |
| LRG1 + CLU + KLKB1 | 0.8889 | 0.4000 | 78 |
| LRG1 + C1R + KLKB1 | 0.9074 | 0.6000 | 79 |
| CLU + CA19-9 | 0.7407 | 0.4000 | 80 |
| CLU + TTR | 0.7333 | 0.3333 | 81 |
| CLU + C1R | 0.7778 | 0.6000 | 82 |
| CLU + KLKB1 | 0.8111 | 0.3333 | 83 |
| CLU + CA19-9 + TTR | 0.8741 | 0.6000 | 84 |
| CLU + CA19-9 + C1R | 0.8185 | 0.7333 | 85 |
| CLU + CA19-9 + KLKB1 | 0.8741 | 0.6000 | 86 |
| CLU + TTR + C1R | 0.8481 | 0.3333 | 87 |

TABLE 19-continued

| 150 | AUC | $Sn|_{Sp=0.9}$ | Fig.# |
|---|---|---|---|
| CLU + TTR + KLKB1 | 0.8333 | 0.4000 | 88 |
| CLU + C1R + KLKB1 | 0.8889 | 0.6000 | 89 |

As can be seen in Table 19 and FIGS. 64 to 89, individual markers or a combination of any two or more thereof according to the present disclosure was observed to have excellent performance of selectively discriminating high-risk IPMN from low-risk IPMN. Particularly, combinations of the markers according to the present disclosure were demonstrated to have higher diagnostic performance for high-risk IPMN than the commercially available diagnostic marker CA19-9 alone.

EXAMPLE 18

Selective Diagnosis Between High-Risk IPMN and Low-Risk IPMN by MRM-MS

Examination was made to see whether ELISA would reproduce results of the MRM-MS assay of the marker combinations for pancreatic cancer discrimination in Example 17. The excellent diagnostic performance of the marker combinations of Table 20 for high-risk IPMN was also confirmed as assayed by ELISA.

To discriminate high-risk IPMN from low-risk IPMN for Test 7 of Example 15, the test shown in Table 20 below was performed in substantially the same manner as in the ELISA of Example 6. Measurements of AUC and $Sn|_{Sp=0.9}$ are given in Table 34 and FIGS. 90 to 100.

TABLE 20

| 150 | AUC | $Sn|_{Sp=0.9}$ | Fig.# |
|---|---|---|---|
| CA19-9 | 0.5667 | 0.2800 | ** |
| LRG1 | 0.6978 | 0.3600 | 90 |
| LRG1 + CA19-9 | 0.8067 | 0.6400 | 91 |
| LRG1 + TTR | 0.7356 | 0.1600 | 92 |
| LRG1 + CLU | 0.8244 | 0.6400 | 93 |
| LRG1 + CA19-9 + TTR | 0.8511 | 0.6000 | 94 |
| LRG1 + CA19-9 + CLU | 0.8689 | 0.5600 | 95 |
| LRG1 + CA19-9 + TTR + CLU | 0.8578 | 0.6000 | 96 |
| LRG1 + TTR + CLU | 0.8511 | 0.5200 | 97 |
| CLU + CA19-9 | 0.7889 | 0.4800 | 98 |
| CLU + TTR | 0.8178 | 0.5600 | 99 |
| CLU + CA19-9 + TTR | 0.7911 | 0.1200 | 100 |

As can be seen in Table 20 and FIGS. 90 to 100, individual markers or a combination of any two or more thereof according to the present disclosure was observed to have excellent performance of selectively discriminating high-risk IPMN from low-risk IPMN. Particularly, combinations of the markers according to the present disclosure were demonstrated to have higher diagnostic performance for high-risk IPMN than the commercially available diagnostic marker CA19-9 alone.

The invention claimed is:

1. A method for detecting the expression of protein in a subject suspected of having high-risk intraductal papillary mucinous neoplasm (IPMN), comprising:
   obtaining a sample from a subject suspected of having pancreatic cancer,
   measuring a protein expression level of LRG1 (Leucine-rich alpha-2-glycoprotein 1) from the sample suspected of having high-risk IPMN, comparing the expression level of LRG1 between the sample from the subject suspected of having high-risk IPMN and a sample from a normal group.

2. The method of claim 1, further comprising examining whether the subject has IPMN prior to the measuring step.

3. The method of claim 2, wherein the examining step is carried out by imaging diagnosis or biopsy, or by using a genetic marker.

4. The method of claim 1, wherein the subject is a patient from which an IPMN tissue has been removed by surgical section.

5. The method of claim 1, wherein the control is a normal group, a patient with a pancreatic disease other than pancreatic ductal adrenocarcinoma, or a subject with low-risk IPMN.

6. The method of claim 1, wherein the high-risk IPMN comprises high grade dysplasia and invasive type IPMN.

7. The method of claim 1, further comprising conducting surgical resection or drug administration when the subject is determined to have high-risk IPMN.

8. The method of claim 3, further comprising conducting drug administration or prognosis monitoring when the subject is determined to have low-risk IPMN.

9. The method of claim 1, wherein onset of high-risk IPMN is determined when the following conditions are satisfied: expression levels of both (a) CA19-9 and (b) LRG1 are higher in the subject than in a normal control; and an expression level of any one of (c) at least one of TTR, CLU, and KLKB1 is lower in the subject than in a normal control or an expression level of C1R is higher than in the subject than in a normal group.

10. The method of claim 1, wherein the high-risk IPMN comprises IPMN-derived pancreatic ductal adenocarcinoma.

11. A method for detecting the expression of protein in a subject suspected of having high-risk intraductal papillary mucinous neoplasm (IPMN), comprising:

obtaining a sample from a subject suspected of having pancreatic cancer, 1measuring from the sample suspected of having high-risk IPMN at least three proteins comprising (a) CA19-9 (carbohydrate antigen 19-9), (b) LRG1 (Leucine-rich alpha-2-glycoprotein 1, LRG), and (c) at least one protein selected from the group consisting of TTR (Transthyretin, ATTR, Prealbumin, TBPA), C1 R (Complement Clr subcomponent precursor), CLU (Clusterin preproprotein), and KLKB1 (Plasma Kallikrein protein), comparing the expression level of LRG1, CA19-9, and at least one of TTR, ATTR, C1R, C1r, CLU or KLKB1 between the sample from the subject suspected of having high-risk IPMN and a sample from a normal group.

12. The method of claim 1, wherein the measuring of expression levels of the proteins utilizes antibodies, oligopeptides, ligands, PNAs (peptide nucleic acids), or aptamers that can specifically bind to corresponding marker proteins.

13. The method of claim 1, wherein the measuring or comparing of expression levels of the proteins is carried out by using at least one selected from the group consisting of protein chip assay, immunoassay, ligand binding assay, MALDI-TOF (Matrix Assisted Laser Desorption/Ionization Time of Flight Mass Spectrometry), SELDI-TOF (Surface Enhanced Laser Desorption/Ionization Time of Flight Mass Spectrometry), radioimmunoassay, radial immunodiffusion, Ouchterlony immunodiffusion, Rocket immunoelectrophoresis, immunohistostaining, complement fixation test, 2-D electrophoresis, liquid chromatography-mass spectrometry (LC-MS), liquid chromatography-mass spectrometry/mass spectrometry (LC-MS/MS), Western blotting, and ELISA (enzyme-linked immunosorbentassay).

* * * * *